United States Patent
Hirata et al.

(10) Patent No.: US 9,193,908 B2
(45) Date of Patent: *Nov. 24, 2015

(54) COMPOUND HAVING DIHYDROPHENANTHRENE, LIQUID CRYSTAL COMPOSITION AND LIQUID CRYSTAL DISPLAY DEVICE

(75) Inventors: Kenji Hirata, Chiba (JP); Hiroki Ookawa, Chiba (JP)

(73) Assignees: JNC CORPORATION, Tokyo (JP); JNC PETROCHEMICAL CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/991,170

(22) PCT Filed: Dec. 9, 2011

(86) PCT No.: PCT/JP2011/078551
§ 371 (c)(1),
(2), (4) Date: Jun. 3, 2013

(87) PCT Pub. No.: WO2012/086437
PCT Pub. Date: Jun. 28, 2012

(65) Prior Publication Data
US 2013/0240784 A1    Sep. 19, 2013

(30) Foreign Application Priority Data
Dec. 21, 2010  (JP) .................. 2010-284260

(51) Int. Cl.
| C09K 19/00 | (2006.01) |
| C09K 19/32 | (2006.01) |
| C07C 25/22 | (2006.01) |
| C09K 19/34 | (2006.01) |
| C07C 25/24 | (2006.01) |
| G02F 1/137 | (2006.01) |

(52) U.S. Cl.
CPC .............. *C09K 19/32* (2013.01); *C07C 25/22* (2013.01); *C07C 25/24* (2013.01); *C09K 19/3402* (2013.01); *C07C 2103/26* (2013.01); *C09K 2019/3425* (2013.01); *G02F 2001/13712* (2013.01); *G02F 2201/086* (2013.01)

(58) Field of Classification Search
CPC .............. C07D 211/46; C09K 2019/0401; C09K 2019/0411; C09K 19/586
USPC .............................................. 252/61
See application file for complete search history.

(56) References Cited

U.S. PATENT DOCUMENTS

| 5,648,021 A | 7/1997 | Wingen et al. |
| 5,888,422 A * | 3/1999 | Manero et al. ........... 252/299.62 |
| 6,929,834 B2 * | 8/2005 | Klasen-Memmer et al. .. 428/1.1 |
| 2004/0099842 A1 | 5/2004 | Klasen-Memmer et al. |
| 2005/0258400 A1 | 11/2005 | Wingen et al. |
| 2006/0177603 A1 | 8/2006 | Taugerbeck et al. |

FOREIGN PATENT DOCUMENTS

| JP | 08-053672 | 2/1996 |
| JP | 11-508890 | 8/1999 |
| JP | 2005-325113 | 11/2005 |
| JP | 2006206887 A * | 8/2006 |
| JP | 2006/520327 | 9/2006 |

OTHER PUBLICATIONS

F. M. Leslie, "Distortion of Twisted Orientation Patterns in Liquid Crystals by Magnetic Fields", Molecular Crystals and Liquid Crystals, Aug. 1970, p. 57, vol. 12, Gordon and Breach Science Publishers, Great Britain.

"International Search Report (Form PCT/ISA/210)", published on Mar. 13, 2012, with English translation thereof, p. 1-p. 4.

"1st Office Action of Taiwan Counterpart Application", issued on Apr. 7, 2015, with English translation thereof, p. 1-p. 9.

* cited by examiner

*Primary Examiner* — Chanceity Robinson
(74) *Attorney, Agent, or Firm* — Jianq Chyun IP Office

(57) ABSTRACT

To provide a liquid crystal compound having a large negative dielectric anisotropy (Δ∈), and having at least one of characteristics such as a high stability to heat, light and so forth, a high clearing point, a suitable refractive index anisotropy (Δn) and an excellent compatibility with other liquid crystal compounds, and an intermediate thereof. A solution is a compound represented by formula (1):

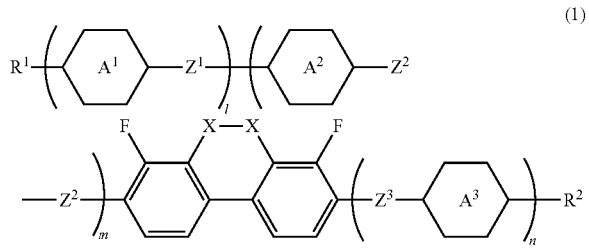

(1)

wherein, for example, $R^1$ and $R^2$ are alkyl having 1 to 12 carbons, alkoxy having 1 to 12 carbons or alkenyl having 2 to 12 carbons; ring $A^1$, ring $A^2$ and ring $A^3$ are 1,4-cyclohexylene or 1,4-phenylene; $Z^1$, $Z^2$ and $Z^3$ are a single bond or —(CH$_2$)$_2$—; X is —CF$_2$— or —CHF—; and l, m and n are 0 or 1.

12 Claims, No Drawings

COMPOUND HAVING DIHYDROPHENANTHRENE, LIQUID CRYSTAL COMPOSITION AND LIQUID CRYSTAL DISPLAY DEVICE

CROSS-REFERENCE TO RELATED APPLICATION

This application is a 371 application of an international PCT application serial no. PCT/JP2011/078551, filed on Dec. 9, 2011, which claims the priority benefit of Japan application no. 2010-284260, filed on Dec. 21, 2010. The entirety of each of the above-mentioned patent applications is hereby incorporated by reference herein and made a part of this specification.

TECHNICAL FIELD

The invention relates to a new liquid crystal compound and liquid crystal composition. More specifically, the invention relates to a liquid crystal compound having a negative dielectric anisotropy ($\Delta\epsilon$), a liquid crystal composition containing the same and a liquid crystal display device including the liquid crystal composition.

BACKGROUND ART

A display device using a liquid crystal compound is widely utilized for a display of a watch, a calculator, a word processor and so forth. The display devices utilize refractive index anisotropy, dielectric anisotropy or the like of the liquid crystal compound.

A liquid crystal phase includes a nematic liquid crystal phase, a smectic liquid crystal phase and a cholesteric liquid crystal phase, but a device utilizing the nematic liquid crystal phase is most widely used. Moreover, examples of display modes include a dynamic scattering (DS) mode, a deformation of aligned phases (DAP) mode, a guest/host (GH) mode, a twisted nematic (TN) mode, a super twisted nematic (STN) mode, a thin film transistor (TFT) mode, a vertical alignment (VA) mode, an in-plane switching (IPS) mode and a polymer sustained alignment (PSA) mode.

The liquid crystal compound used in the display modes should show the liquid crystal phase in a wide temperature range centering on room temperature, be sufficiently stable under an environment in which the display device is used, and have sufficient characteristics for driving the display device, but any single liquid crystal compound satisfying the conditions is not currently found.

Consequently, a liquid crystal composition having required characteristics is prepared by mixing several kinds to tens of kinds of liquid crystal compounds under an actual situation. The liquid crystal compositions are required to be stable to moisture, light, heat or air ordinarily present under conditions in which the display device is used, and also stable to an electric field or electromagnetic radiation, and also chemically stable to a compound to be mixed. Moreover, the liquid crystal composition is required to have suitable values of various physical properties such as refractive index anisotropy ($\Delta n$) and dielectric anisotropy ($\Delta\epsilon$) depending on the display mode or a shape of the display device. Furthermore, each component in the liquid crystal composition should have a good solubility with each other as an important requirement.

As a mode for overcoming narrowness of viewing angle being a biggest problem of a liquid crystal display device, among the display modes, a mode such as the IPS mode, the VA mode, the OCB mode and the PSA mode has attracted attention in recent years. Among the liquid crystal display devices having the modes, in particular, a device having the VA mode or the IPS mode has been actively developed because such a device has a wide viewing angle and also an excellent responsiveness, and further achieves a high contrast display. Features of the liquid crystal composition used for the liquid crystal display devices having the display modes are in a negative dielectric anisotropy ($\Delta\epsilon$). Then, a liquid crystal composition having a large negative dielectric anisotropy ($\Delta\epsilon$) is known to allow a decrease in a driving voltage of a liquid crystal display device including the liquid crystal composition (Non-patent literature No. 1). Therefore, the liquid crystal compound being a constituent of the liquid crystal composition is also required to have a larger negative dielectric anisotropy ($\Delta\epsilon$).

As a component of the liquid crystal composition having a negative dielectric anisotropy ($\Delta\epsilon$), a liquid crystal compound having a fluorine-substituted phenanthrene ring or a fluorine-substituted dihydrophenanthrene ring has been examined so far (Patent literature No. 1, 2, 3, 4 or 5).

In JP H8-53672 A (Patent literature No. 1), a compound as described below is proposed, but dielectric anisotropy ($\Delta\epsilon$) is not large.

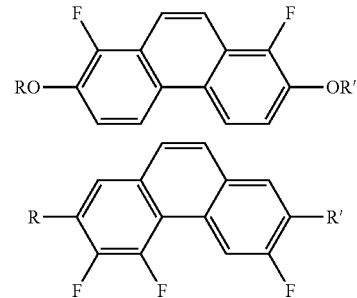

In JP 2005-325113 A (Patent literature No. 2), a compound as described below is proposed, but is unsuitable as a liquid crystal compound because a shape of a molecule is nonlinear.

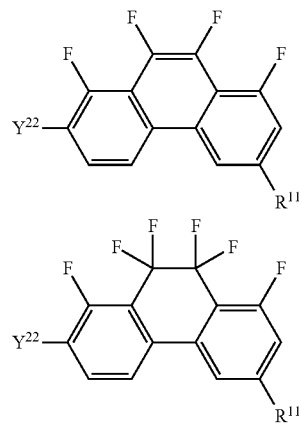

In U.S. Pat. No. 6,929,834 B (Patent literature No. 3), a liquid crystal composition using a compound represented by formula (a) is proposed.

(a)

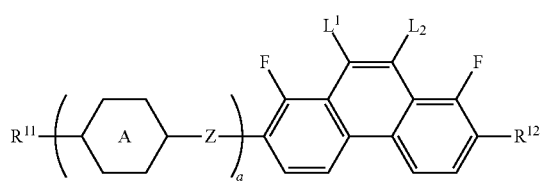

In the formula, $L^1$ and $L^2$ are independently hydrogen or fluorine. The compound represented by formula (a) has a large negative dielectric anisotropy ($\Delta\epsilon$), but is not sufficient in order to decrease a driving voltage of a liquid crystal display device having the VA mode, the IPS mode or the like. Moreover, the compound generally has a significantly low solubility, and is unstable to light.

In JP 2006-520327 A (Patent literature No. 4), benzo-chromene derivative (b) is proposed.

(b)

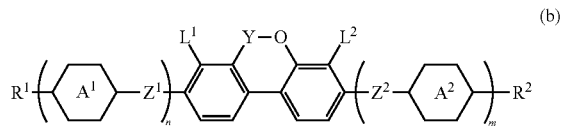

In the formula, Y is —CO—, —CS—, —CH$_2$—, —CF$_2$— or —CHF—, and $L^1$ and $L^2$ are independently hydrogen, fluorine, chlorine or —CN. When Y is —CF$_2$—, and $L^1$ and $L^2$ are fluorine, the derivative has a large negative dielectric anisotropy ($\Delta\epsilon$), but a basic skeleton is different from the art of the invention.

In JP H11-508890 A (Patent literature No. 5), a fluorine-substituted dihydrophenanthrene derivative represented by formula (C) is proposed.

(c)

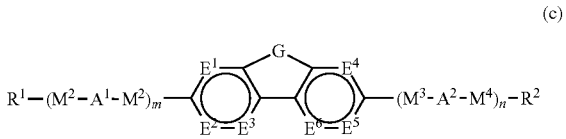

In the formula, $E^1$, $E^2$, $E^3$, $E^4$, $E^5$ and $E^6$ are independently —CF— or —CH—, and G is —CF$_2$CF$_2$— or —CF=CF—.

In Examples in the identical Patent literature, compounds as described below are disclosed. However, no Examples of a compound having fluorine on 1-position and 8-position of a 9,10-dihydrophenanthrene ring are found, and physical properties thereof are not explained, either.

(C-1)

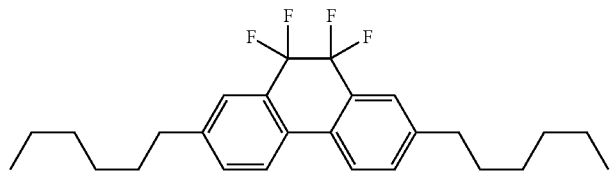

(C-2)

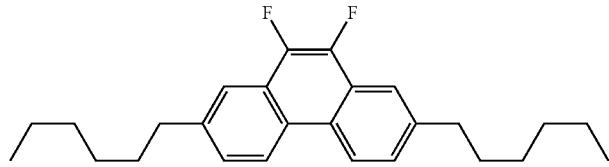

(C-3)

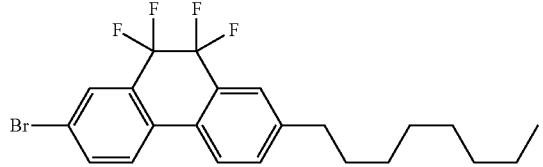

(C-4)

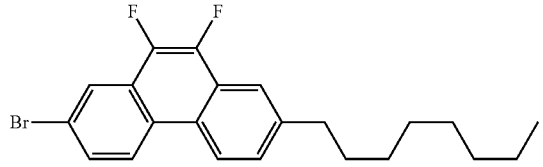

(C-5)

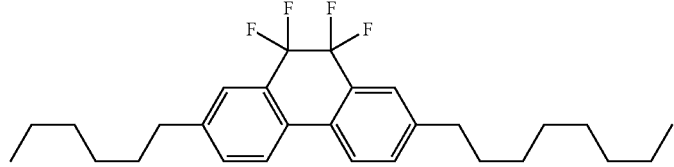

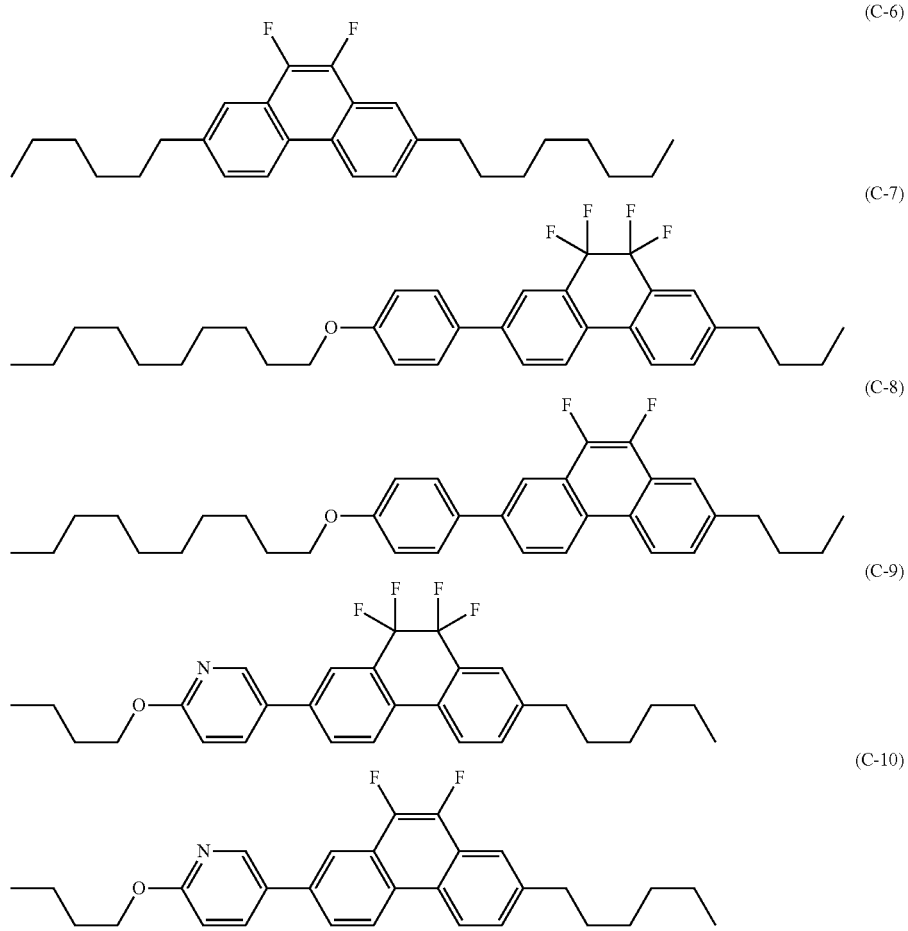

(C-6)

(C-7)

(C-8)

(C-9)

(C-10)

In order to decrease the driving voltage of a liquid crystal display device having the VA mode, the IPS mode or the like, a liquid crystal compound having a larger negative dielectric anisotropy (Δ∈), a liquid crystal composition and a liquid crystal display device are desired.

CITATION LIST

Patent Literature

Patent literature No. 1: JP H8-53672 A.
Patent literature No. 2: JP 2005-325113 A.
Patent literature No. 3: U.S. Pat. No. 6,929,834 B.
Patent literature No. 4: JP 2006-520327 A.
Patent literature No. 5: JP H11-508890 A.

Non-Patent Literature

Non-patent literature No. 1: Mol. Cryst. Liq. Cryst., 12, 57 (1970).

SUMMARY OF INVENTION

Technical Problem

A first object of the invention is to provide a liquid crystal compound having a large negative dielectric anisotropy (Δ∈). And having at least one of characteristics such as a high stability to heat, light and so forth, a high clearing point, a suitable refractive index anisotropy (Δn) and an excellent compatibility with other liquid crystal compounds, and to provide an intermediate thereof.

A second object of the invention is to provide a liquid crystal composition containing the compound, having at least one of characteristics such as a low viscosity, a suitable refractive index anisotropy (Δn) and a suitable negative dielectric anisotropy (Δ∈), a low threshold voltage, a high maximum temperature of a nematic phase (maximum temperature: phase transition temperature between the nematic phase and an isotropic phase) and a low minimum temperature of the nematic phase, or having a suitable balance regarding at least two of the characteristics.

A third object of the invention is to provide a liquid crystal display device including the composition, and having at least one of characteristics such as a short response time, a small electric power consumption and a small driving voltage, a large contrast and a capability of using the device in a wide temperature range, or having a suitable balance regarding at least two of the characteristics.

Solution to Problem

The present inventors have conducted research for achieving the objects, as a result, have found that, when a liquid crystal compound includes an element of

1)

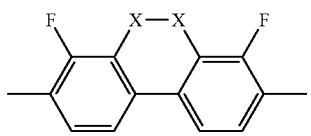

wherein, in the formula, X is independently —C(=O)—, —CHF— or —CF$_2$—, an excellent effect of an excellent compatibility with other liquid crystal compounds, in particular, a large negative value of dielectric anisotropy (Δ∈) is developed. The present inventors have found that the objects can be achieved by utilizing the effect, and thus have completed the invention.

The invention has constitutions of items 1 to 14 and so forth.

Item 1. A compound represented by formula (1):

(1)

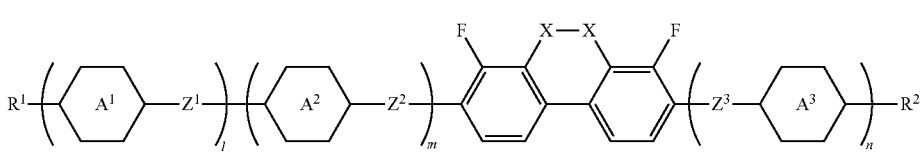

wherein, in formula (1), $R^1$ and $R^2$ are independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, and in the alkyl, the alkenyl, the alkoxy, the alkoxyalkyl and the alkenyloxy, at least one of hydrogen may be replaced by fluorine; ring $A^1$, ring $A^2$ and ring $A^3$ are independently 1,4-cyclohexylene, 1,4-cyclohexenylene, 1,4-phenylene, tetrahydropyran-2,5-diyl or 1,3-dioxane-2,5-diyl, and in the rings, at least one of hydrogen may be replaced by fluorine;
$Z^1$, $Z^2$ and $Z^3$ are independently a single bond, —(CH$_2$)$_2$—, —OCH$_2$—, —CH$_2$O—, —COO—, —COO—, —CF$_2$O— or —OCF$_2$—;
X is independently —C(=O)—, —CHF— or —CF$_2$—; and
l, m and n are independently 0 or 1.

Item. 2. The compound according to item 1, wherein, in formula (1), $R^1$ and $R^2$ are independently alkyl having 1 to 10 carbons, alkenyl having 2 to 10 carbons or alkoxy having 1 to 9 carbons; and ring $A^1$, ring $A^2$ and ring $A^3$ are independently 1,4-cyclohexylene, 1,4-cyclohexenylene, 1,4-phenylene, tetrahydropyran-2,5-diyl, 1,3-dioxane-2,5-diyl, 2-fluoro-1,4-phenylene, 3-fluoro-1,4-phenylene or 2,3-difluoro-1,4-phenylene.

Item 3. The compound according to item 2, wherein, in formula (1), ring $A^1$, ring $A^2$ and ring $A^3$ are independently 1,4-cyclohexylene, 1,4-cyclohexenylene, 1,4-phenylene, 2-fluoro-1,4-phenylene, 3-fluoro-1,4-phenylene or 2,3-difluoro-1,4-phenylene.

Item 4. The compound according to any one of items 1 to 3, wherein, in formula (1), a sum of l, m and n is 0, 1 or 2.

Item 5. The compound according to item 1, represented by formula (1-1):

(1-1)

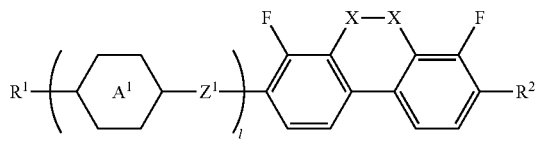

wherein, in formula (1-1), ring $A^1$ is 1,4-cyclohexylene, 1,4-cyclohexenylene, 1,4-phenylene, 2-fluoro-1,4-phenylene, 3-fluoro-1,4-phenylene or 2,3-difluoro-1,4-phenylene;

$R^1$ and $R^2$ are independently alkyl having 1 to 10 carbons, alkenyl having 2 to 10 carbons or alkoxy having 1 to 9 carbons;

$Z^1$ is a single bond, —(CH$_2$)$_2$—, —OCH$_2$—, —CH$_2$O—, —COO—, —COO—, —CF$_2$O— or —OCF$_2$—;

X is independently —C(=O)—, —CHF— or —CF$_2$—; and
l is 0 or 1.

Item 6. The compound according to item 5, wherein, in formula (1), $Z^1$ is a single bond, —(CH$_2$)$_2$—, —CH$_2$O—, —COO— or —CF$_2$O—.

Item 7. The compound according to item 5 or 6, wherein, in formula (1-1), ring $A^1$ is 1,4-cyclohexylene, 1,4-cyclohexenylene, 1,4-phenylene or 2,3-difluoro-1,4-phenylene.

Item 8. A liquid crystal composition containing at least one compound according to any one of items 1 to 7.

Item 9. The liquid crystal composition according to item 8, further containing at least one compound selected from the group of compounds represented by formulas (2), (3), (4), (5), (6) and (7):

(2)

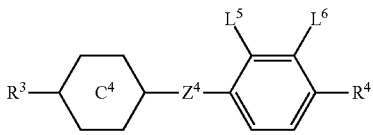

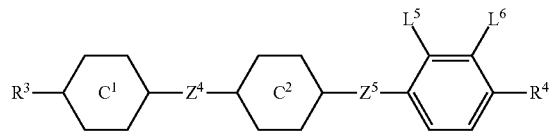
(3)

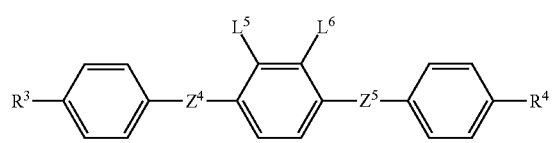
(4)

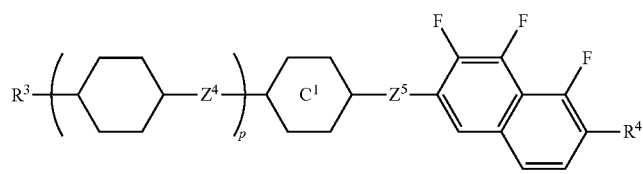
(5)

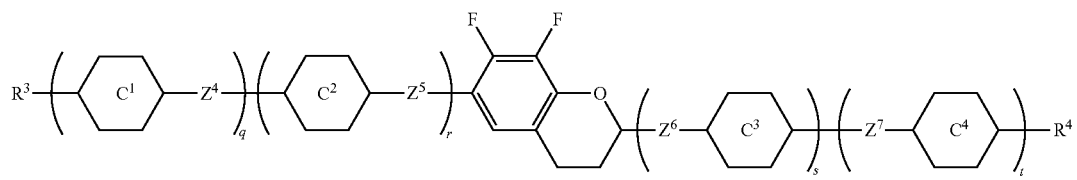
(6)

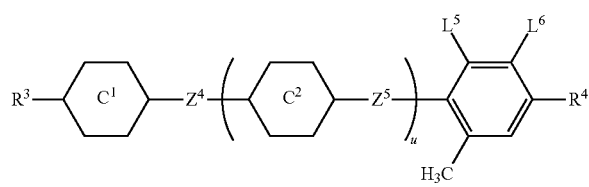
(7)

wherein, in the formulas, $R^3$ and $R^4$ are independently alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—; ring $C^1$, ring $C^2$, ring $C^3$ and ring $C^4$ are independently 1,4-cyclohexylene, 1,4-cyclohexenylene, 1,4-phenylene in which at least one of hydrogen may be replaced by fluorine, tetrahydropyran-2,5-diyl or decahydro-2,6-naphthalene;

$Z^4$, $Z^5$, $Z^6$ and $Z^7$ are independently —$(CH_2)_2$—, —COO—, —$CH_2O$—, —$OCF_2$—, —$OCF_2(CH_2)_2$— or a single bond; $L^5$ and $L^6$ are independently fluorine or chlorine; and p, q, r, s, t and u are independently 0 or 1, and a sum of q, r, s and t is 1 or 2.

Item 10. The liquid crystal composition according to item 8, further containing at least one compound selected from the group of compounds represented by formulas (8), (9) and (10):

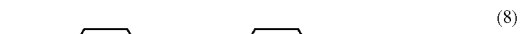
(8)

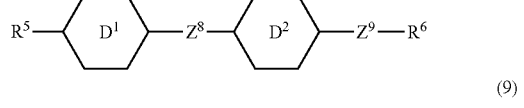
(9)

(10)

wherein, in the formulas, $R^5$ and $R^6$ are independently alkyl having 1 to 10 carbons or alkenyl having 2 to 10 carbons, and in the alkyl and the alkenyl, at least one of hydrogen may be replaced by fluorine and at least one of —$CH_2$— may be replaced by —O—; ring $D^1$, ring $D^2$ and ring $D^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^8$ and $Z^9$ are independently —C≡C—, —COO—, —$(CH_2)_2$—, —CH=CH— or a single bond.

Item 11. The liquid crystal composition according to item 9, further containing at least one compound selected from the group of compounds represented by formulas (8), (9) and (10).

Item 12. The liquid crystal composition according to any one of items 8 to 11, further containing at least one optically active compound and/or one polymerizable compound.

Item 13. The liquid crystal composition according to any one of items 8 to 12, containing at least one antioxidant and/or one ultraviolet light absorber.

Item 14. A liquid crystal display device including the liquid crystal composition according to any one of items 8 to 13.

Advantageous Effects of Invention

According to the invention, a liquid crystal compound having a large negative dielectric anisotropy (Δ∈), and having at least one of characteristics such as a high stability to heat, light and so forth, a high clearing point, a suitable refractive index anisotropy (Δn), a nematic phase in a wide temperature range and an excellent compatibility with other liquid crystal compounds, or an intermediate thereof is obtained.

Moreover, according to the invention, a liquid crystal composition having at least one of characteristics such as a low viscosity, a suitable refractive index anisotropy (Δn), a suitable negative dielectric anisotropy (Δ∈), a low threshold voltage and a high maximum temperature of a nematic phase and a low minimum temperature of the nematic phase is obtained.

Furthermore, a liquid crystal display device of the invention has at least one of characteristics such as a short response time, a small electric power consumption and a small driving voltage, a large contrast, and a capability of using the device in a wide temperature range, can be suitably used for a liquid crystal display device having a display mode such as a PC mode, a TN mode, a STN mode, an ECB mode, an OCB mode, an IPS mode, a VA mode and a PSA mode, in particular, for a liquid crystal display device having the IPS mode, the VA mode and the PSA mode.

DESCRIPTION OF EMBODIMENTS

Usage of terms herein is as described below. A liquid crystal compound and a liquid crystal composition according to the invention may be occasionally abbreviated as "compound" and "composition," respectively. Moreover, a liquid crystal display device may be occasionally abbreviated as "display device" or "device." The liquid crystal display device is a generic term for a liquid crystal display panel and a liquid crystal display module. "Liquid crystal compound" means a compound having a liquid crystal phase such as a nematic phase and a smectic phase, or a compound having no liquid crystal phase but being useful as a component of the composition. Such a useful compound includes a 6-membered ring such as 1,4-cyclohexylene and 1,4-phenylene and has a rod like molecular structure. An optically active compound may be occasionally added to the composition. Even when the compound is liquid crystalline, the compound is classified as an additive herein. At least one compound selected from the group of compounds represented by formula (1) may be occasionally abbreviated as "compound (1)." "Compound (1)" means one compound or two or more compounds represented by formula (1). A same rule applies to any other compound represented by any other formula. An expression "A and/or B" means that selection "A and B" and selection "A or B" can be arbitrarily performed. "At least one" in the context of "may be replaced" represents any of positions and also the number. An expression "at least one of A may be replaced by B, C or D" means a case where arbitrary A is replaced by B, a case where arbitrary A is replaced by C, and a case where arbitrary A is replaced by D, and also a case where a plurality of A are replaced by at least two of B to D. For example, alkyl in which at least one of —CH$_2$— may be replaced by —O— or —CH=CH— includes alkyl, alkenyl, alkoxy, alkoxyalkyl, alkoxyalkenyl and alkenyloxyalkyl.

Hereinafter, the invention will be explained in more detail.

A compound of the invention includes a liquid crystal compound represented by formula (1) as described below, or an intermediate thereof.

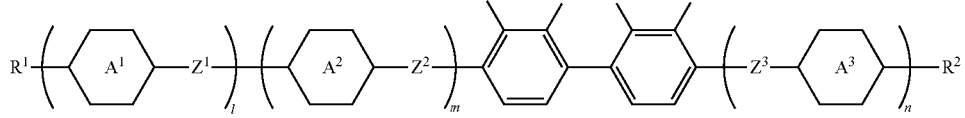

(1)

In formula (1), $R^1$ and $R^2$ are independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, and in the alkyl, the alkenyl, the alkoxy, the alkoxyalkyl and the alkenyloxy, at least one of hydrogen may be replaced by fluorine.

An alkyl chain in the groups is preferably linear. When the alkyl chain is linear, a temperature range of the liquid crystal phase can be extended, and viscosity can be decreased. Moreover, alkenyl preferably has a double bond in an odd-numbered position, and a trans configuration as a configuration. When a plurality double bonds are included in alkenyl, the plurality of double bonds are preferably non-conjugated.

Specific examples of alkyl include —CH$_3$, —C$_2$H$_5$, —C$_3$H$_7$, —C$_4$H$_9$, —C$_5$H$_{11}$, —O$_6$H$_{13}$, —C$_7$H$_{15}$ and —C$_8$H$_{17}$;

specific examples of alkenyl include —CH=CH$_2$, —CH=CHCH$_3$, —CH=CHC$_2$H$_5$, —(CH$_2$)$_2$CH=CH$_2$, —CH=CHC$_3$H$_7$, —(CH$_2$)$_2$CH=CHCH$_3$, —(CH$_2$)$_3$CH=CH$_2$, —CH=CH(CH$_2$)$_2$CH=CH$_2$ and —(CH$_2$)$_2$CH=CH(CH$_2$)$_2$CH=CH$_2$;

specific examples of alkoxy include —OCH$_3$, —OC$_2$H$_5$, —OC$_3$H$_7$, —OC$_4$H$_9$, —OC$_5$H$_{11}$, —OC$_6$H$_{13}$ and —OC$_7$H$_{15}$;

specific examples of alkoxyalkyl include —CH$_2$OCH$_3$, —CH$_2$OC$_2$H$_5$, —(CH$_2$)$_2$OCH$_3$ and —(CH$_2$)$_2$OC$_2$H$_5$; and specific examples of alkenyloxy include —OCH$_2$CH=CH$_2$, —OCH$_2$CH=CHCH$_3$ and —OCH$_2$CH=CHC$_2$H$_5$.

Preferred $R^1$ and $R^2$ include —CH$_3$, —O$_2$H$_5$, —O$_3$H$_7$, —O$_4$H$_9$, —O$_5$H$_{11}$, —C$_6$H$_{13}$, —C$_7$H$_{15}$, —CH=CH$_2$, —CH=CHCH$_3$, —(CH$_2$)$_2$CH=CH$_2$, —(CH$_2$)$_2$CH=CHCH$_3$, —CH=CH(CH$_2$)$_2$CH_CH$_2$, —(CH$_2$)$_2$CH=CH(CH$_2$)$_2$CH=CH$_2$, —OCH$_3$, —OC$_2$H$_5$, —OC$_3$H$_7$, —OC$_4$H$_9$ and —OC$_5$H$_{11}$.

Further preferred $R^1$ and $R^2$ include —CH$_3$, —C$_2$H$_5$, —O$_3$H$_7$, —O$_4$H$_9$, —C$_5$H$_{11}$, —CH=CH$_2$—CH=CHCH$_3$, —(CH$_2$)$_2$CH=CH$_2$—(CH$_2$)$_2$CH=CHCH$_3$, —OCH$_3$, —OC$_2$H$_5$, —OC$_3$H$_7$ and —OC$_4$H$_9$.

In formula (1), ring $A^1$, ring $A^2$ and ring $A^3$ are independently 1,4-cyclohexylene, 1,4-cyclohexenylene, 1,4-phenylene, tetrahydropyran-2,5-diyl or 1,3-dioxane-2,5-diyl, and in the groups, at least one of hydrogen may be replaced by fluorine.

When the rings are 1,4-cyclohexylene, refractive index anisotropy (Δn) can be decreased, the viscosity can be decreased, and further if the liquid crystal compound is added to a liquid crystal composition, the maximum temperature of the nematic phase can be increased.

Moreover, when the rings are 1,4-phenylene in which hydrogen may be replaced by halogen, the refractive index anisotropy (Δn) can be relatively increased, and simultaneously an orientational order parameter can be increased.

Among the rings, ring $A^1$, ring $A^2$ and ring $A^3$ are preferably 1,4-cyclohexylene, 1,4-cyclohexenylene, 1,4-phenylene, 2-fluoro-1,4-phenylene, 3-fluoro-1,4-phenylene, 2,3-difluoro-1,4-phenylene or tetrahydropyran-2,5-diyl.

Further preferred ring $A^1$, ring $A^2$ and ring $A^3$ are 1,4-cyclohexylene, 1,4-phenylene or 2,3-difluoro-1,4-phenylene.

In formula (1), $Z^1$, $Z^2$ and $Z^3$ are independently a single bond, —(CH$_2$)$_2$—, —OCH$_2$—, —CH$_2$O—, —COO—, —OCO—, —CF$_2$O— or —COF$_2$—.

A case where the bonding groups are a single bond is preferred from a viewpoint of extending the temperature range of the liquid crystal phase or decreasing the viscosity.

Moreover, a case where the bonding groups are —(CH$_2$)$_2$— is preferred from a viewpoint of a high solubility with other liquid crystal compounds and decreasing the viscosity.

Moreover, a case where the bonding groups are —OCH$_2$—, —CH$_2$O—, —COO—, —OCO—, —CF$_2$O— or —OCF$_2$— is preferred from a viewpoint of a large negative dielectric anisotropy, an excellent compatibility with other liquid crystal compounds and decreasing the viscosity.

In formula (1), X is independently —C(=O)—, —CHF— or —CF$_2$—. A case where X is —CHF— or —CF$_2$— is preferred from a viewpoint of a large negative dielectric anisotropy and an excellent compatibility with other liquid crystal compounds.

Then, l, m and n are independently 0 or 1.

With regard to the liquid crystal compounds represented by formula (1), when terminal groups $R^1$ and $R^2$, ring $A^1$, ring $A^2$ and ring $A^3$, and bonding groups $Z^1$, $Z^2$ and $Z^3$ are appropriately selected in the range described above, physical properties such as the refractive index anisotropy (Δn), the dielectric anisotropy (Δ∈) and the viscosity can be adjusted to desired levels.

Particularly preferred examples of the liquid crystal compounds represented by formula (1) include compounds (1-1-1) to (1-1-6).

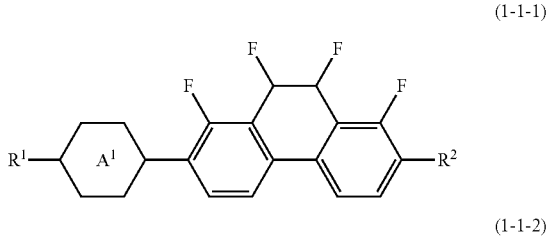
(1-1-1)

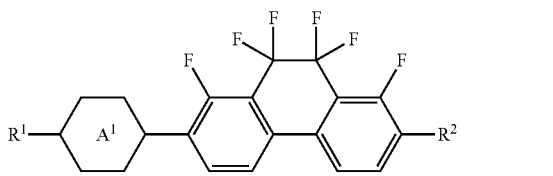
(1-1-2)

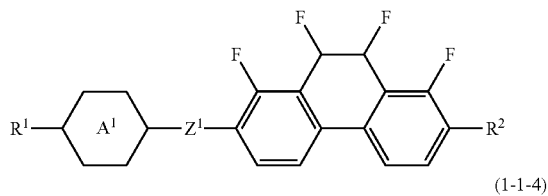
(1-1-3)

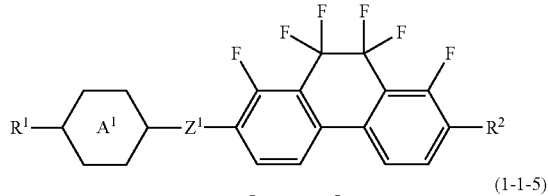
(1-1-4)

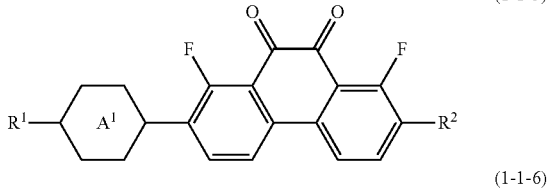
(1-1-5)

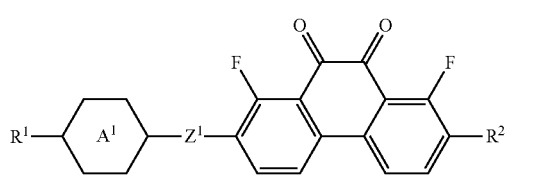
(1-1-6)

In the formulas, $R^1$ and $R^2$ are independently alkyl having 1 to 10 carbons, alkenyl having 2 to 10 carbons or alkoxy having 1 to 9 carbons;

ring $A^1$ is 1,4-cyclohexylene, 1,4-cyclohexenylene, 1,4-phenylene, 2-fluoro-1,4-phenylene, 3-fluoro-1,4-phenylene or 2,3-difluoro-1,4-phenylene; and $Z^1$ is —(CH$_2$)$_2$—, —OCH$_2$—, —CH$_2$O—, —COO—, —OCO—, —CF$_2$O— or —OCF$_2$—.

Compound (1) can be prepared by suitably combining techniques in synthetic organic chemistry. Methods for introducing an objective terminal group, ring structure and bonding group into a starting material are described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co. Ltd.).

With regard to one example of methods for forming bonding groups $Z^1$, $Z^2$ or $Z^3$, a scheme is first shown, and explained in section (I) to section (V). In the scheme, MSG$^1$ or MSG$^2$ is a monovalent organic group having at least one ring. A plurality of MSG$^1$ (or MSG$^2$) used in the scheme may be identical or different. Compounds (1A) to (1F) correspond to compound (1).

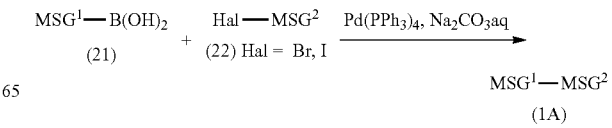
(1A)

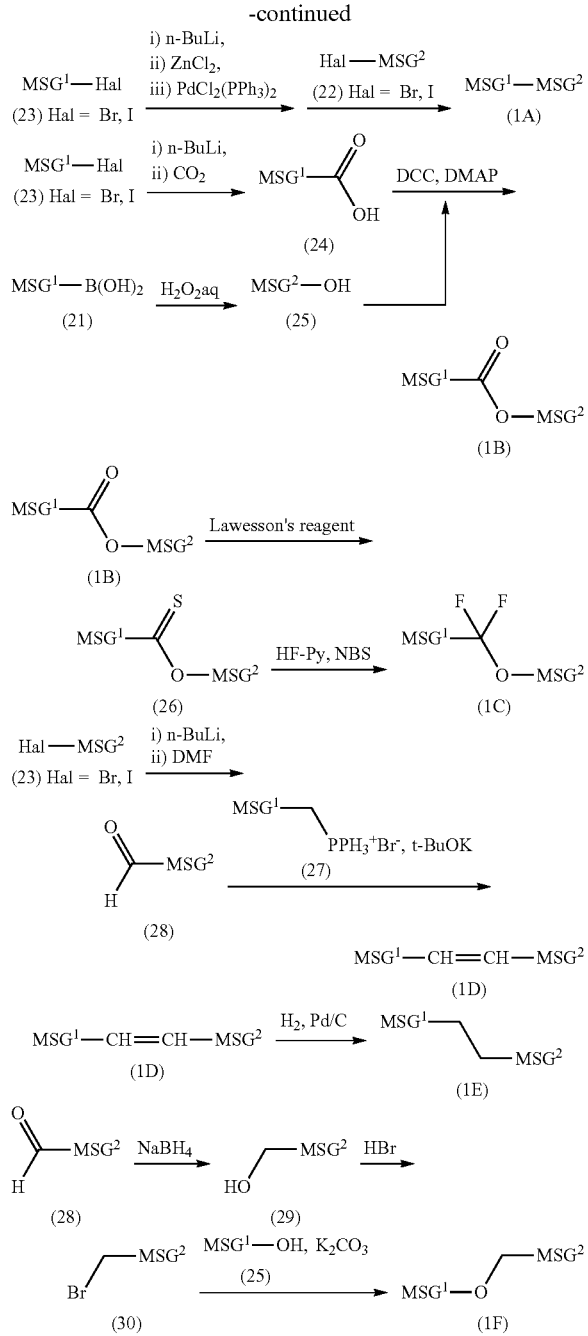

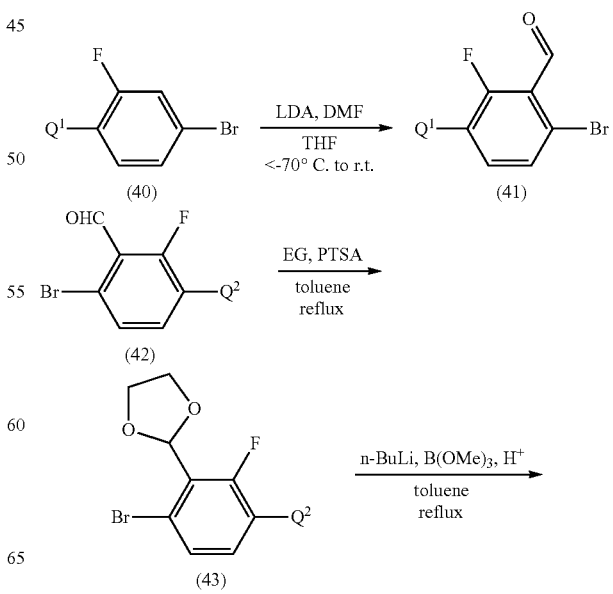

pared by dehydrating compound (24) and phenol (25) to be prepared according to a publicly known method, in the presence of 1,3-dicyclohexylcarbodiimide (DCC) and 4-dimethylaminopyridine (DMAP). A compound having —COO— can also be prepared according to the method.

(III) Formation of —CF$_2$O— and —OCF$_2$—

Compound (26) is obtained by treating compound (1B) with a thiation reagent such as Lawesson's reagent. Compound (1C) having —CF$_2$O— can be prepared by fluorinating compound (26) with a hydrogen fluoride-pyridine complex and N-bromosuccinimide (NBS) (M. Kuroboshi et al., Chem. Lett., 1992, 827). Compound (1C) can also be prepared by fluorinating compound (26) with (diethylamino) sulfurtrifluoride (DAST) (W. H. Bunnelle et al., J. Org. Chem. 1990, 55, 768). A compound having —OCF$_2$— can also be prepared according to the method. The bonding groups can also be formed according to the method described in Peer. Kirsch et al., Angew. Chem. Int. Ed. 2001, 40, 1480.

(IV) Formation of —(CH$_2$)$_2$—

Aldehyde (28) is obtained by treating compound (23) with n-butyllithium, and then allowing the treated product to react with formamide such as N,N-dimethylformamide (DMF). Compound (1D) can be prepared by allowing aldehyde (28) to react with phosphorus ylide generated by treating phosphonium salt (27) to be prepared according to a publicly known method with a base such as potassium tert-butoxide. Compound (1E) can be prepared by hydrogenating compound (1D) in the presence of a palladium on carbon catalyst.

(V) Formation of —CH$_2$O— or —OCH$_2$—

Compound (29) is obtained by reducing compound (28) with a reducing agent such as sodium borohydride. Compound (30) is obtained by halogenating compound (29) with hydrobromic acid or the like. Compound (1F) can be prepared by allowing compound (30) to react with compound (25) in the presence of potassium carbonate or the like.

Next, one example of methods for synthesizing a compound represented by formula (1) is shown in a scheme. A scheme for preparing intermediate (45) will be first explained.

(I) Formation of a Single Bond

Compound (1A) can be prepared by allowing arylboronic acid (21) to react, in the presence of an aqueous solution of carbonate and a tetrakis(triphenylphosphine) palladium catalyst, with compound (22) to be prepared according to a publicly known method. Compound (1A) can also be prepared by allowing compound (23) to be prepared according to a publicly known method to react with n-butyllithium, and subsequently with zinc chloride, and further with compound (22) in the presence of a dichlorobis(triphenylphosphine) palladium catalyst.

(II) Formation of —COO— and —COO—

Carboxylic acid (24) is obtained by allowing compound (23) to react with n-butyllithium, and subsequently with carbon dioxide. Compound (1B) having —COO— can be pre-

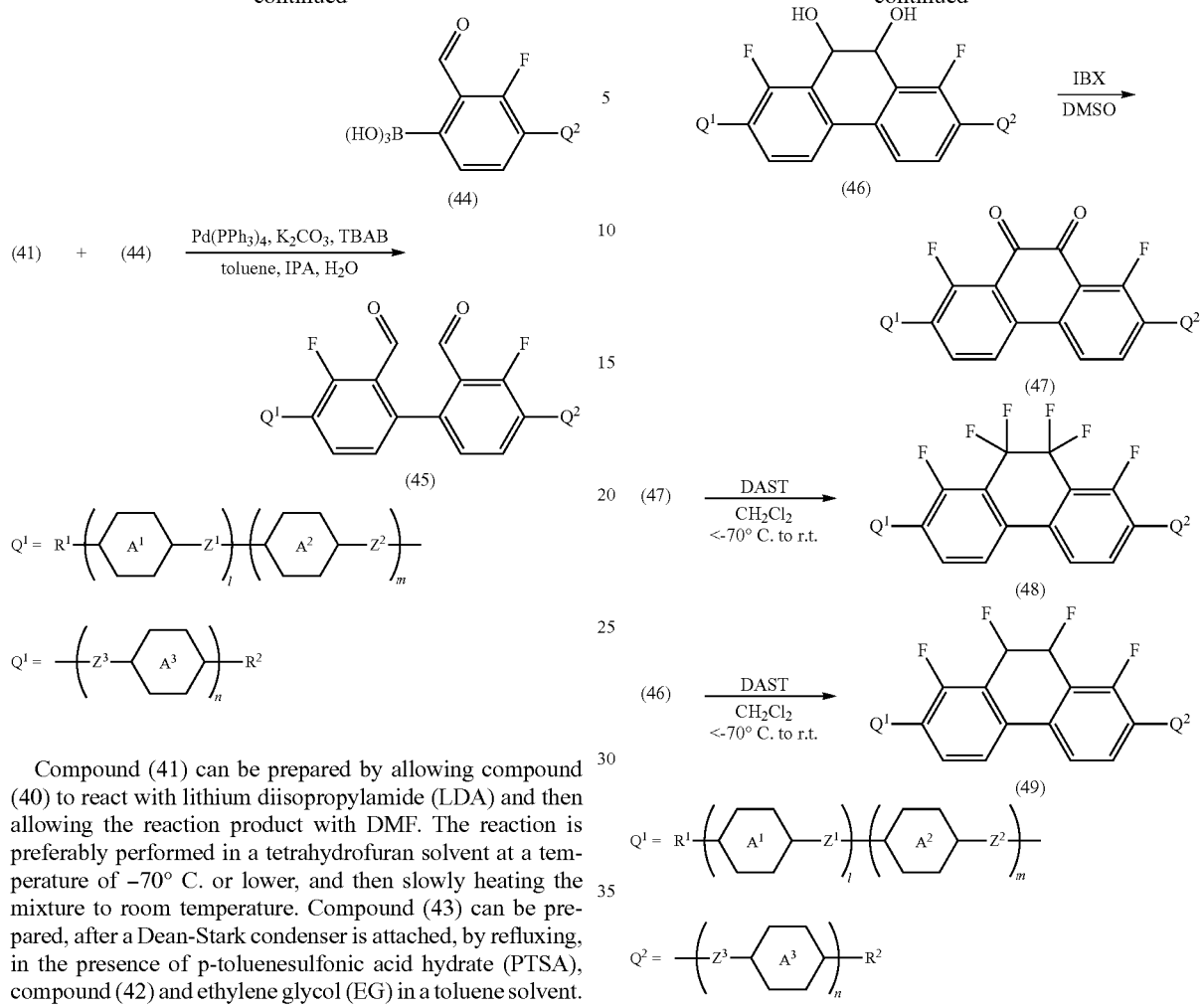

Compound (41) can be prepared by allowing compound (40) to react with lithium diisopropylamide (LDA) and then allowing the reaction product with DMF. The reaction is preferably performed in a tetrahydrofuran solvent at a temperature of −70° C. or lower, and then slowly heating the mixture to room temperature. Compound (43) can be prepared, after a Dean-Stark condenser is attached, by refluxing, in the presence of p-toluenesulfonic acid hydrate (PTSA), compound (42) and ethylene glycol (EG) in a toluene solvent. Compound (43) is allowed to react with n-butyllithium in a tetrahydrofuran solvent, and then allowing the reaction product to react with trimethoxy borane. The reaction is preferably performed at a temperature of −60° C. or lower, and then slowly heating the mixture to room temperature. Subsequently, compound (44) is obtained by treating the reaction product with an acid. Compound (45) can be prepared by allowing compound (41) to react with compound (44) in the presence of a tetrakis(triphenylphosphine)palladium catalyst and a base. The reaction is preferably performed by refluxing, in the presence of a phase transition catalyst such as tetrabutylammonium bromide (TBAB), the mixture in a mixed solvent of toluene-alcohol-water.

Subsequently, one example of methods for preparing compound (47), compound (48) and compound (49) using synthetic intermediate (45) as a starting material is described.

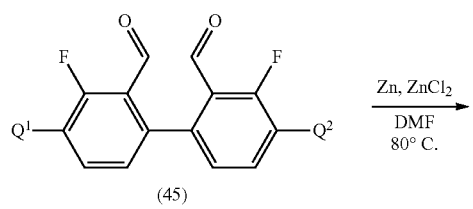

Compound (46) can be prepared by allowing, in the presence of zinc and $ZnCl_2$, reaction of compound (45) in DMF (Tetrahedron, 64 (2008), 9906-9910). Compound (47) can be prepared by allowing compound (46) to react with 1-hydroxy-1,2-benziodoxy-3(1H)-one (IBX) in dimethyl sulfoxide (DMSO). Compound (48) can be prepared by allowing compound (47) to react with DAST in dichloromethane. The reaction is preferably performed at a temperature of −70° C. or lower, and then slowly heating the mixture to room temperature. In a similar manner, compound (49) is obtained from compound (46).

In compounds (40) to (49), $Q^1$ and $Q^2$ represent the structural unit in formula (1). The structural unit is shown in the scheme. $R^1$, $R^2$, $A^1$, $A^2$, $A^3$, $Z^1$, $Z^2$, $Z^3$, l, m and n in the compounds are defined in a manner identical with the definitions of the identical symbols as described in item 1.

The compound of the invention has a superior compatibility with other liquid crystal compounds and a lower viscosity, and a wider liquid crystal temperature range in comparison with a compound having a similar structure. Moreover, the compound has a lower threshold voltage and also shows a relatively lower viscosity in comparison with the compound having the similar structure. Furthermore, the compound of the invention is physically and chemically sufficiently stable under an environment in which the liquid crystal display device is ordinarily used, and is superb as a constituent of a nematic liquid crystal composition, and can be suitably used as a constituent of a liquid crystal composition for the TN mode, the STN mode, the TFT mode, the VA mode, the IPS mode and the PSA mode.

The liquid crystal composition of the invention is required to contain compound (1) as component A. The liquid crystal composition of the invention may contain only component A, or component A and any other component that is not particularly named herein. However, when a component selected from components B and C as shown below is added to the component A, a liquid crystal composition having various characteristics according to the invention can be provided.

As the component to be added to component A, component B including at least one compound selected from the group of compounds represented by formulas (2), (3), (4), (5), (6) and (7) is preferred. Furthermore, when component C including at least one compound selected from the group of compounds represented by formula (8), (9) and (10) is added to component A, the threshold voltage, the liquid crystal phase temperature range, the refractive index anisotropy, the dielectric anisotropy, the viscosity or the like can be adjusted.

Even when each component used in the liquid crystal composition of the invention is an analog including an isotopic element of each element, the liquid crystal composition of the invention has no large difference in physical characteristics.

Component B including compounds (2) to (7) is preferred when preparing a liquid crystal composition having a negative dielectric anisotropy used for the vertical alignment mode (VA mode), a polymer sustained alignment mode (PSA mode) according to the invention.

Suitable examples of compounds (2) to (7) being component B include compounds (2-1) to (2-6), (3-1) to (3-15), (4-1), (5-1) to (5-3), (6-1) to (0.6-11) and (7-1) to (7-10).

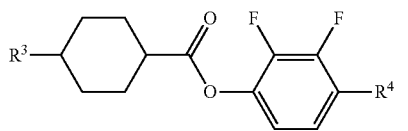
(2-1)

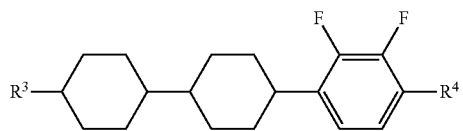
(2-2)

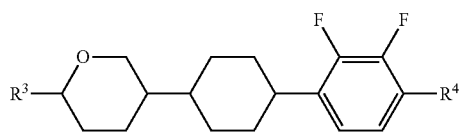
(2-3)

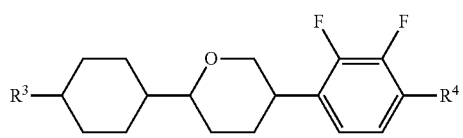
(2-4)

(2-5)

(2-6)

(3-1)

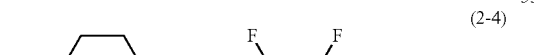
(3-2)

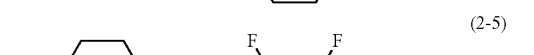
(3-3)

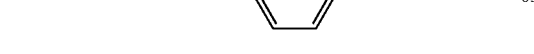
(3-4)

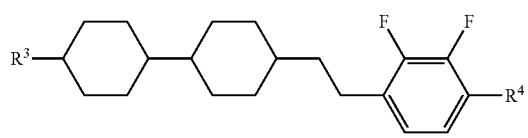
(3-5)

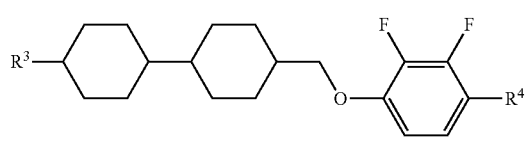
(3-6)

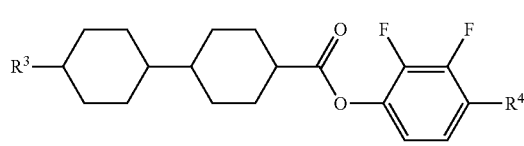
(3-7)

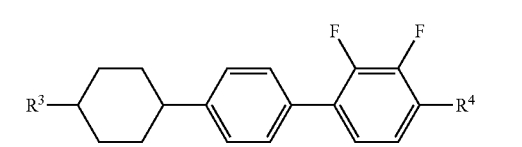
(3-8)

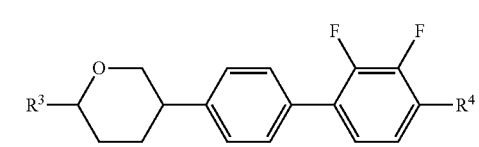
(3-9)

(3-10)
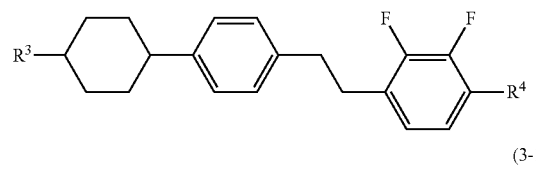
(3-11)
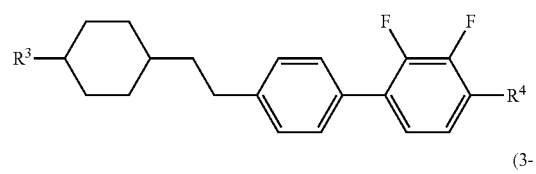
(3-12)
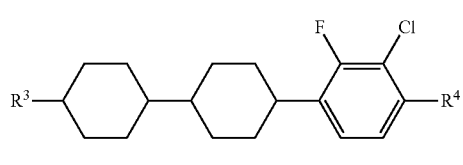
(3-13)
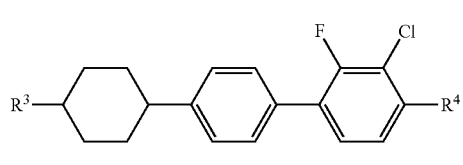
(3-14)
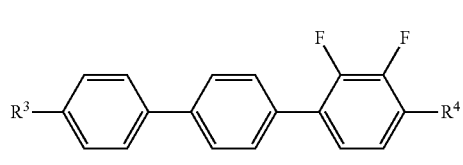
(3-15)
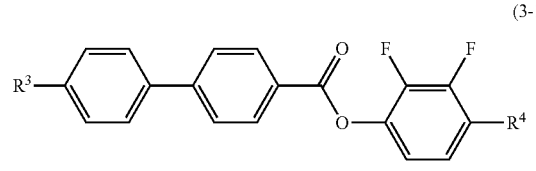
(4-1)
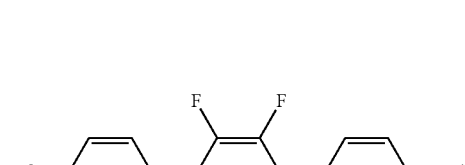
(5-1)
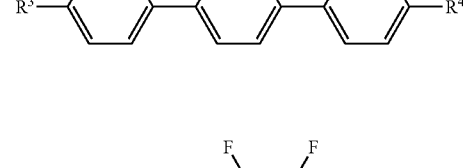
(5-2)
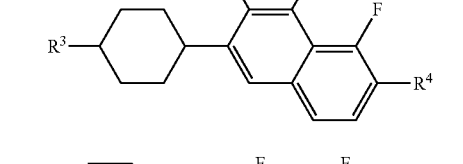
(5-3)
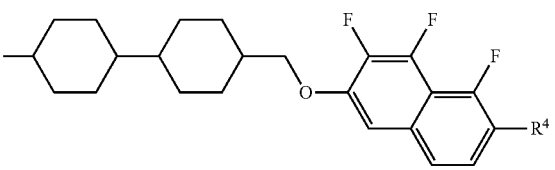
(6-1)
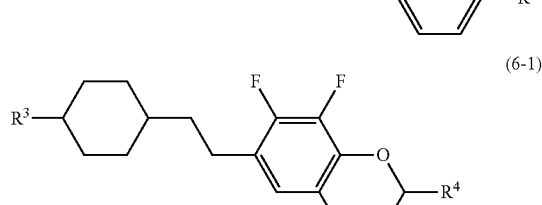
(6-2)
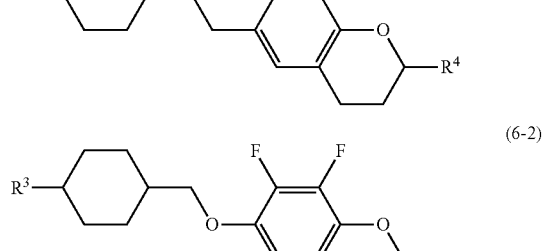
(6-3)
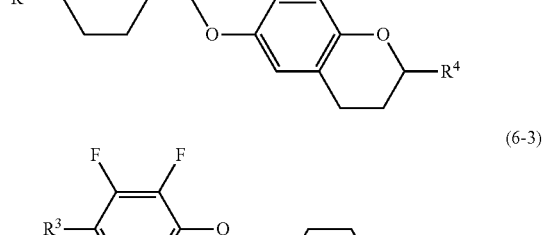
(6-4)
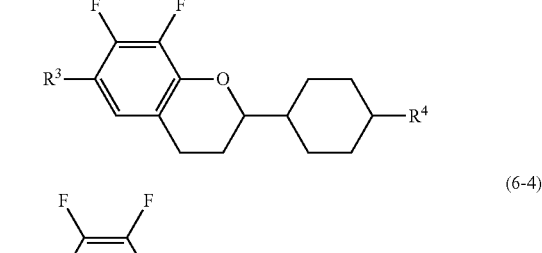
(6-5)
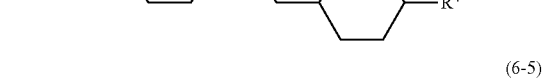
(6-6)
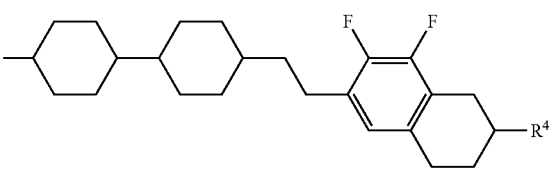
(6-7)
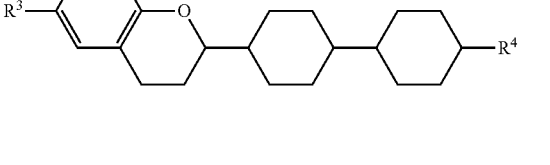

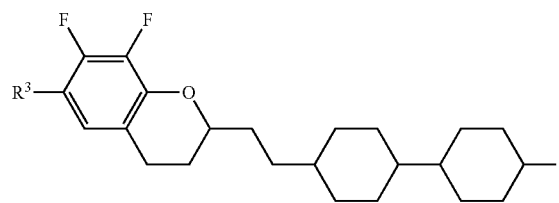 (6-8)

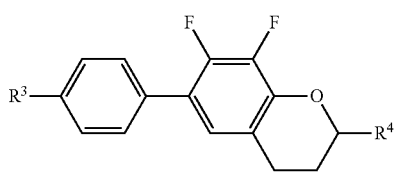 (6-9)

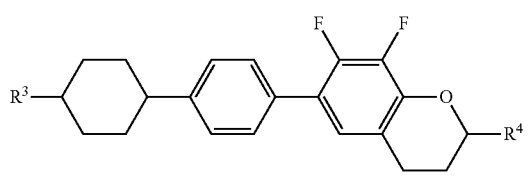 (6-10)

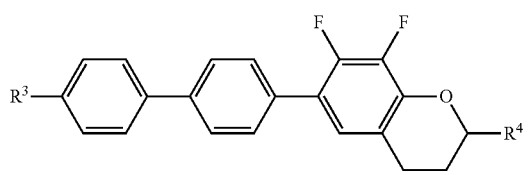 (6-11)

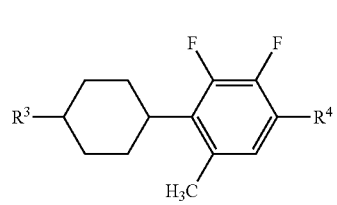 (7-1)

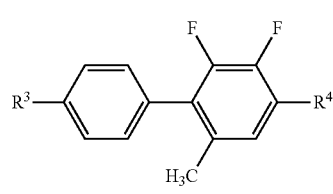 (7-2)

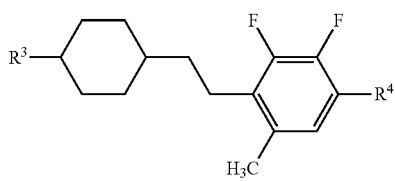 (7-3)

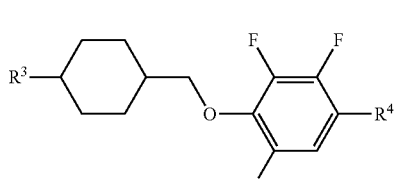 (7-4)

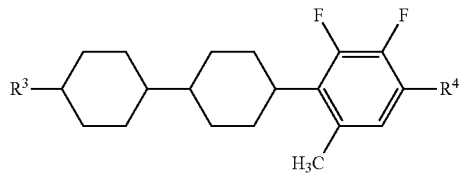 (7-5)

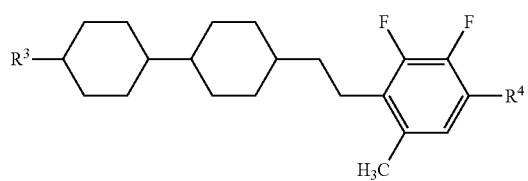 (7-6)

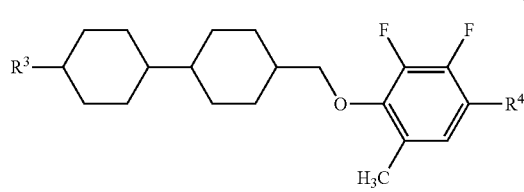 (7-7)

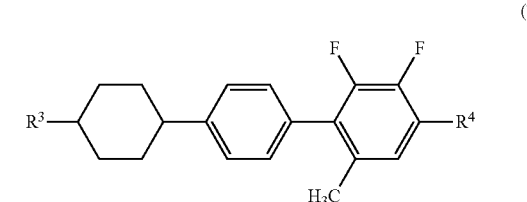 (7-8)

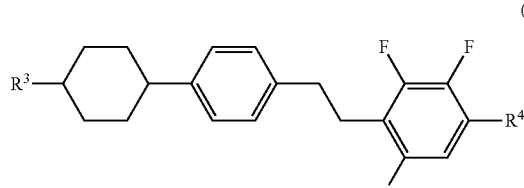 (7-9)

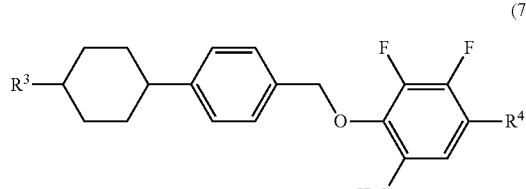 (7-10)

In the formulas, $R^3$ and $R^4$ are defined in a manner identical with the definitions described above.

The compounds of component B are used for a liquid crystal composition having a negative value of dielectric anisotropy for the VA mode or the PSA mode. If the content is increased, the threshold voltage of the composition decreases, but the viscosity increases, and therefore the content is preferably decreased, as long as a required value of the threshold voltage is satisfied. However, an absolute value of dielectric anisotropy is about 5. Therefore, when the content decreases to a level less than 40% by weight, no voltage driving may be occasionally allowed.

Among types of component B, compound (2) is a bicyclic compound, and therefore mainly effective in adjusting the threshold voltage, adjusting the viscosity or adjusting the refractive index anisotropy. Moreover, compounds (3) and (4) are a tricyclic compound, and therefore effective in increasing the clearing point, extending the nematic range, decreasing the threshold voltage, increasing the refractive index anisotropy or the like. Moreover, compounds (5), (6) and (7) are effective in decreasing the threshold voltage.

When preparing a composition for the VA mode or the PSA mode, content of component B is preferably in the range of 40% by weight or more, further preferably, in the range of 50 to 95% by weight, based on the total amount of the composition. Moreover, when component B is mixed, an elastic constant can be controlled, and a voltage-transmittance curve of the device can be controlled.

Suitable examples of compounds (8), (9) and (10) being component C include compounds (8-1) to (8-11), (9-1) to (9-19) and (10-1) to (10-6).

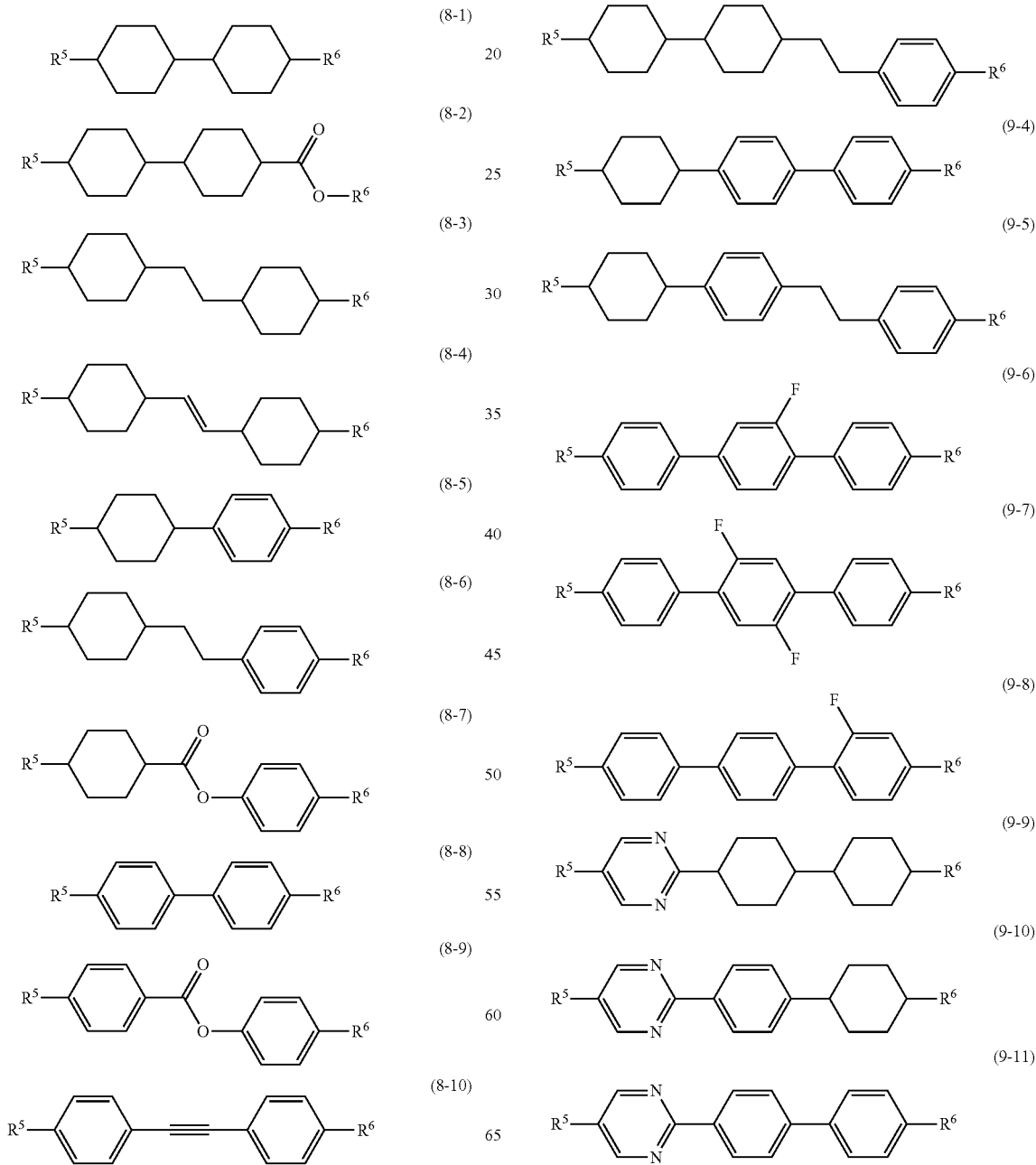

(9-12)
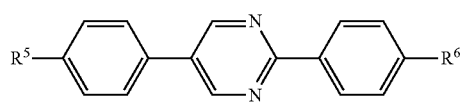

(9-13)
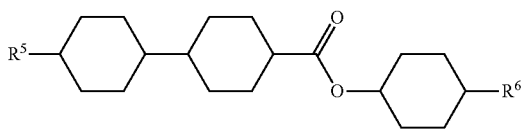

(9-14)
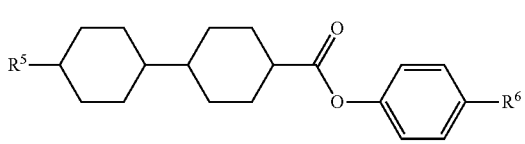

(9-15)
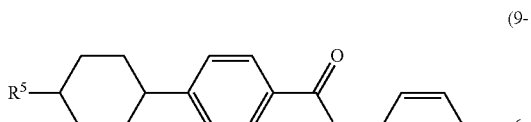

(9-16)
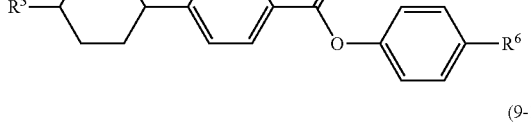

(9-17)
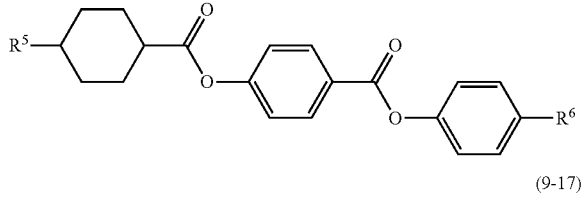

(9-18)
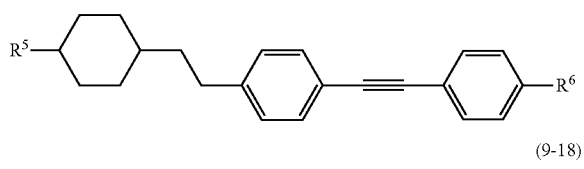

(9-19)
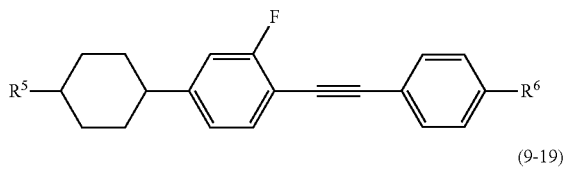

(10-1)
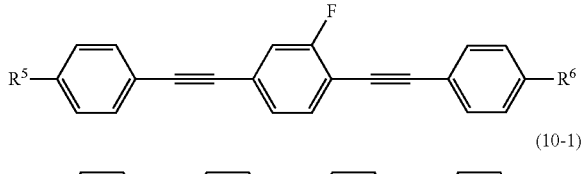

(10-2)
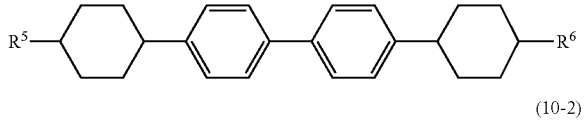

(10-3)
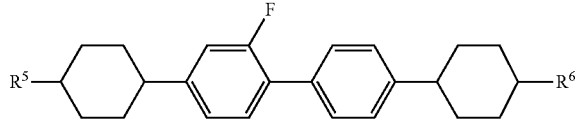

(10-4)
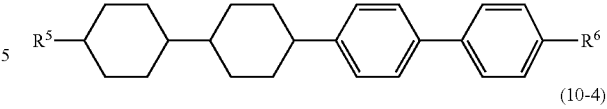

(10-5)
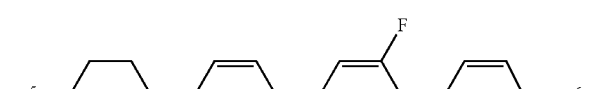

(10-6)
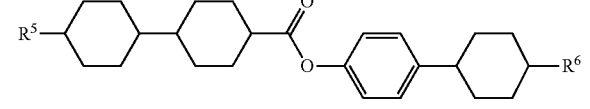

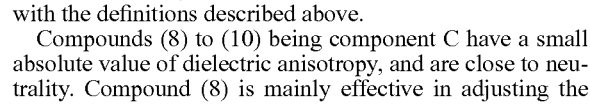

In the formulas, $R^5$ and $R^6$ are defined in a manner identical with the definitions described above.

Compounds (8) to (10) being component C have a small absolute value of dielectric anisotropy, and are close to neutrality. Compound (8) is mainly effective in adjusting the viscosity or adjusting the refractive index anisotropy, and compounds (9) and (10) are effective in extending the nematic range such as increasing the clearing point or effective in adjusting the refractive index anisotropy.

If content of component C is increased, the threshold voltage of the liquid crystal composition increases and the viscosity decreases. Therefore, the content is desirably increased, as long as a required value of the threshold voltage of the liquid crystal composition is satisfied. When preparing a liquid crystal composition for the TFT mode or the PSA mode, the content of component C is preferably in the range of 30% by weight or more, further preferably, 50% by weight or more, based on the total amount of the composition. Moreover, when preparing a liquid crystal composition for the TN mode, the STN mode or the PSA mode, the content of component C is preferably in the range of 30% by weight or more, further preferably, in the range of 40% by weight or more, based on the total amount of the composition.

The liquid crystal composition of the invention preferably contains at least one of compound (1) of the invention at a ratio of 0.1 to 99% by weight in order to develop excellent characteristics.

The liquid crystal composition of the invention is generally prepared according to a publicly known method, for example, a method for dissolving required components under a high temperature. Moreover, the additive well known to those skilled in the art is added depending on an application. Thus, for example, a liquid crystal composition containing the optically active compound, a polymerizable compound or a polymerization initiator, or a liquid crystal composition for a GH mode in which a dye is added can be prepared. Ordinarily, the additive is well known to those skilled in the art, and described in detail in literatures or the like.

The liquid crystal composition of the invention may further contain at least one optically active compound. As the optically active compound, a publicly known chiral dopant is added. The chiral dopant is effective in inducing a helical structure of liquid crystals to adjust a required twist angle, and preventing an inverted twist, or the like. Specific examples of the chiral dopants include optically active compounds (Op-1) to (Op-13) as described below.

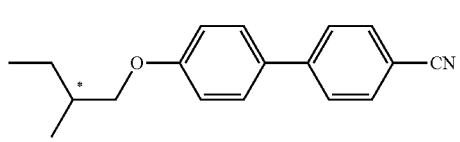 (Op-1)
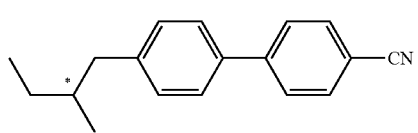 (Op-2)
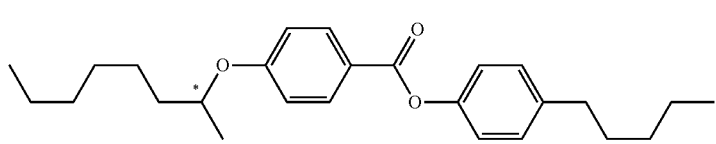 (Op-3)
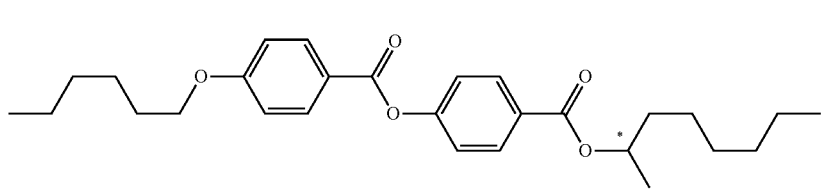 (Op-4)
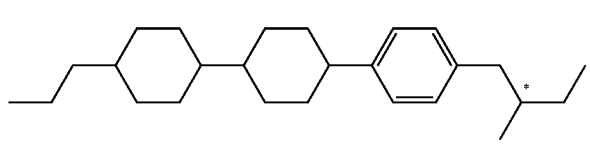 (Op-5)
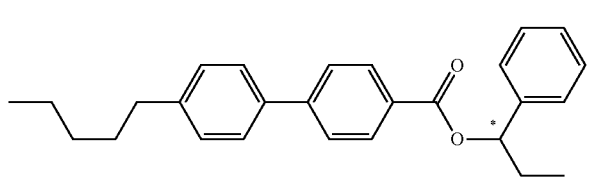 (Op-6)
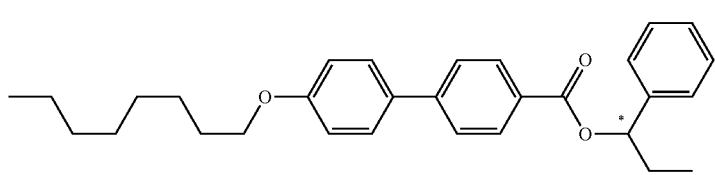 (Op-7)
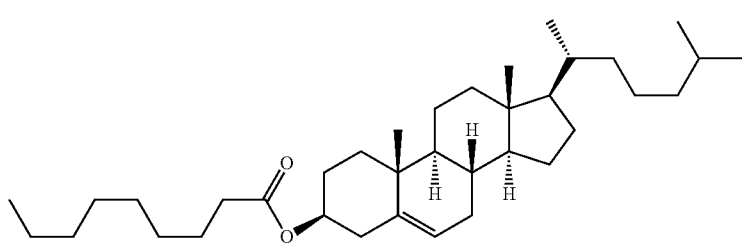 (Op-8)
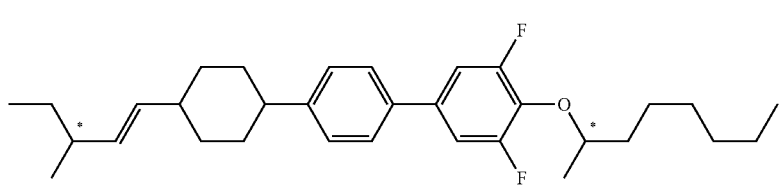 (Op-9)

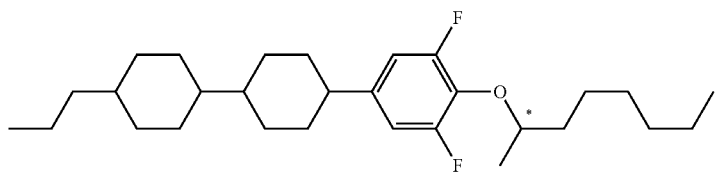
(Op-10)

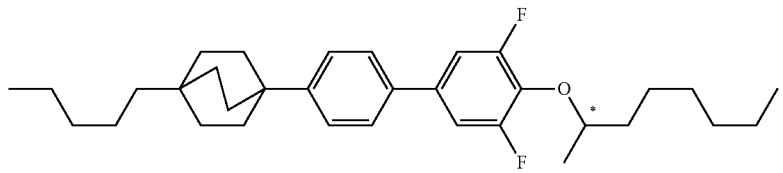
(Op-11)

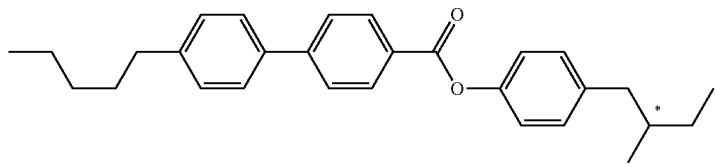
(Op-12)

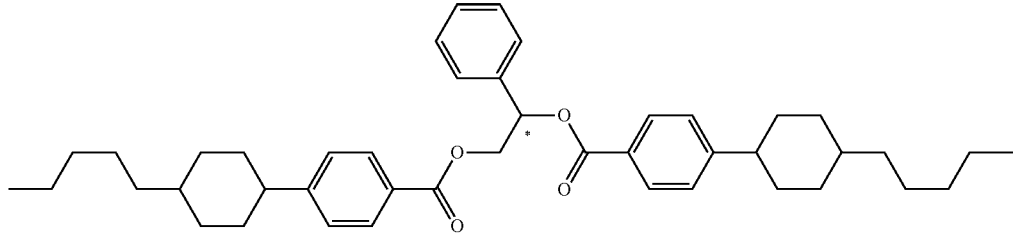
(Op-13)

A helical pitch of the liquid crystal composition of the invention is ordinarily adjusted by adding the optically active compounds. The helical pitch is preferably adjusted in the range of 40 to 200 micrometers for a liquid crystal composition for the TFT mode or the TN mode. The helical pitch is preferably adjusted in the range of 6 to 20 micrometers for a liquid crystal composition for the STN mode. Moreover, the helical pitch is adjusted in the range of 1.5 to 4 micrometers in the case of a bistable twisted nematic (BTN) mode use. Moreover, two or more kinds of optically active compounds may be added for the purpose of adjusting temperature dependence of the pitch.

The liquid crystal composition of the invention can also be used as a liquid crystal composition for the GH mode if a dichroic dye of a merocyanine type, a styryl type, an azo type, an azomethine type, an azoxy type, a quinophthalone type, an anthraquinone type, a tetrazine type o the like is added to the liquid crystal composition.

The liquid crystal composition of the invention can also be used for a NCAP device prepared by microencapsulating nematic liquid crystals, and a polymer dispersed liquid crystal display (PDLCD) device prepared by forming a three-dimensional network polymer in the liquid crystals, for example, a polymer network liquid crystal display (PNLCD) device, and an electrically controlled birefringence (ECB) mode device or a DS mode device.

Moreover, the liquid crystal composition of the invention can also be used for the polymer sustained alignment (PSA) mode by adding the polymerizable compound. Specific examples of the polymerizable compounds include a compound having a polymerizable group such as acrylate, methacrylate, vinyl, vinyloxy, propenyl ether, epoxy, vinyl ketone and oxetane. The polymerizable compound is preferably polymerized by irradiation with ultraviolet light or the like in the presence of a suitable polymerization initiator such as a photopolymerization initiator. Suitable conditions for polymerization, suitable types and suitable amounts of the polymerization initiator are known to those skilled in the art and described in literatures. For example, Irgacure 651 (registered trade name), Irgacure 184 (registered trade name) or Darocure 1173 (registered trade name) (Ciba Japan K. K.), each being the photopolymerization initiator, are suitable for radical polymerization.

EXAMPLES

Hereinafter, the invention will be explained in more detail by way of Examples. The invention is not limited by the Examples. In each Example, C stands for a crystal, SA stands for a smectic A phase, SB stands for a nematic B phase, SX stands for a smectic phase of which structure is unanalyzed, N stands for a nematic phase, and I stands for an isotropic phase. All of units of a phase transition temperature are ° C. In addition, unless otherwise noted, "%" means "% by weight."

A compound obtained was identified by a $^1$H NMR analysis, a mass spectrum analysis or the like. First, analytical methods will be explained.

$^1$H NMR Analysis

As a measuring apparatus, DRX-500 (made by Bruker BioSpin Corporation) was used. A sample manufactured in Examples and so forth was dissolved into a deuterated solvent such as $CDCl_3$ in which the sample was soluble, and measurement was carried out under the conditions of room temperature, 500 MHz and 24 times of accumulation. As a reference material for a zero point of chemical shifts (δ values), tetramethylsilane (TMS) was used.

GC Analysis

As a measuring apparatus, GC-2014 Gas Chromatograph made by Shimadzu Corporation was used. As a column, capillary column DB-1 (length 30 m, bore 0.25 mm, film thickness 0.25 micrometers; stationary liquid phase: dimethylpolysiloxane; non-polar) made by Agilent Technologies Inc. was used. Helium was used as a carrier gas, and a flow rate was adjusted at 1 milliliter per minute. Temperature in a sample injector was set at 300° C. and temperature of a detector (FID) part was set at 300° C.

A sample was dissolved into toluene and prepared to be a 1% solution, and 1 microliter of the resultant solution was injected into the sample injector.

As a recorder, C-R6A Chromatopac (made by Shimadzu Corporation) or the equivalent thereof was used. The resultant gas chromatogram showed a retention time of a peak and a value of a peak area corresponding to each of component compounds.

In addition, as a solvent for diluting the sample, for example, chloroform or hexane may also be used. Moreover, as the column, capillary column CBP1-M25-025 (length 25 m, bore 0.25 mm, film thickness 0.25 µm) made by Shimadzu Corporation), HP-1 (length 30 m, bore 0.25 mm, film thickness 0.25 µm) made by Agilent Technologies Inc., Rtx-1 (length 30 m, bore 0.32 mm, film thickness 0.25 µm) made by Restek Corporation, BP-1 (length 30 m, bore 0.32 mm, film thickness 0.25 µm) made by SGE International Pty. Ltd. and so forth may also be used.

A ratio of peak areas in the gas chromatogram corresponds to a ratio of component compounds. In general, weight percent of each of the component compounds in an analytical sample is not completely identical with a percentage of each of the peak areas in the analytical sample. However, when the column described above was used in the invention, the weight percent of each of the component compounds in the analytical sample substantially corresponds to the percentage of each of the peak areas in the analytical sample because a correction coefficient is essentially (one).

GCMS Analysis

As a measuring apparatus, GCMS-QP2010 Gas Chromatograph Mass Spectrometer made by Shimadzu Corporation was used. As a column, capillary column DB-1MS (length 60 m, bore 0.25 mm, film thickness 0.25 µm) made by Agilent Technologies Inc. was used. Helium was used as a carrier gas, and a flow rate was adjusted at 1 milliliter per minute. Temperature in a sample injector was set at 300° C., temperature of an ion source part was set at 200° C., ionizing voltage was set at 70 eV, and an emission current was set at 150 µA.

Sample for Determining Values of Physical Properties

As a sample for determining values of physical properties of a liquid crystal compound, two kinds of samples were used, namely, in a case where a compound per se was used as the sample, and in a case where a sample was prepared by mixing the compound with a base liquid crystal.

In the case of using the sample prepared by mixing the compound with the base liquid crystal, measurement was carried out by methods as described below. First, a sample was prepared by mixing 15% of liquid crystal compound obtained and 85% of base liquid crystal. Then, extrapolated values were calculated according to an extrapolation method shown in an equation below from measured values of the sample obtained, and the extrapolated values were described as the values of physical properties of the compound.

(Extrapolated value)={100×(measured value of a sample)−(% of base liquid crystal)×(measured value of the base liquid crystal)}/(% of liquid crystal compound).

When a smectic phase was maintained at 25° C. or a crystal precipitated at 25° C. even at the ratio of the liquid crystal compound to the base liquid crystal, a ratio of the liquid crystal compound to the base liquid crystal was changed in the order of (10%:90%), (5%:95%) and (1%:99%), and a sample was measured at a ratio at which no smectic phase was maintained at 25° C. or no crystal precipitated at 25° C. Then, the extrapolated values were determined according to the equation from the measured values of the sample obtained, and described as the values of physical properties of the liquid crystal compound.

Various kinds of base liquid crystals are present as the base liquid crystal used for the measurement, but according to the invention, base liquid crystal A having a composition as described below was used.

Base Liquid Crystal A:

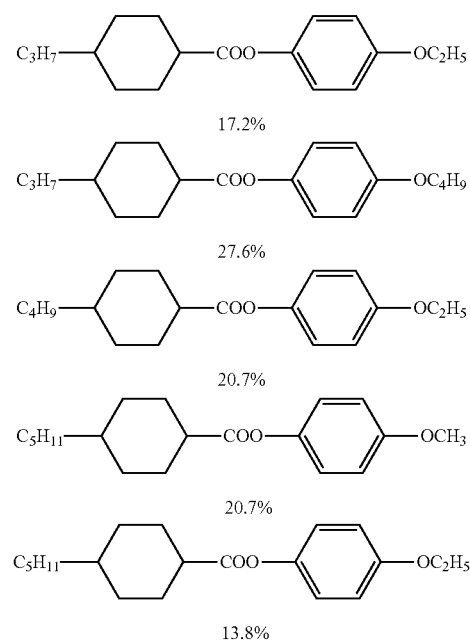

In addition, the liquid crystal composition per se was used as the sample for determining the values of physical properties value of the liquid crystal composition.

Method for Determining Values of Physical Properties

Values of physical properties were determined according to the methods described below. Most of the measuring methods are applied as described in EIAJ ED-2521A of the Standard of Electronic Industries Association of Japan, or as modified thereon. Moreover, no TFT was attached to a TN device or a VA device used for measurement.

Among the measured values, values obtained using the liquid crystal compound per se as the sample, and values obtained using the liquid crystal composition per se as the sample were described as were. When measurement was carried out by mixing the compound with the base liquid crystal, values obtained according to the extrapolation method were described as the values of physical properties.

Phase Structure and Phase Transition Temperature (° C.)

Measurement was carried out according to methods (1) and (2) as described below.

(1) A compound was placed on a hot plate of a melting point apparatus (FP-52 Hot Stage made by Mettler-Toledo International Inc.) equipped with a polarizing microscope, and a state of phase and a change thereof were observed with the polarizing microscope while heating the compound at a rate of 3° C. per minute, and a kind of the phase was specified.

(2) A sample was heated and then cooled at a rate of 3° C. per minute using a differential scanning calorimeter, DSC-7 System or Diamond DSC System, made by PerkinElmer, Inc. A starting point (on set) of an endothermic peak or an exothermic peak caused by a phase change of the sample was determined by extrapolation, and thus a phase transition temperature was determined.

Hereinafter, the crystal was expressed as C. When the crystals were further distinguishable, each of the crystals was expressed as $C_1$ or $C_2$. The smectic phase was expressed as S and the nematic phase as N. A liquid (isotropic) was expressed as Iso. When smectic B phase or smectic A phase was distinguishable among the smectic phases, the phases were expressed as $S_B$ or $S_A$, respectively. As an expression of the phase transition temperature, for example, "C 50.0N 100.0 Iso" shows that a phase transition temperature (CN) from the crystal to the nematic phase is 50.0° C., and a phase transition temperature (NI) from the nematic phase to the liquid is 100.0° C. A same rule applied to other expressions.

Maximum Temperature of a Nematic Phase ($T_{NI}$; ° C.)

A sample (a liquid crystal composition, or a mixture of a liquid crystal compound and a base liquid crystal) was placed on a hot plate of a melting point apparatus (FP-52 Hot Stage made by Mettler-Toledo International Inc.) equipped with a polarizing microscope, and was observed with the polarizing microscope while heating the sample at a rate of 1° C. per minute. Temperature when part of the sample changed from the nematic phase to the isotropic liquid was described as a maximum temperature of the nematic phase. The maximum temperature of the nematic phase may be occasionally abbreviated simply as "maximum temperature."

Compatibility at a Low Temperature

Samples were prepared in which the base liquid crystal and a liquid crystal compound were mixed for an amount of the liquid crystal compound to be 20%, 15%, 10%, 5%, 3% and 1%, and the samples were put in glass vials. The glass vials were kept in freezers at −10° C. or −20° C. for a fixed period of time, and then whether the crystal or the smectic phase precipitated was observed.

Viscosity (Bulk Viscosity; η; Measured at 20° C.; mPa·s)

Bulk viscosity was measured using a cone-plate (E type) rotational viscometer.

Viscosity (Rotational Viscosity; $\gamma_1$; Measured at 25° C.; mPa·s)

Measurement was carried out according to the method described in M. Imai et al., Molecular Crystals and Liquid Crystals, Vol. 259, p. 37 (1995). A sample (a liquid crystal composition, or a mixture of a liquid crystal compound and a base liquid crystal) was put in a VA device in which a distance (cell gap) between two glass substrates was 20 micrometers. Voltage was stepwise applied to the device in the range of 30 V to 50 V at an increment of 1 V. After a period of 0.2 second with no application, voltage was applied repeatedly under the conditions of only one of rectangular waves (rectangular pulse; 0.2 second) and no application (2 seconds). A peak current and a peak time of a transient current generated by the application were measured. A value of rotational viscosity was obtained from the measured values and a calculation equation (8) described on page 40 of the paper presented by M. Imai et al.

In addition, as dielectric anisotropy (Δ∈) required for the calculation, a value obtained in measuring dielectric anisotropy (Δ∈) as described below was used.

Refractive Index Anisotropy (Δn; Measured at 25° C.)

Measurement was carried out by Abbe refractometer with a polarizing plate mounted on an ocular, using light at a wavelength of 589 nanometers. A surface of a main prism was rubbed in one direction, and then a sample (a liquid crystal composition, or a mixture of a liquid crystal compound and a base liquid crystal) was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of refractive index anisotropy was calculated from an equation: (Δn)=(n∥)−(n⊥).

Dielectric Anisotropy (Δ∈; Measured at 25° C.)

An ethanol (20 mL) solution of octadecyl triethoxysilane (0.16 mL) was applied onto a well-washed glass substrate. After rotating the glass substrate with a spinner, the glass substrate was heated at 150° C. for 1 hour. A VA device in which a distance (cell gap) was 20 micrometers was assembled from two glass substrates.

In a similar manner, an alignment film of polyimide was formed on the glass substrate. After rubbing treatment was applied to the alignment film obtained on the glass substrate, a TN device in which a cell gap between two glass substrates was 9 micrometers and a twist angle was 80 degrees was assembled.

A sample (a liquid crystal composition, or a mixture of a liquid crystal compound and a base liquid crystal) was put into the VA device obtained, a voltage of 0.5 V (1 kHz, sine waves) was applied to the device, and a dielectric constant (∈∥) in the major axis direction of liquid crystal molecules was measured.

Moreover, a sample (a liquid crystal composition, or a mixture of a liquid crystal compound and a base liquid crystal) was put into the TN device obtained, a voltage of 0.5V (1 kHz, sine waves) was applied to the device, and a dielectric constant (∈⊥) in the minor axis direction of the liquid crystal molecules was measured.

A value of dielectric anisotropy (Δ∈) was calculated from an equation: (Δ∈)=(∈∥)−(∈⊥).

Examples of Synthesis of Liquid Crystal Compounds and Intermediates

Examples 1 and 2

Synthesis of 2-ethoxy-1,8-difluoro-7-propylphenanthrene-9,10-dione (58) and 2-ethoxy-1,8,9,9,10,10-hexafluoro-7-propyl-9,10-dihydrophenanthrene (No. 1)

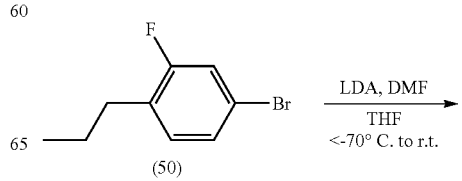

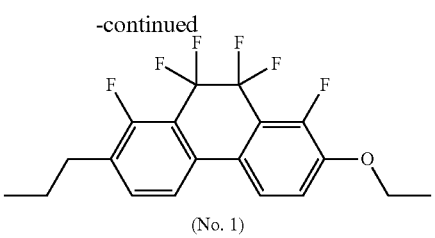

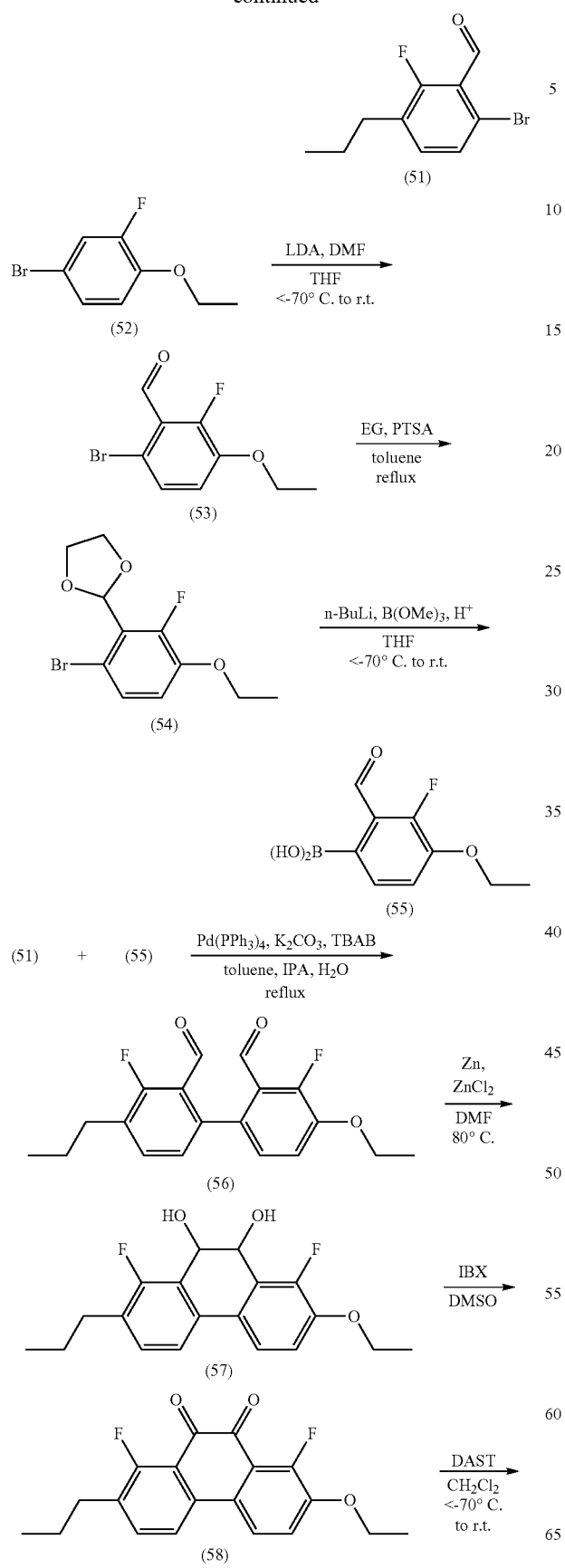

Example 1

First Step

Under a nitrogen atmosphere, LDA (50.7 mL, 56.25 mmol) was slowly added dropwise, at −70° C. or lower, to a THF (100 mL) solution of 4-bromo-2-fluoro-1-propylbenzene (50) (11.1 g, 51.13 mmol). The reaction mixture was agitated at −70° C. or lower for 1 hour, and then DMF (6.15 g, 76.70 mmol) was slowly added dropwise thereto. The reaction mixture was returned to room temperature, and then quenched with 100 mL of 1N hydrochloric acid aqueous solution, and extracted with 60 mL of toluene 3 times. Combined organic layers were washed with a saturated aqueous solution of sodium hydrogencarbonate, water and saturated brine, dried over magnesium sulfate and a solvent was distilled off by evaporator. The residue was purified by silica gel column chromatography, and thus 6-bromo-2-fluoro-3-propylbenzaldehyde (51) (5.0 g, yield 36%) was obtained.

Second Step

In a manner similar to the operations for synthesizing compound (51), 6-bromo-3-ethoxy-2-fluorobenzaldehyde (53) (17.0 g, yield 75.4%) was obtained from 4-bromo-1-ethoxy-2-fluorobenzene (52) (20.0 g, 91.30 mmol).

Third Step

A Dean-Stark condenser was attached, and a mixture of compound (53) (17.0 g, 68.81 mmol), EG (12.8 g, 200.2 mmol) and PTSA (0.17 g, 1 wt %) was refluxed in a toluene (200 mL) solvent for 3 hours. The reaction mixture was washed with a saturated aqueous solution of sodium hydrogencarbonate, water and saturated brine, and dried over magnesium sulfate. Toluene was distilled off by evaporator, and thus 2-(6-bromo-3-ethoxy-2-fluorophenyl)-1,3-dioxolane (54) (19.8 g, yield 98.8%) was obtained.

Fourth Step

Under a nitrogen atmosphere, n-BuLi (43.3 mL, 71.42 mmol) was slowly added dropwise, at −70° C. or lower, to a THF (200 mL) solution of compound (54) (19.8 g, 68.02 mmol). The reaction mixture was agitated at −70° C. or lower for 1 hour, and then trimethyl borate (10.6 g, 102.0 mmol) was slowly added dropwise thereto. The reaction mixture was returned to room temperature, and then quenched with 200 mL of 2N hydrochloric acid aqueous solution, and extracted with 100 mL of toluene three times. Combined organic layers were washed with a saturated aqueous solution of sodium hydrogencarbonate, water and saturated brine, and then dried over magnesium sulfate, and a solvent was distilled off by an evaporator. The residue was washed with heptane, and thus (4-ethoxy-3-fluoro-2-formylphenyl)boronic acid (55) (9.85 g, yield 68.3%) was obtained.

Fifth Step

Under a nitrogen atmosphere, a mixture of compound (51) (4.9 g, 19.99 mmol), compound (55) (4.9 g, 23.12 mmol), tetrakis(triphenylphosphine)palladium (0.23 g, 0.199 mmol), sodium carbonate (4.9 g, 46.23 mmol) and TBAB (0.96 g, 2.978 mmol) was refluxed in a toluene (30 mL)-ethanol (20 mL)-water (50 mL) solvent for 5 hours. The reaction mixture was extracted with 30 mL of toluene three times. Combined organic layers were washed with a saturated aqueous solution of sodium hydrogencarbonate, water and saturated brine, and then dried over magnesium sulfate, and a solvent was distilled off by an evaporator. The residue was purified by silica gel column chromatography, and thus 4-ethoxy-3,3'-difluoro-4'-propyl-[1,1'-biphenyl]-2,2'-dicarboaldehyde (56) (5.35 g, yield 80.5%) was obtained.

Sixth Step

Under a nitrogen atmosphere, zinc powder (0.295 g, 4.513 mmol) and zinc chloride (0.1 g, 0.752 mmol) were added to a DMF (5 mL) solution of compound (56) (0.5 g, 1.504 mmol), and the resultant mixture was agitated at 80° C. for 8 hours. The reaction mixture was quenched with 20 mL of 1N hydrochloric acid aqueous solution, and extracted with 10 mL of toluene three times. Combined organic layers were washed with a saturated aqueous solution of sodium hydrogencarbonate, water and saturated brine, and then dried over magnesium sulfate, and a solvent was distilled off by an evaporator. The residue was purified by silica gel column chromatography, and thus 2-ethoxy-1,8-difluoro-7-propyl-9,10-dihydrophenanthrene-9,10-diol (57) (0.3 g, yield 59.7%) was obtained.

Seventh Step

IBX (31.5 g, 112.5 mmol) was added to 100 mL of DMSO, and the resultant mixture was agitated at room temperature for 30 minutes, and then compound (57) (9.4 g, 28.11 mmol) was added and the resultant mixture was further agitated for 3 hours. The reaction mixture was filtered, 200 mL of water was added to a filtrate, and the resultant mixture was extracted with 100 mL of ethyl acetate three times. Combined organic layers were washed with a saturated aqueous solution of sodium hydrogencarbonate, water and saturated brine, and then dried over magnesium sulfate, and a solvent was distilled off by an evaporator. The residue was recrystallized from toluene, and thus 2-ethoxy-1,8-difluoro-7-propylphenanthrene-9,10-dione (58) (3.2 g, yield 34.5%) was obtained.

Chemical shifts (δ (ppm)) by $^1$H-NMR analysis were as described below, and the compound obtained was identified to be 2-ethoxy-1,8-difluoro-7-propylphenanthrene-9,10-dione (58).

$^1$H-NMR (CDCl$_3$) δ: 7.68 (d, 1H), 7.61 (d, 1H), 7.52-7.47 (m, 1H), 7.28-7.23 (m, 1H), 4.18 (q, 2H), 2.65 (t, 2H), 1.66 (tq, 2H), 1.49 (t, 3H), 0.98 (t, 3H).

A liquid crystal composition was prepared using 1% of compound (58) and 99% of base liquid crystal A. Physical properties of the liquid crystal composition obtained were measured, and values of physical properties of compound (58) were determined by extrapolating measured values. The results were as described below.

Maximum temperature (NI)=4.6° C.; dielectric anisotropy (Δ∈)=−28.4; refractive index anisotropy (Δn)=0.187; viscosity (η)=247.8 mPa·s.

Example 2

Under a nitrogen atmosphere, DAST (2.93 g, 18.16 mmol) was slowly added dropwise, at −70° C. or lower, to a dichloromethane (10 mL) suspension of compound (58) (1.0 g, 3.027 mmol) prepared in Example 1. The reaction mixture was slowly returned to room temperature, and then quenched with 10 mL of water. The dichloromethane layer was washed with a saturated aqueous solution of sodium hydrogencarbonate, water and saturated brine, and then dried over magnesium sulfate, and a solvent was distilled off by an evaporator. The residue was purified by silica gel column chromatography, and thus 2-ethoxy-1,8,9,9,10,10-hexafluoro-7-propyl-9,10-dihydrophenanthrene (No. 1) (0.8 g, yield 70.6%) was obtained.

Chemical shifts (δ (ppm)) by $^1$H-NMR analysis were as described below, and the compound obtained was identified to be 2-ethoxy-1,8,9,9,10,10-hexafluoro-7-propyl-9,10-dihydrophenanthrene (No. 1).

$^1$H-NMR (CDCl$_3$) δ: 7.50 (d, 1H), 7.45 (d, 1H), 7.40-7.36 (m, 1H), 7.16-7.11 (m, 1H), 4.17 (q, 2H), 2.66 (t, 2H), 1.67 (tq, 2H), 1.49 (t, 3H), 0.99 (t, 3H).

A phase transition temperature of compound (No. 1) obtained was as described below.

Phase transition temperature: C 89.5 Iso.

A liquid crystal composition was prepared using 15% of compound No. 1 and 85% of base liquid crystal A. Physical properties of the liquid crystal composition obtained were measured, and values of physical properties of compound No. 1 were determined by extrapolating measured values. The results were as described below.

Maximum temperature (NI)=−18.1° C.; dielectric anisotropy (Δ∈)=−18.2; refractive index anisotropy (Δn)=0.1197; viscosity (η)=139.8 mPa·s.

Examples 3 and 4

Synthesis of 2-ethoxy-1,8-difluoro-7-((4-propylcyclohexyl)methoxy)phenanthrene-9,10-dione (65) and 2-ethoxy-1,8,9,9,10,10-hexafluoro-7-((4-propylcyclohexyl)methoxy)-9,10-dihydrophenanthrene (No. 211)

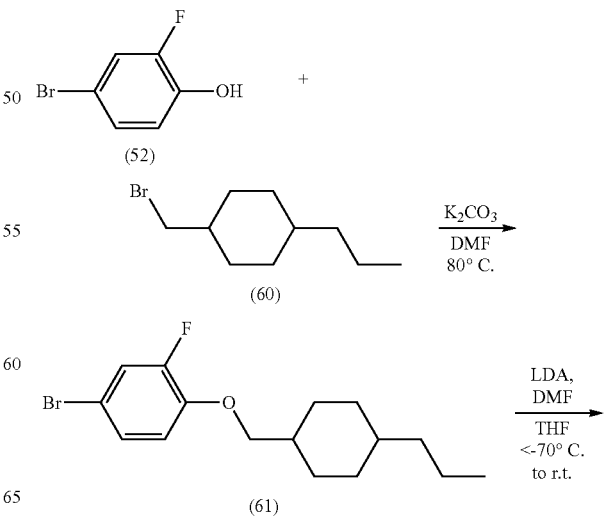

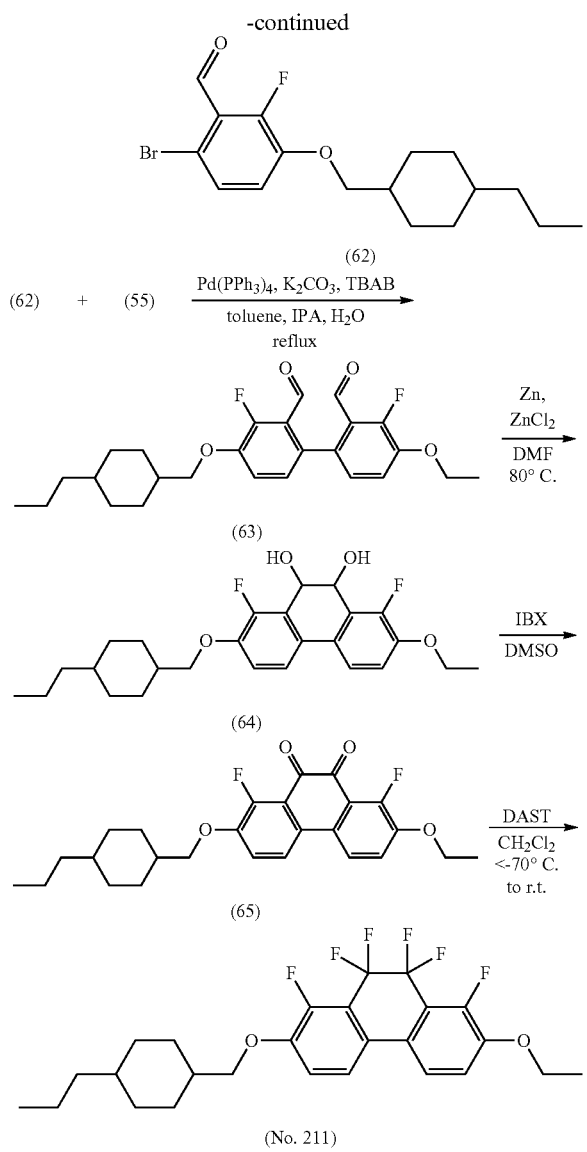

(100 mL) solution of compound (61) (11.4 g, 34.62 mmol). The reaction mixture was agitated at −70° C. or lower for 1 hour, and then DMF (4.17 g, 52.07 mmol) was slowly added dropwise thereto. The reaction mixture was returned to room temperature, and then quenched with 100 mL of 1N hydrochloric acid aqueous solution, and extracted with 60 mL of toluene three times. Combined organic layers were washed with a saturated aqueous solution of sodium hydrogencarbonate, water and saturated brine, and then dried over magnesium sulfate, and a solvent was distilled off by an evaporator. The residue was purified by silica gel column chromatography, and thus 6-bromo-2-fluoro-3-((4-propylcyclohexyl)methoxy)benzaldehyde (62) (4.20 g, yield 33.9%) was obtained.

Third Step

Under a nitrogen atmosphere, a mixture of compound (62) (4.20 g, 11.76 mmol), compound (55) (2.74 g, 12.93 mmol) prepared in Example 1, tetrakis(triphenylphosphine)palladium (0.14 g, 0.121 mmol), potassium carbonate (3.25 g, 23.51 mmol) and TBAB (0.76 g, 2.351 mmol) was refluxed in a toluene (20 mL)-ethanol (10 mL)-water (50 mL) solvent for 5 hours. The reaction mixture was extracted with 20 mL of toluene three times, combined organic layers were washed with water and saturated brine, and then dried over magnesium sulfate, and a solvent was distilled off by an evaporator. The residue was purified by silica gel column chromatography, and thus 4-ethoxy-3,3'-difluoro-4'-((4-propylcyclohexyl)methoxy)-[1,1'-biphenyl]-2,2'-dicarboaldehyde (63) (4.20 g, yield 80.3%) was obtained.

Fourth Step

Under a nitrogen atmosphere, zinc powder (1.85 g, 28.30 mmol) and zinc chloride (0.64 g, 4.696 mmol) were added to a DMF (50 mL) solution of compound (63) (4.20 g, 9.449 mmol), and the resultant mixture was agitated at 80° C. for 8 hours. The reaction mixture was quenched with 100 mL of 1N hydrochloric acid aqueous solution, and extracted with 50 mL of toluene three times. Combined organic layers were washed with a saturated aqueous solution of sodium hydrogencarbonate, water and saturated brine, and then dried over magnesium sulfate, and a solvent was distilled off by an evaporator. The residue was purified by silica gel column chromatography, and thus 2-ethoxy-1,8-difluoro-7-((4-propylcyclohexyl)methoxy)-9,10-dihydrophenanthrene-9,10-diol (64) (3.6 g, yield 85.4%) was obtained.

Fifth Step

IBX (9.03 g, 32.25 mmol) was added to 100 mL of DMSO, the resultant mixture was agitated at room temperature for 30 minutes, and then compound (64) (3.6 g, 8.062 mmol) was added thereto, and the resultant mixture was further agitated for 3 hours. The reaction mixture was filtered, 200 mL of water was added to a filtrate, and the resultant mixture was extracted with 100 mL of ethyl acetate three times. Combined organic layers were washed with a saturated aqueous solution of sodium hydrogencarbonate, water and saturated brine, and then dried over magnesium sulfate, and a solvent was distilled off by an evaporator. The residue was recrystallized from toluene, and thus 2-ethoxy-1,8-difluoro-7-((4-propylcyclohexyl)methoxy)phenanthrene-9,10-dione (65) (3.2 g, yield 34.5%) was obtained.

Chemical shifts (δ (ppm)) by $^1$H-NMR analysis were as described below, and the compound obtained was identified Example 3

First Step

Under a nitrogen atmosphere, a mixture of 4-bromo-2-fluoro-1-phenol (52) (10.8 g, 56.58 mmol), 1-(bromomethyl)-4-propylcyclohexane (60) (12.4 g, 56.58 mmol) and potassium carbonate (15.6 g, 112.9 mmol) was agitated at 80° C. for 5 hours in 100 mL of DMF. The reaction mixture was quenched with 100 mL of water, and extracted with 60 mL of toluene three times. Combined organic layers were washed with a 2N sodium hydroxide aqueous solution, water and saturated brine, and then dried over magnesium sulfate, and a solvent was distilled off by an evaporator. The residue was purified by silica gel column chromatography, and thus 4-bromo-2-fluoro-1-(4-propylcyclohexyl)benzene (61) (11.4 g, yield 61.2%) was obtained.

Second Step

Under a nitrogen atmosphere, LDA (34.4 mL, 38.18 mmol) was slowly added dropwise, at −70° C. or lower, to a THF to be 2-ethoxy-1,8-difluoro-7-((4-propylcyclohexyl)methoxy)phenanthrene-9,10-dione (65).

¹H-NMR (CDCl₃) δ: 7.58-7.55 (m, 2H), 7.24-7.19 (m, 2H), 4.17 (q, 2H), 3.87 (d, 2H), 1.92-1.88 (m, 2H), 1.85-1.75 (m, 3H), 1.48 (t, 3H), 1.37-1.28 (m, 2H), 1.28-1.15 (m, 3H), 1.13-1.02 (m, 2H), 1.01-0.86 (m, 5H).

Example 4

Under a nitrogen atmosphere, DAST (2.16 g, 13.56 mmol) was slowly added dropwise, at −70° C. or lower, to a dichloromethane (10 mL) suspension of compound (65) (1.2 g, 2.712 mmol) prepared in Example 3. The reaction mixture was slowly returned to room temperature, and quenched with 10 mL of water. The dichloromethane layer was washed with a saturated aqueous solution of sodium hydrogencarbonate, water and saturated brine, and then dried over magnesium sulfate, and a solvent was distilled off by an evaporator. The residue was purified by silica gel column chromatography, and thus 2-ethoxy-1,8,9,9,10,10-hexafluoro-7-((4-propylcyclohexyl)meth oxy)-9,10-dihydrophenanthrene (No. 211) (0.73 g, yield 55.4%) was obtained.

Chemical shifts (δ (ppm)) by ¹H-NMR analysis were as described below, and the compound obtained was identified to be 2-ethoxy-1,8,9,9,10,10-hexafluoro-7-((4-propylcyclohexyl)meth oxy)-9,10-dihydrophenanthrene (No. 211).

¹H-NMR (CDCl₃) δ: 7.45-7.41 (m, 2H), 7.14-7.08 (m, 2H), 4.16 (q, 2H), 3.86 (d, 2H), 1.95-1.89 (m, 2H), 1.85-1.77 (m, 3H), 1.49 (t, 3H), 1.38-0.91 (m, 9H), 0.89 (t, 3H).

A phase transition temperature of compound No. 211 obtained was as described below.

Phase transition temperature: C 115.0 Iso.

A liquid crystal composition was prepared using 15% of compound No. 211 and 85% of base liquid crystal A. Physical properties of the liquid crystal composition obtained were measured, and values of physical properties of compound No. 211 were determined by extrapolating measured values. The results were as described below.

Maximum temperature (NI)=99.3° C.; dielectric anisotropy (Δ∈)=−24.4; refractive index anisotropy (an)=0.167; viscosity (η)=174.8 mPa·s.

Example 5

Synthesis of 2-ethoxy-1,8,9,9,10,10-hexafluoro-7-((4-pentylcyclohexyl)meth oxy)-9,10-dihydrophenanthrene (No. 513)

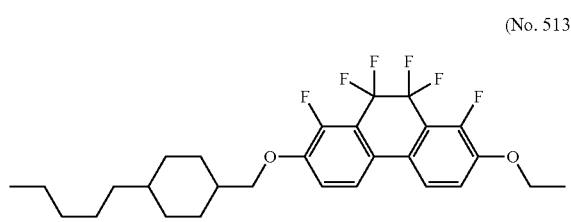

(No. 513)

Then, 2-ethoxy-1,8,9,9,10,10-hexafluoro-7-((4-pentylcyclohexyl)meth oxy)-9,10-dihydrophenanthrene (No. 513) was obtained by changing 1-(bromomethyl)-4-propylcyclohexane (60) as described in Example 3 to 1-(bromomethyl)-4-pentylcyclohexane and by performing a reaction in a manner similar to the operations described in Example 3 and 4.

Chemical shifts (δ (ppm)) by ¹H-NMR analysis were as described below, and the compound obtained was identified to be 2-ethoxy-1,8,9,9,10,10-hexafluoro-7-((4-pentylcyclohexyl)meth oxy)-9,10-dihydrophenanthrene (No. 513).

¹H-NMR (CDCl₃) δ: 7.49-7.37 (m, 2H), 7.18-7.05 (m, 2H), 4.15 (q, 2H), 3.85 (d, 2H), 1.97-1.87 (m, 2H), 1.87-1.75 (m, 3H), 1.48 (t, 3H), 1.38-1.15 (m, 9H), 1.14-1.02 (m, 2H), 1.01-0.85 (m, 5H).

A phase transition temperature of compound No. 513 obtained was as described below.

Phase transition temperature: C 109.7 Iso.

A liquid crystal composition was prepared using 15% of compound No. 513 and 85% of base liquid crystal A. Physical properties of the liquid crystal composition obtained were measured, and values of physical properties of compound No. 513 were determined by extrapolating measured values. The results were as described below.

Maximum temperature (NI)=101.3° C.; dielectric anisotropy (Δ∈)=−23.7; refractive index anisotropy (Δn)=0.158; viscosity (η)=169.3 mPa·s.

Example 6

Synthesis of 2-ethoxy-1,8,9,9,10,10-hexafluoro-7-(4-propylcyclohexyl)-9,10-dihydrophenanthrene (No. 11)

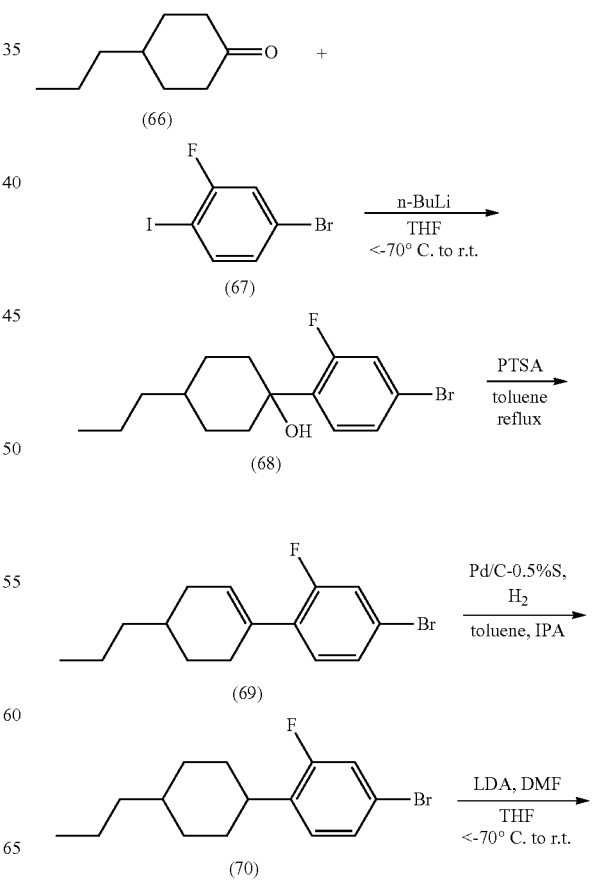

-continued

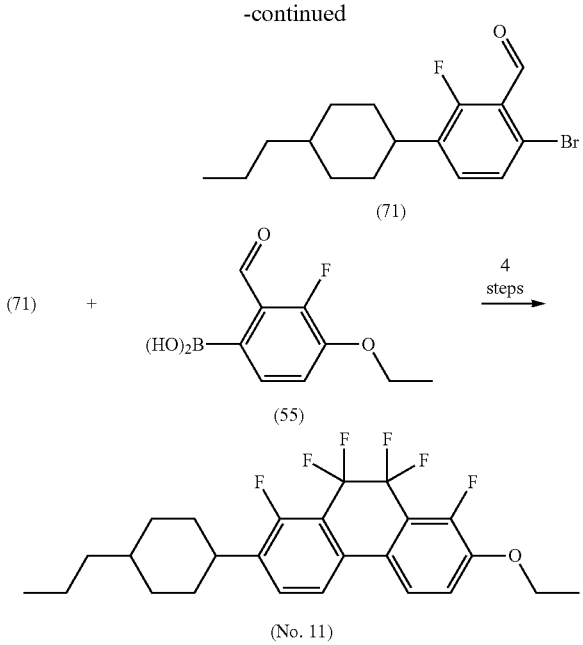

First Step

Under a nitrogen atmosphere, n-BuLi (108.0 mL, 174.0 mmol) was slowly added dropwise, at −70° C. or lower, to a THF (300 mL) solution of 4-bromo-2-fluoro-1-iodobenzene (67) (50.0 g, 166.0 mmol). The reaction mixture was agitated at −70° C. or lower for 1 hour, and then 4-propylcyclohexanone (66) (24.5 g, 174.0 mmol) was slowly added dropwise thereto. The reaction mixture was returned to room temperature, and then quenched with 200 mL of 1N hydrochloric acid aqueous solution, and extracted with 100 mL of toluene three times. Combined organic layers were washed with a saturated aqueous solution of sodium hydrogencarbonate, water and saturated brine, and then dried over magnesium sulfate, and a solvent was distilled off by an evaporator. The residue was purified by silica gel column chromatography, and thus 1-(4-bromo-2-fluorophenyl)-4-propylcyclohexanol (68) (42.0 g, yield 80.2%) was obtained.

Second Step

A Dean-Stark condenser was attached, and a mixture of compound (68) (42.0 g, 133.2 mmol) and PTSA (0.42 g, 1 wt %) was refluxed in a toluene (300 mL) solvent for 3 hours. The reaction mixture was washed with a saturated aqueous solution of sodium hydrogencarbonate, water and saturated brine, and dried over magnesium sulfate. Toluene was distilled off by an evaporator, and thus 4'-bromo-2'-fluoro-4-propyl-2,3,4,5-tetrahydro-1,1'-biphenyl (69) (39.2 g, yield 99.0%) was obtained.

Third Step

A mixture of compound (69) (39.2 g, 131.9 mmol) and 5%-palladium on carbon (0.5% sulfur, 50% water-containing article) (1.18 g, 3 wt %) was agitated for 18 hours under a hydrogen atmosphere in a toluene (200 mL)-IPA (100 mL) solvent. The reaction mixture was filtered and a solvent in a filtrate was distilled off by an evaporator. The residue was passed through silica gel column chromatography and then a low-boiling-point material was distilled off by distillation, and thus 4-bromo-2-fluoro-1-(4-propylcyclohexyl)benzene (70) (30.8 g, yield 78.1%) was obtained.

Fourth Step

Under a nitrogen atmosphere, LDA (11.6 mL, 12.87 mmol) was slowly added dropwise, at −70° C. or lower, to a THF (30 mL) solution of compound (70) (3.5 g, 11.70 mmol). The reaction mixture was agitated at −70° C. or lower for 1 hour, and then DMF (1.28 g, 17.55 mmol) was slowly added dropwise thereto. The reaction mixture was returned to room temperature, and then quenched with 50 mL of 1 N hydrochloric acid aqueous solution, and extracted with 20 mL of toluene three times. Combined organic layers were washed with a saturated aqueous solution of sodium hydrogencarbonate, water and saturated brine, and then dried over magnesium sulfate, and a solvent was distilled off by an evaporator. The residue was purified by silica gel column chromatography, and thus 6-bromo-2-fluoro-3-(4-propylcyclohexyl)benzaldehyde (71) (2.3 g, yield 89.7%) was obtained.

Fifth Step

Then, 2-ethoxy-1,8,9,9,10,10-hexafluoro-7-(4-propylcyclohexyl)-9,10-dihydrophenanthrene (No. 11) was obtained from compound (71) and compound (55) prepared in Example 1 by performing a reaction in a manner similar to the operations in Examples 1 and 2.

Chemical shifts (δ (ppm)) by $^1$H-NMR analysis were as described below, and the compound obtained was identified to be 2-ethoxy-1,8,9,9,10,10-hexafluoro-7-(4-propylcyclohexyl)-9,10-dihydrophenanthrene (No. 11).

$^1$H-NMR (CDCl$_3$) δ: 7.52-7.40 (m, 3H), 7.15-7.10 (m, 1H), 4.17 (q, 2H), 2.89 (tt, 1H), 1.93-1.86 (m, 4H), 1.53-1.42 (m, 5H), 1.40-1.27 (m, 3H), 1.27-1.20 (m, 2H), 1.15-1.05 (m, 2H), 0.91 (t, 3H).

A phase transition temperature of compound No. 11 obtained was as described below.

Phase transition temperature: C 100.7N 110.7 Iso.

A liquid crystal composition was prepared using 15% of compound No. 11 and 85% of base liquid crystal A. Physical properties of the liquid crystal composition obtained were measured, and values of physical properties of compound No. 11 were determined by extrapolating measured values. The results were as described below.

Maximum temperature (NI)=101.9° C.; dielectric anisotropy (Δ∈)=−20.1; refractive index anisotropy (Δn)=0.163; viscosity (η)=154.5 mPa·s.

Example 7

Synthesis of 2-ethoxy-1,8,9,9,10,10-hexafluoro-7-(4-pentylcyclohexyl)-9,10-dihydrophenanthrene (No. 514)

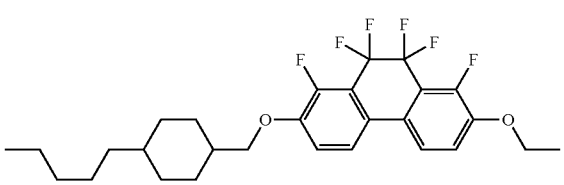

Then, 2-ethoxy-1,8,9,9,10,10-hexafluoro-7-(4-pentylcyclohexyl)-9,10-dihydrophenanthrene (No. 514) was obtained by changing 4-propylcyclohexanone (66) as described in Example 6 to 4-pentylcyclohexanone and by performing a reaction in a manner similar to the operations in Example 6.

Chemical shifts (δ (ppm)) by $^1$H-NMR analysis were as described below, and the compound obtained was identified to be 2-ethoxy-1,8,9,9,10,10-hexafluoro-7-(4-pentylcyclohexyl)-9,10-dihydrophenanthrene (No. 514).

$^1$H-NMR (CDCl$_3$) δ: 7.55-7.37 (m, 3H), 7.13 (m, 1H), 4.17 (q, 2H), 2.95-2.82 (m, 1H), 1.95-1.84 (m, 4H), 1.52-1.40 (m, 5H), 1.38-1.19 (m, 9H), 1.17-1.03 (m, 2H), 0.90 (t, 3H).

A phase transition temperature of compound No. 514 obtained was as described below.

Phase transition temperature: C 107.5N 122.2 Iso.

A liquid crystal composition was prepared using 15% of compound No. 514 and 85% of base liquid crystal A. Physical properties of the liquid crystal composition obtained were measured, and values of physical properties of compound No. 514 were determined by extrapolating measured values. The results were as described below.

Maximum temperature (NI)=111.3° C.; dielectric anisotropy (Δ∈)=−19.2; refractive index anisotropy (Δn)=0.161; viscosity (η)=154.5 mPa·s.

Example 8

2-Ethoxy-1,8,9,9,10,10-hexafluoro-7-(4-propylcyclohexa-1-en-1-yl)-9,10-dihydrophenanthrene (No. 101)

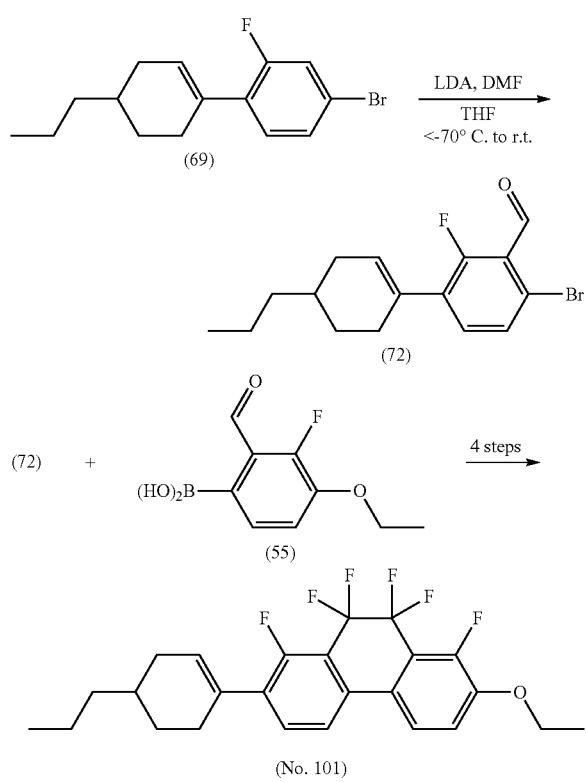

First step Under a nitrogen atmosphere, LDA (93.6 mL, 103.9 mmol) was slowly added dropwise, at −70° C. or lower, to a THF (300 mL) solution of compound (69) (27.8 g, 93.54 mmol) prepared in Example 6. The reaction mixture was agitated at −70° C. or lower for 1 hour, and then DMF (11.2 g, 139.8 mmol) was slowly added dropwise thereto. The reaction mixture was returned to room temperature, and then quenched with 300 mL of 1N hydrochloric acid aqueous solution, and extracted with 100 mL of toluene three times. Combined organic layers were washed with a saturated aqueous solution of sodium hydrogencarbonate, water and saturated brine, and then dried over magnesium sulfate, and a solvent was distilled off by an evaporator. The residue was purified by silica gel column chromatography, and thus 4-bromo-2-fluoro-4'-propyl-2',3',4',5'-tetrahydro-[1,1'-biphenyl]-3-carboaldehyde (72) (28.2 g, yield 92.7%) was obtained.

Second Step

Then, 2-ethoxy-1,8,9,9,10,10-hexafluoro-7-(4-propylcyclohexa-1-en-1-yl)-9,10-dihydrophenanthrene (No. 101) was obtained from compound (72) and compound (55) prepared in Example 1 by performing a reaction in a manner similar to the operations in Example 6.

Chemical shifts (δ (ppm)) by $^1$H-NMR analysis were as described below, and the compound obtained was identified to be 2-ethoxy-1,8,9,9,10,10-hexafluoro-7-(4-propylcyclohexa-1-en-1-yl)-9,10-dihydrophenanthrene (No. 101).

$^1$H-NMR (CDCl$_3$) δ: 7.52-7.48 (m, 1H), 7.47-7.39 (m, 2H), 7.16-7.11 (m, 1H), 6.00-5.96 (m, 1H), 4.17 (q, 2H), 2.53-2.42 (m, 1H), 2.41-2.29 (m, 2H), 1.92-1.79 (m, 2H), 1.70-1.59 (m, 1H), 1.49 (t, 3H), 1.45-1.26 (m, 5H), 0.93 (t, 3H).

A phase transition temperature of compound No. 101 obtained was as described below.

Phase transition temperature: C 93.3N 103.1 Iso.

A liquid crystal composition was prepared using 15% of compound No. 101 and 85% of base liquid crystal A. Physical properties of the liquid crystal composition obtained were measured, and values of physical properties of compound No. 101 were determined by extrapolating measured values. The results were as described below.

Maximum temperature (NI)=97.9° C.; dielectric anisotropy (Δ∈)=−19.5; refractive index anisotropy (Δn)=0.194; viscosity (η)=141.3 mPa·s.

Example 9

Synthesis of 2-ethoxy-1,8,9,9,10,10-hexafluoro-7-(2-(4-propylcyclohexyl)ethyl)-9,10-dihydrophenanthrene (No. 121)

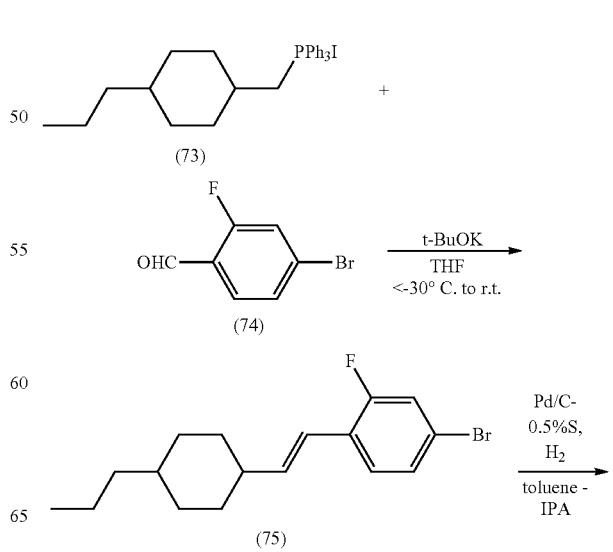

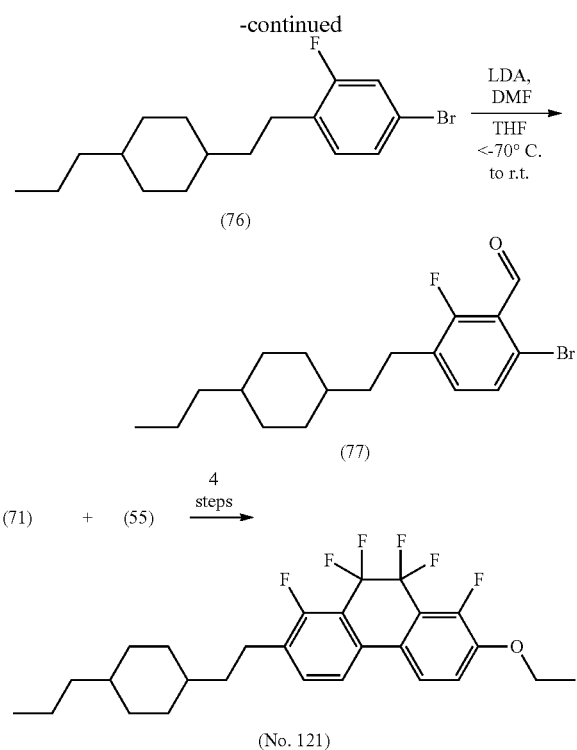

First Step

Under a nitrogen atmosphere, potassium t-butoxide (30.4 g, 271.0 mmol) was added, at −30° C. or lower, to a THF (500 mL) suspension of iodotriphenyl((4-propylcyclohexyl)methyl)phosphine (73) (143.0 g, 271.0 mmol). The reaction mixture was agitated at −30° C. or lower for 1 hour, and then a THF (100 mL) solution of 4-bromo-2-fluorobenzaldehyde (50.0 g, 246.0 mmol) was added dropwise thereto. The reaction mixture was returned to room temperature, and then quenched with 500 mL of water, and extracted with 200 mL of toluene three times. Combined organic layers were washed with water and saturated brine, and then dried over magnesium sulfate, and a solvent was distilled off by an evaporator. The residue was purified by silica gel column chromatography, and thus 4-bromo-2-fluoro-1-(2-(4-propylcyclohexyl)vinyl)benzene (75) (75.0 g, yield 94.0%) was obtained.

Second Step

A mixture of compound (75) (75.0 g, 231.0 mmol) and 5%-palladium on carbon (0.5% sulfur, 50% water-containing article) (2.82 g, 3 wt %) was agitated for 18 hours under a hydrogen atmosphere in a toluene (300 mL)-IPA (100 mL) solvent. The reaction mixture was filtered and a solvent of a filtrate was distilled off by an evaporator. The residue was passed through silica gel column chromatography and recrystallized from heptane-ethanol, and thus 4-bromo-2-fluoro-1-(2-(4-propylcyclohexyl)ethyl)benzene (76) (57.1 g, yield 75.5%) was obtained.

Third Step

Under a nitrogen atmosphere, LDA (299.0 mL, 328.9 mmol) was slowly added dropwise, at −70° C. or lower, to a THF (400 mL) solution of compound (76) (89.7 g, 274.1 mmol). The reaction mixture was agitated at −70° C. or lower for 1 hour, and then DMF (30.1 g, 411.1 mmol) was slowly added dropwise thereto. The reaction mixture was returned to room temperature, and then quenched with 400 mL of 1N hydrochloric acid aqueous solution, and extracted with 200 mL of toluene three times. Combined organic layers were washed with a saturated aqueous solution of sodium hydrogencarbonate, water and saturated brine, and then dried over magnesium sulfate, and a solvent was distilled off by an evaporator. The residue was purified by silica gel column chromatography, and thus 6-bromo-2-fluoro-3-(2-(4-propylcyclohexyl)ethyl)benzaldehyde (77) (61.4 g, yield 63.1%) was obtained.

Fourth Step

Then, 2-ethoxy-1,8,9,9,10,10-hexafluoro-7-(2-(4-propylcyclohexyl)ethyl)-9,10-dihydrophenanthrene (No. 121) was obtained from compound (77) and compound (55) prepared in Example 1 by performing a reaction in a manner similar to the operations in Examples 1 and 2.

Chemical shifts (δ (ppm)) by $^1$H-NMR analysis were as described below, and the compound obtained was identified to be 2-ethoxy-1,8,9,9,10,10-hexafluoro-7-(2-(4-propylcyclohexyl)ethyl)-9,10-dihydrophenanthrene (No. 121).

$^1$H-NMR (CDCl$_3$) δ: 7.51-7.48 (m, 1H), 7.46-7.42 (m, 1H), 7.40-7.35 (m, 1H), 7.15-7.11 (m, 1H), 4.17 (q, 2H), 2.71-2.66 (m, 2H), 1.84-1.72 (m, 4H), 1.54-1.47 (m, 5H), 1.36-1.12 (m, 6H), 1.00-0.84 (m, 7H).

A phase transition temperature of compound No. 121 obtained was as described below.

Phase transition temperature: C 87.8N 101.7 Iso.

A liquid crystal composition was prepared using 15% of compound No. 121 and 85% of base liquid crystal A. Physical properties of the liquid crystal composition obtained were measured, and values of physical properties of compound No. 121 were determined by extrapolating measured values. The results were as described below.

Maximum temperature (NI)=97.9° C.; dielectric anisotropy (Δ∈)=−17.7; refractive index anisotropy (Δn)=0.158; viscosity (η)=144.4 mPa·s.

Example 10

Synthesis of 1,8,9,9,10,10-hexafluoro-2-propyl-7-(2-(4-propylcyclohexyl)ethyl)-9,10-dihydrophenanthrene (No. 512)

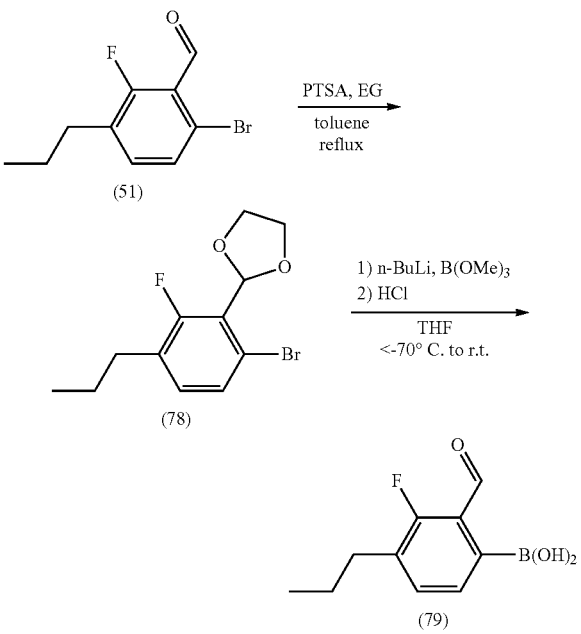

-continued

(77) + (79) —4 steps→

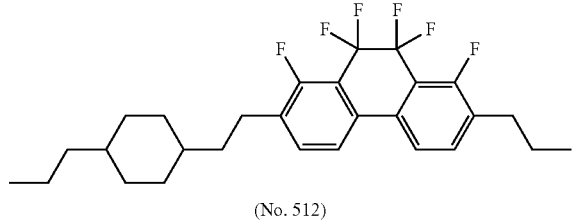

(No. 512)

First Step

A Dean-Stark condenser was attached, and a mixture of compound (51) (52.4 g, 213.8 mmol) prepared in Example 1, EG (39.8 g, 641.4 mmol) and PTSA (0.52 g, 1 wt %) was refluxed in a toluene (300 mL) solvent for 3 hours. The reaction mixture was washed with a saturated aqueous solution of sodium hydrogencarbonate, water and saturated brine, and dried over magnesium sulfate. Toluene was distilled off by an evaporator, and thus 2-(6-bromo-2-fluoro-3-propylphenyl)-1,3-dioxolane (78) (61.2 g, yield 99.0%) was obtained.

Second Step

Under a nitrogen atmosphere, n-BuLi (141.1 mL, 232.8 mmol) was slowly added dropwise, at −70° C. or lower, to a THF (500 mL) solution of compound (78) (61.2 g, 213.0 mmol). The reaction mixture was agitated at −70° C. or lower for 1 hour, and then trimethyl borate (33.0 g, 317 mmol) was slowly added dropwise thereto. The reaction mixture was returned to room temperature, and then quenched with 400 mL of 2N hydrochloric acid aqueous solution, and extracted with 200 mL of toluene three times. Combined organic layers were washed with a saturated aqueous solution of sodium hydrogencarbonate, water and saturated brine, and then dried over magnesium sulfate, and a solvent was distilled off by an evaporator. The residue was washed with heptane, and thus (3-fluoro-2-formyl-4-ethoxyphenyl)boronic acid (79) (38.1 g, yield 86.0%) was obtained.

Fourth Step

Then, 1,8,9,9,10,10-hexafluoro-2-propyl-7-(2-(4-propylcyclohexyl)ethyl)-9,10-dihydrophenanthrene (No. 512) was obtained from compound (77) prepared in Example 9 and compound (79) by performing a reaction in a manner similar to the operations in Examples 1 and 2.

Chemical shifts (δ (ppm)) by $^1$H-NMR analysis were as described below, and the compound obtained was identified to be 1,8,9,9,10,10-hexafluoro-2-propyl-7-(2-(4-propylcyclohexyl)ethyl)-9,10-dihydrophenanthrene (No. 512).

$^1$H-NMR (CDCl$_3$) δ: 7.52-7.48 (m, 2H), 7.42-7.33 (m, 2H), 2.72-2.65 (m, 4H), 1.85-1.73 (m, 4H), 1.72-1.64 (m, 2H), 1.57-1.49 (m, 2H) 1.36-1.12 (m, 6H), 1.01-0.83 (m, 10H).

A phase transition temperature of compound No. 512 obtained was as described below.

Phase transition temperature: C 76.4 Iso.

A liquid crystal composition was prepared using 15% of compound No. 512 and 85% of base liquid crystal A. Physical properties of the liquid crystal composition obtained were measured, and values of physical properties of compound No. 512 were determined by extrapolating measured values. The results were as described below.

Maximum temperature (NI)=65.9° C.; dielectric anisotropy (Δ∈)=−13.4; refractive index anisotropy (Δn)=0.1297; viscosity (η)=119.4 mPa·s.

Example 11

Synthesis of 2-(4-(but-3-en-1-yl)phenyl)-7-ethoxy-1,8,9,9,10,10-hexafluoro-9,10-dihydrophenanthrene (No. 24)

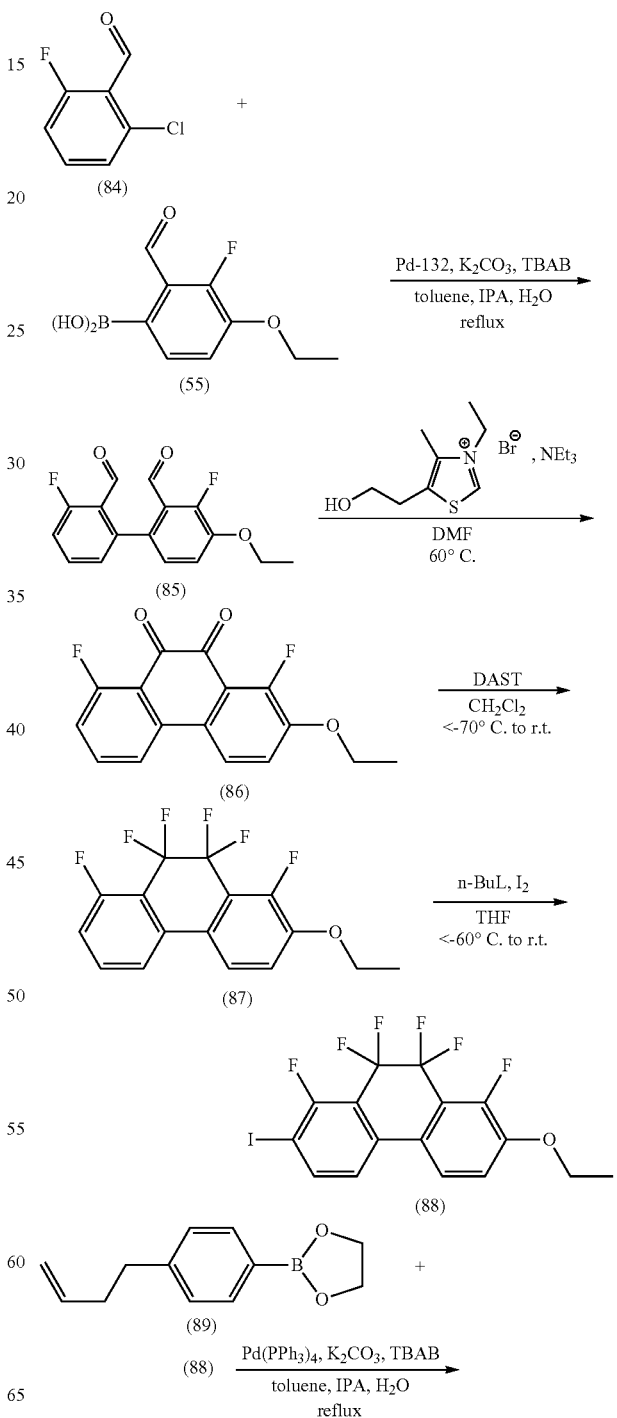

-continued

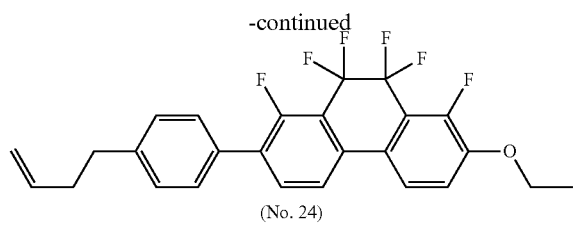

(No. 24)

First Step

Under a nitrogen atmosphere, a mixture of 2-chloro-6-fluorobenzaldehyde (84) (50.0 g, 315 mmol), compound (55) (73.5 g, 347 mmol), Pd-132 (made by Johnson Matthey Catalysis and Chiral Technologies) (0.223 g, 0.315 mmol), potassium carbonate (87 g, 631 mmol) and TBAB (20.33 g, 63.1 mmol) was refluxed in a toluene 500 mL)-ethanol (100 mL)-water (500 mL) solvent for 5 hours. The reaction mixture was extracted with 300 mL of toluene three times. Combined organic layers were washed with a saturated aqueous solution of sodium hydrogencarbonate, water and saturated brine, and then dried over magnesium sulfate, and a solvent was distilled off by an evaporator. The residue was purified by silica gel column chromatography, and thus 4-ethoxy-3,3'-difluoro-[1,1'-biphenyl]-2,2'-dicarboaldehyde (85) (77.25 g, yield 84%) was obtained.

Second Step

Under a nitrogen atmosphere, a DMF (50 mL) solution of compound (85) (10.0 g, 3.45 mmol), 3-ethyl-5-(2-hydroxyethyl)-4-methylthiazole-3-iumbromide (1.74 g, 6.89 mmol) and triethylamine (1.05 g, 10.34 mmol) was agitated at 60° C. for 6 hours. The reaction mixture was quenched with 150 mL of water, and extracted with 50 mL of dichloromethane three times. Combined organic layers were washed with a 1N hydrochloric acid aqueous solution, water and saturated brine, and then dried over magnesium sulfate, and a solvent was distilled off by an evaporator. The residue was washed with toluene, and thus 2-ethoxy-1,8-difluorophenanthrene-9,10-dione (86) (7.0 g, yield 70.5%) was obtained.

Third Step

Under a nitrogen atmosphere, DAST (15.63 g, 97.00 mmol) was slowly added dropwise, at −70° C. or lower, to a dichloromethane (50 mL) solution of compound (86) (6.21 g, 21.54 mmol). The reaction mixture was slowly returned to room temperature, and then quenched with 100 mL of water. The dichloromethane layer was washed with a saturated aqueous solution of sodium hydrogencarbonate, water and saturated brine, and then dried over magnesium sulfate, and a solvent was distilled off by an evaporator. The residue was purified by silica gel column chromatography, and thus 2-ethoxy-1,8,9,9,10,10-hexafluoro-9,10-dihydrophenanthrene (87) (6.44 g, yield 90.0%) was obtained.

Fourth Step

Under a nitrogen atmosphere, n-butyllithium (1.65 M, 14.1 mL, 23.26 mmol) was slowly added dropwise, at −60° C. or lower, to a THF (50 mL) solution of compound (87) (6.44 g, 19.38 mmol). The reaction mixture was agitated at −60° C. or lower for 1 hour, and then a THF (30 mL) solution of iodine (5.9 g, 23.26 mmol) was added dropwise thereto. The reaction mixture was returned to room temperature, and then quenched with a saturated aqueous solution of ammonium chloride, and extracted with 50 mL of toluene three times. Combined organic layers were washed with a sodium thiosulfate aqueous solution, a saturated aqueous solution of sodium hydrogencarbonate, water and saturated brine, and then dried over magnesium sulfate, and a solvent was distilled off by an evaporator. The residue was purified by silica gel column chromatography, and thus 2-ethoxy-1,8,9,9,10,10-hexafluoro-7-iodo-9,10-dihydrophenanthrene (88) (6.7 g, yield 74.5%) was obtained.

Fifth Step

Under a nitrogen atmosphere, a mixture of 2-(4-(but-3-en-1-yl)phenyl)-1,3,2-dioxoborolane (89) (1.76 g, 8.73 mmol), compound (88) (2.0 g, 4.37 mmol), tetrakis(triphenylphosphine)palladium (5.04 mg, 4.37 μmol), potassium carbonate (1.21 g, 8.73 mmol) and TBAB (0.035 g, 0.11 mmol) was refluxed in a toluene (10 mL)-ethanol (5 mL)-water (10 mL) solvent for 5 hours. The reaction mixture was extracted with 10 mL of toluene three times. Combined organic layers were washed with water and saturated brine, and then dried over magnesium sulfate, and a solvent was distilled off by an evaporator. The residue was purified by silica gel column chromatography, and thus 2-(4-(but-3-en-1-yl)phenyl)-7-ethoxy-1,8,9,9,10,10-hexafluoro-9,10-dihydrophenanthrene (No. 24) (1.85 g, yield 87%) was obtained.

Chemical shifts (δ (ppm)) by $^1$H-NMR analysis were as described below, and the compound obtained was identified to be 2-(4-(but-3-en-1-yl)phenyl)-7-ethoxy-1,8,9,9,10,10-hexafluoro-9,10-dihydrophenanthrene (No. 24).

$^1$H-NMR (CDCl$_3$) δ: 7.65-7.54 (m, 3H), 7.51-7.47 (m, 2H), 7.32-7.29 (m, 2H), 7.19-7.14 (m, 1H), 5.94-5.85 (m, 1H), 5.11-5.05 (m, 1H), 5.03-4.99 (m, 1H), 4.19 (q, 2H), 2.78 (t, 2H), 2.46-2.40 (m, 2H), 1.50 (t, 3H).

A phase transition temperature of compound No. 24 obtained was as described below.

Phase transition temperature: C 108.0N 118.8 Iso.

A liquid crystal composition was prepared using 15% of compound No. 24 and 85% of base liquid crystal A. Physical properties of the liquid crystal composition obtained were measured, and values of physical properties of compound No. 24 were determined by extrapolating measured values. The results were as described below.

Maximum temperature (NI)=103.9° C.; dielectric anisotropy (Δ∈)=−18.8; refractive index anisotropy (Δn)=0.244; viscosity (η)=155.3 mPa·s.

Example 12

Synthesis of 2-ethoxy-7-(4-ethoxy-2,3-difluorophenyl)-1,8,9,9,10,10-hexafluoro-9,10-dihydrophenanthrene (No. 509)

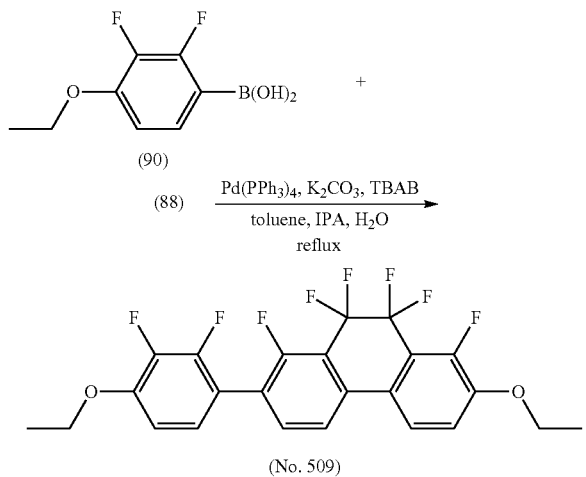

(No. 509)

Then, 2-ethoxy-7-(4-ethoxy-2,3-difluorophenyl)-1,8,9,9,10,10-hexafluoro-9,10-dihydrophenanthrene (No. 509) was obtained by changing 2-(4-(but-3-en-1-yl)phenyl)-1,3,2-dioxoborolane (89) of Example to (4-ethoxy-2,3-difluorophenyl)boronic acid (90) and by performing a reaction in a manner similar to the operations in Example 11.

Chemical shifts (δ (ppm)) by $^1$H-NMR analysis were as described below, and the compound obtained was identified to be 2-ethoxy-7-(4-ethoxy-2,3-difluorophenyl)-1,8,9,9,10,10-hexafluoro-9,10-dihydrophenanthrene (No. 509).

$^1$H-NMR (CDCl$_3$) δ: 7.61-7.54 (m, 3H), 7.19-7.14 (m, 1H), 7.12-7.06 (m, 1H), 6.86-6.81 (m, 1H), 4.22-4.15 (m, 4H), 1.53-1.47 (m, 6H).

A phase transition temperature of compound No. 509 obtained was as described below.

Phase transition temperature: C 154.5 Iso.

A liquid crystal composition was prepared using 15% of compound No. 509 and 85% of base liquid crystal A. Physical properties of the liquid crystal composition obtained were measured, and values of physical properties of compound No. 509 were determined by extrapolating measured values. The results were as described below.

Maximum temperature (NI)=106.6° C.; dielectric anisotropy (Δϵ)=−21.9; refractive index anisotropy (Δn)=0.243; viscosity (η)=156.2 mPa·s.

Example 13

Synthesis of 2-(difluoro(4-propylcyclohexyl)methoxy)-7-ethoxy-1,8,9,9,10,10-hexafluoro-9,10-dihydrophenanthrene (No. 411)

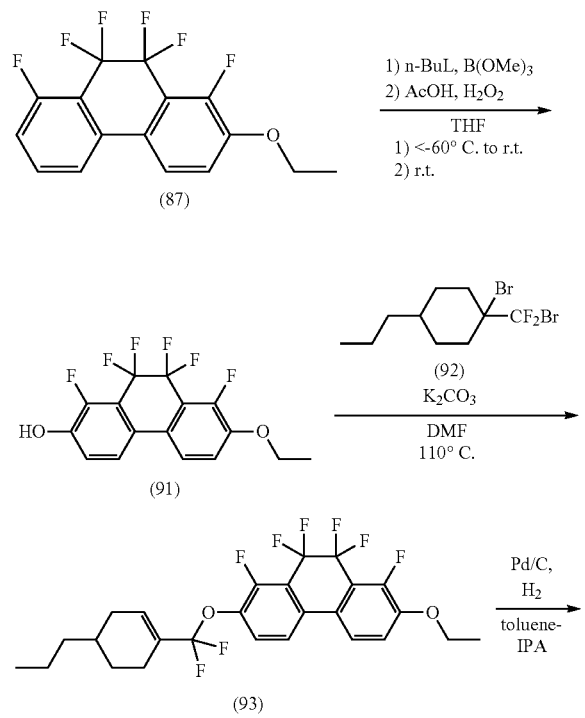

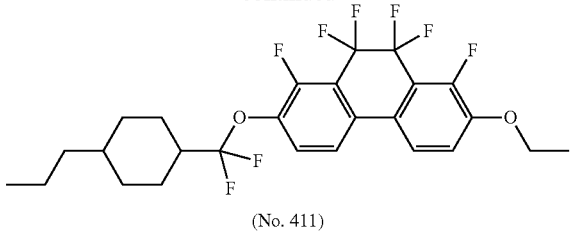

(No. 411)

First Step

Under a nitrogen atmosphere, n-butyllithium (1.63 M, 8.71 mL, 14.20 mmol) was slowly added dropwise, at −60° C. or lower, to a THF (40 mL) solution of compound (87) (4.29 g, 12.91 mmol) prepared in Example 11. The reaction mixture was agitated at −60° C. or lower for 1 hour, and then trimethyl borate (1.61 g, 15.49 mmol) was slowly added dropwise thereto. The reaction mixture was returned to room temperature, and then acetic acid (1.16 g, 19.37 mmol) and hydrogen peroxide water (2.93 g, 25.80 mmol) were added thereto, and the resultant mixture was agitated for 3 hours. The reaction mixture was quenched with a saturated aqueous solution of ammonium chloride, and extracted with 50 mL of toluene three times. Combined organic layers were washed with a sodium thiosulfate aqueous solution, a saturated aqueous solution of sodium hydrogencarbonate, water and saturated brine, and then dried over magnesium sulfate, and a solvent was distilled off by an evaporator. The residue was purified by silica gel column chromatography, and thus 7-ethoxy-1,8,9,9,10,10-hexafluoro-9,10-dihydrophenanthrene-2-ol (91) (3.76 g, yield 84.0%) was obtained.

Second Step

Under a nitrogen atmosphere, a mixture of compound (91) (3.76 g, 10.80 mmol) and potassium carbonate (4.48 g, 32.4 mmol) was heated and agitated at 110° C. for 1 hour in a DMF (40 mL) solvent. Subsequently, 1-bromo-1-(bromodifluoromethyl)-4-propylcyclohexane (92) (7.21 g, 21.59 mmol) was added dropwise to the reaction mixture at 110° C., and the resultant mixture was further agitated for 3 hours. The reaction mixture was quenched with water, and extracted with 50 mL of toluene three times. Combined organic layers were washed with water and saturated brine, and then dried over magnesium sulfate, and a solvent was distilled off by an evaporator. The residue was purified by silica gel column chromatography, and thus 2-(difluoro(4-propylcyclohexa-1-en-1-yl)methoxy)-7-ethoxy-1,8,9,9,10,10-hexafluoro-9,10-dihydrophenanthrene (93) (4.40 g, yield 78.0%) was obtained.

Third Step

A mixture of compound (93) (4.40 g, 8.45 mmol) and 5%-palladium on carbon (50% water-containing article) (0.132 g, 3 wt %) was agitated for 24 hours under a hydrogen atmosphere in a toluene (10 mL)-IPA (10 mL) solvent. The reaction mixture was filtered and a solvent in a filtrate was distilled off by an evaporator. The residue was purified by silica gel column chromatography, and thus 2-(difluoro(4-propylcyclohexyl)methoxy)-7-ethoxy-1,8,9,9,10,10-hexafluoro-9,10-dihydrophenanthrene (No. 411) was obtained.

Chemical shifts (δ (ppm)) by $^1$H-NMR analysis were as described below, and the compound obtained was identified to be 2-(difluoro(4-propylcyclohexyl)methoxy)-7-ethoxy-1,8,9,9,10,10-hexafluoro-9,10-dihydrophenanthrene (No. 411).

$^1$H-NMR (CDCl$_3$) δ: 7.54-7.45 (m, 3H), 7.17-7.12 (m, 1H), 4.17 (q, 2H), 2.16-2.03 (m, 3H), 1.92-1.85 (m, 2H), 1.54-1.17 (m, 10H), 1.00-0.87 (m, 5H).

A phase transition temperature of compound No. 411 obtained was as described below.

Phase transition temperature: C 97.8N 132.6 Iso.

A liquid crystal composition was prepared using 15% of compound No. 411 and 85% of base liquid crystal A. Physical properties of the liquid crystal composition obtained were measured, and values of physical properties of compound No. 411 were determined by extrapolating measured values. The results were as described below.

Maximum temperature (NI)=115.3° C.; dielectric anisotropy (Δ∈)=−15.1; refractive index anisotropy (Δn)=0.1483; viscosity (η)=137.5 mPa·s.

Example 14

Synthesis of 2-ethoxy-1,8,9,10-tetrafluoro-7-propyl-9,10-dihydrophenanthrene (No. 6)

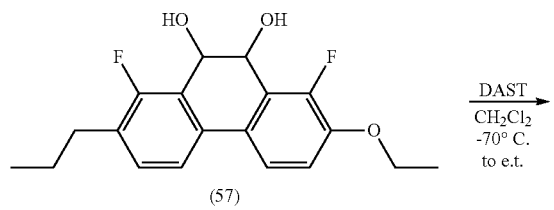

(57)

DAST
CH$_2$Cl$_2$
-70° C.
to r.t.

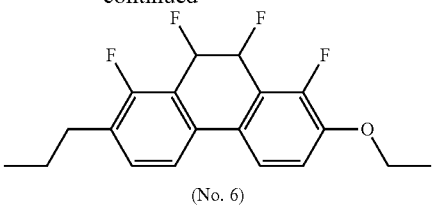

(No. 6)

DAST (0.2 g, 1.26 mmol) was slowly added dropwise, at −70° C. or lower, to a dichloromethane (5 mL) solution of 2-ethoxy-1,8-difluoro-7-propyl-9,10-dihydrophenanthrene-9,10-diol (57) (0.2 g, 0.598 mmol) prepared in Example 1. The reaction mixture was slowly returned to room temperature, and then quenched with 5 mL of water, and the dichloromethane layer was washed with a saturated aqueous solution of sodium hydrogencarbonate and water. When the dichloromethane layer was analyzed by GCMS, formation of 2-ethoxy-1,8,9,10-tetrafluoro-7-propyl-9,10-dihydrophenanthrene (No. 6) was confirmed.

Fragments of peaks obtained by the GCMG analysis are as described below to support a structure of 2-ethoxy-1,8,9,10-tetrafluoro-7-propyl-9,10-dihydrophenanthrene (No. 6).

Fragments: m/z (%)=338.15 (M$^+$, 38.46), 281.05 (100.00), 29.20 (72.58), 27.20 (35.61), 310.10 (25.08), 282.05 (19.46)

According to synthetic processes as described in Examples 1 to 14, compounds as described below can be prepared.

| No. | |
|---|---|
| 1 | 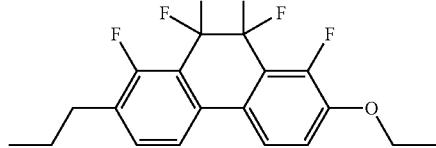 |
| 2 | 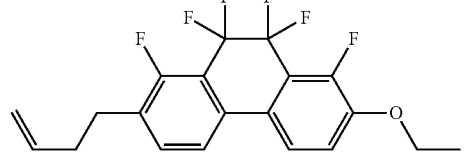 |
| 3 | 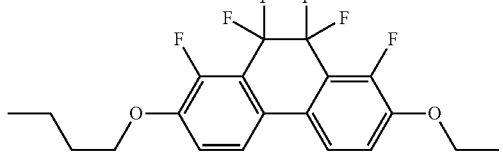 |
| 4 | 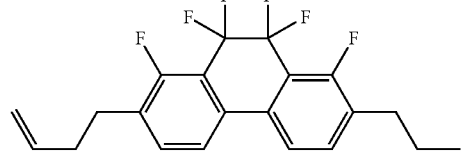 |

-continued
| No. | |
|---|---|
| 5 | 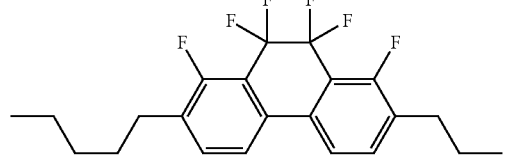 |
| 6 | 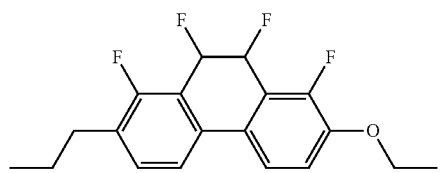 [SMILES: CCCc1ccc2c(c1F)C(F)C(F)c1c-2ccc(OCC)c1F] |
| 7 | 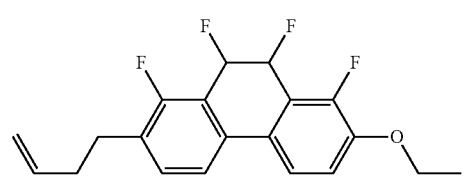 |
| 8 | 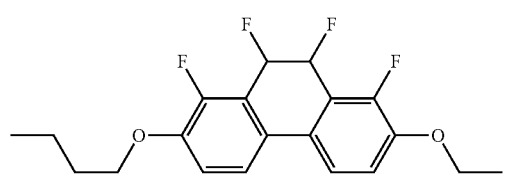 [SMILES: CCCCOc1ccc2c(c1F)C(F)C(F)c1c-2ccc(OCC)c1F] |
| 9 | 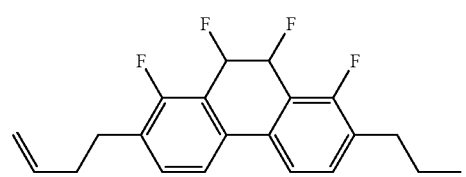 [SMILES: C=CCCc1ccc2c(c1F)C(F)C(F)c1c-2ccc(CCC)c1F] |
| 10 | 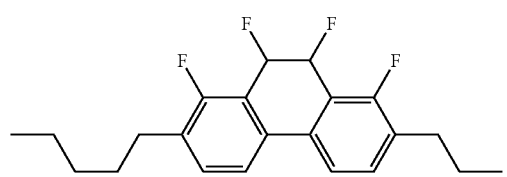 [SMILES: CCCCCc1ccc2c(c1F)C(F)C(F)c1c-2ccc(CCC)c1F] |
| 11 | 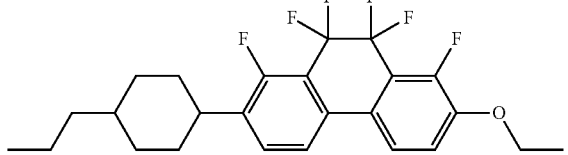 |
| 12 | 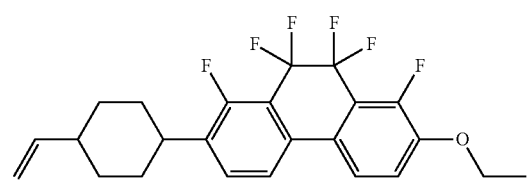 [SMILES: C=CC1CCC(c2ccc3c(c2F)C(F)(F)C(F)(F)c2c-3ccc(OCC)c2F)CC1] |
| 13 | 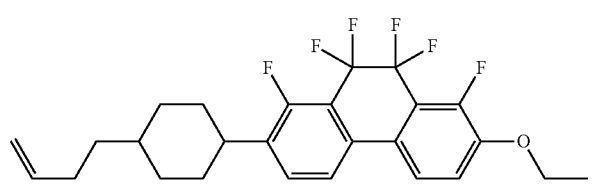 |

-continued
| No. | |
|---|---|
| 14 | 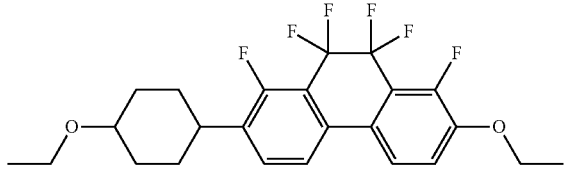 [SMILES: CCOc1ccc2c(c1F)C(F)(F)C(F)(F)c1c-2ccc(C2CCC(OCC)CC2)c1F] |
| 15 | 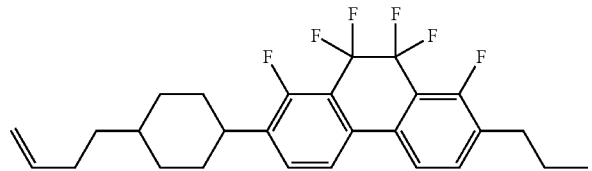 |
| 16 | 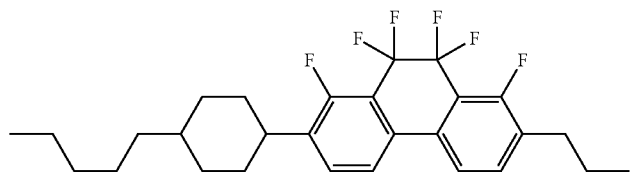 |
| 17 | 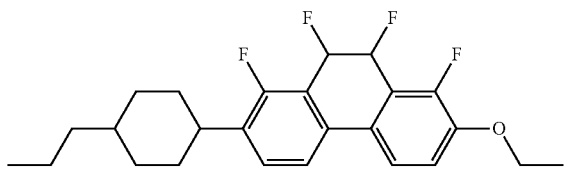 |
| 18 | 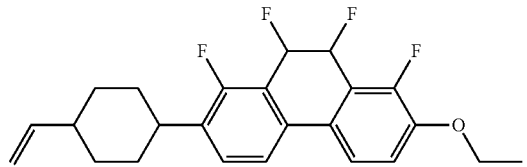 [SMILES: C=CC1CCC(c2ccc3c(c2F)C(F)C(F)c2c-3ccc(OCC)c2F)CC1] |
| 19 | 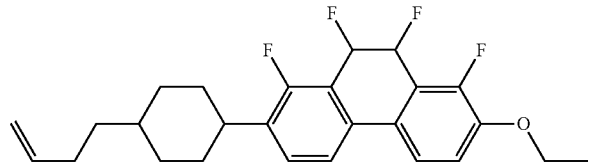 |
| 20 | 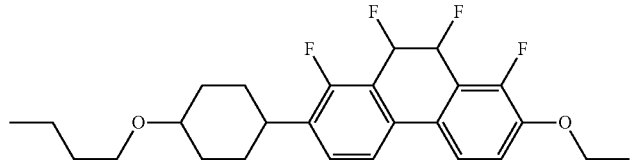 |
| 21 | 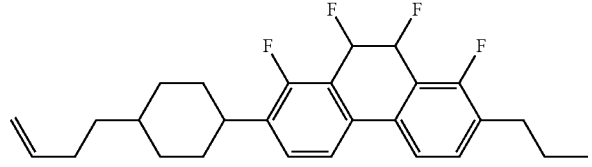 [SMILES: C=CCCC1CCC(c2ccc3c(c2F)C(F)C(F)c2c-3ccc(OCC)c2F)CC1] |

-continued
| No. | |
|---|---|
| 22 | 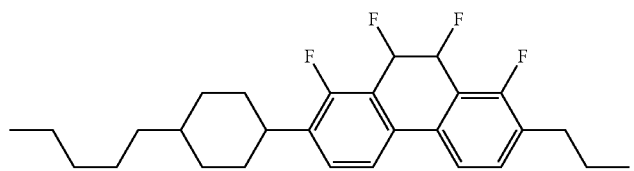 [SMILES: CCCCCC1CCC(c2ccc3c(c2F)C(F)C(F)c2c-3ccc(CCC)c2F)CC1] |
| 23 | 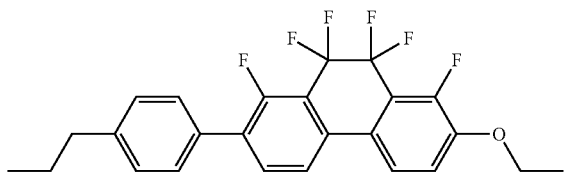 |
| 24 | 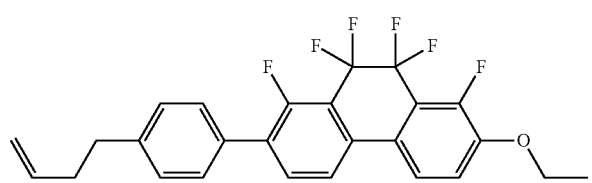 [SMILES: C=CCCc1ccc(-c2ccc3c(c2F)C(F)(F)C(F)(F)c2c-3ccc(OCC)c2F)cc1] |
| 25 | 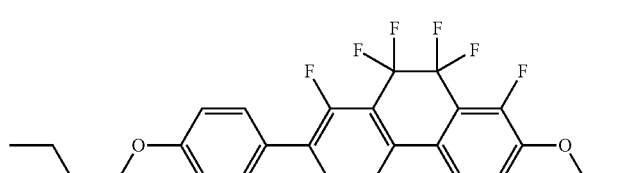 |
| 26 | 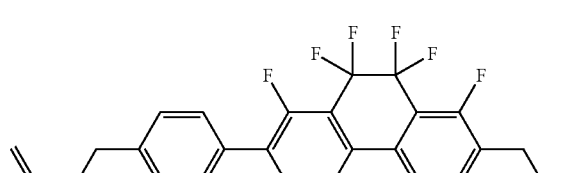 |
| 27 | 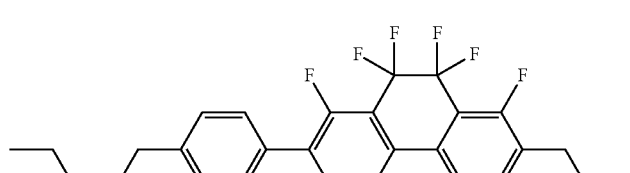 |
| 28 | 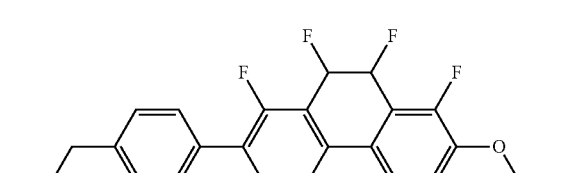 |
| 29 | 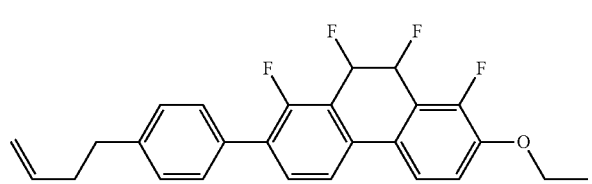 [SMILES: C=CCCc1ccc(-c2ccc3c(c2F)C(F)C(F)c2c-3ccc(OCC)c2F)cc1] |

| No. | |
|---|---|
| 30 | 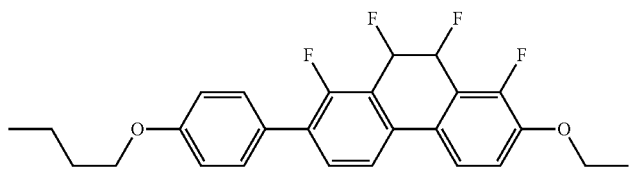 [SMILES: CCCCOc1ccc(-c2ccc3c(c2F)C(F)C(F)c2c-3ccc(OCC)c2F)cc1] |
| 31 | 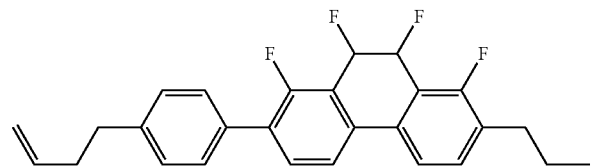 |
| 32 | 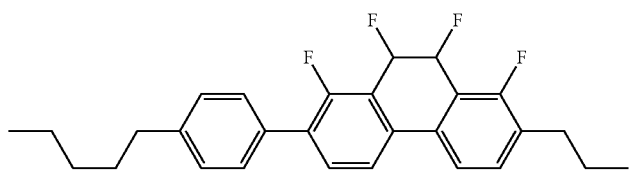 |
| 33 | 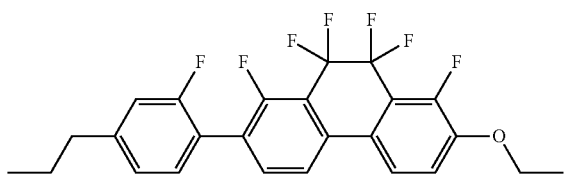 |
| 34 | 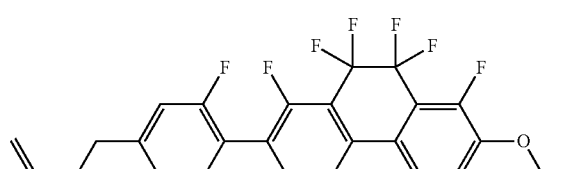 |
| 35 | 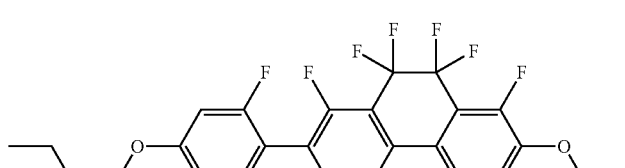 |
| 36 | 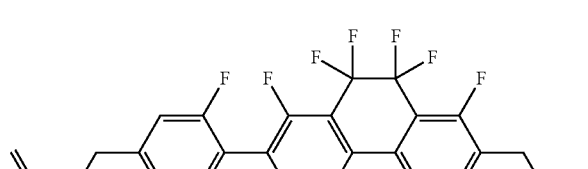 |
| 37 | 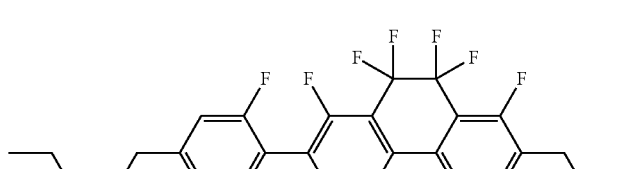 |

| No. |
|---|
| 38 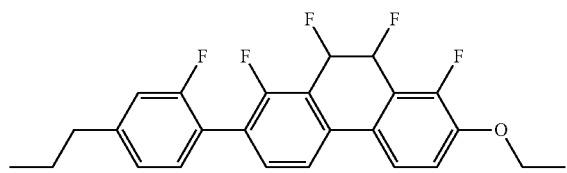 [SMILES: CCCc1ccc(-c2ccc3c(c2F)C(F)C(F)c2c-3ccc(OCC)c2F)c(F)c1] |
| 39 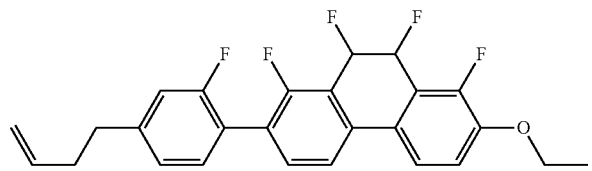 [SMILES: C=CCCc1ccc(-c2ccc3c(c2F)C(F)C(F)c2c-3ccc(OCC)c2F)c(F)c1] |
| 40 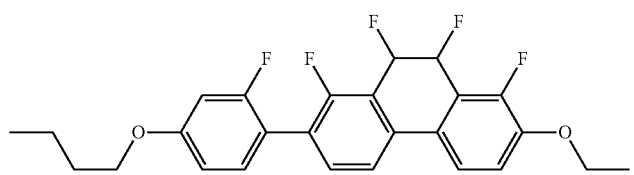 |
| 41 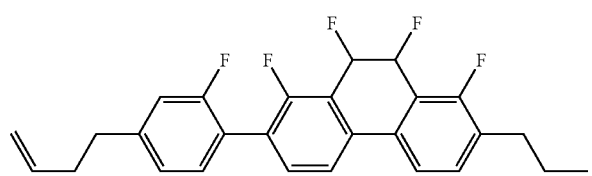 |
| 42 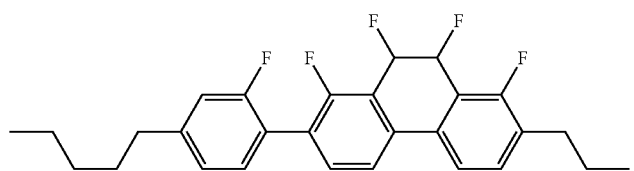 [SMILES: CCCCOc1ccc(-c2ccc3c(c2F)C(F)C(F)c2c-3ccc(OCC)c2F)c(F)c1] |
| 43 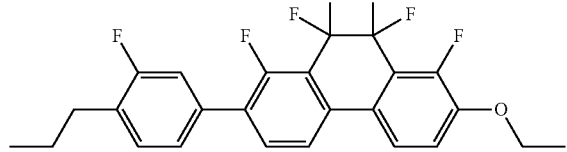 |
| 44 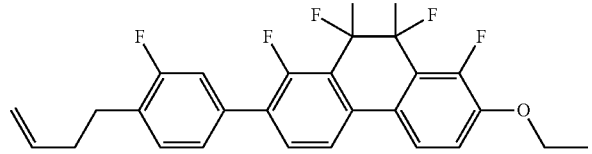 |
| 45 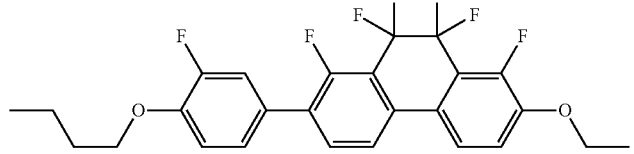 |
| 46 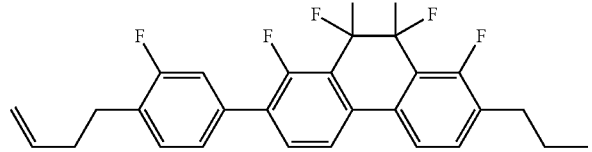 |

| No. | |
|---|---|
| 47 | 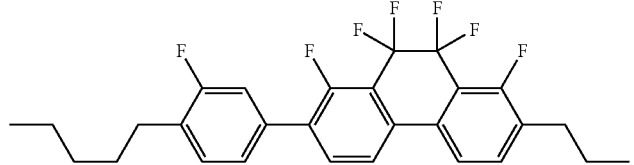 [SMILES: CCCCCc1ccc(-c2ccc3c(c2F)C(F)(F)C(F)(F)c2c-3ccc(CCC)c2F)cc1F] |
| 48 | 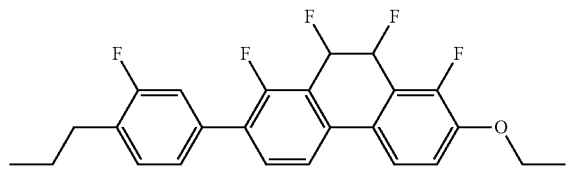 [SMILES: CCCc1ccc(-c2ccc3c(c2F)C(F)C(F)c2c-3ccc(OCC)c2F)cc1F] |
| 49 | 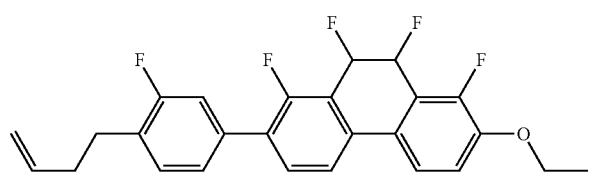 [SMILES: C=CCCc1ccc(-c2ccc3c(c2F)C(F)C(F)c2c-3ccc(OCC)c2F)cc1F] |
| 50 | 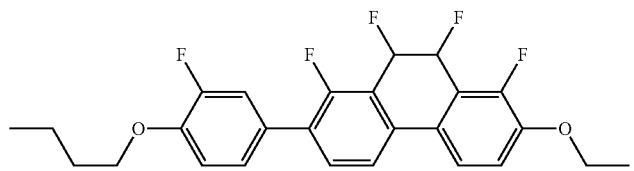 |
| 51 | 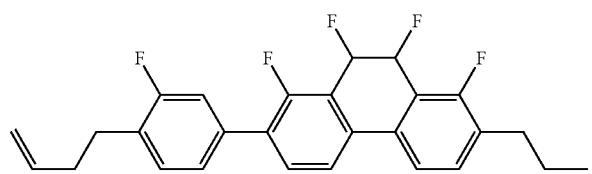 [SMILES: C=CCCc1ccc(-c2ccc3c(c2F)C(F)C(F)c2c-3ccc(CCC)c2F)cc1F] |
| 52 | 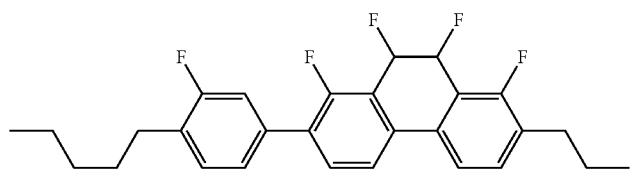 |
| 53 | 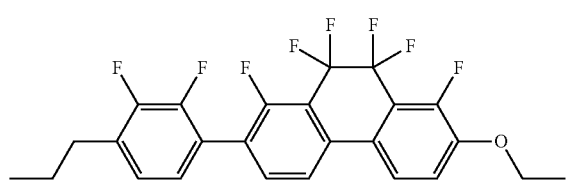 |
| 54 | 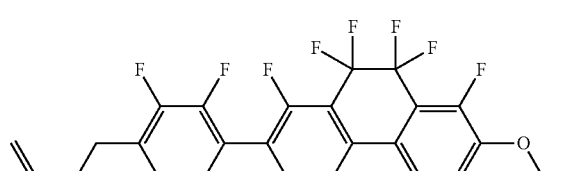 |

-continued
| No. | |
|---|---|
| 55 | 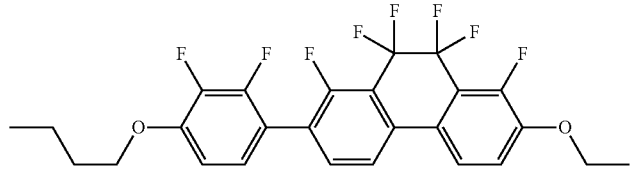 |
| 56 | 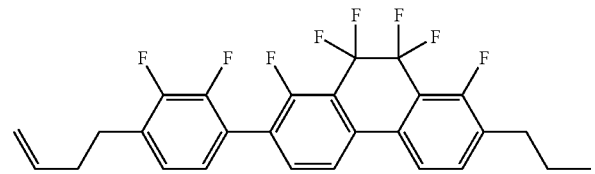 |
| 57 | 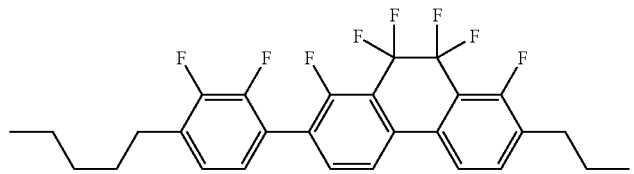 |
| 58 | 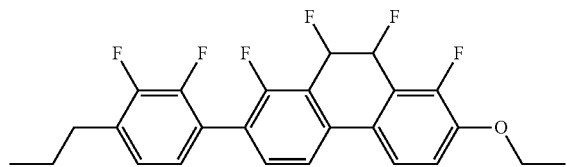 |
| 59 | 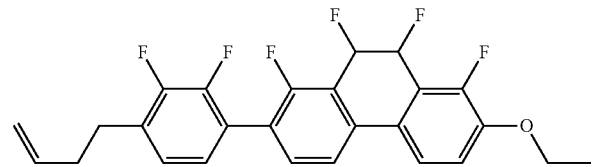 [SMILES: C=CCCc1ccc(-c2ccc3c(c2F)C(F)C(F)c2c-3ccc(OCC)c2F)c(F)c1F] |
| 60 | 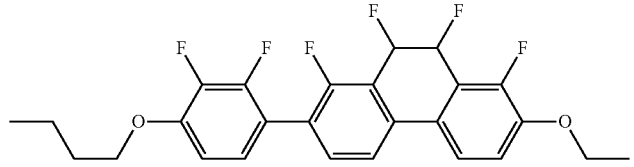 |
| 61 | 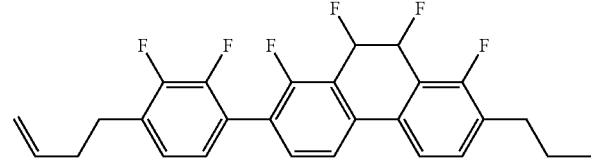 |
| 62 | 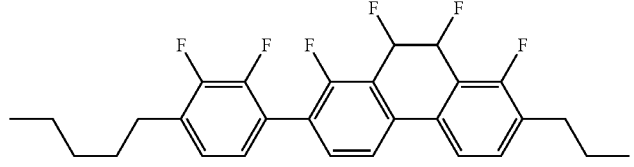 [SMILES: CCCCCc1ccc(-c2ccc3c(c2F)C(F)C(F)c2c-3ccc(CCC)c2F)c(F)c1F] |
| 63 | 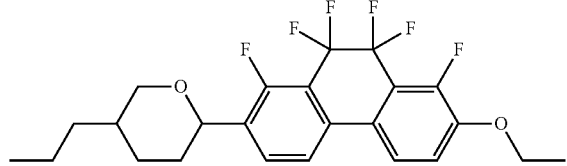 |

| No. | |
|---|---|
| 64 | 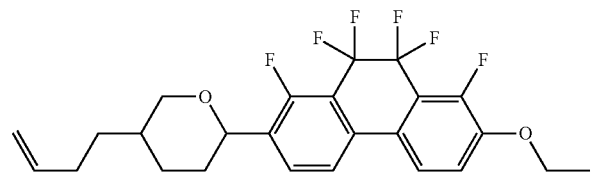 |
| 65 | 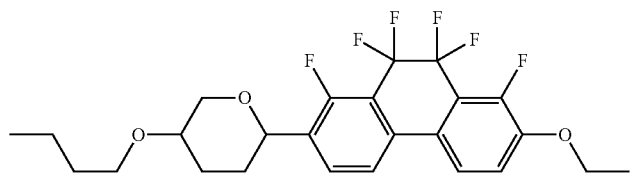 |
| 66 | 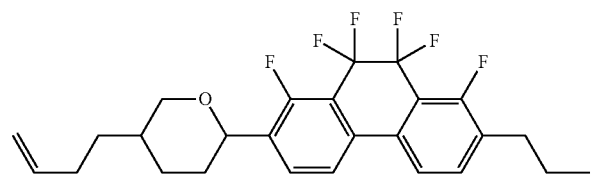 |
| 67 | 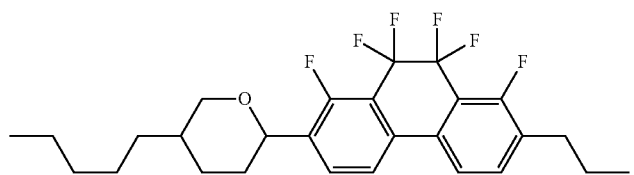 [SMILES: CCCCCC1CCC(c2ccc3c(c2F)C(F)(F)C(F)(F)c2c-3ccc(CCC)c2F)OC1] |
| 68 | 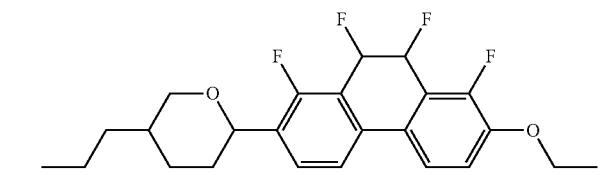 [SMILES: CCCC1CCC(c2ccc3c(c2F)C(F)C(F)c2c-3ccc(OCC)c2F)OC1] |
| 69 | 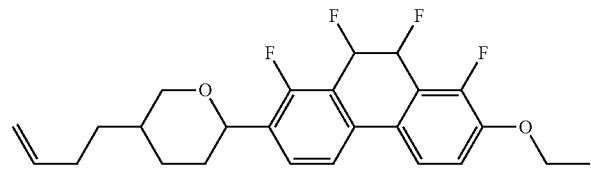 [SMILES: C=CCCC1CCC(c2ccc3c(c2F)C(F)C(F)c2c-3ccc(OCC)c2F)OC1] |
| 70 | 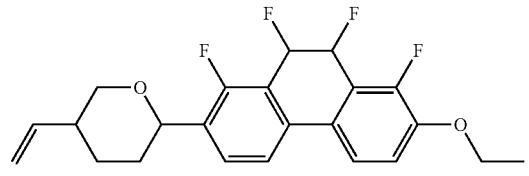 [SMILES: C=CC1CCC(c2ccc3c(c2F)C(F)C(F)c2c-3ccc(OCC)c2F)OC1] |
| 71 | 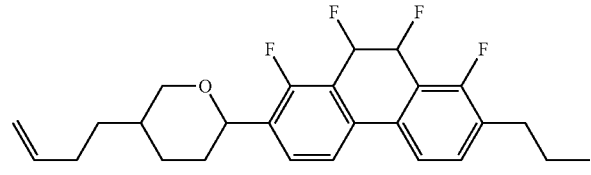 |

| No. | |
|---|---|
| 72 | 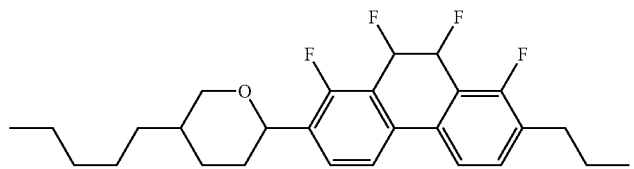 [SMILES: CCCCCC1CCC(c2ccc3c(c2F)C(F)C(F)c2c-3ccc(CCC)c2F)OC1] |
| 73 | 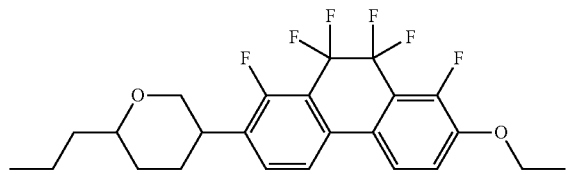 [SMILES: CCCC1CCC(c2ccc3c(c2F)C(F)(F)C(F)(F)c2c-3ccc(OCC)c2F)CO1] |
| 74 | 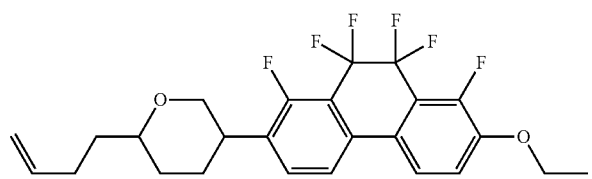 [SMILES: C=CCCC1CCC(c2ccc3c(c2F)C(F)(F)C(F)(F)c2c-3ccc(OCC)c2F)CO1] |
| 75 | 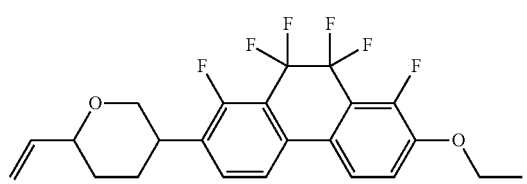 |
| 76 | 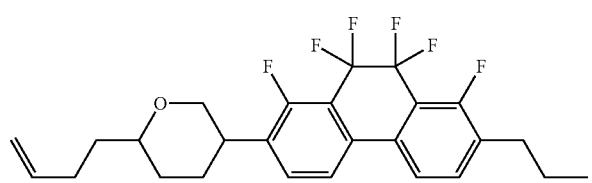 |
| 77 | 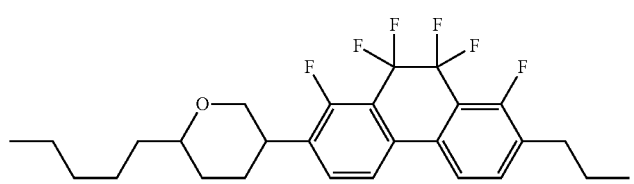 [SMILES: CCCCCC1CCC(c2ccc3c(c2F)C(F)(F)C(F)(F)c2c-3ccc(CCC)c2F)CO1] |
| 78 | 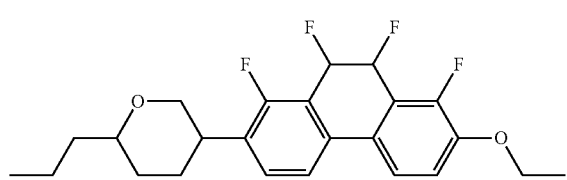 [SMILES: CCCC1CCC(c2ccc3c(c2F)C(F)C(F)c2c-3ccc(OCC)c2F)CO1] |
| 79 | 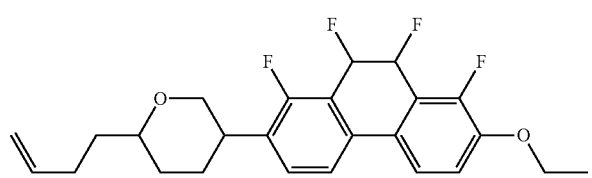 [SMILES: C=CCCC1CCC(c2ccc3c(c2F)C(F)C(F)c2c-3ccc(OCC)c2F)CO1] |

| No. | |
|---|---|
| 80 | 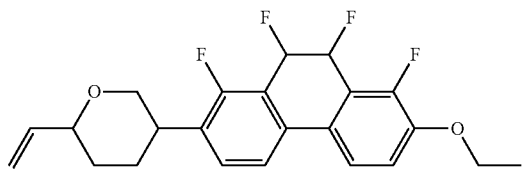 |
| 81 | 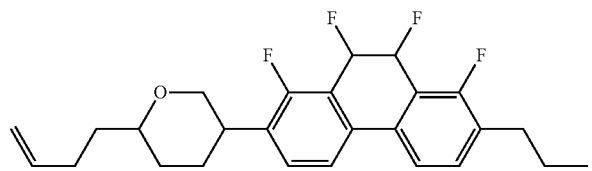 |
| 82 | 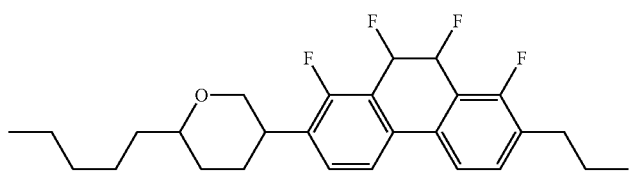 [SMILES: CCCCCC1CCC(c2ccc3c(c2F)C(F)C(F)c2c-3ccc(CCC)c2F)CO1] |
| 83 | 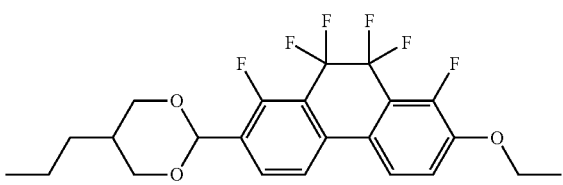 |
| 84 | 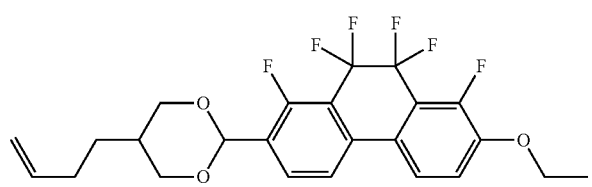 [SMILES: C=CCCC1COC(c2ccc3c(c2F)C(F)(F)C(F)(F)c2c-3ccc(OCC)c2F)OC1] |
| 85 | 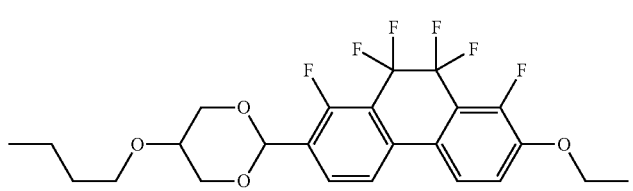 [SMILES: CCCCOC1COC(c2ccc3c(c2F)C(F)(F)C(F)(F)c2c-3ccc(OCC)c2F)OC1] |
| 86 | 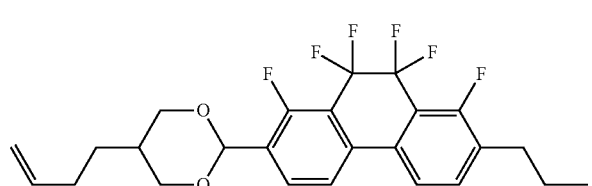 |
| 87 | 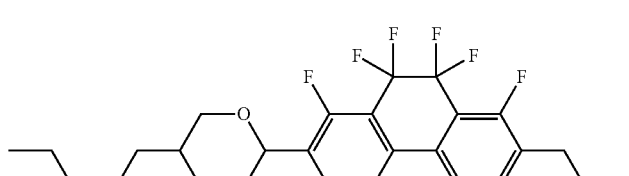 |

-continued
| No. |
|---|
| 88 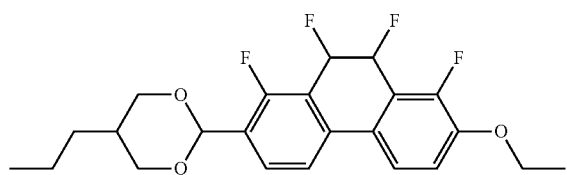 [SMILES: CCCC1COC(c2ccc3c(c2F)C(F)C(F)c2c-3ccc(OCC)c2F)OC1] |
| 89 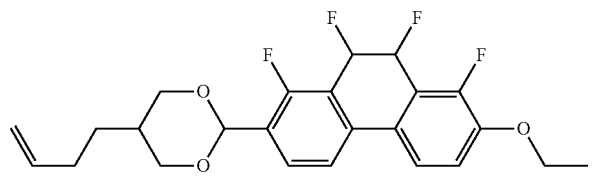 |
| 90 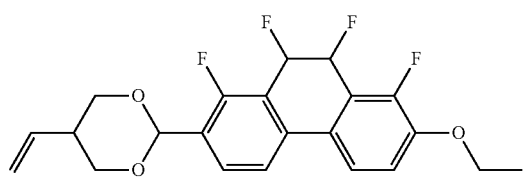 [SMILES: C=CC1COC(c2ccc3c(c2F)C(F)C(F)c2c-3ccc(OCC)c2F)OC1] |
| 91 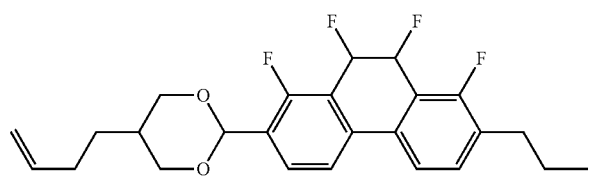 [SMILES: C=CCCC1COC(c2ccc3c(c2F)C(F)C(F)c2c-3ccc(CCC)c2F)OC1] |
| 92 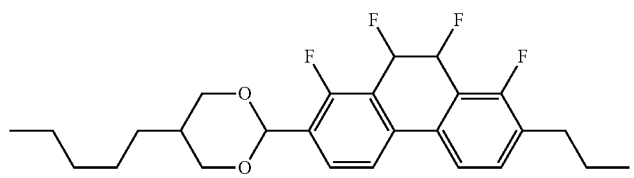 [SMILES: CCCCCC1COC(c2ccc3c(c2F)C(F)C(F)c2c-3ccc(CCC)c2F)OC1] |
| 93 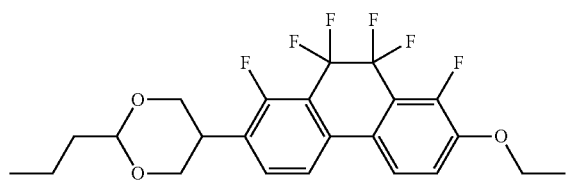 |
| 94 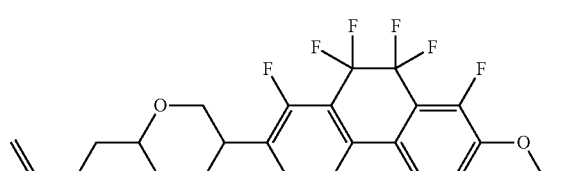 |
| 95 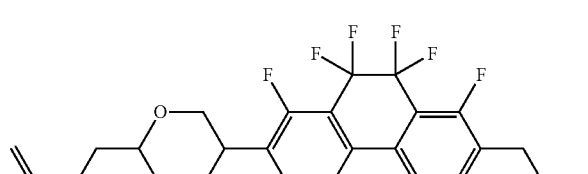 |

US 9,193,908 B2
81                                                              82
-continued
| No. | |
|---|---|
| 96 | 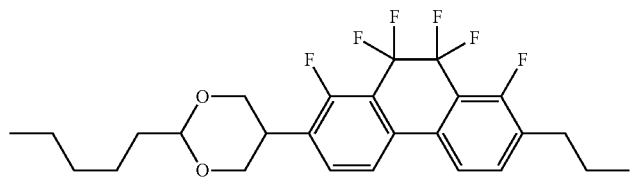 [SMILES: CCCCCC1OCC(c2ccc3c(c2F)C(F)(F)C(F)(F)c2c-3ccc(CCC)c2F)CO1] |
| 97 | 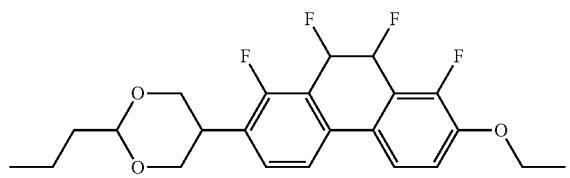 [SMILES: CCCC1OCC(c2ccc3c(c2F)C(F)C(F)c2c-3ccc(OCC)c2F)CO1] |
| 98 | 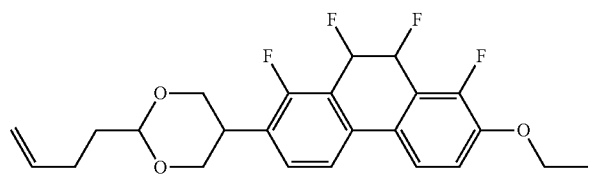 |
| 99 | 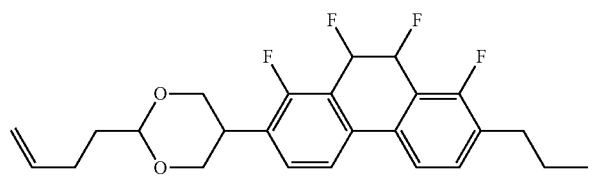 |
| 100 | 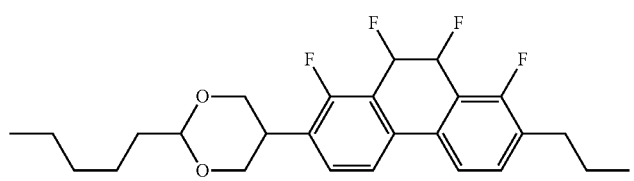 [SMILES: CCCCCC1OCC(c2ccc3c(c2F)C(F)C(F)c2c-3ccc(CCC)c2F)CO1] |
| 101 | 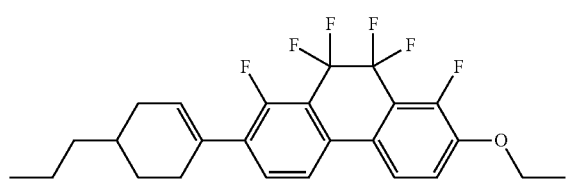 |
| 102 | 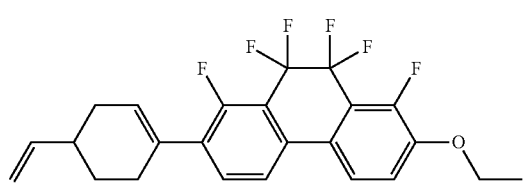 |
| 103 | 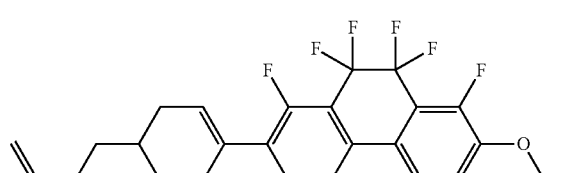 |

| No. |
|---|
| 104 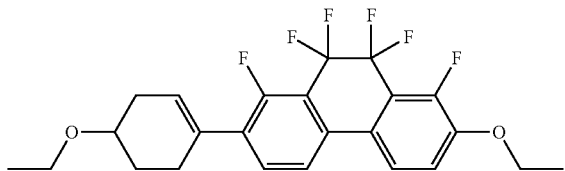 [SMILES: CCCC1CC=C(c2ccc3c(c2F)C(F)(F)C(F)(F)c2c-3ccc(OCC)c2F)CC1] |
| 105 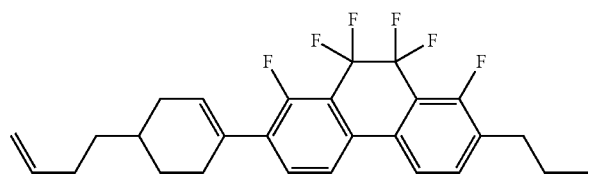 |
| 106 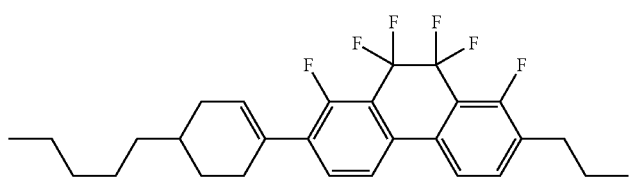 [SMILES: CCCCCC1CC=C(c2ccc3c(c2F)C(F)(F)C(F)(F)c2c-3ccc(CCC)c2F)CC1] |
| 107 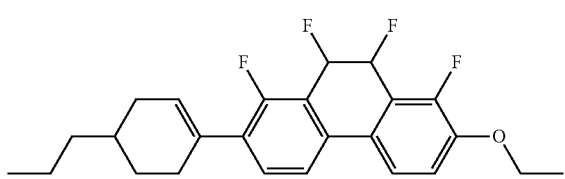 |
| 108 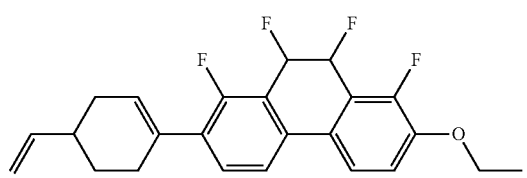 |
| 109 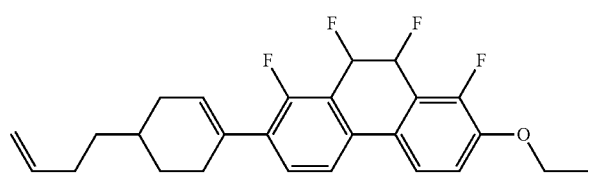 |
| 110 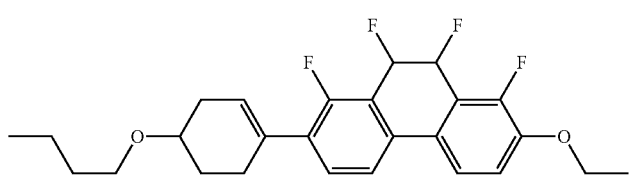 [SMILES: CCCCOC1CC=C(c2ccc3c(c2F)C(F)C(F)c2c-3ccc(OCC)c2F)CC1] |
| 111 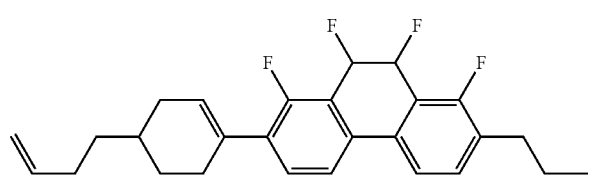 [SMILES: C=CCCC1CC=C(c2ccc3c(c2F)C(F)C(F)c2c-3ccc(CCC)c2F)CC1] |
| 112 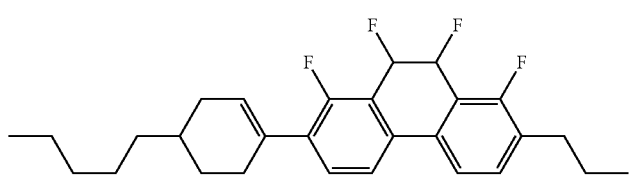 [SMILES: CCCCCC1CC=C(c2ccc3c(c2F)C(F)C(F)c2c-3ccc(CCC)c2F)CC1] |

-continued
| No. | |
|---|---|
| 113 | 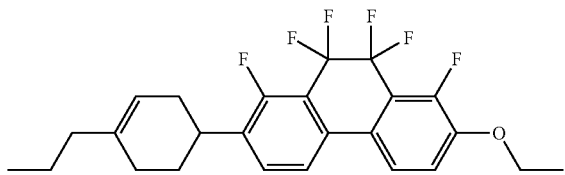 |
| 114 | 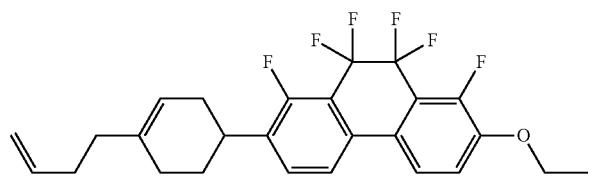 |
| 115 | 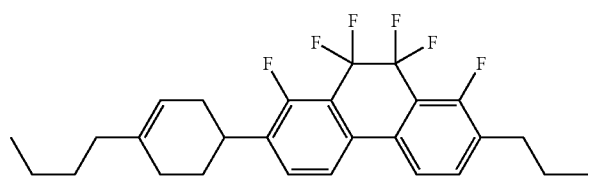 |
| 116 | 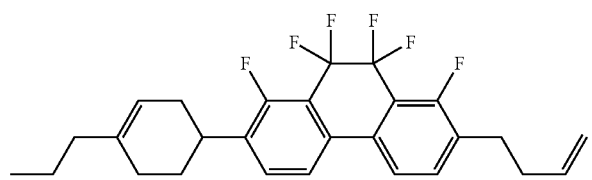 [SMILES: C=CCCc1ccc2c(c1F)C(F)(F)C(F)(F)c1c-2ccc(C2CC=C(CCC)CC2)c1F] |
| 117 | 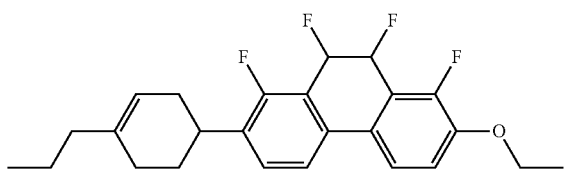 [SMILES: CCCC1=CCC(c2ccc3c(c2F)C(F)C(F)c2c-3ccc(OCC)c2F)CC1] |
| 118 | 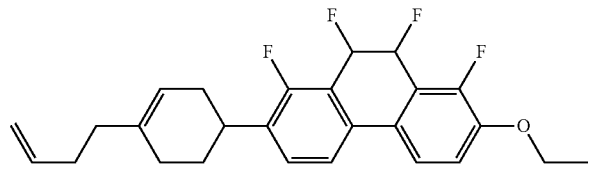 |
| 119 | 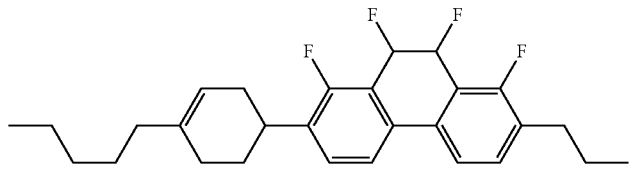 |
| 120 | 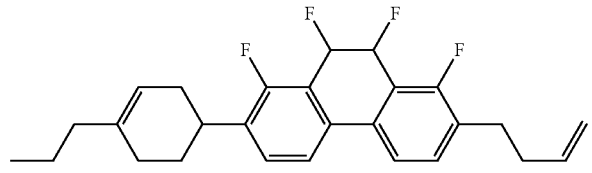 [SMILES: C=CCCc1ccc2c(c1F)C(F)C(F)c1c-2ccc(C2CC=C(CCC)CC2)c1F] |

| No. |
|---|
| 121 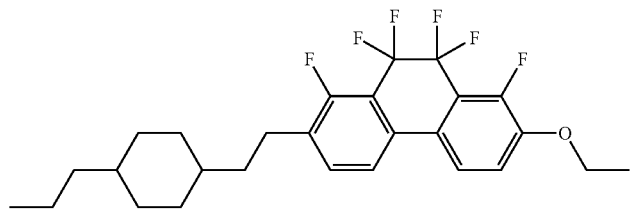 |
| 122 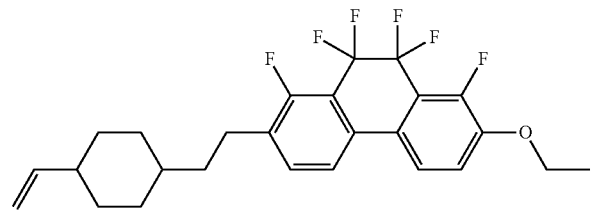 [SMILES: C=CC1CCC(CCc2ccc3c(c2F)C(F)(F)C(F)(F)c2c-3ccc(OCC)c2F)CC1] |
| 123 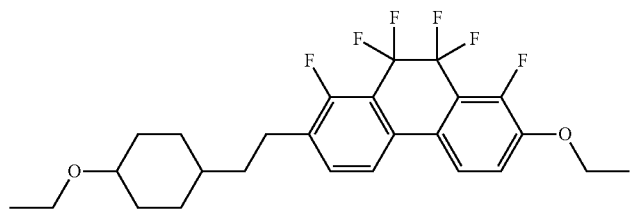 [SMILES: CCOc1ccc2c(c1F)C(F)(F)C(F)(F)c1c-2ccc(CCC2CCC(OCC)CC2)c1F] |
| 124 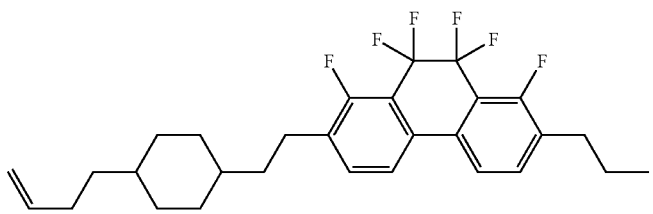 |
| 125 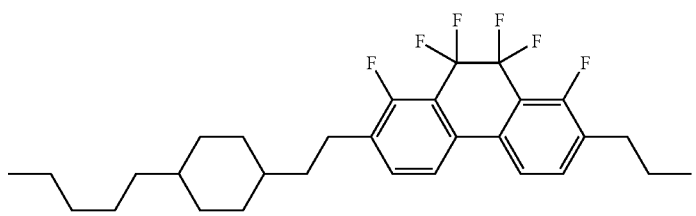 |
| 126 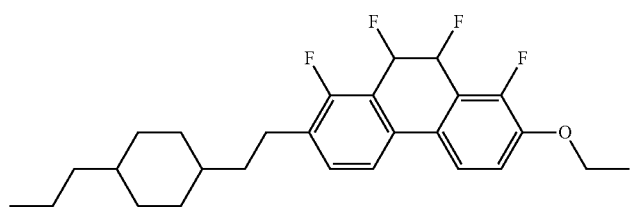 [SMILES: CCCC1CCC(CCc2ccc3c(c2F)C(F)C(F)c2c-3ccc(OCC)c2F)CC1] |
| 127 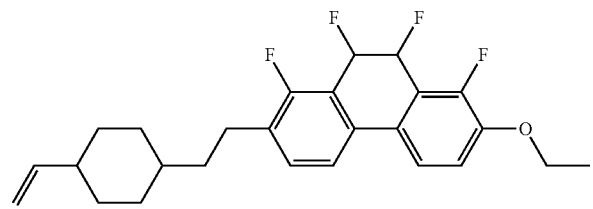 [SMILES: C=CC1CCC(CCc2ccc3c(c2F)C(F)C(F)c2c-3ccc(OCC)c2F)CC1] |

| No. | |
|---|---|
| 128 | 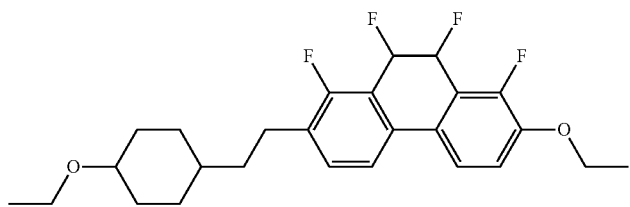 |
| 129 | 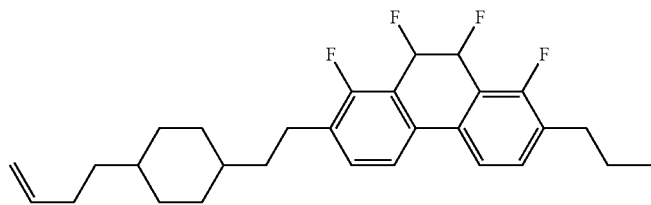 |
| 130 | 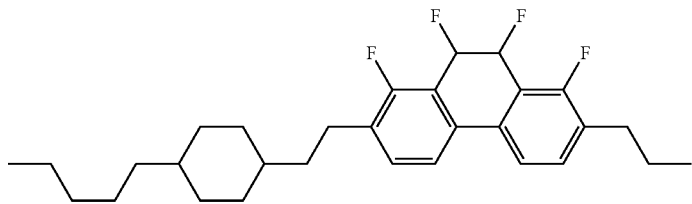 |
| 131 | 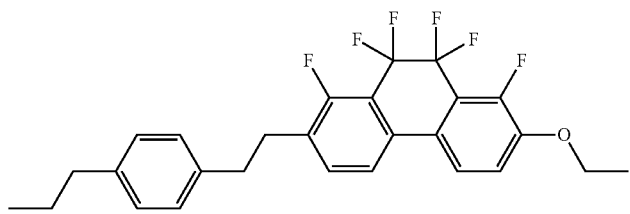 |
| 132 | 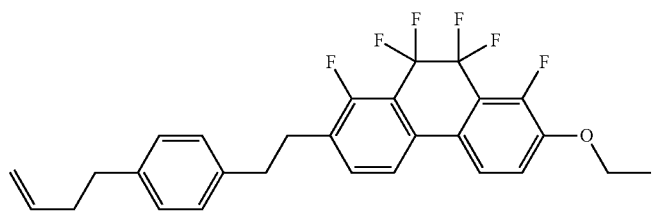 |
| 133 | 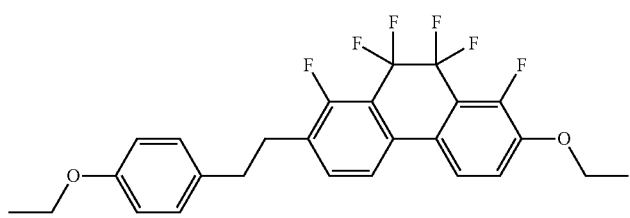 [SMILES: CCCc1ccc(CCc2ccc3c(c2F)C(F)(F)C(F)(F)c2c-3ccc(OCC)c2F)cc1] |
| 134 | 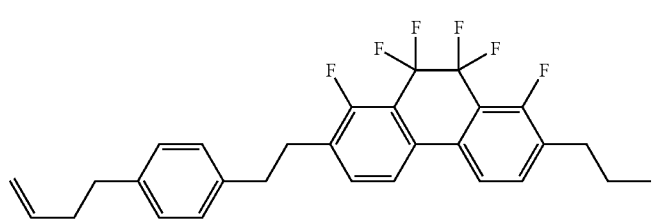 [SMILES: C=CCCc1ccc(CCc2ccc3c(c2F)C(F)(F)C(F)(F)c2c-3ccc(OCC)c2F)cc1] |

-continued
| No. |
| --- |
135
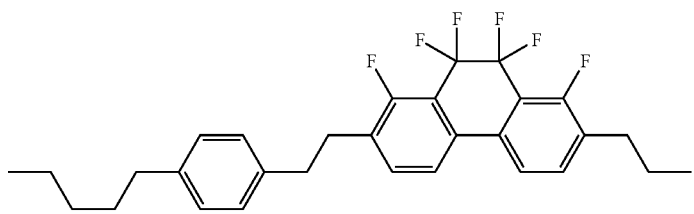
136
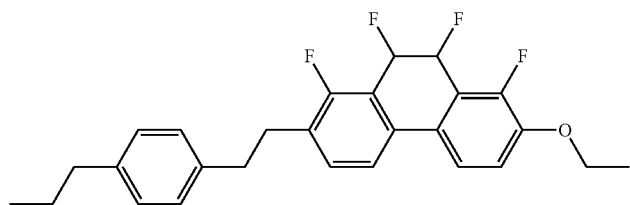
137
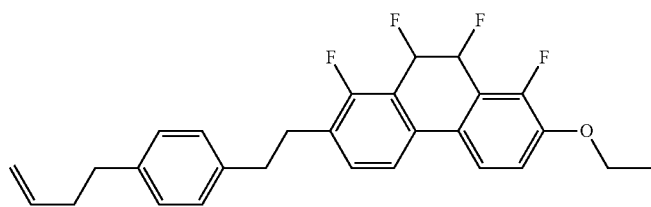
138
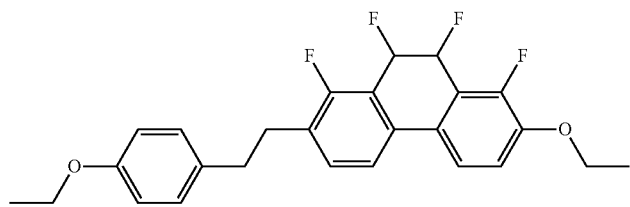
139
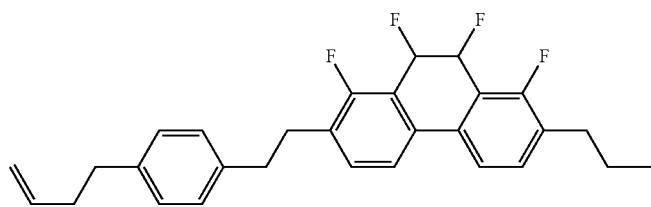
140
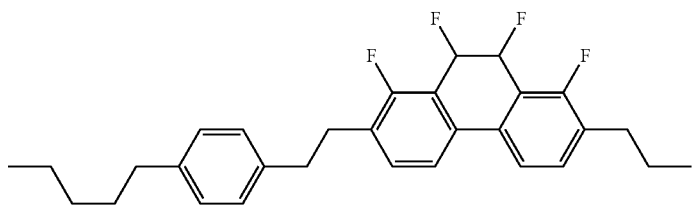
141
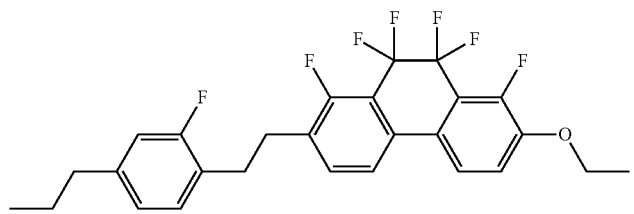 [SMILES: CCOc1ccc(CCc2ccc3c(c2F)C(F)(F)C(F)(F)c2c-3ccc(OCC)c2F)cc1]

| No. |
| --- |
| 142 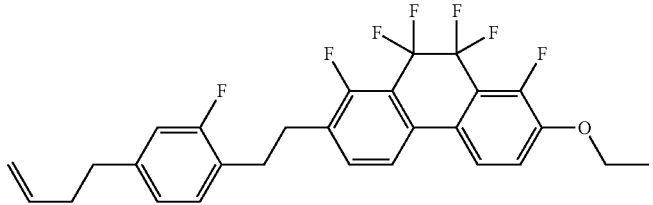 |
| 143 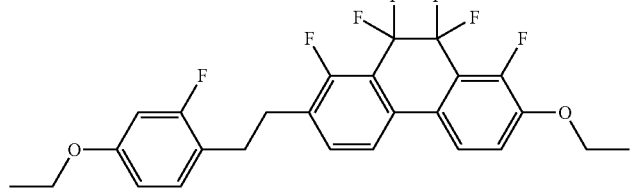 |
| 144 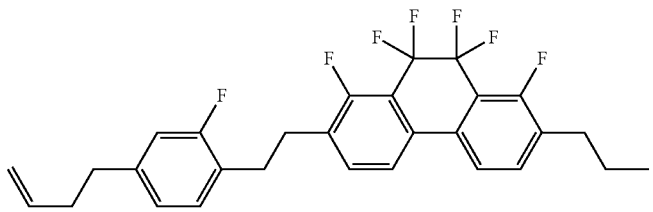 [SMILES: C=CCCc1ccc(CCc2ccc3c(c2F)C(F)(F)C(F)(F)c2c-3ccc(OCC)c2F)c(F)c1] |
| 145 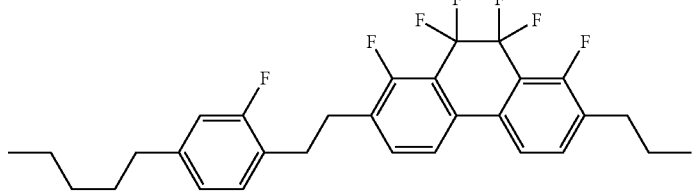 |
| 146 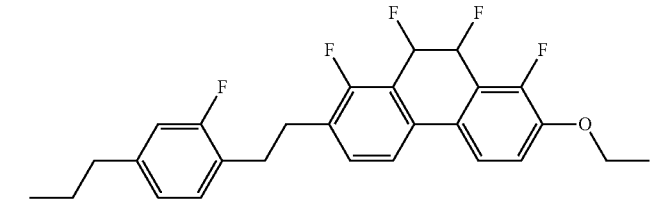 |
| 147 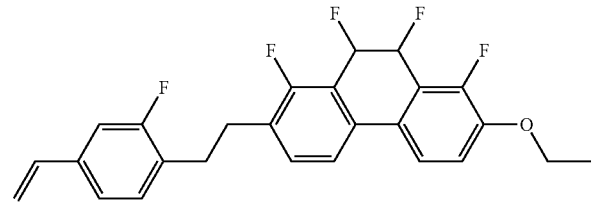 [SMILES: C=Cc1ccc(CCc2ccc3c(c2F)C(F)C(F)c2c-3ccc(OCC)c2F)c(F)c1] |
| 148 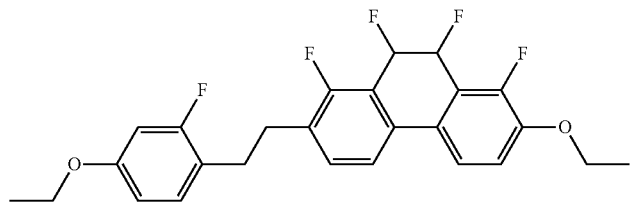 [SMILES: CCOc1ccc(CCc2ccc3c(c2F)C(F)C(F)c2c-3ccc(OCC)c2F)c(F)c1] |

-continued
| No. | |
|---|---|
| 149 | 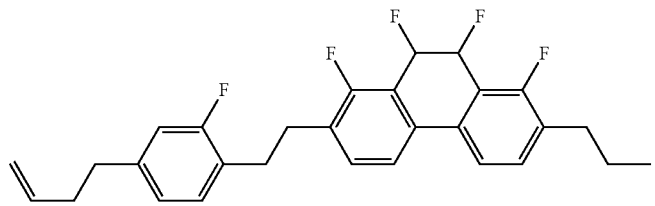 |
| 150 | 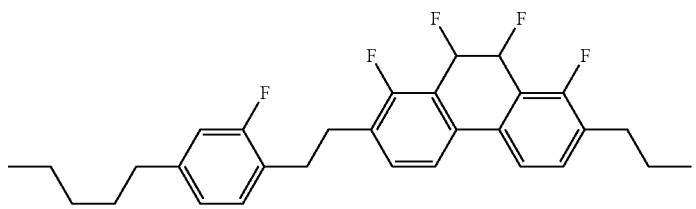 |
| 151 | 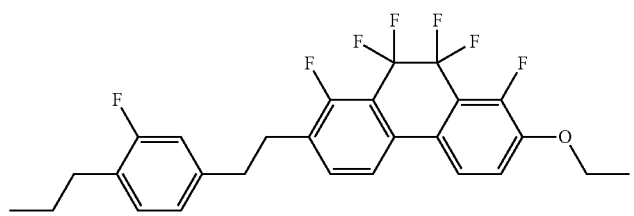 |
| 152 | 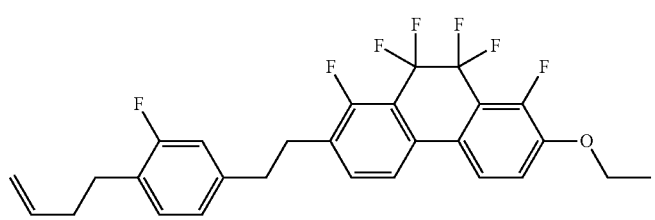 |
| 153 | 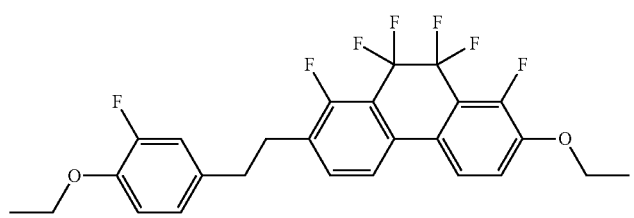 |
| 154 | 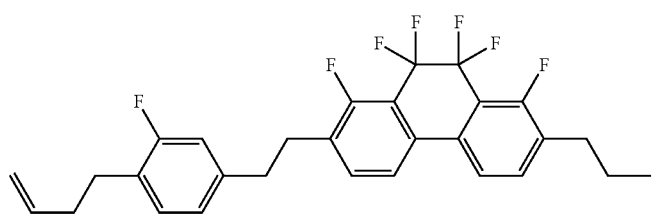 |
| 155 | 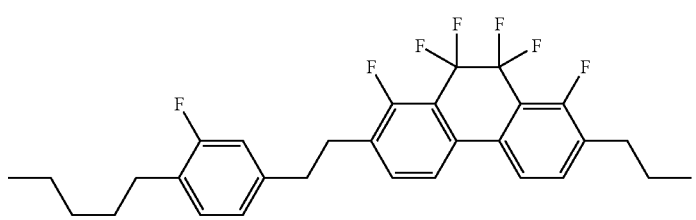 |

-continued
| No. | |
|---|---|
| 156 | 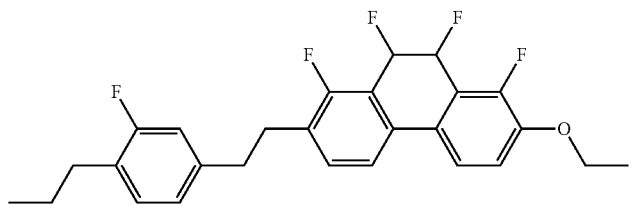 |
| 157 | 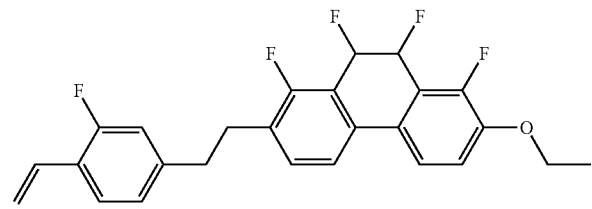 [SMILES: C=Cc1ccc(CCc2ccc3c(c2F)C(F)C(F)c2c-3ccc(OCC)c2F)cc1F] |
| 158 | 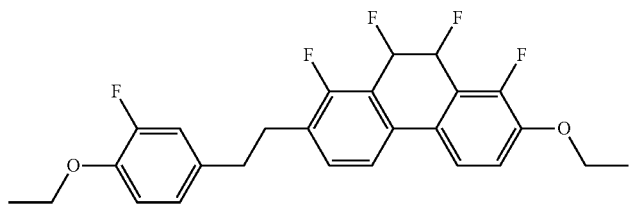 [SMILES: CCOc1ccc(CCc2ccc3c(c2F)C(F)C(F)c2c-3ccc(OCC)c2F)cc1F] |
| 159 | 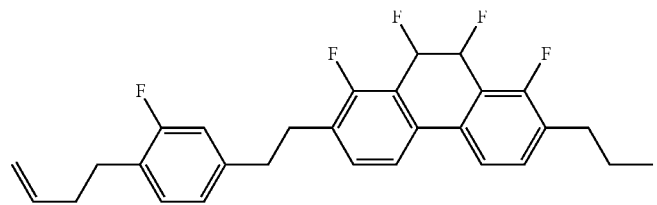 |
| 160 | 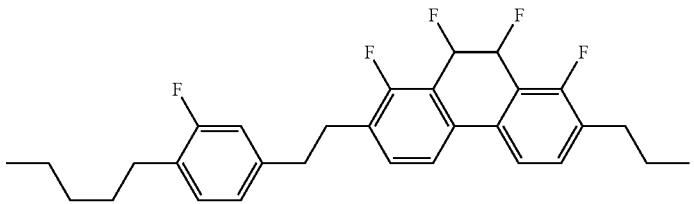 |
| 161 | 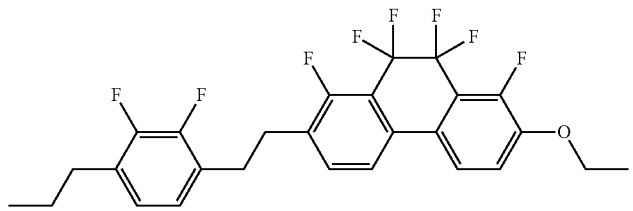 |
| 162 | 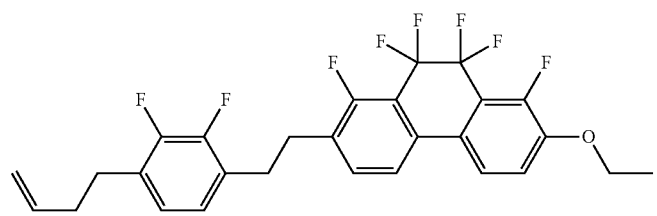 [SMILES: C=CCCc1ccc(CCc2ccc3c(c2F)C(F)(F)C(F)(F)c2c-3ccc(OCC)c2F)c(F)c1F] |

| No. |
|---|
| 163 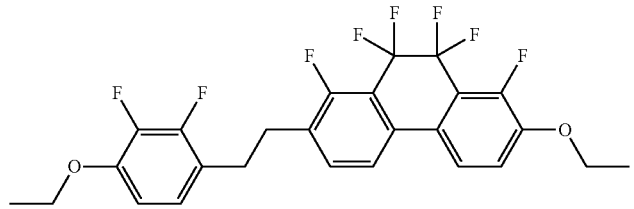 |
| 164 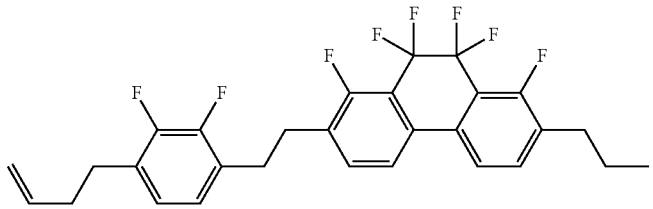 |
| 165 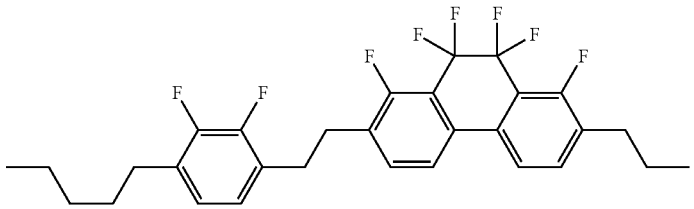 |
| 166 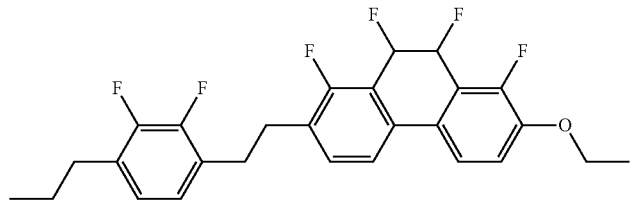 [SMILES: CCOc1ccc(CCc2ccc3c(c2F)C(F)C(F)c2c-3ccc(OCC)c2F)c(F)c1F] |
| 167 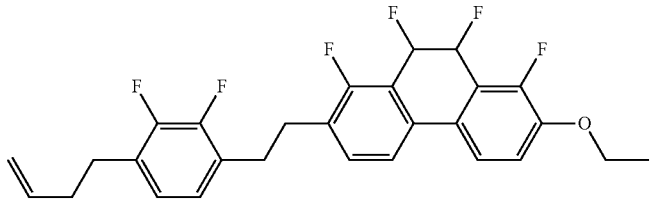 |
| 168 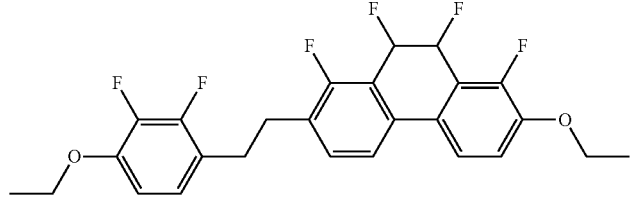 |
| 169 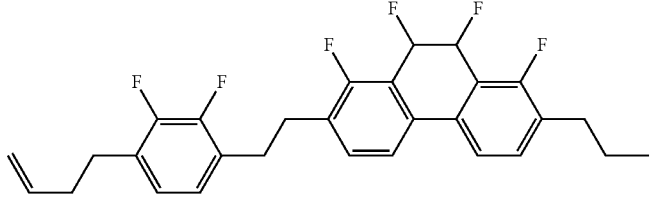 |

-continued
| No. |
|---|
| 170 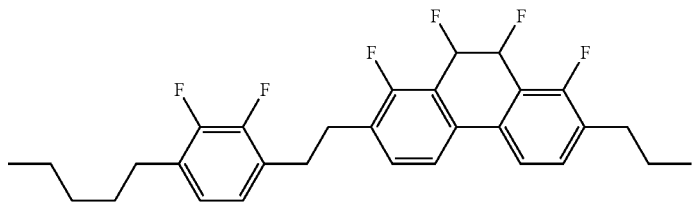 |
| 171 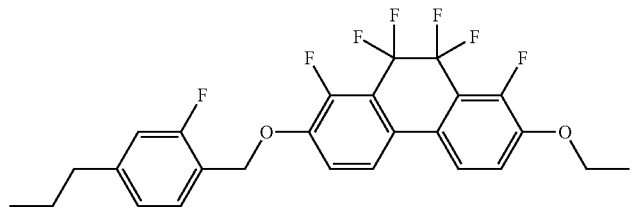 [SMILES: CCCc1ccc(COc2ccc3c(c2F)C(F)(F)C(F)(F)c2c-3ccc(OCC)c2F)c(F)c1] |
| 172 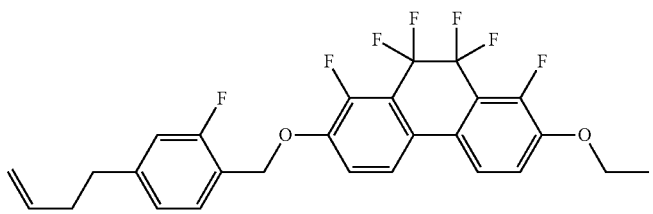 [SMILES: C=CCCc1ccc(COc2ccc3c(c2F)C(F)(F)C(F)(F)c2c-3ccc(OCC)c2F)c(F)c1] |
| 173 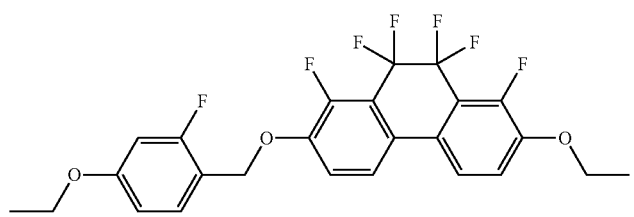 |
| 174 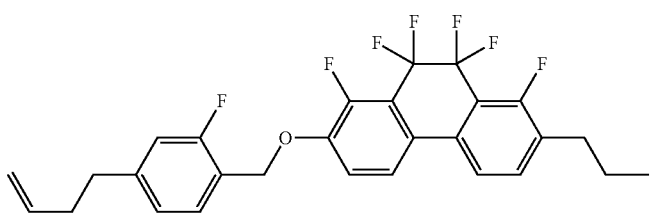 |
| 175 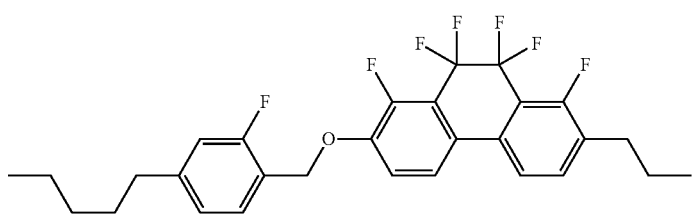 |
| 176 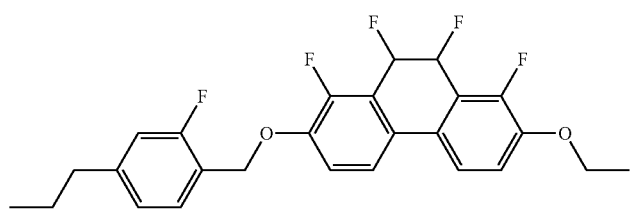 |

| No. | |
|---|---|
| 177 | 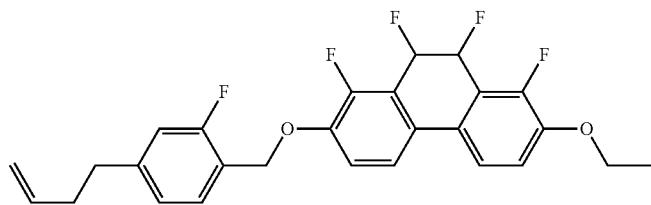 |
| 178 | 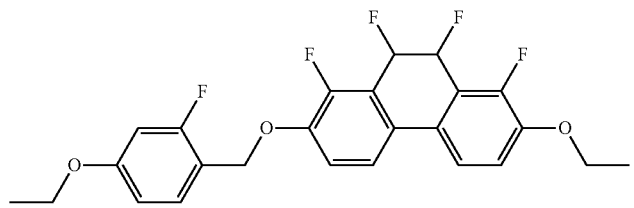 |
| 179 | 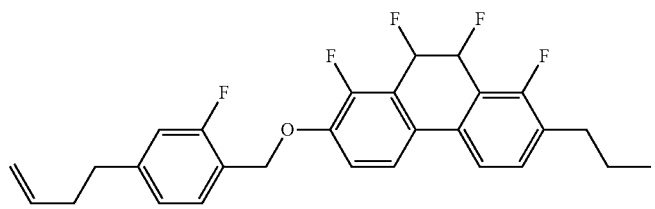 [SMILES: C=CCCc1ccc(COc2ccc3c(c2F)C(F)C(F)c2c-3ccc(CCC)c2F)c(F)c1] |
| 180 | 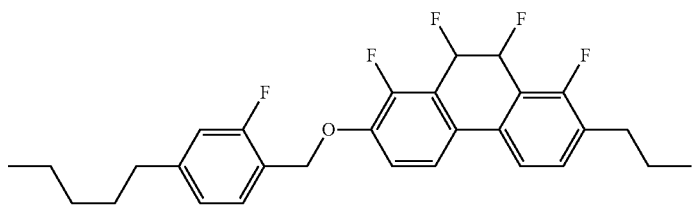 [SMILES: CCCCCc1ccc(COc2ccc3c(c2F)C(F)C(F)c2c-3ccc(CCC)c2F)c(F)c1] |
| 181 | 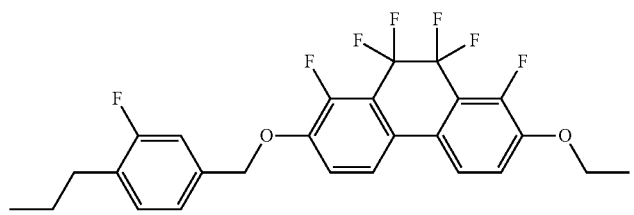 |
| 182 | 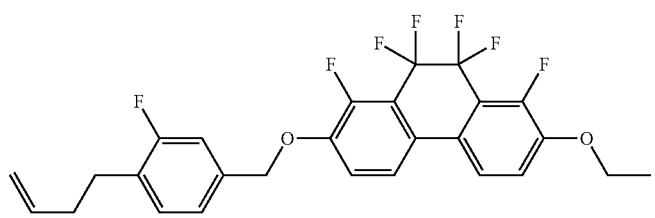 |
| 183 | 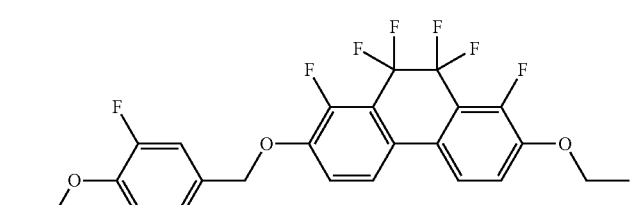 |

| No. | |
|---|---|
| 184 | 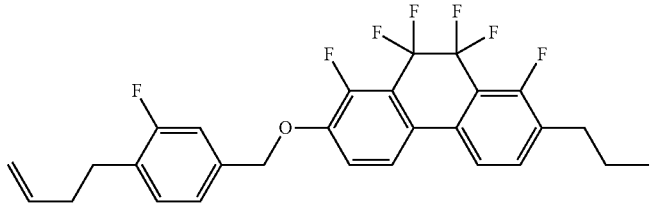 |
| 185 | 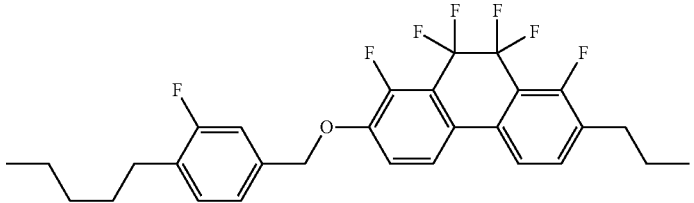 [SMILES: CCCCCc1ccc(COc2ccc3c(c2F)C(F)(F)C(F)(F)c2c-3ccc(CCC)c2F)cc1F] |
| 186 | 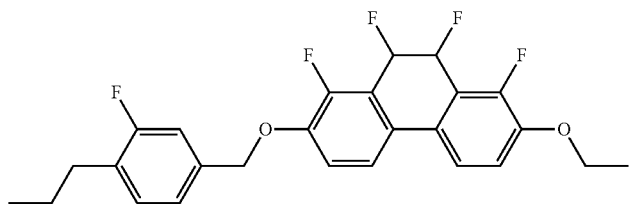 |
| 187 | 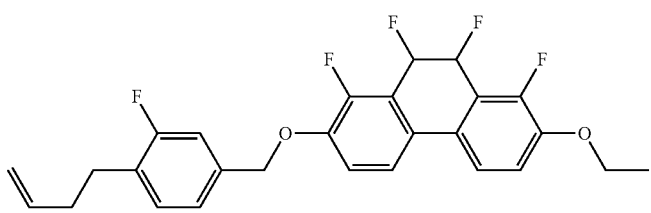 |
| 188 | 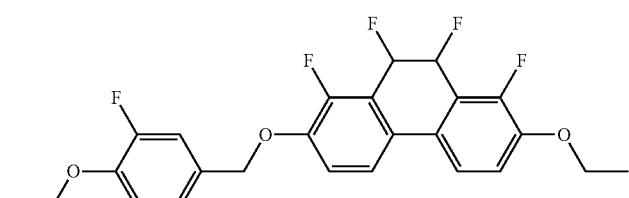 |
| 189 | 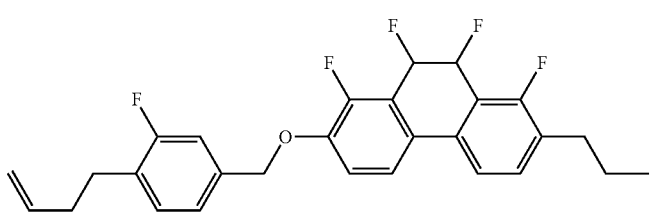 |
| 190 | 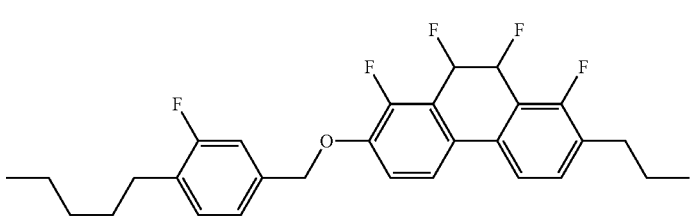 [SMILES: CCCCCc1ccc(COc2ccc3c(c2F)C(F)C(F)c2c-3ccc(CCC)c2F)cc1F] |

-continued
| No. | |
|---|---|
| 191 | 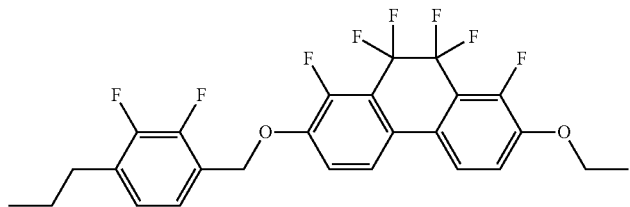 |
| 192 | 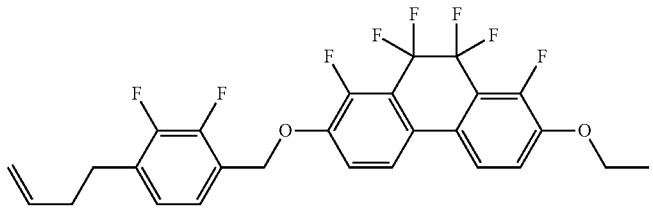 |
| 193 | 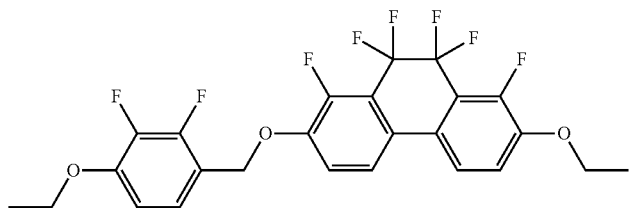 |
| 194 | 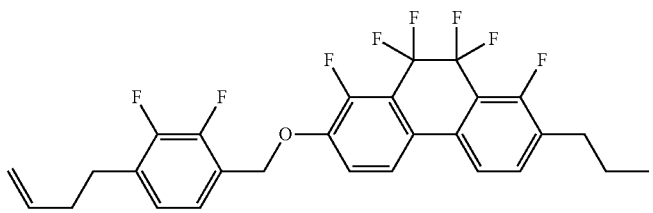 |
| 195 | 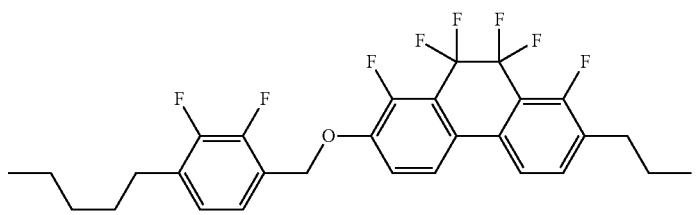 [SMILES: CCCCCc1ccc(COc2ccc3c(c2F)C(F)(F)C(F)(F)c2c-3ccc(CCC)c2F)c(F)c1F] |
| 196 | 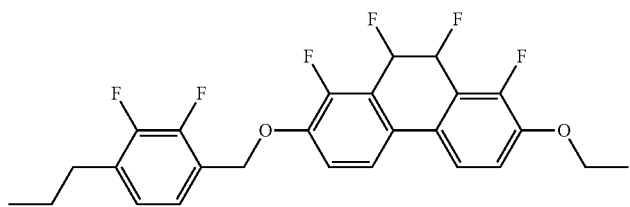 |
| 197 | 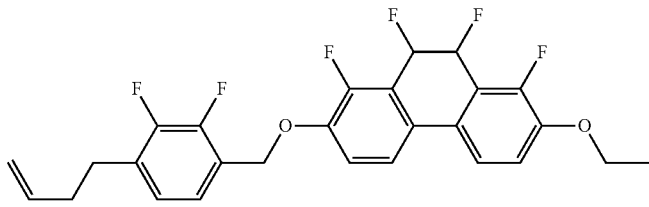 |

-continued
| No. | |
|---|---|
| 198 | 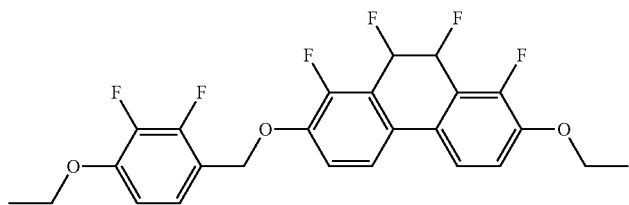 |
| 199 | 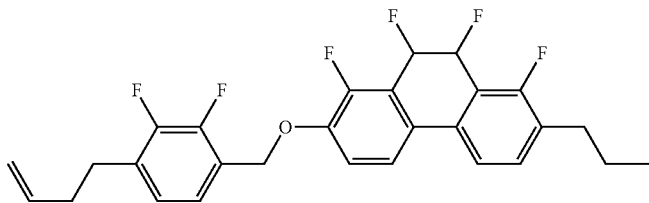 [SMILES: C=CCCc1ccc(COc2ccc3c(c2F)C(F)C(F)c2c-3ccc(CCC)c2F)c(F)c1F] |
| 200 | 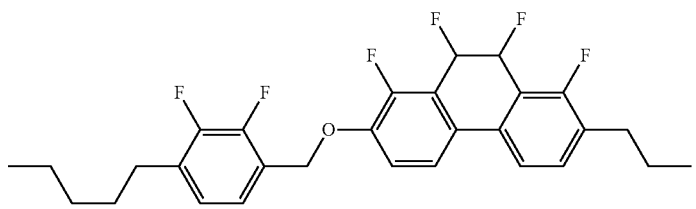 |
| 201 | 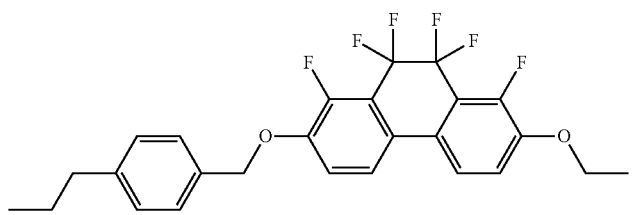 |
| 202 | 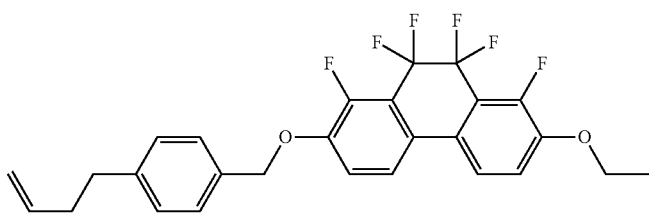 |
| 203 | 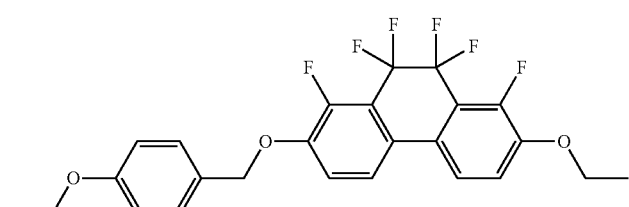 |
| 204 | 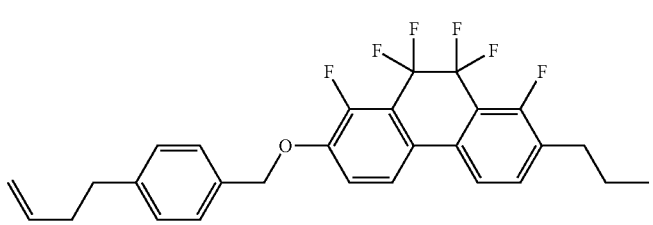 |

| No. |
| --- |
| 205 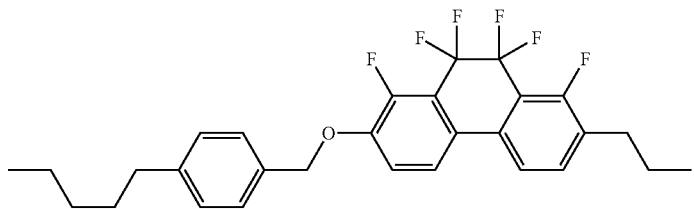 |
| 206 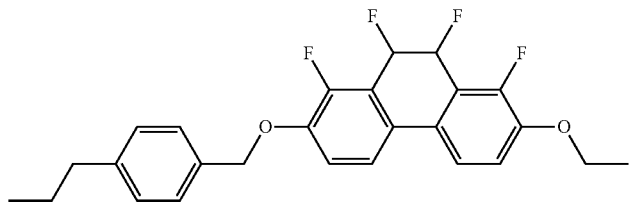 |
| 207 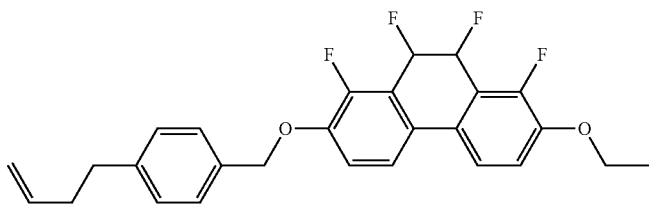 |
| 208 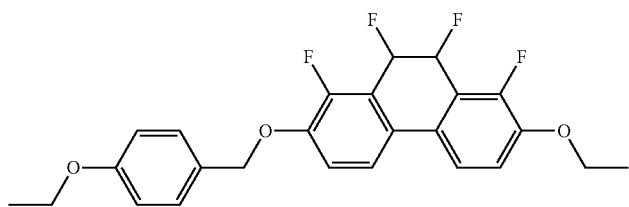 [SMILES: CCOc1ccc(COc2ccc3c(c2F)C(F)C(F)c2c-3ccc(OCC)c2F)cc1] |
| 209 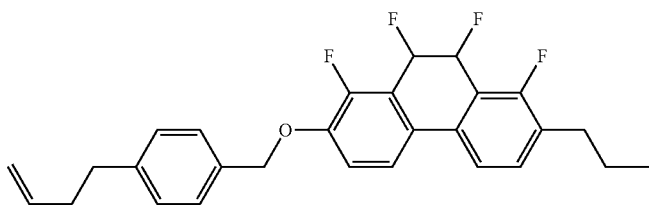 [SMILES: C=CCCc1ccc(COc2ccc3c(c2F)C(F)C(F)c2c-3ccc(CCC)c2F)cc1] |
| 210 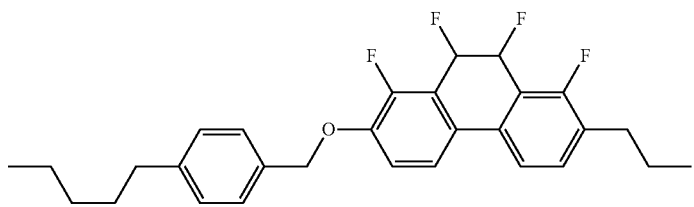 [SMILES: CCCCCc1ccc(COc2ccc3c(c2F)C(F)C(F)c2c-3ccc(CCC)c2F)cc1] |
| 211 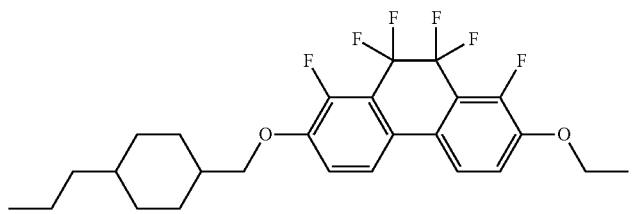 |

| No. |
|---|
| 212 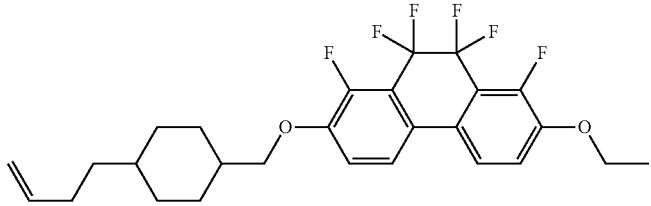 [SMILES: C=CCCC1CCC(COc2ccc3c(c2F)C(F)(F)C(F)(F)c2c-3ccc(OCC)c2F)CC1] |
| 213 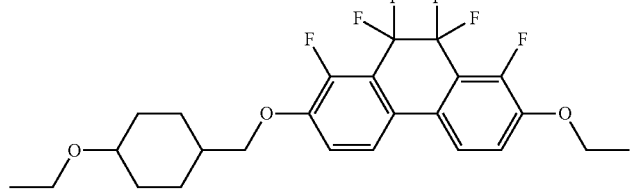 |
| 214 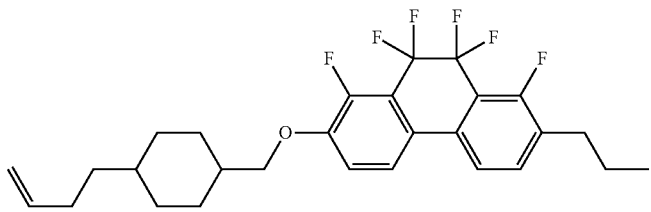 |
| 215 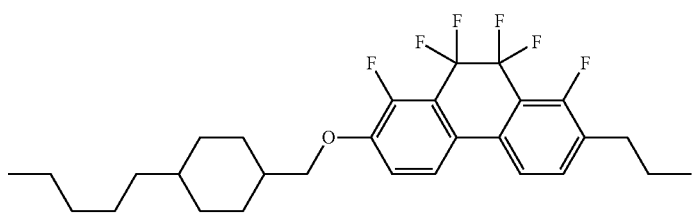 |
| 216 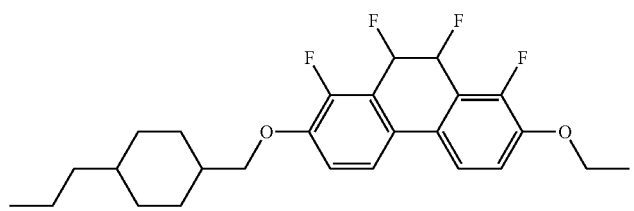 |
| 217 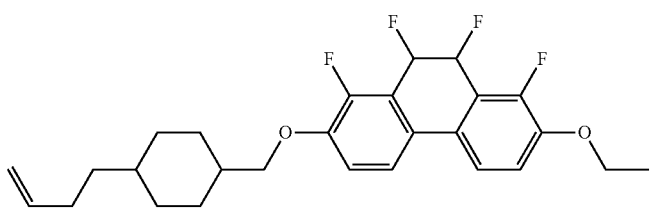 |
| 218 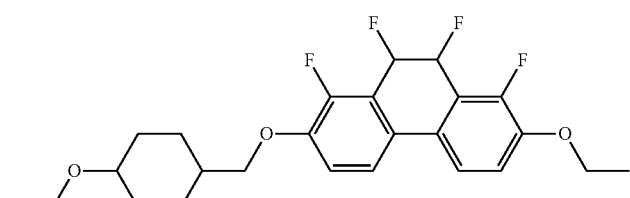 |

| No. |
|---|
| 219 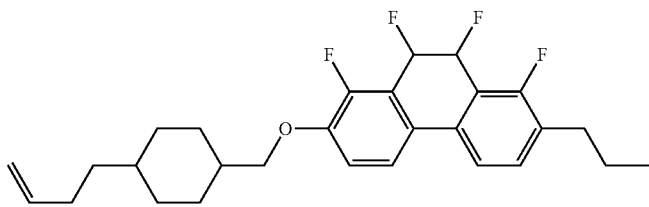 |
| 220 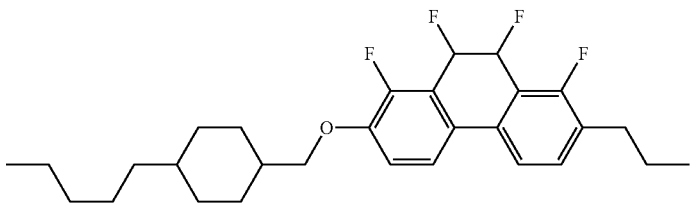 |
| 221 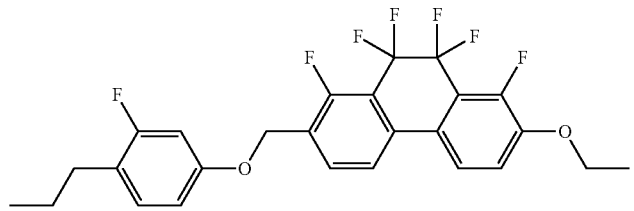 |
| 222 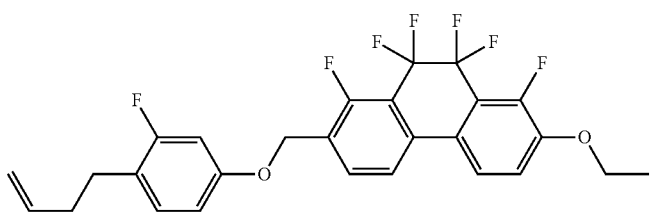 |
| 223 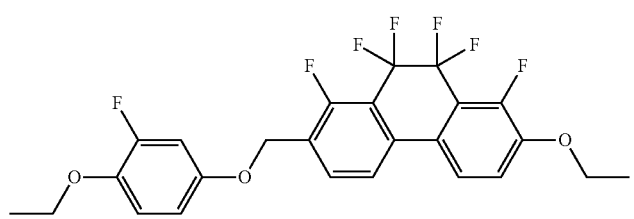 [SMILES: CCCc1ccc(OCc2ccc3c(c2F)C(F)(F)C(F)(F)c2c-3ccc(OCC)c2F)cc1F] |
| 224 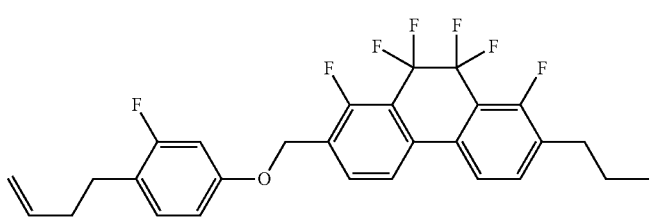 |
| 225 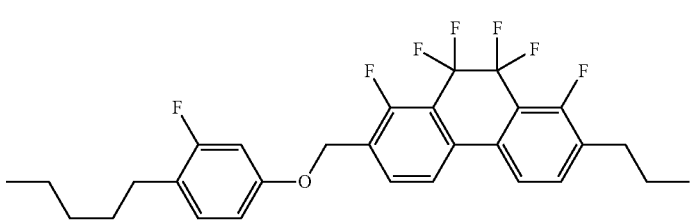 |

| No. |
| --- |
| 226 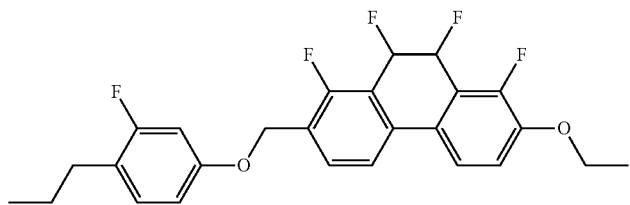 |
| 227 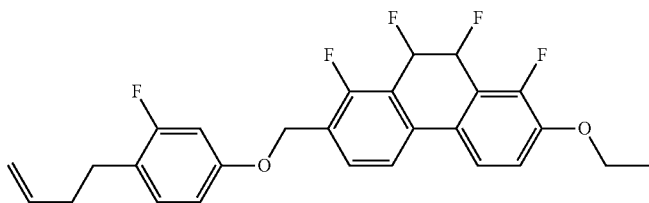 |
| 228 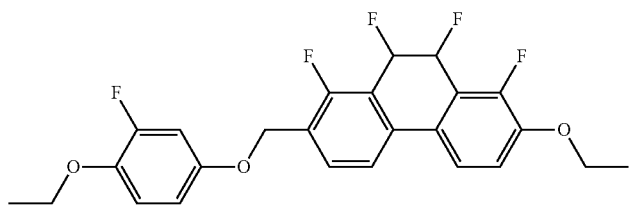 |
| 229 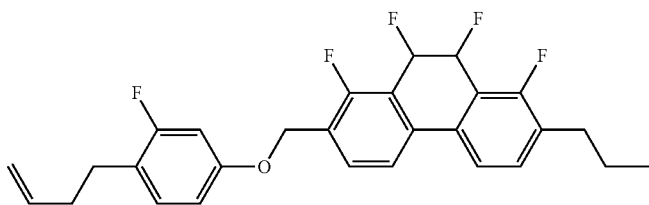 [SMILES: C=CCCc1ccc(OCc2ccc3c(c2F)C(F)C(F)c2c-3ccc(CCC)c2F)cc1F] |
| 230 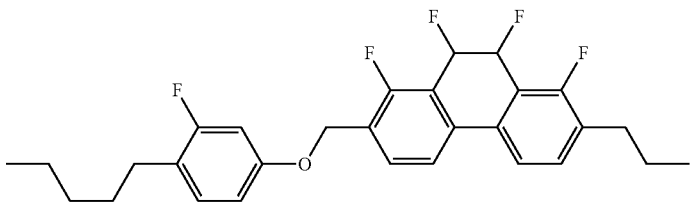 [SMILES: CCCCCc1ccc(OCc2ccc3c(c2F)C(F)C(F)c2c-3ccc(CCC)c2F)cc1F] |
| 231 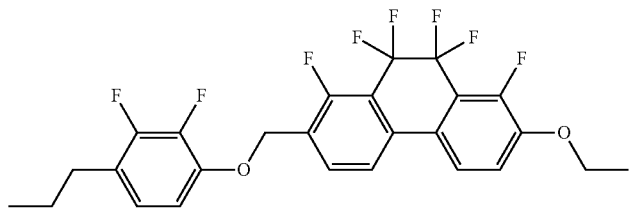 |
| 232 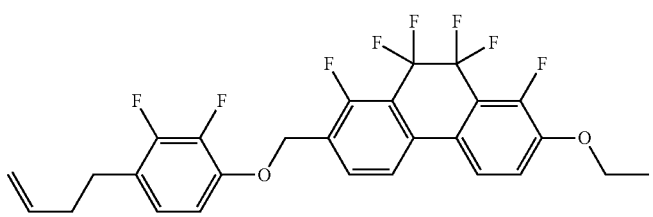 [SMILES: C=CCCc1ccc(OCc2ccc3c(c2F)C(F)(F)C(F)(F)c2c-3ccc(OCC)c2F)c(F)c1F] |

| No. |
|---|
| 233 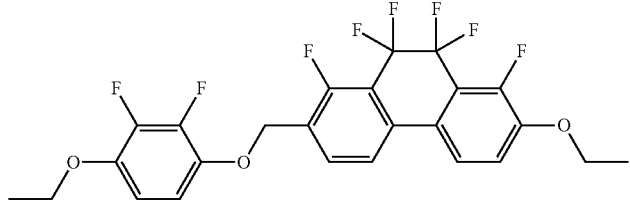 [SMILES: CCOc1ccc(OCc2ccc3c(c2F)C(F)(F)C(F)(F)c2c-3ccc(OCC)c2F)c(F)c1F] |
| 234 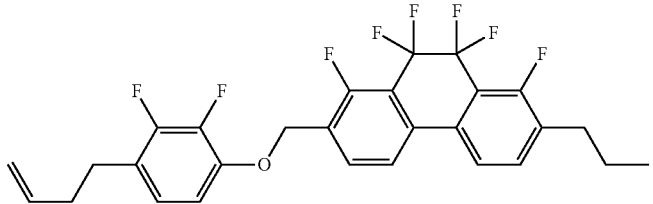 |
| 235 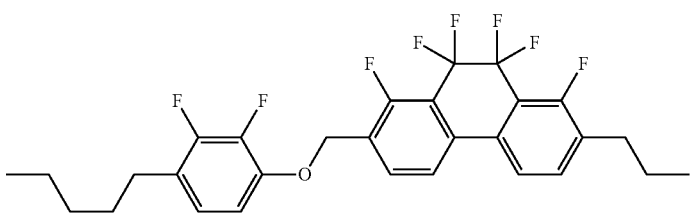 [SMILES: CCCCCc1ccc(OCc2ccc3c(c2F)C(F)(F)C(F)(F)c2c-3ccc(CCC)c2F)c(F)c1F] |
| 236 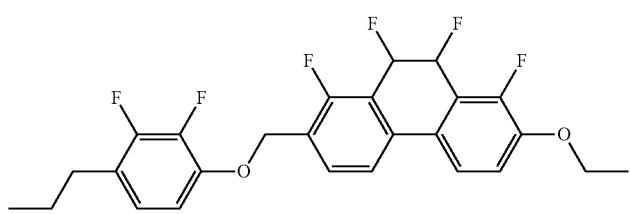 |
| 237 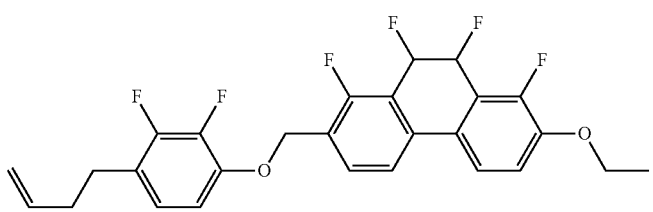 [SMILES: C=CCCc1ccc(OCc2ccc3c(c2F)C(F)C(F)c2c-3ccc(OCC)c2F)c(F)c1F] |
| 238 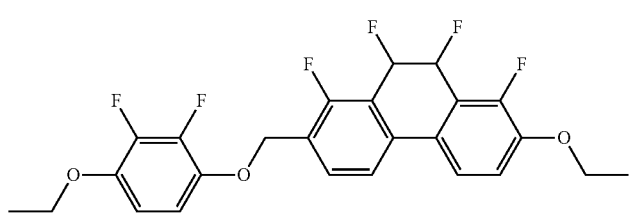 [SMILES: CCOc1ccc(OCc2ccc3c(c2F)C(F)C(F)c2c-3ccc(OCC)c2F)c(F)c1F] |
| 239 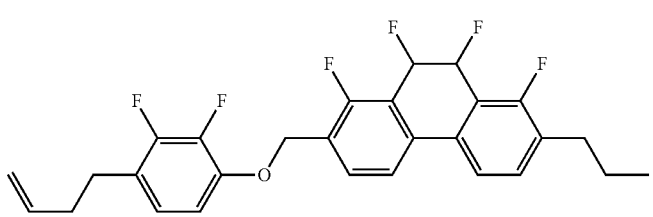 |

-continued
| No. | |
|---|---|
| 240 | 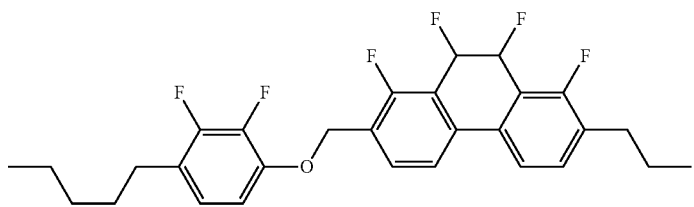 |
| 241 | 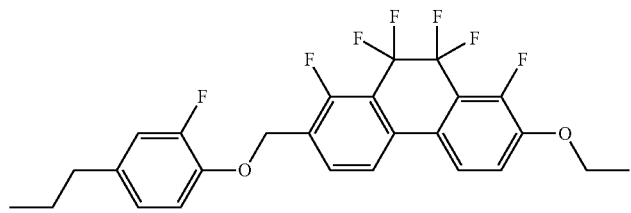 |
| 242 | 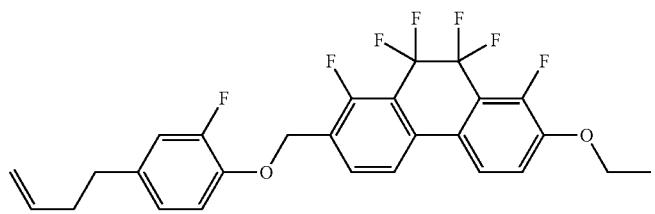 |
| 243 | 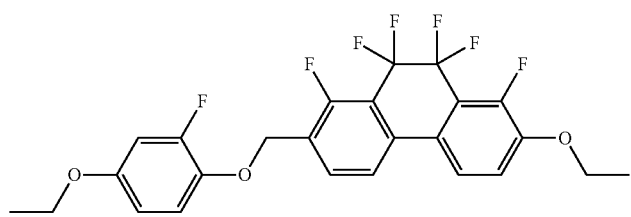 |
| 244 | 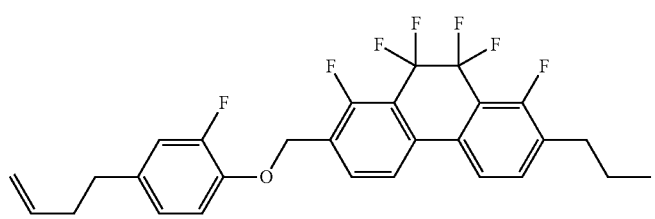 [SMILES: C=CCCc1ccc(OCc2ccc3c(c2F)C(F)(F)C(F)(F)c2c-3ccc(OCC)c2F)c(F)c1] |
| 245 | 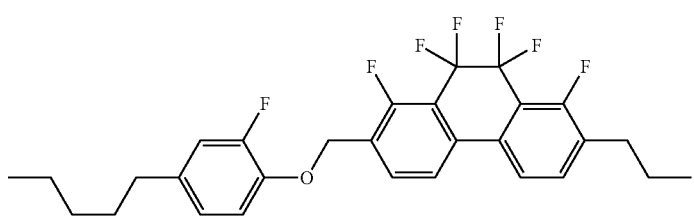 [SMILES: CCCCCc1ccc(OCc2ccc3c(c2F)C(F)(F)C(F)(F)c2c-3ccc(CCC)c2F)c(F)c1] |
| 246 | 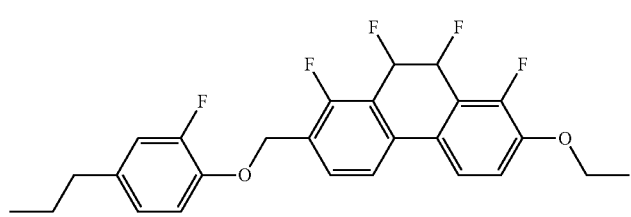 |

-continued
| No. | |
|---|---|
| 247 | 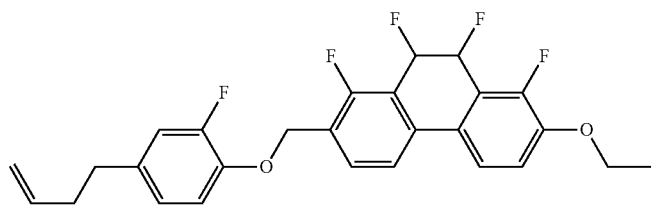 |
| 248 | 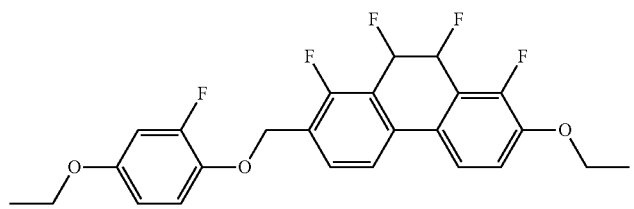 |
| 249 | 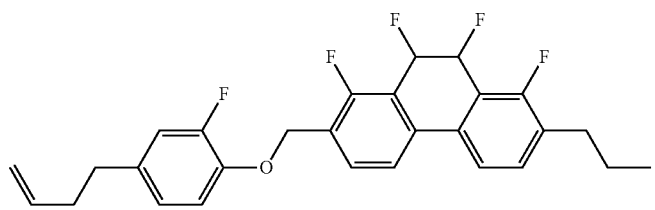 |
| 250 | 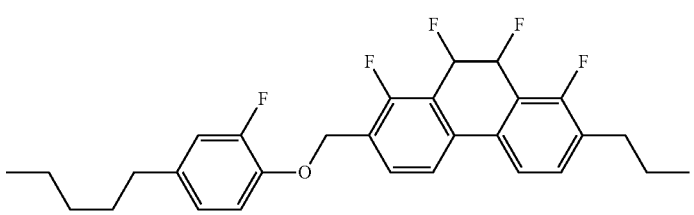 |
| 251 | 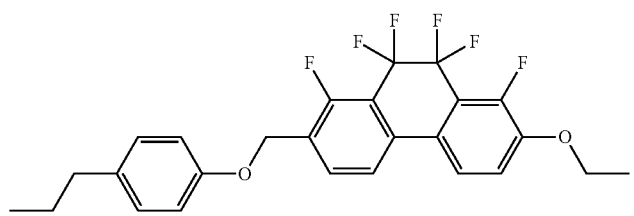 |
| 252 | 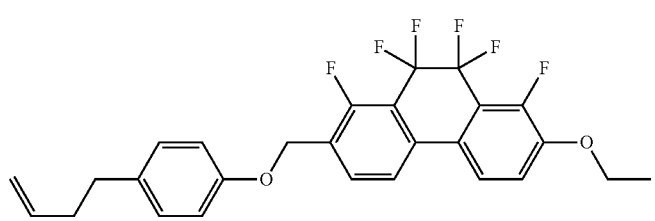 |
| 253 | 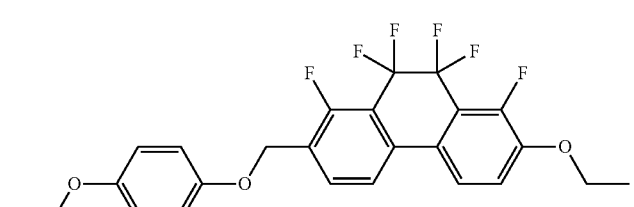 |

| No. | |
|---|---|
| 254 | 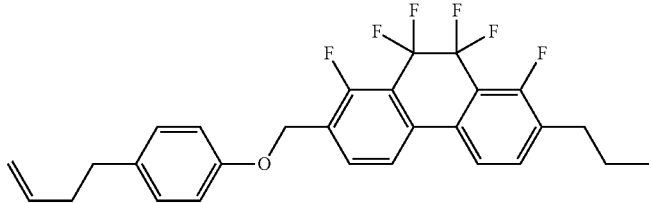 |
| 255 | 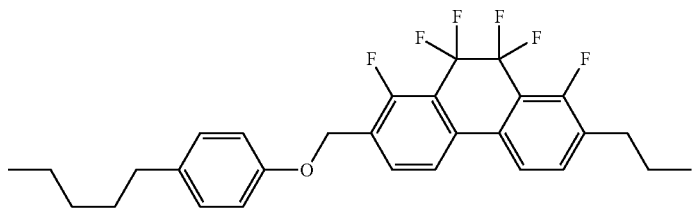 [SMILES: CCCCCc1ccc(OCc2ccc3c(c2F)C(F)(F)C(F)(F)c2c-3ccc(CCC)c2F)cc1] |
| 256 | 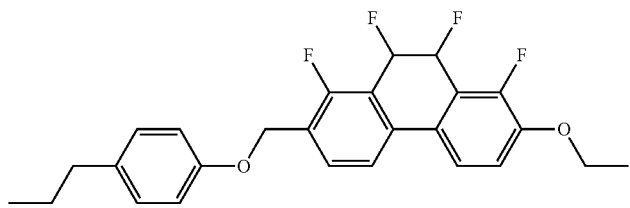 |
| 257 | 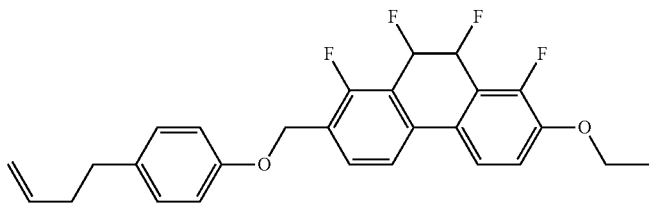 |
| 258 | 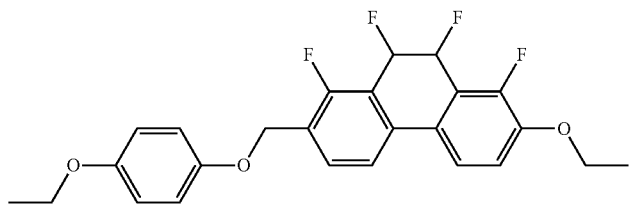 |
| 259 | 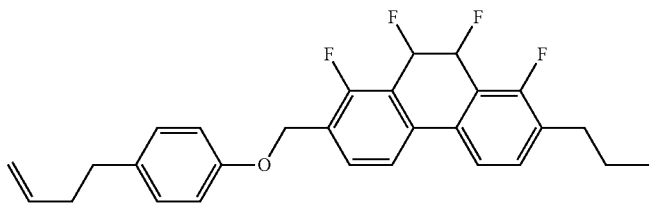 |
| 260 | 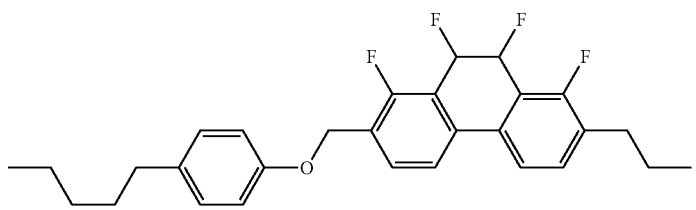 |

| No. |
|---|
| 261 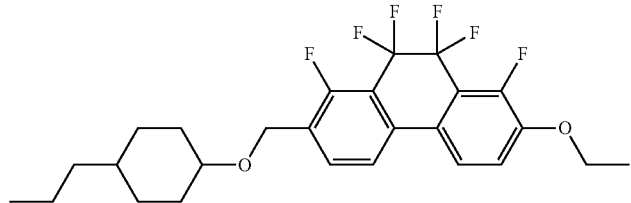 |
| 262 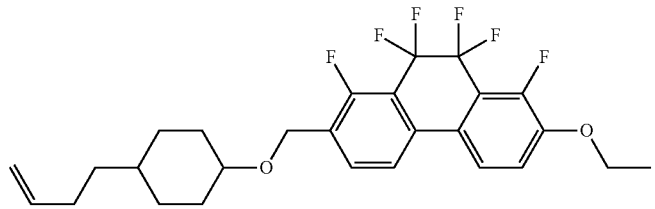 |
| 263 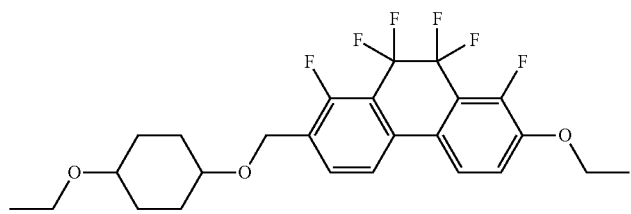 [SMILES: CCCC1CCC(OCc2ccc3c(c2F)C(F)(F)C(F)(F)c2c-3ccc(OCC)c2F)CC1] |
| 264 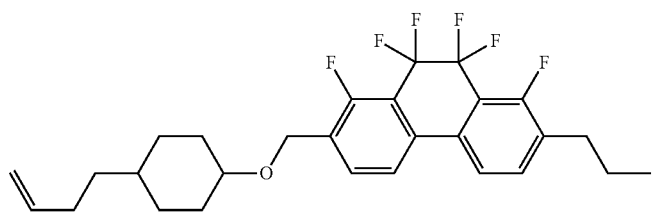 |
| 265 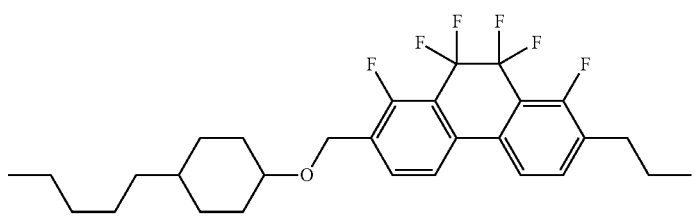 |
| 266 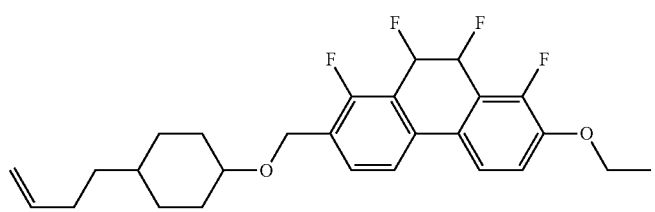 |
| 267 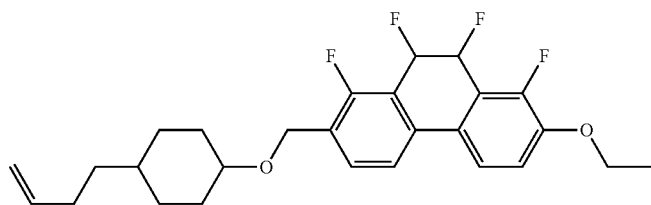 [SMILES: C=CCCC1CCC(OCc2ccc3c(c2F)C(F)C(F)c2c-3ccc(OCC)c2F)CC1] |

-continued
| No. |
|---|
| 268 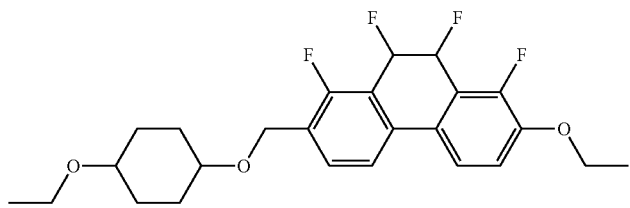 [SMILES: CCOc1ccc2c(c1F)C(F)C(F)c1c-2ccc(COC2CCC(OCC)CC2)c1F] |
| 269 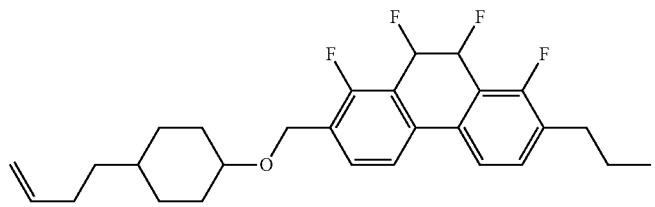 |
| 270 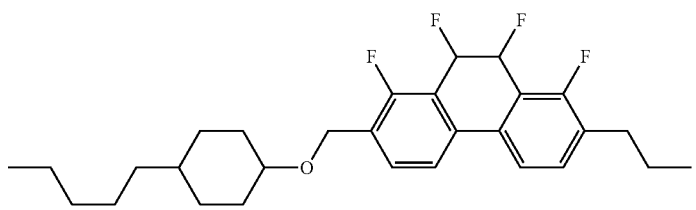 |
| 271 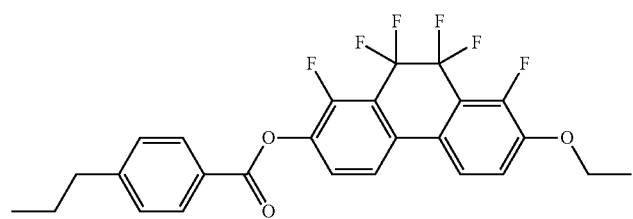 |
| 272 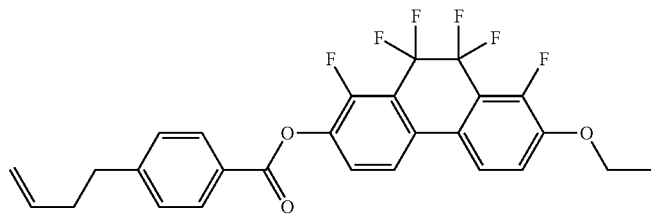 |
| 273 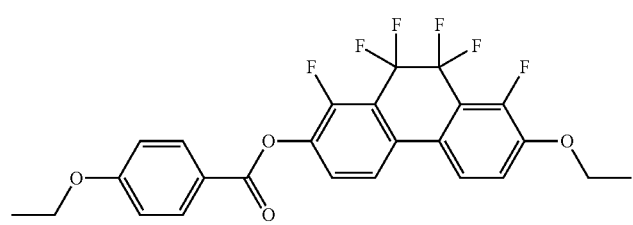 |
| 274 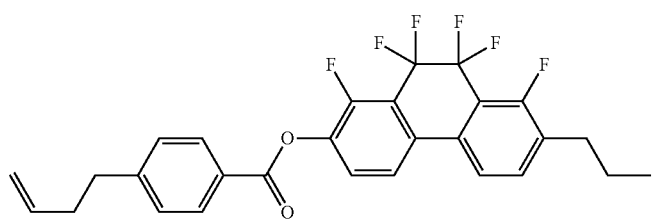 |

-continued
| No. |
|---|
| 275 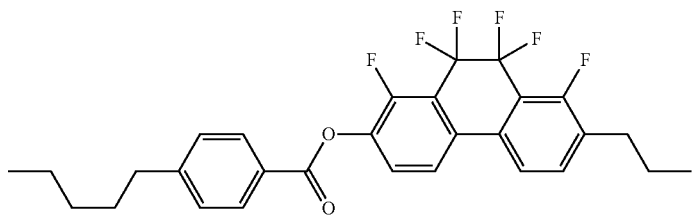 [SMILES: CCCCCc1ccc(C(=O)Oc2ccc3c(c2F)C(F)(F)C(F)(F)c2c-3ccc(CCC)c2F)cc1] |
| 276 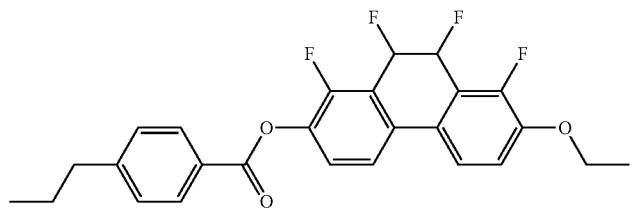 [SMILES: CCCc1ccc(C(=O)Oc2ccc3c(c2F)C(F)C(F)c2c-3ccc(OCC)c2F)cc1] |
| 277 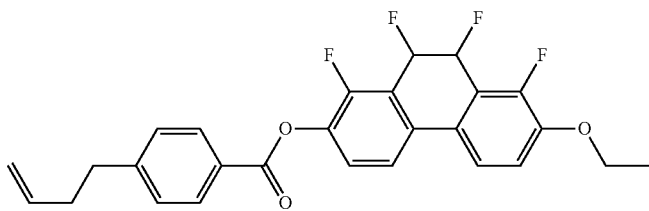 [SMILES: C=CCCc1ccc(C(=O)Oc2ccc3c(c2F)C(F)C(F)c2c-3ccc(OCC)c2F)cc1] |
| 278 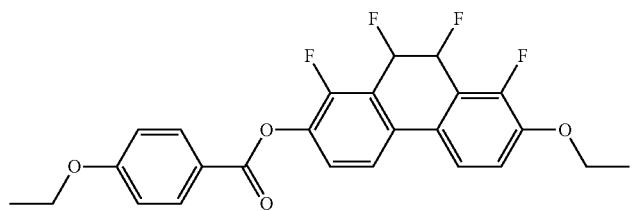 [SMILES: CCOc1ccc(C(=O)Oc2ccc3c(c2F)C(F)C(F)c2c-3ccc(OCC)c2F)cc1] |
| 279 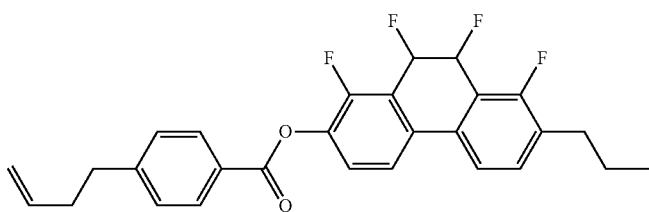 [SMILES: C=CCCc1ccc(C(=O)Oc2ccc3c(c2F)C(F)C(F)c2c-3ccc(CCC)c2F)cc1] |
| 280 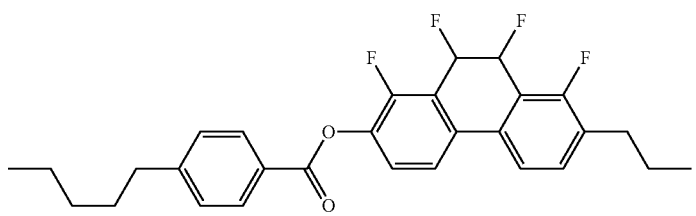 [SMILES: CCCCCc1ccc(C(=O)Oc2ccc3c(c2F)C(F)C(F)c2c-3ccc(CCC)c2F)cc1] |
| 281 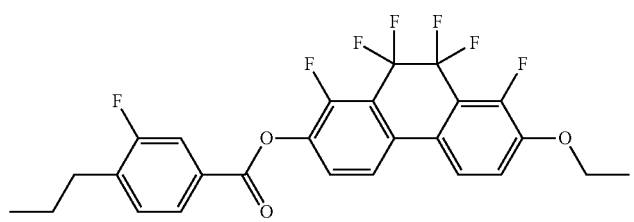 |

| No. | |
|---|---|
| 282 | 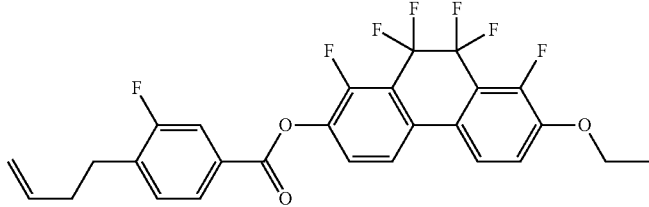 [SMILES: C=CCCc1ccc(C(=O)Oc2ccc3c(c2F)C(F)(F)C(F)(F)c2c-3ccc(OCC)c2F)cc1F] |
| 283 | 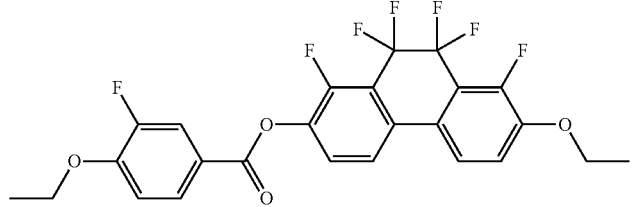 |
| 284 | 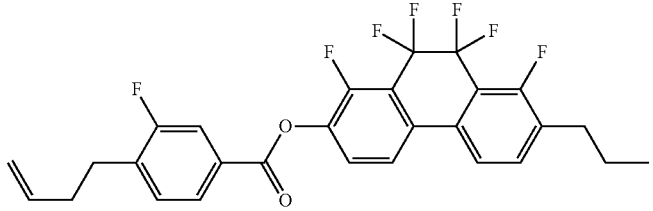 |
| 285 | 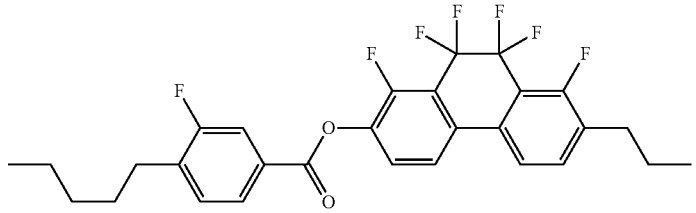 |
| 286 | 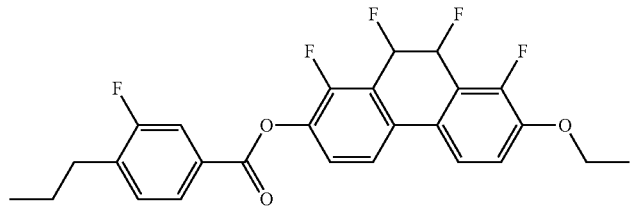 [SMILES: CCCc1ccc(C(=O)Oc2ccc3c(c2F)C(F)C(F)c2c-3ccc(OCC)c2F)cc1F] |
| 287 | 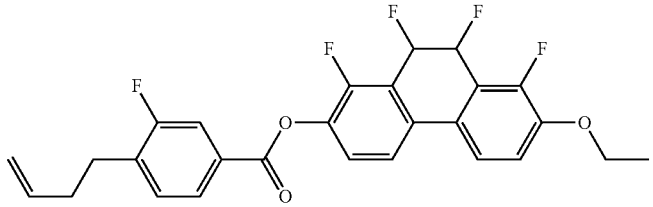 |
| 288 | 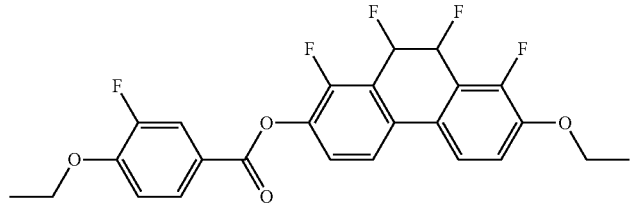 [SMILES: CCOc1ccc(C(=O)Oc2ccc3c(c2F)C(F)C(F)c2c-3ccc(OCC)c2F)cc1F] |

-continued
| No. |
|---|
| 289 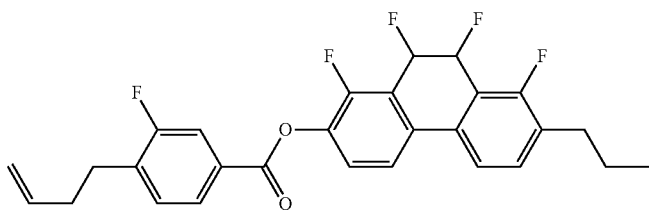 |
| 290 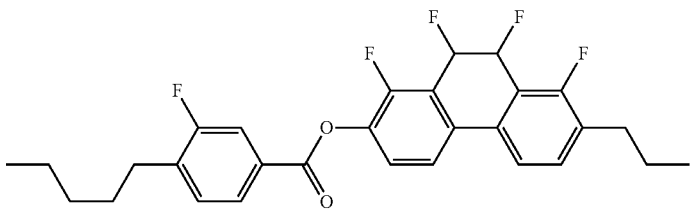 |
| 291 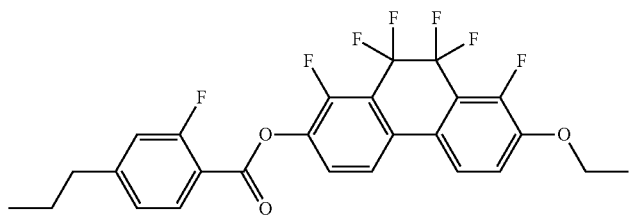 |
| 292 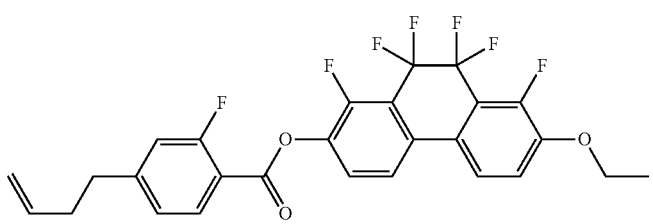 [SMILES: C=CCCc1ccc(C(=O)Oc2ccc3c(c2F)C(F)(F)C(F)(F)c2c-3ccc(OCC)c2F)c(F)c1] |
| 293 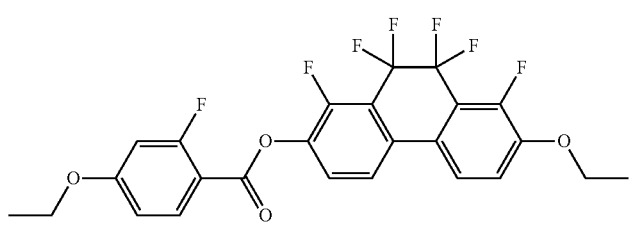 [SMILES: CCOc1ccc(C(=O)Oc2ccc3c(c2F)C(F)(F)C(F)(F)c2c-3ccc(OCC)c2F)c(F)c1] |
| 294 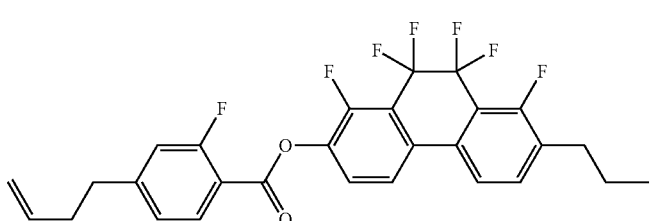 |
| 295 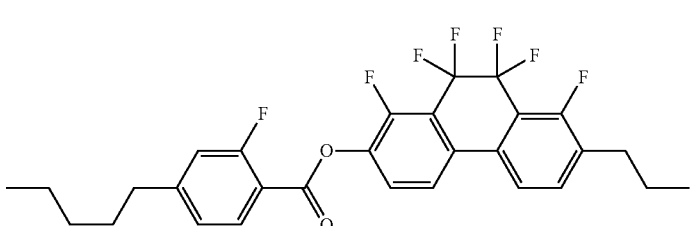 |

-continued
| No. | |
|---|---|
| 296 | 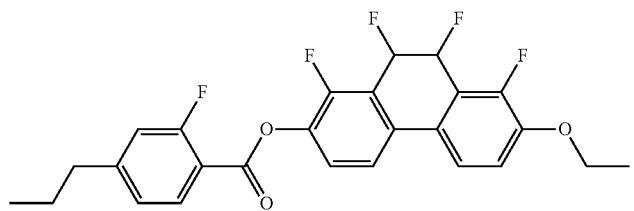 |
| 297 | 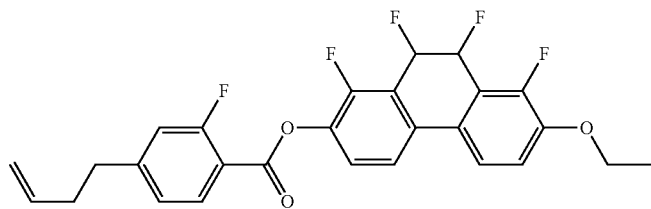 |
| 298 | 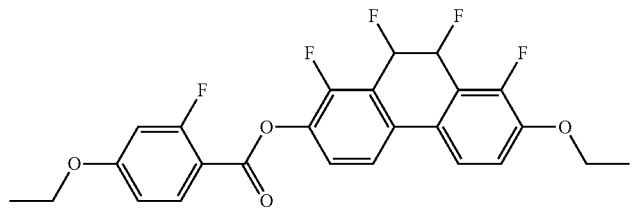 [SMILES: CCCc1ccc(C(=O)Oc2ccc3c(c2F)C(F)C(F)c2c-3ccc(OCC)c2F)c(F)c1] |
| 299 | 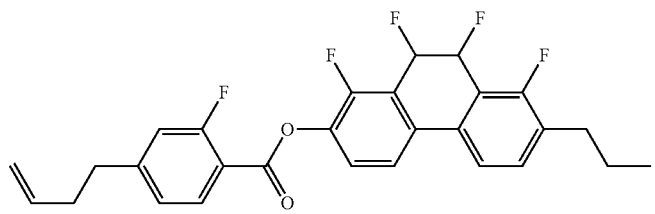 [SMILES: C=CCCc1ccc(C(=O)Oc2ccc3c(c2F)C(F)C(F)c2c-3ccc(CCC)c2F)c(F)c1] |
| 300 | 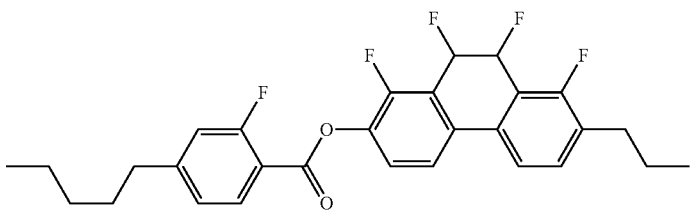 |
| 301 | 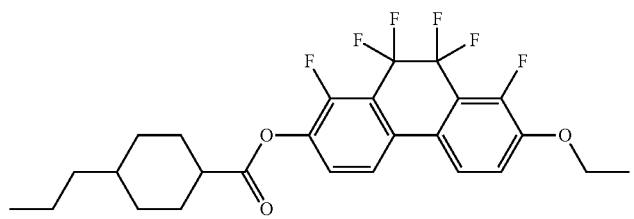 [SMILES: CCCC1CCC(C(=O)Oc2ccc3c(c2F)C(F)(F)C(F)(F)c2c-3ccc(OCC)c2F)CC1] |
| 302 | 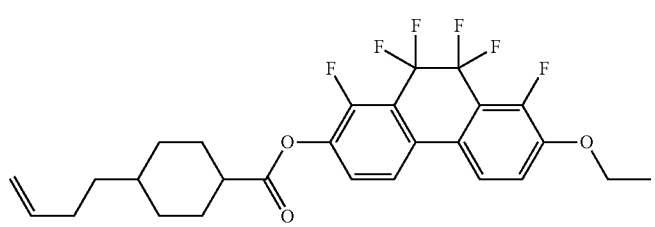 |

-continued
| No. |
| --- |
303
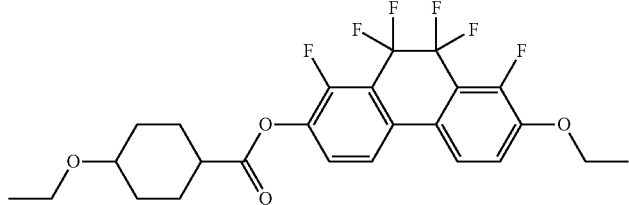 [SMILES: CCOc1ccc2c(c1F)C(F)(F)C(F)(F)c1c-2ccc(OC(=O)C2CCC(OCC)CC2)c1F]
304
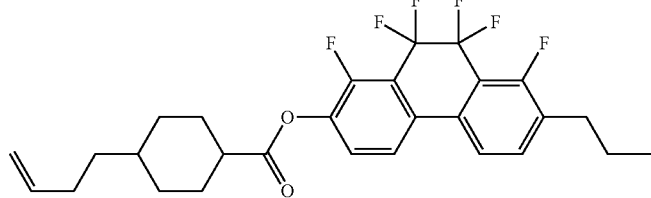
305
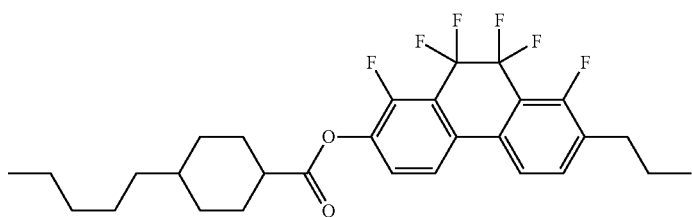 [SMILES: CCCCCC1CCC(C(=O)Oc2ccc3c(c2F)C(F)(F)C(F)(F)c2c-3ccc(CCC)c2F)CC1]
306
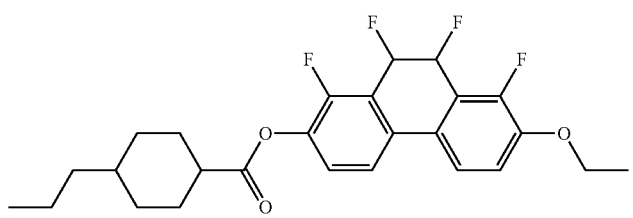
307
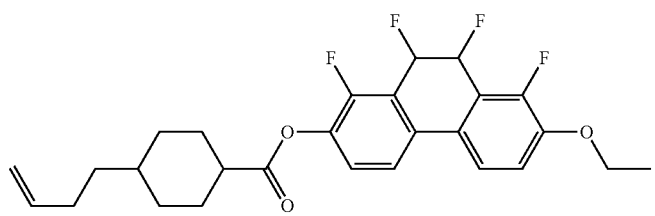 [SMILES: C=CCCC1CCC(C(=O)Oc2ccc3c(c2F)C(F)C(F)c2c-3ccc(OCC)c2F)CC1]
308
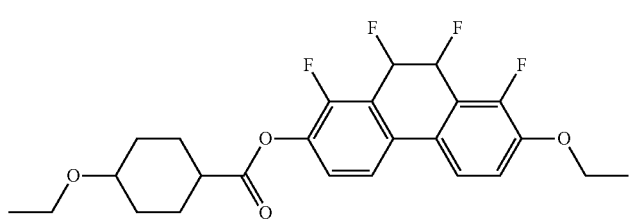
309
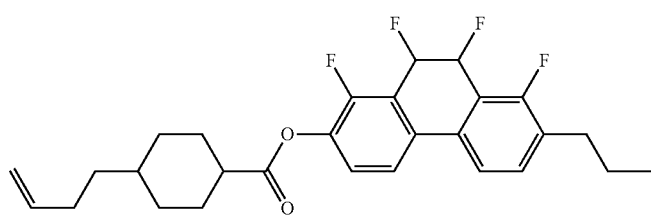

| No. |
|---|
| 310 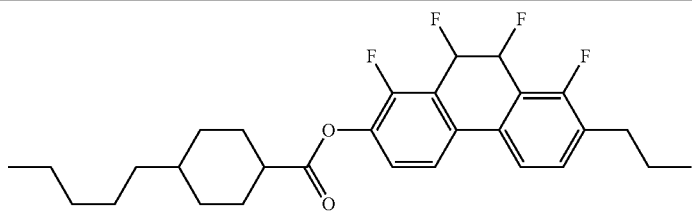 [SMILES: CCCCCC1CCC(C(=O)Oc2ccc3c(c2F)C(F)C(F)c2c-3ccc(CCC)c2F)CC1] |
| 311 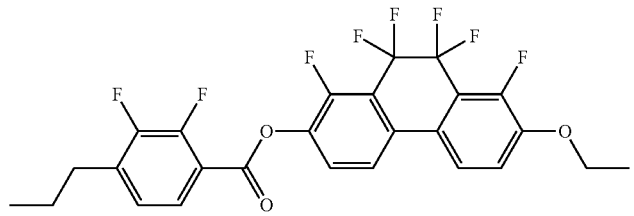 |
| 312 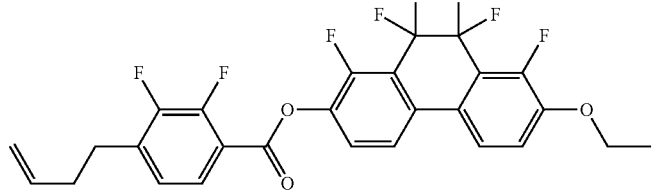 |
| 313 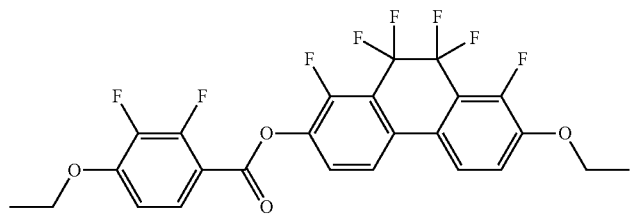 |
| 314 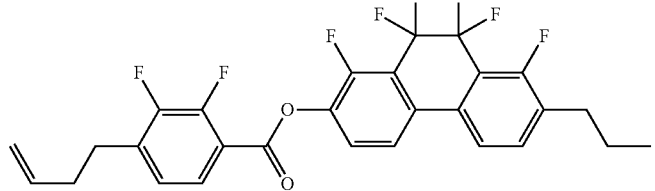 |
| 315 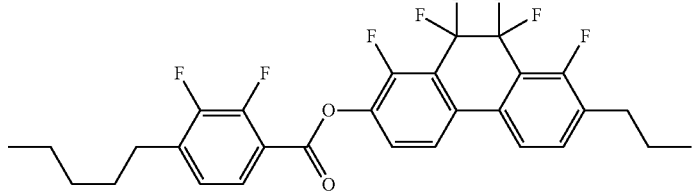 |
| 316 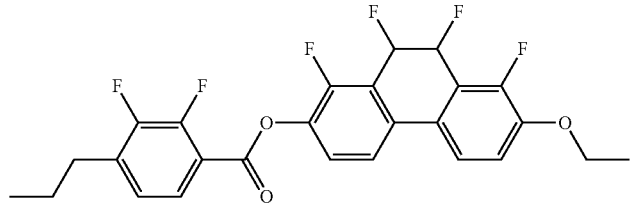 [SMILES: CCCc1ccc(C(=O)Oc2ccc3c(c2F)C(F)C(F)c2c-3ccc(OCC)c2F)c(F)c1F] |

| No. |
|---|
| 317 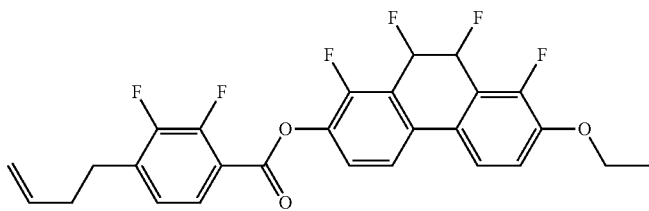 [SMILES: C=CCCc1ccc(C(=O)Oc2ccc3c(c2F)C(F)C(F)c2c-3ccc(OCC)c2F)c(F)c1F] |
| 318 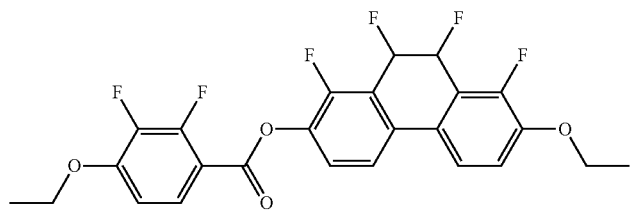 [SMILES: CCOc1ccc(C(=O)Oc2ccc3c(c2F)C(F)C(F)c2c-3ccc(OCC)c2F)c(F)c1F] |
| 319 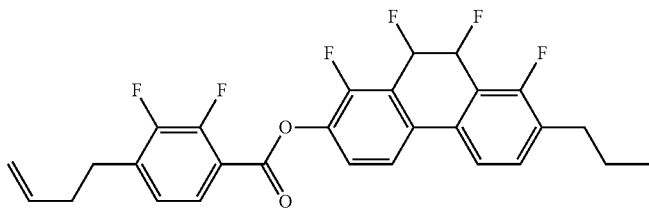 |
| 320 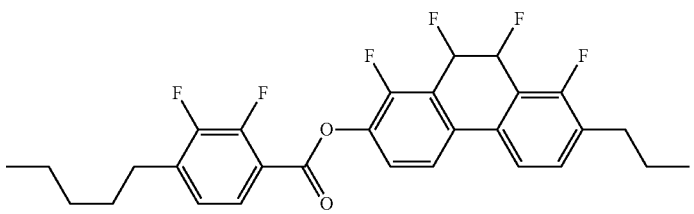 |
| 321 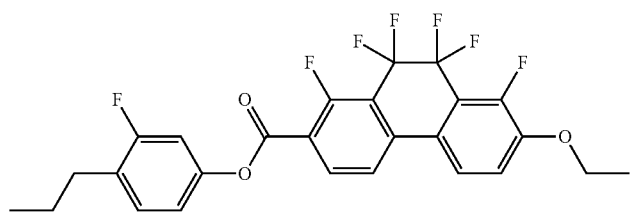 |
| 322 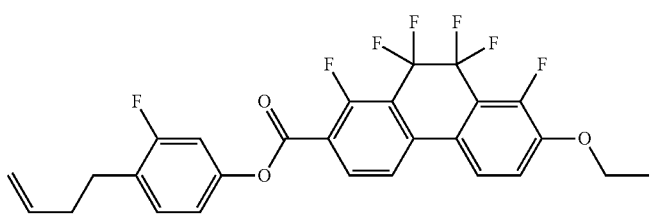 [SMILES: C=CCCc1ccc(OC(=O)c2ccc3c(c2F)C(F)(F)C(F)(F)c2c-3ccc(OCC)c2F)cc1F] |
| 323 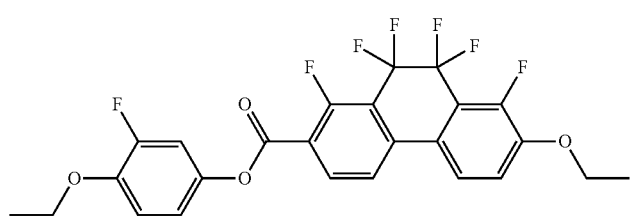 [SMILES: CCOc1ccc(OC(=O)c2ccc3c(c2F)C(F)(F)C(F)(F)c2c-3ccc(OCC)c2F)cc1F] |

| No. | |
|---|---|
| 324 | 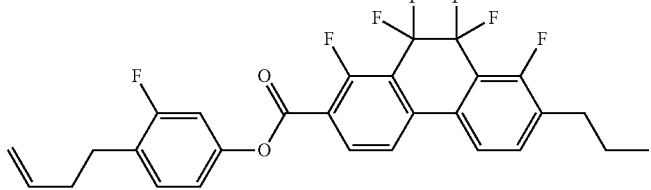 |
| 325 | 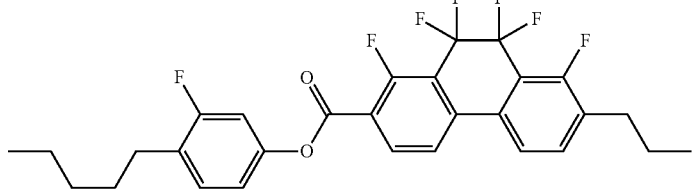 |
| 326 | 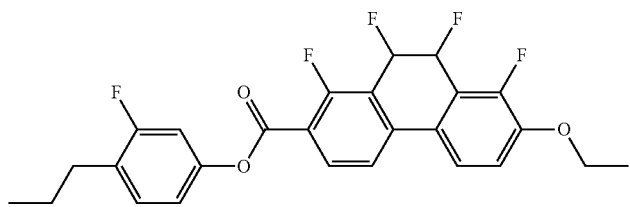 |
| 327 | 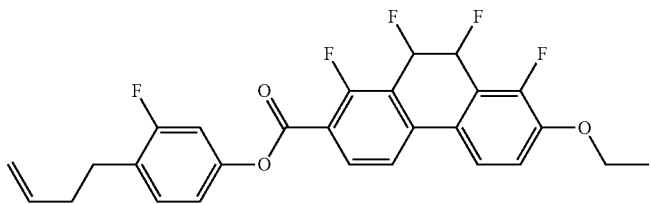 |
| 328 | 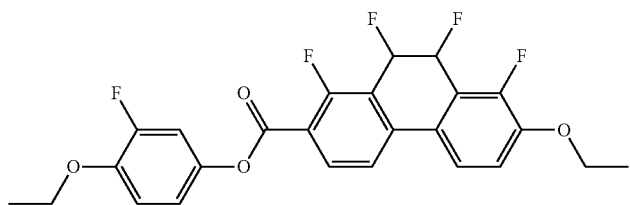 |
| 329 | 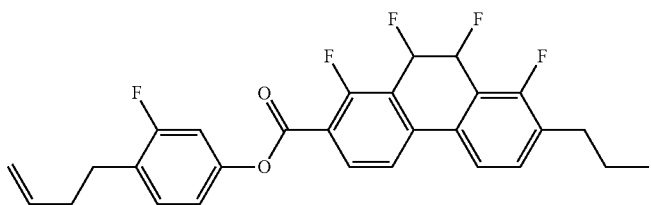 |
| 330 | 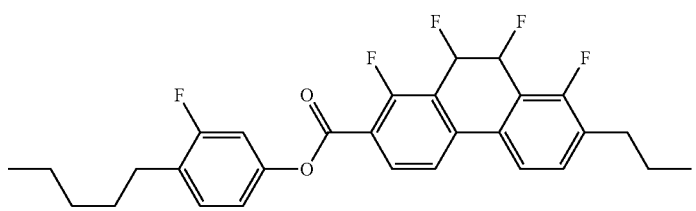 |

-continued
| No. | |
|---|---|
| 331 | 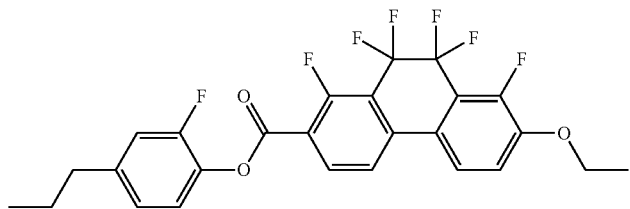 [SMILES: CCCc1ccc(OC(=O)c2ccc3c(c2F)C(F)(F)C(F)(F)c2c-3ccc(OCC)c2F)c(F)c1] |
| 332 | 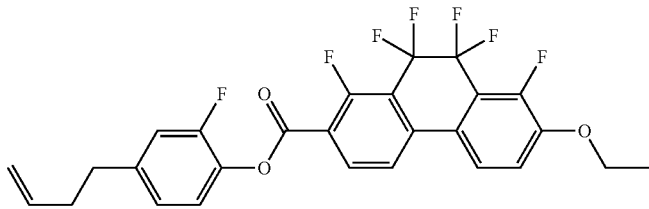 |
| 333 | 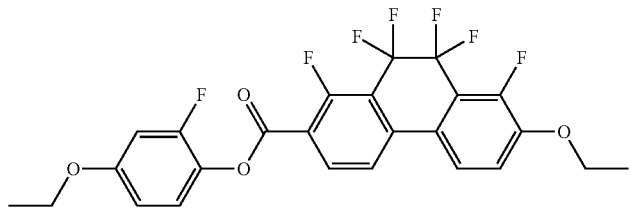 |
| 334 | 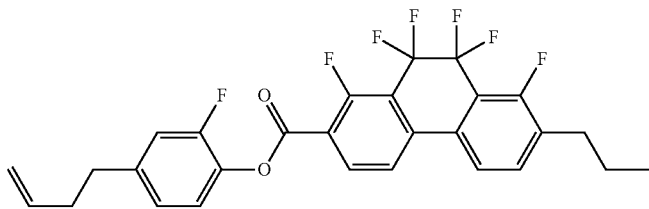 |
| 335 | 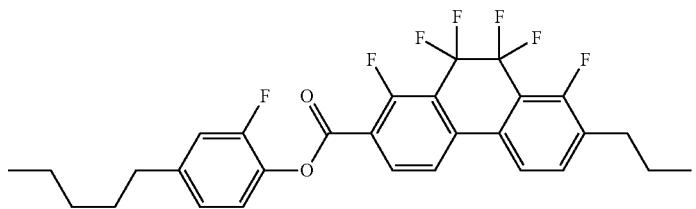 |
| 336 | 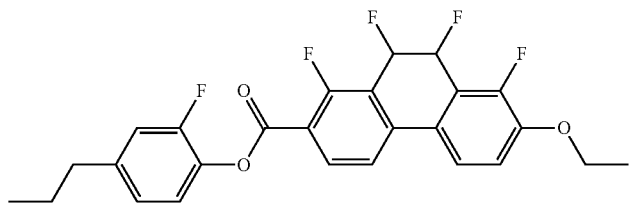 [SMILES: CCCc1ccc(OC(=O)c2ccc3c(c2F)C(F)C(F)c2c-3ccc(OCC)c2F)c(F)c1] |
| 337 | 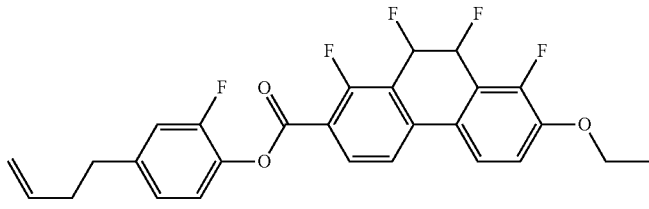 [SMILES: C=CCCc1ccc(OC(=O)c2ccc3c(c2F)C(F)C(F)c2c-3ccc(OCC)c2F)c(F)c1] |

| No. |
| --- |
| 338 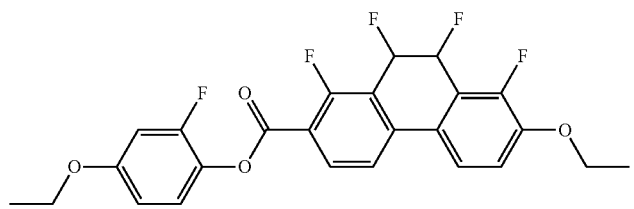 |
| 339 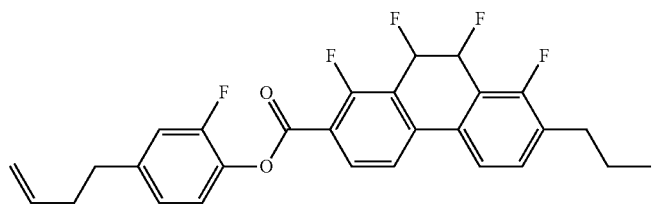 [SMILES: C=CCCc1ccc(OC(=O)c2ccc3c(c2F)C(F)C(F)c2c-3ccc(CCC)c2F)c(F)c1] |
| 340 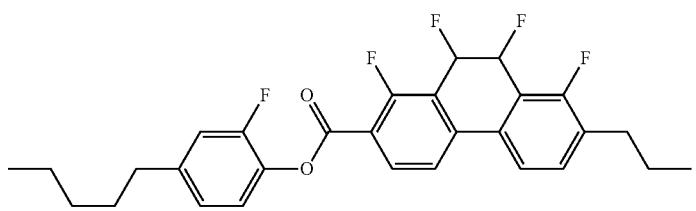 |
| 341 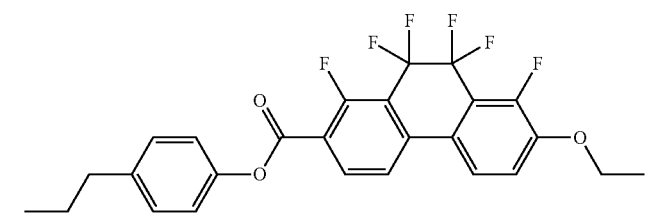 |
| 342 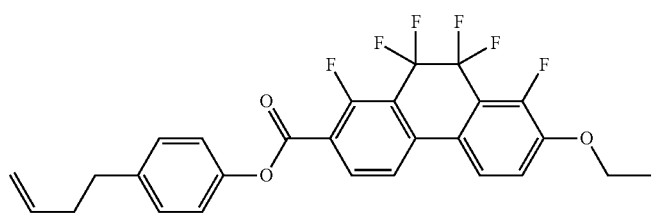 [SMILES: C=CCCc1ccc(OC(=O)c2ccc3c(c2F)C(F)(F)C(F)(F)c2c-3ccc(OCC)c2F)cc1] |
| 343 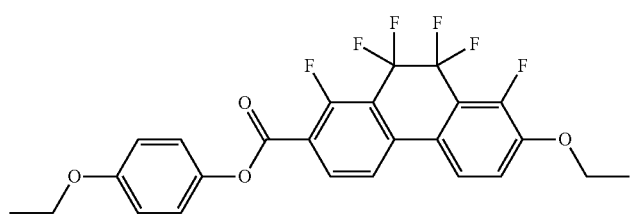 |
| 344 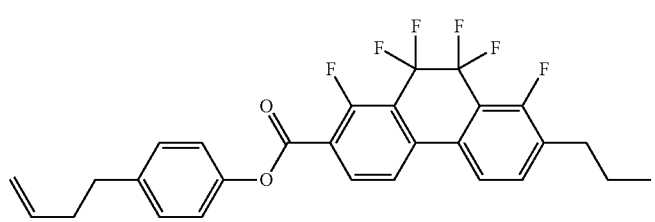 [SMILES: C=CCCc1ccc(OC(=O)c2ccc3c(c2F)C(F)(F)C(F)(F)c2c-3ccc(CCC)c2F)cc1] |

-continued
| No. | |
|---|---|
| 345 | 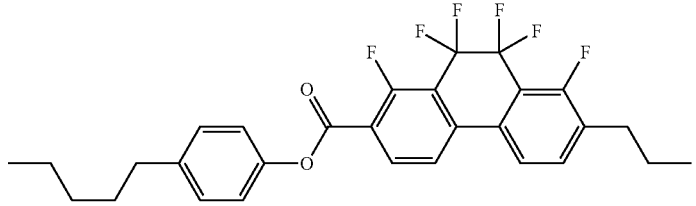 |
| 346 | 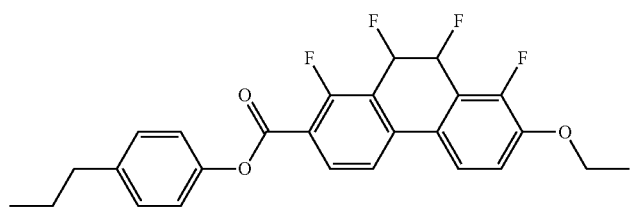 |
| 347 | 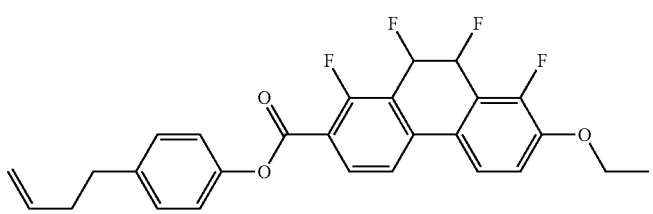 |
| 348 | 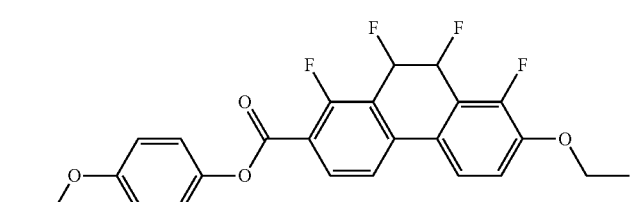 |
| 349 | 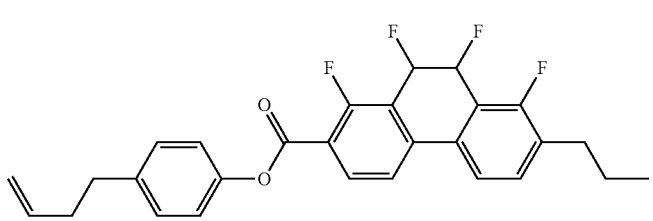 [SMILES: C=CCCc1ccc(OC(=O)c2ccc3c(c2F)C(F)C(F)c2c-3ccc(OCC)c2F)cc1] |
| 350 | 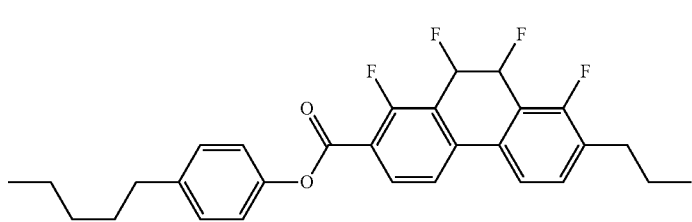 [SMILES: CCCCCc1ccc(OC(=O)c2ccc3c(c2F)C(F)C(F)c2c-3ccc(CCC)c2F)cc1] |
| 351 | 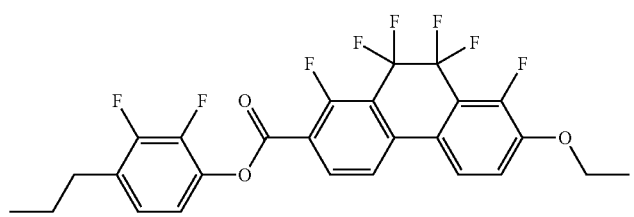 [SMILES: CCOc1ccc(OC(=O)c2ccc3c(c2F)C(F)(F)C(F)(F)c2c-3ccc(OCC)c2F)c(F)c1F] |

-continued
| No. | |
|---|---|
| 352 | 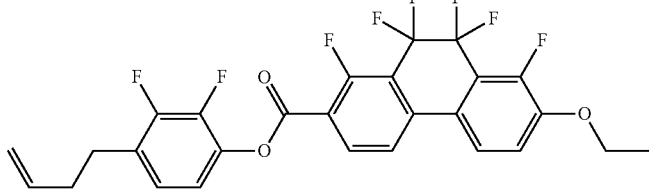 |
| 353 | 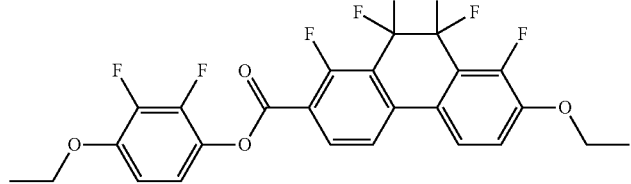 |
| 354 | 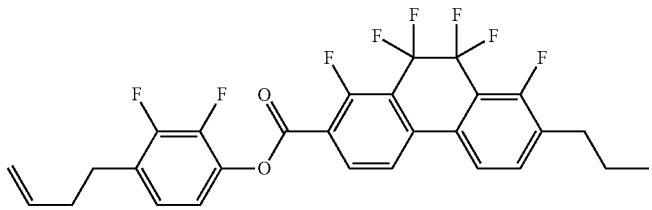 |
| 355 | 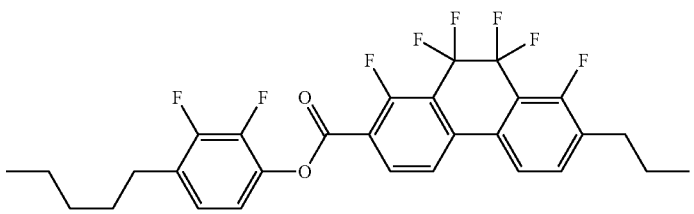 |
| 356 | 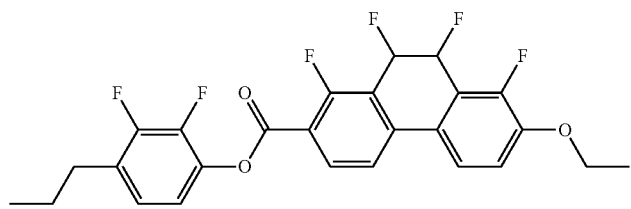 |
| 357 | 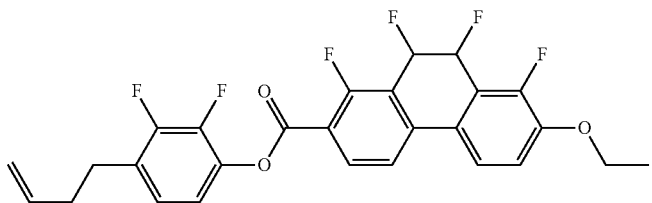 |
| 358 | 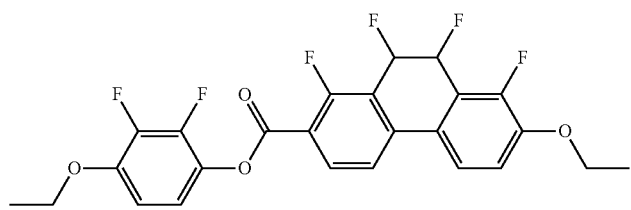 |

-continued
| No. |
|---|
| 359 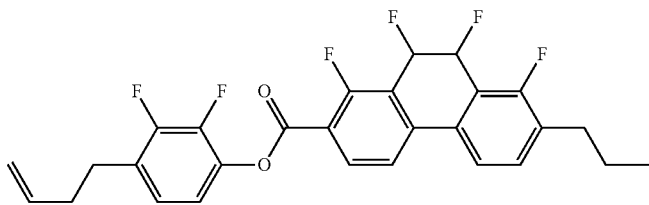 |
| 360 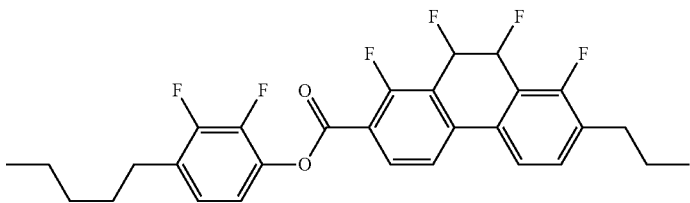 |
| 361 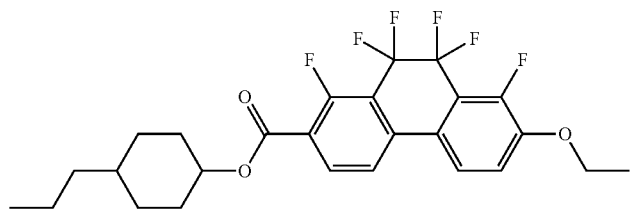 [SMILES: CCCC1CCC(OC(=O)c2ccc3c(c2F)C(F)(F)C(F)(F)c2c-3ccc(OCC)c2F)CC1] |
| 362 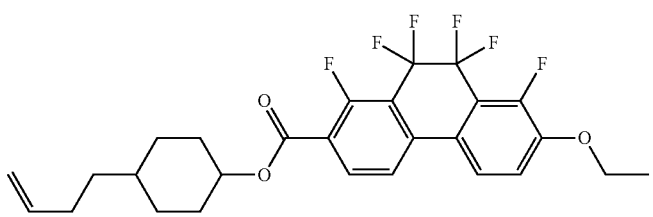 [SMILES: C=CCCC1CCC(OC(=O)c2ccc3c(c2F)C(F)(F)C(F)(F)c2c-3ccc(OCC)c2F)CC1] |
| 363 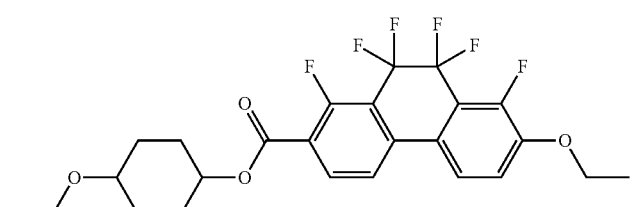 |
| 364 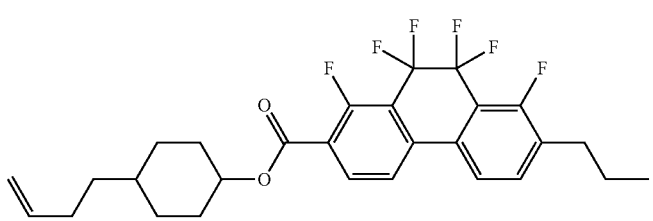 [SMILES: C=CCCC1CCC(OC(=O)c2ccc3c(c2F)C(F)(F)C(F)(F)c2c-3ccc(CCC)c2F)CC1] |
| 365 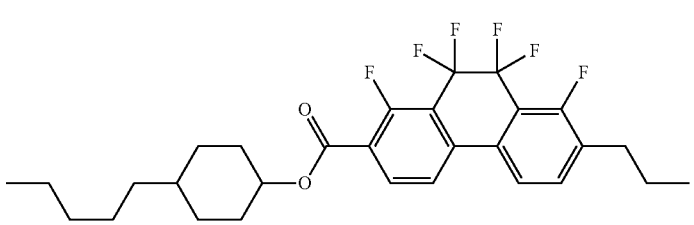 [SMILES: CCCCCC1CCC(OC(=O)c2ccc3c(c2F)C(F)(F)C(F)(F)c2c-3ccc(CCC)c2F)CC1] |

-continued
| No. |
|---|
| 366 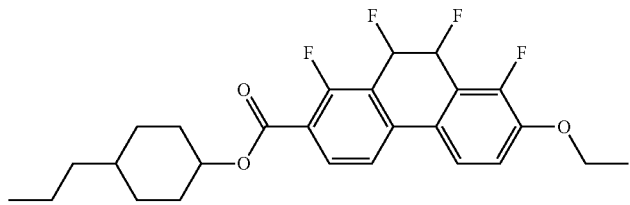 |
| 367 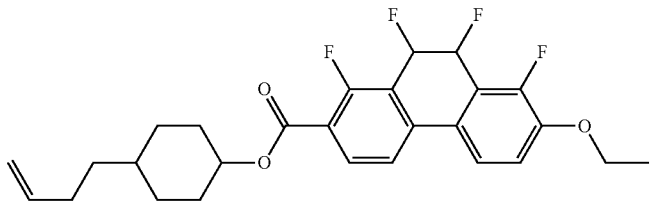 [SMILES: C=CCCC1CCC(OC(=O)c2ccc3c(c2F)C(F)C(F)c2c-3ccc(OCC)c2F)CC1] |
| 368 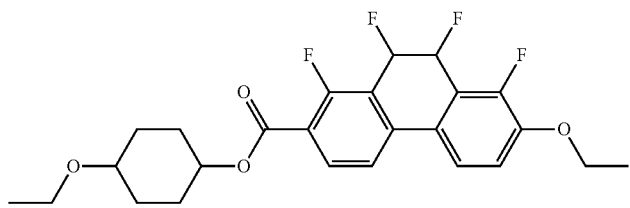 [SMILES: CCOc1ccc2c(c1F)C(F)C(F)c1c-2ccc(C(=O)OC2CCC(OCC)CC2)c1F] |
| 369 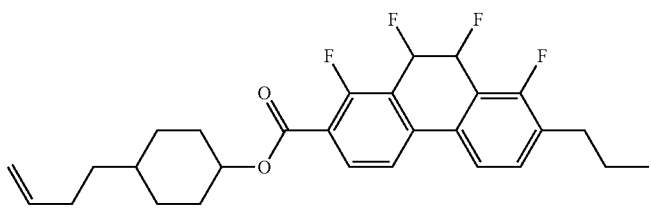 [SMILES: C=CCCC1CCC(OC(=O)c2ccc3c(c2F)C(F)C(F)c2c-3ccc(CCC)c2F)CC1] |
| 370 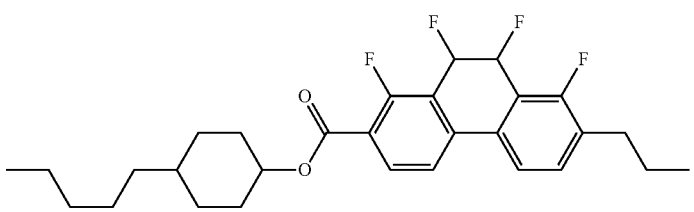 |
| 371 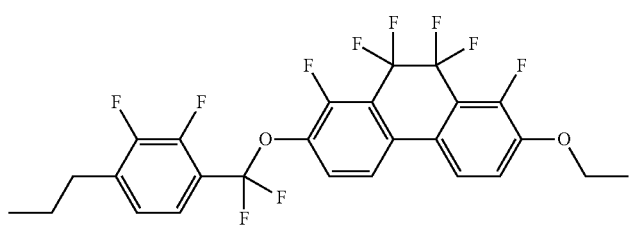 [SMILES: CCCc1ccc(C(F)(F)Oc2ccc3c(c2F)C(F)(F)C(F)(F)c2c-3ccc(OCC)c2F)c(F)c1F] |
| 372 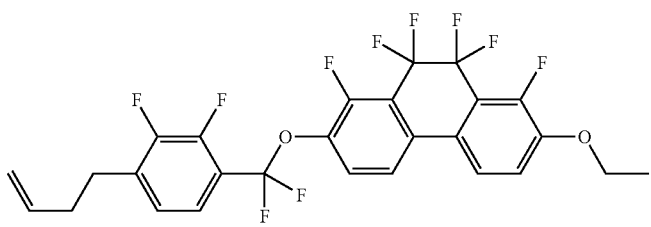 [SMILES: C=CCCc1ccc(C(F)(F)Oc2ccc3c(c2F)C(F)(F)C(F)(F)c2c-3ccc(OCC)c2F)c(F)c1F] |

| No. |
| --- |
| 373 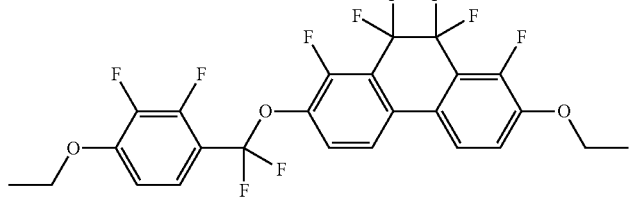 |
| 374 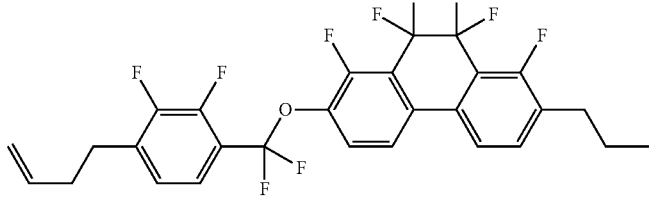 |
| 375 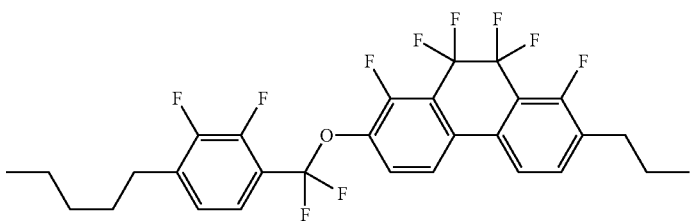 [SMILES: CCCCCc1ccc(C(F)(F)Oc2ccc3c(c2F)C(F)(F)C(F)(F)c2c-3ccc(CCC)c2F)c(F)c1F] |
| 376 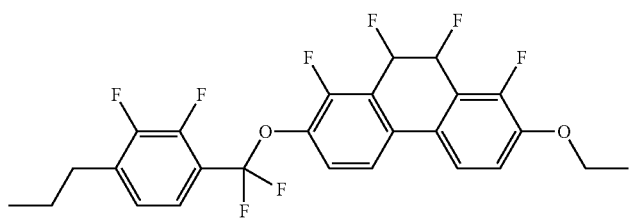 [SMILES: CCCc1ccc(C(F)(F)Oc2ccc3c(c2F)C(F)C(F)c2c-3ccc(OCC)c2F)c(F)c1F] |
| 377 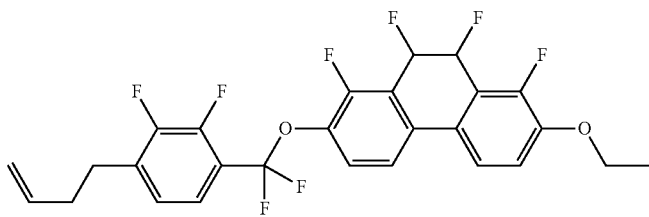 |
| 378 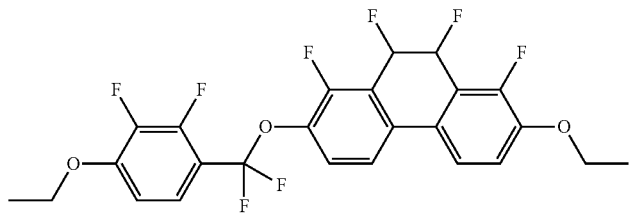 |
| 379 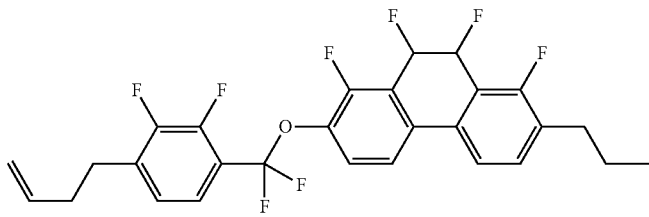 [SMILES: C=CCCc1ccc(C(F)(F)Oc2ccc3c(c2F)C(F)C(F)c2c-3ccc(CCC)c2F)c(F)c1F] |

| No. |
|---|
| 380 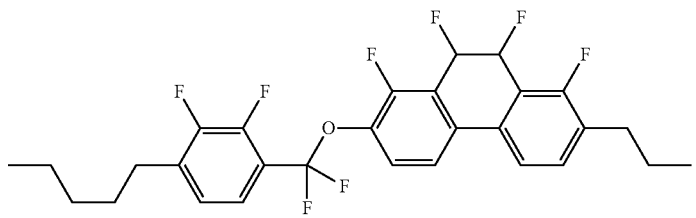 |
| 381 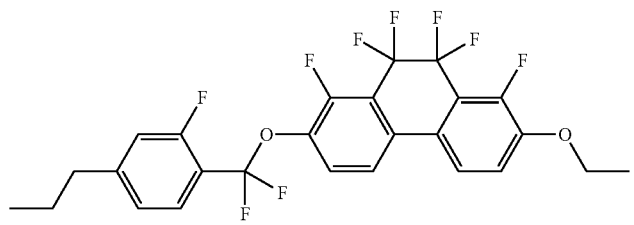 |
| 382 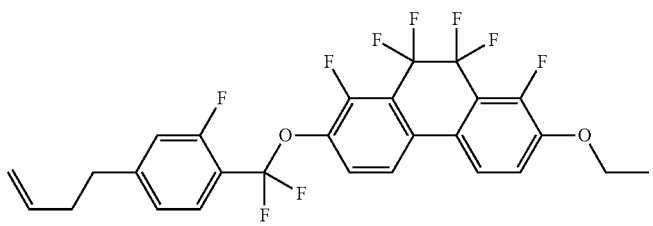 |
| 383 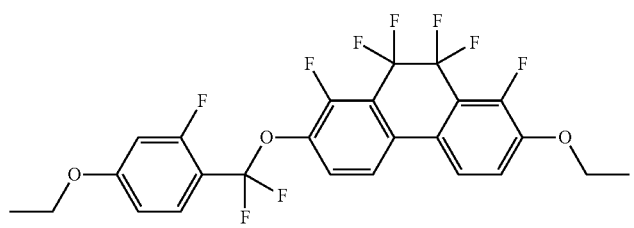 [SMILES: CCCc1ccc(C(F)(F)Oc2ccc3c(c2F)C(F)(F)C(F)(F)c2c-3ccc(OCC)c2F)c(F)c1] |
| 384 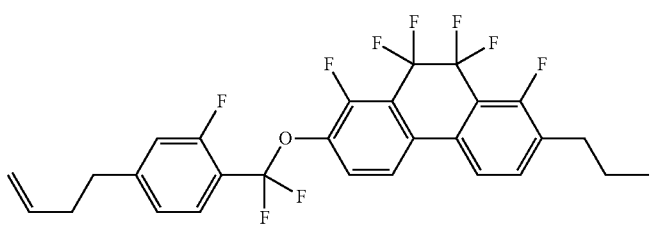 [SMILES: C=CCCc1ccc(C(F)(F)Oc2ccc3c(c2F)C(F)(F)C(F)(F)c2c-3ccc(CCC)c2F)c(F)c1] |
| 385 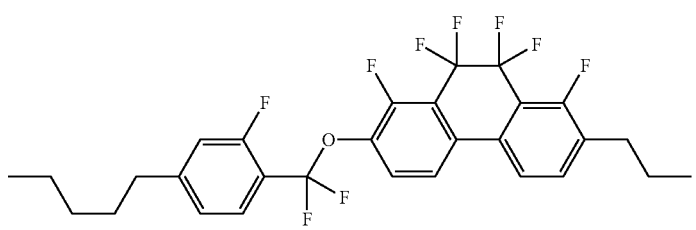 [SMILES: CCCCCc1ccc(C(F)(F)Oc2ccc3c(c2F)C(F)(F)C(F)(F)c2c-3ccc(CCC)c2F)c(F)c1] |
| 386 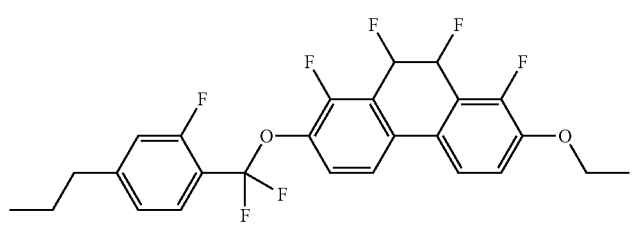 |

-continued
| No. | |
|---|---|
| 387 | 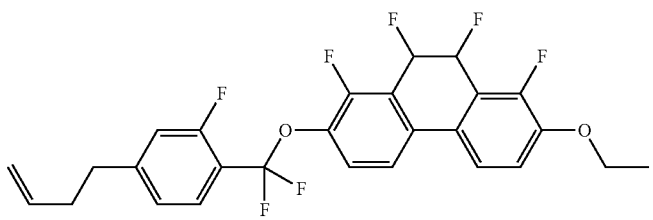 |
| 388 | 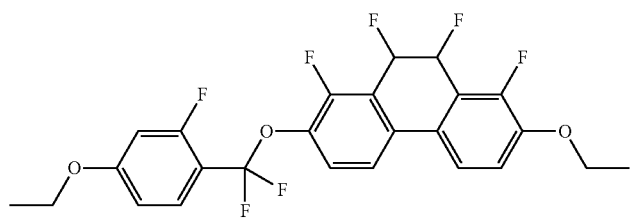 |
| 389 | 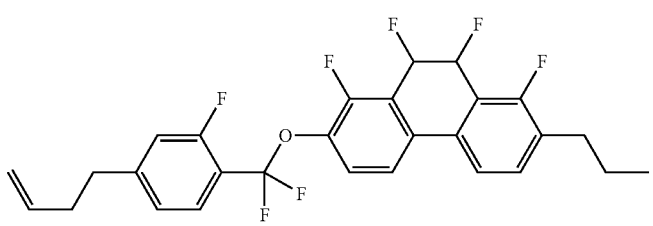 [SMILES: C=CCCc1ccc(C(F)(F)Oc2ccc3c(c2F)C(F)C(F)c2c-3ccc(OCC)c2F)c(F)c1] |
| 390 | 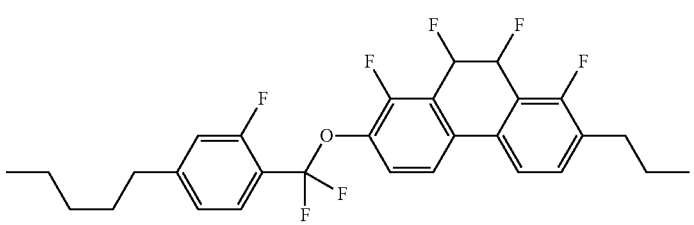 |
| 391 | 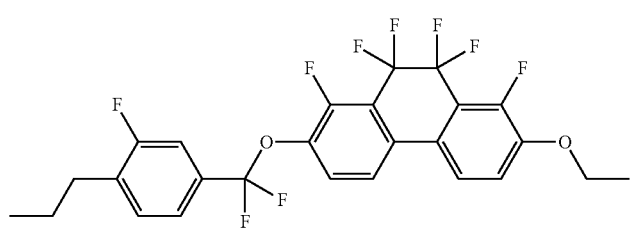 [SMILES: CCCc1ccc(C(F)(F)Oc2ccc3c(c2F)C(F)(F)C(F)(F)c2c-3ccc(OCC)c2F)cc1F] |
| 392 | 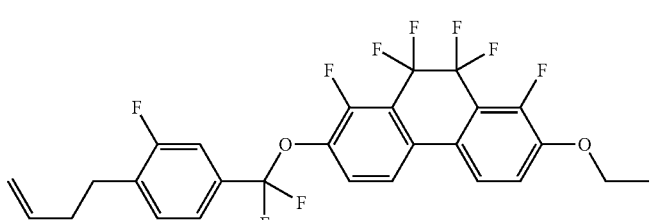 |
| 393 | 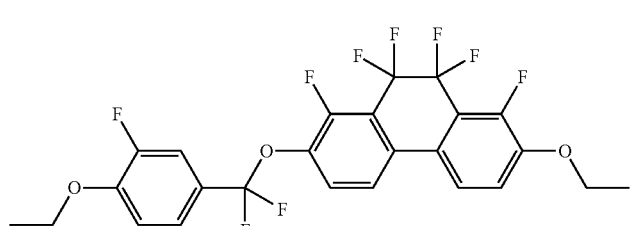 |

-continued
| No. | |
|---|---|
| 394 | 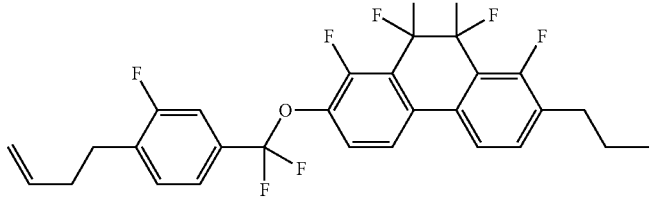 |
| 395 | 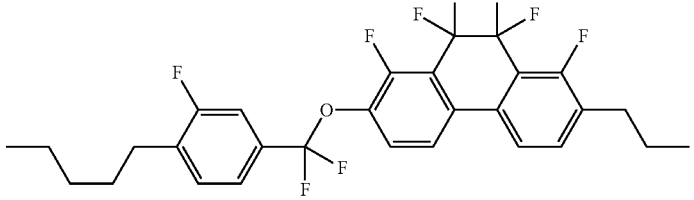 |
| 396 | 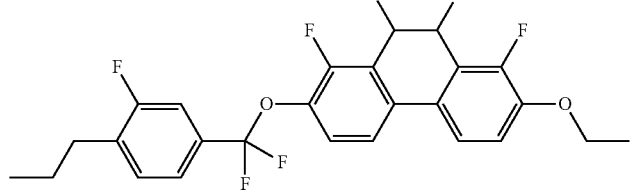 |
| 397 | 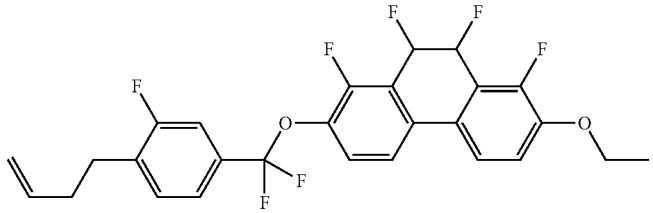 [SMILES: C=CCCc1ccc(C(F)(F)Oc2ccc3c(c2F)C(F)C(F)c2c-3ccc(OCC)c2F)cc1F] |
| 398 | 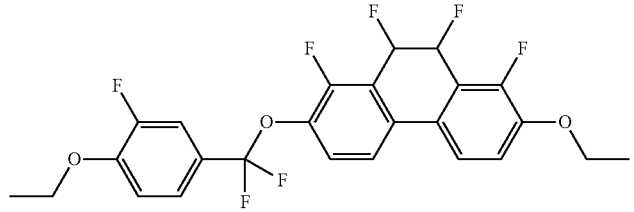 [SMILES: CCOc1ccc(C(F)(F)Oc2ccc3c(c2F)C(F)C(F)c2c-3ccc(OCC)c2F)cc1F] |
| 399 | 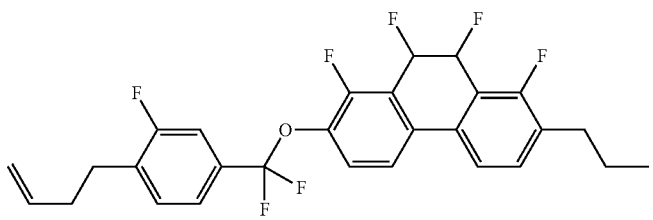 |
| 400 | 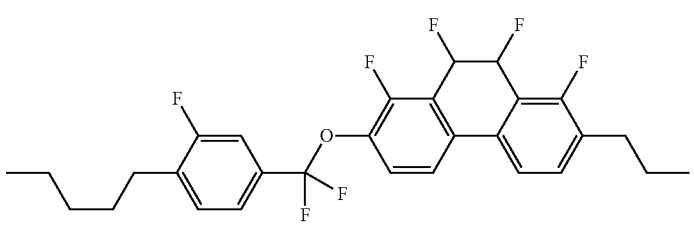 |

-continued
| No. |  |
|---|---|
| 401 | 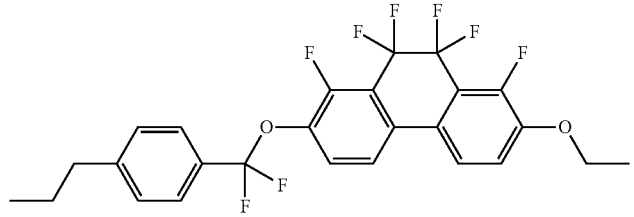 |
| 402 | 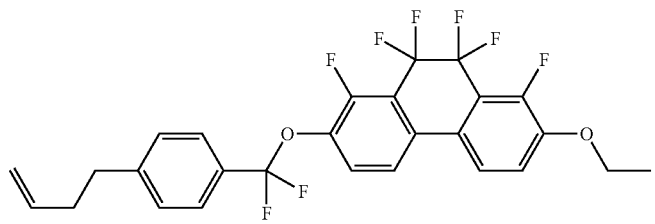 [SMILES: C=CCCc1ccc(C(F)(F)Oc2ccc3c(c2F)C(F)(F)C(F)(F)c2c-3ccc(OCC)c2F)cc1] |
| 403 | 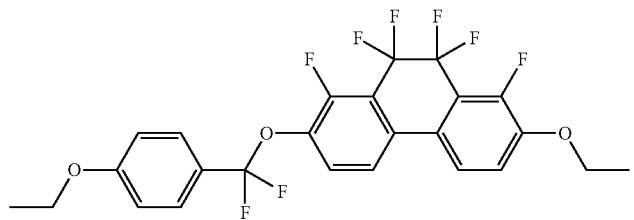 [SMILES: CCOc1ccc(C(F)(F)Oc2ccc3c(c2F)C(F)(F)C(F)(F)c2c-3ccc(OCC)c2F)cc1] |
| 404 | 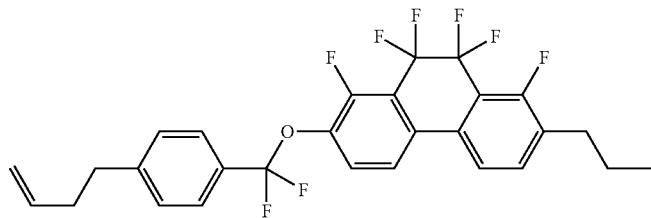 [SMILES: C=CCCc1ccc(C(F)(F)Oc2ccc3c(c2F)C(F)(F)C(F)(F)c2c-3ccc(CCC)c2F)cc1] |
| 405 | 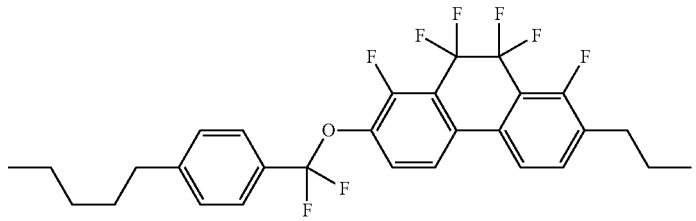 |
| 406 | 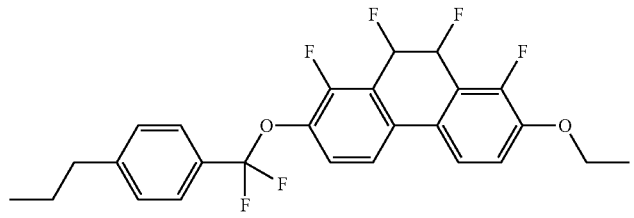 |
| 407 | 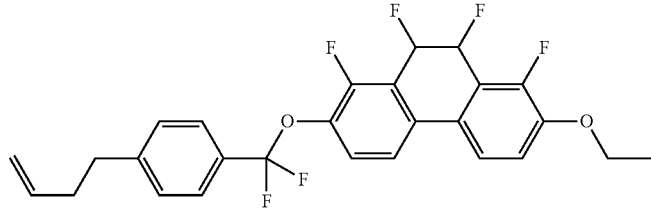 [SMILES: C=CCCc1ccc(C(F)(F)Oc2ccc3c(c2F)C(F)C(F)c2c-3ccc(OCC)c2F)cc1] |

-continued
| No. |
|---|
| 408 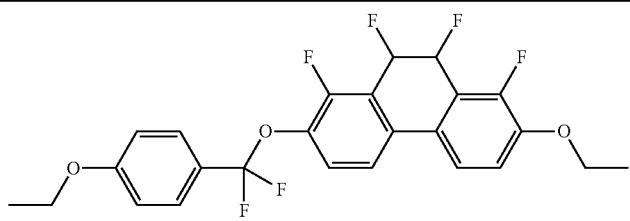 |
| 409 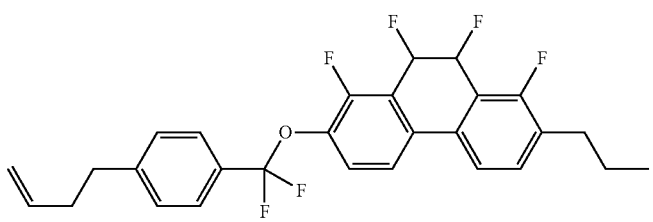 [SMILES: C=CCCc1ccc(C(F)(F)Oc2ccc3c(c2F)C(F)C(F)c2c-3ccc(CCC)c2F)cc1] |
| 410 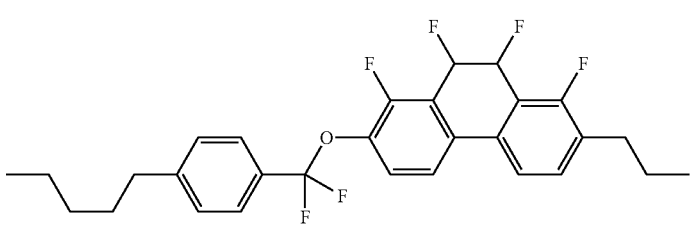 [SMILES: CCCCCc1ccc(C(F)(F)Oc2ccc3c(c2F)C(F)C(F)c2c-3ccc(CCC)c2F)cc1] |
| 411 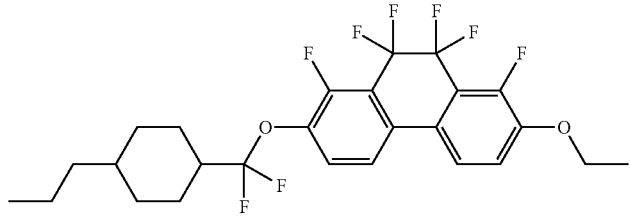 [SMILES: CCCC1CCC(C(F)(F)Oc2ccc3c(c2F)C(F)(F)C(F)(F)c2c-3ccc(OCC)c2F)CC1] |
| 412 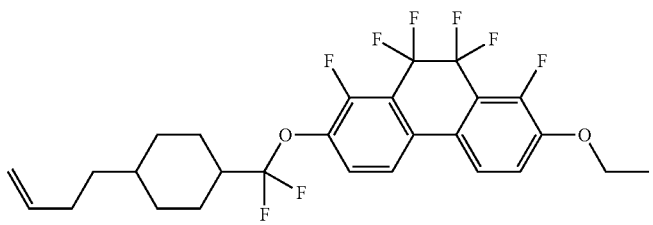 [SMILES: C=CCCC1CCC(C(F)(F)Oc2ccc3c(c2F)C(F)(F)C(F)(F)c2c-3ccc(OCC)c2F)CC1] |
| 413 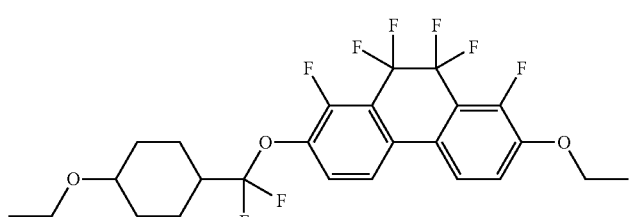 |
| 414 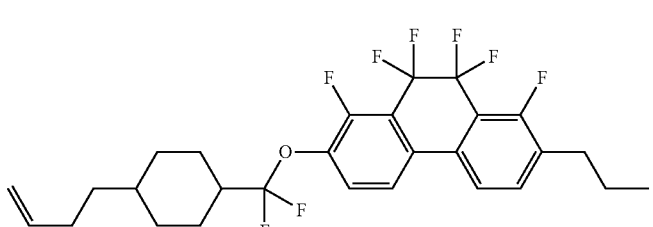 |

| No. |
|---|
| 415 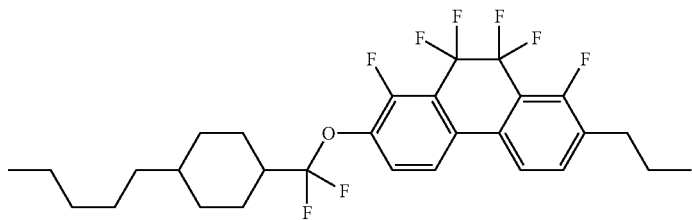 [SMILES: CCCCCC1CCC(C(F)(F)Oc2ccc3c(c2F)C(F)(F)C(F)(F)c2c-3ccc(CCC)c2F)CC1] |
| 416 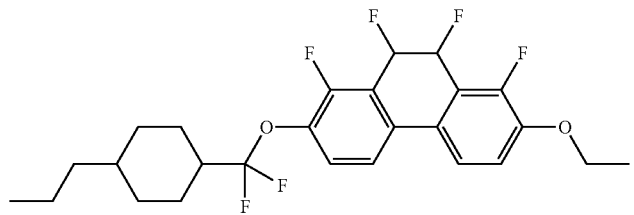 |
| 417 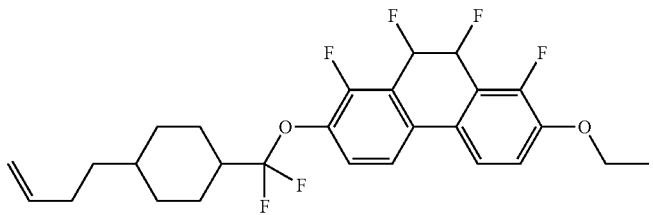 [SMILES: C=CCCC1CCC(C(F)(F)Oc2ccc3c(c2F)C(F)C(F)c2c-3ccc(OCC)c2F)CC1] |
| 418 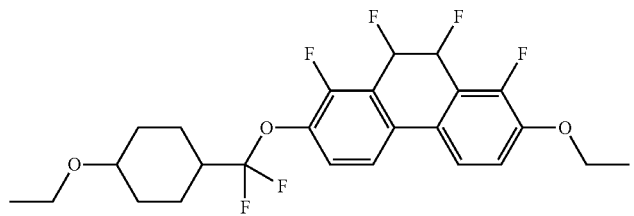 |
| 419 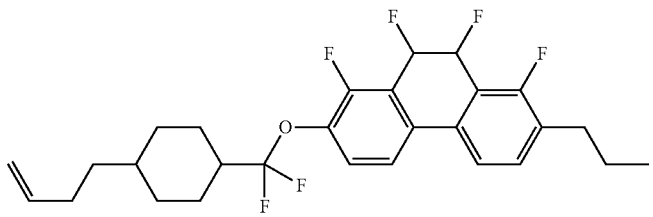 |
| 420 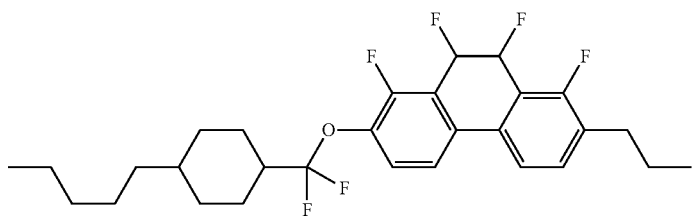 [SMILES: CCCCCC1CCC(C(F)(F)Oc2ccc3c(c2F)C(F)C(F)c2c-3ccc(CCC)c2F)CC1] |
| 421 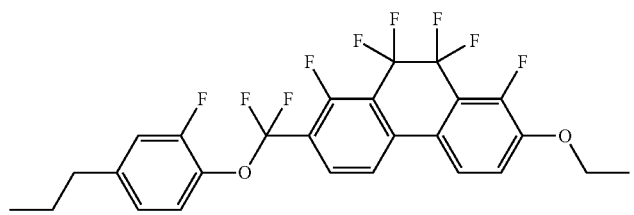 [SMILES: CCCc1ccc(OC(F)(F)c2ccc3c(c2F)C(F)(F)C(F)(F)c2c-3ccc(OCC)c2F)c(F)c1] |

| No. |
|---|
| 422 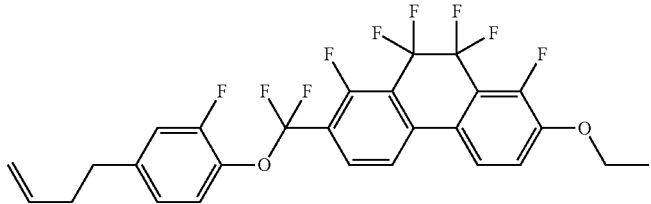 [SMILES: C=CCCc1ccc(OC(F)(F)c2ccc3c(c2F)C(F)(F)C(F)(F)c2c-3ccc(OCC)c2F)c(F)c1] |
| 423 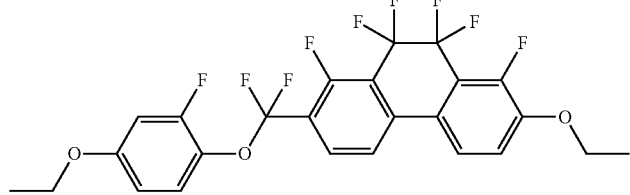 |
| 424 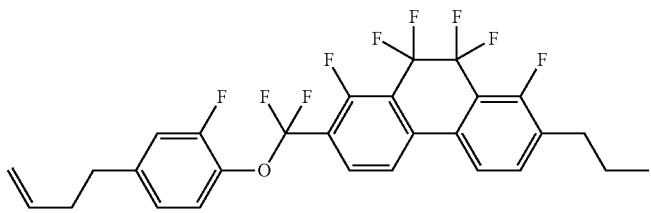 |
| 425 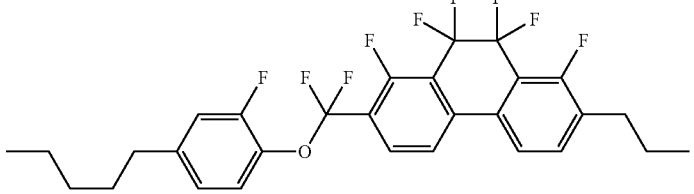 |
| 426 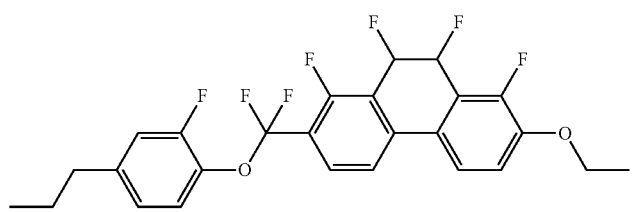 [SMILES: CCCc1ccc(OC(F)(F)c2ccc3c(c2F)C(F)C(F)c2c-3ccc(OCC)c2F)c(F)c1] |
| 427 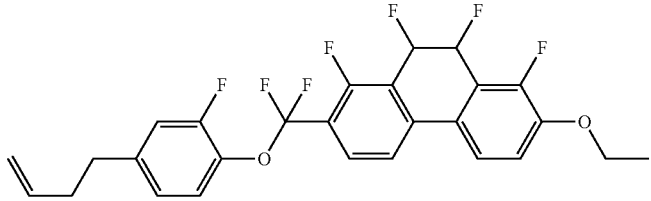 |
| 428 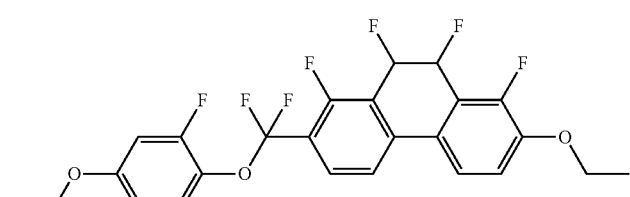 |

| No. |
|---|
| 429 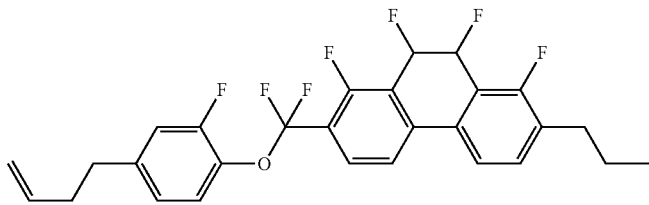 |
| 430 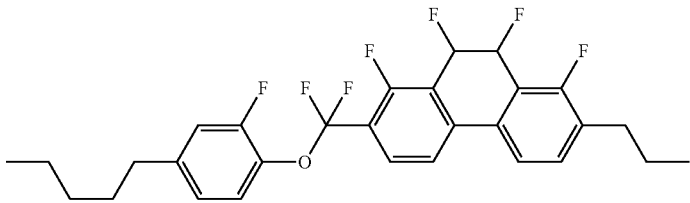 |
| 431 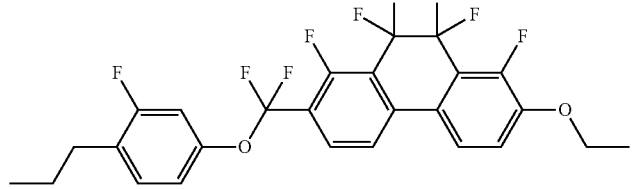 |
| 432 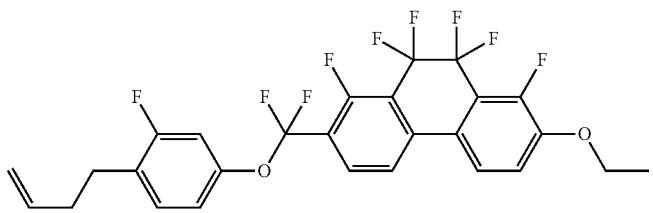 [SMILES: C=CCCc1ccc(OC(F)(F)c2ccc3c(c2F)C(F)(F)C(F)(F)c2c-3ccc(OCC)c2F)cc1F] |
| 433 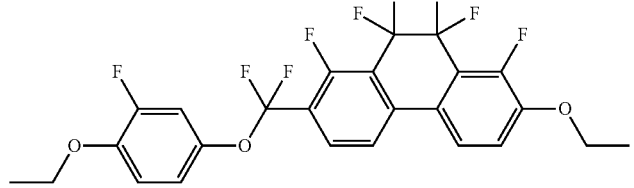 |
| 434 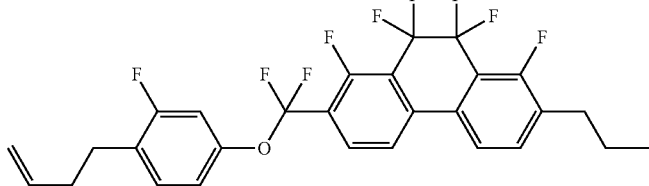 |
| 435 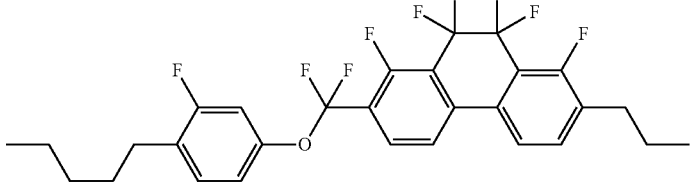 |

| No. |
|---|
| 436 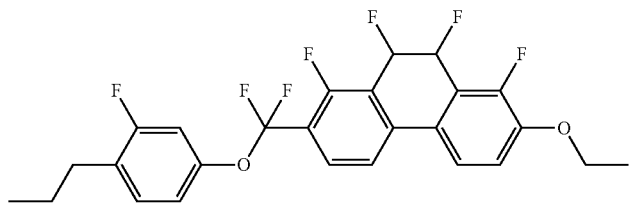 |
| 437 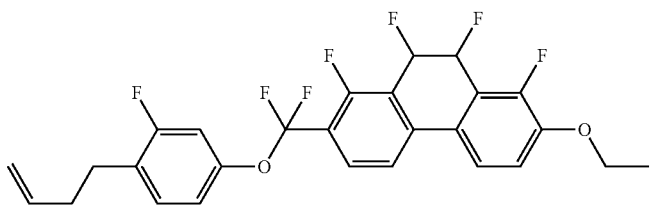 |
| 438 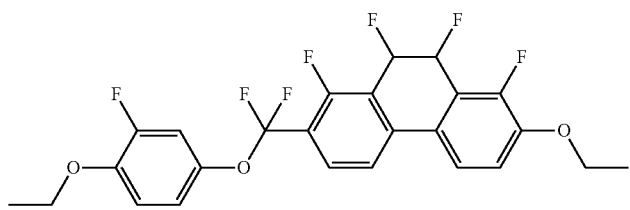 [SMILES: CCCc1ccc(OC(F)(F)c2ccc3c(c2F)C(F)C(F)c2c-3ccc(OCC)c2F)cc1F] |
| 439 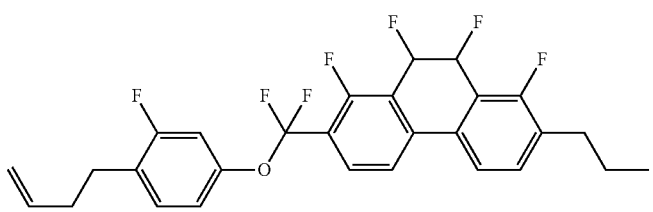 |
| 440 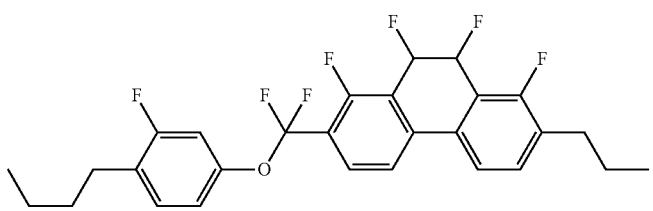 [SMILES: CCCCc1ccc(OC(F)(F)c2ccc3c(c2F)C(F)C(F)c2c-3ccc(CCC)c2F)cc1F] |
| 441 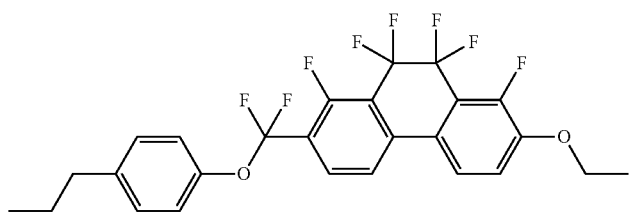 [SMILES: CCCc1ccc(OC(F)(F)c2ccc3c(c2F)C(F)(F)C(F)(F)c2c-3ccc(OCC)c2F)cc1] |
| 442 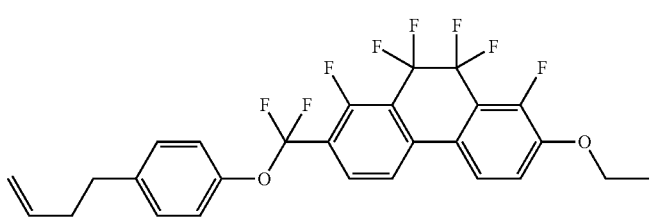 [SMILES: C=CCCc1ccc(OC(F)(F)c2ccc3c(c2F)C(F)(F)C(F)(F)c2c-3ccc(OCC)c2F)cc1] |

-continued
| No. |
| --- |
| 443 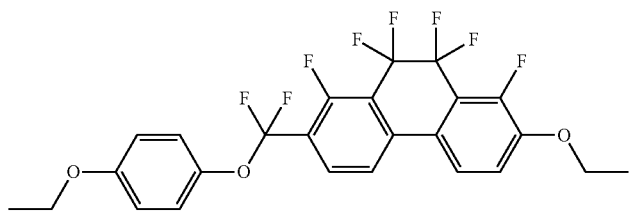 |
| 444 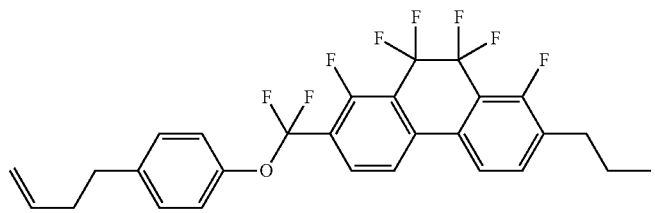 [SMILES: C=CCCc1ccc(OC(F)(F)c2ccc3c(c2F)C(F)(F)C(F)(F)c2c-3ccc(CCC)c2F)cc1] |
| 445 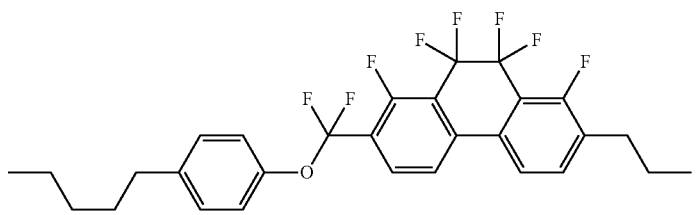 [SMILES: CCCCCc1ccc(OC(F)(F)c2ccc3c(c2F)C(F)(F)C(F)(F)c2c-3ccc(CCC)c2F)cc1] |
| 446 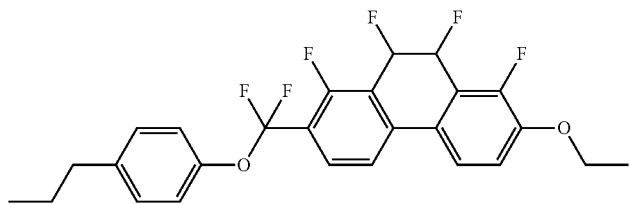 [SMILES: CCCc1ccc(OC(F)(F)c2ccc3c(c2F)C(F)C(F)c2c-3ccc(OCC)c2F)cc1] |
| 447 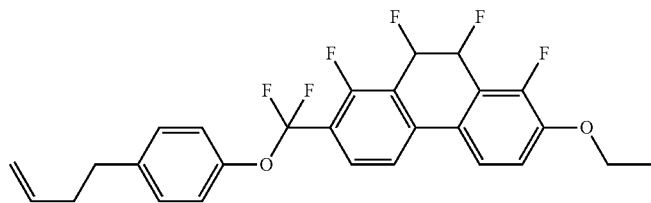 [SMILES: C=CCCc1ccc(OC(F)(F)c2ccc3c(c2F)C(F)C(F)c2c-3ccc(OCC)c2F)cc1] |
| 448 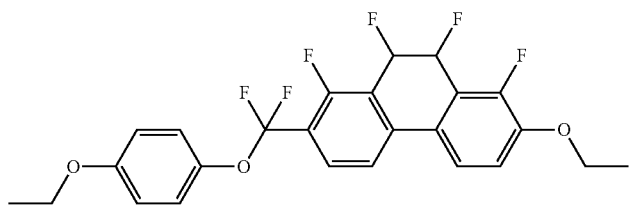 [SMILES: CCOc1ccc(OC(F)(F)c2ccc3c(c2F)C(F)C(F)c2c-3ccc(OCC)c2F)cc1] |
| 449 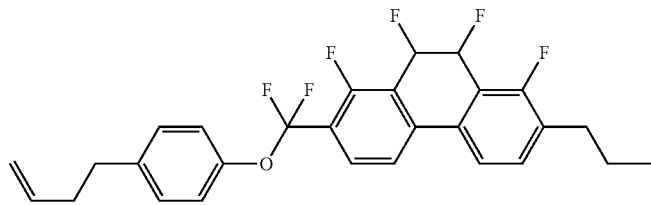 |

-continued
| No. | |
|---|---|
| 450 | 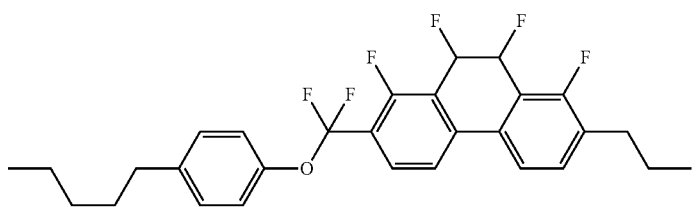 |
| 451 | 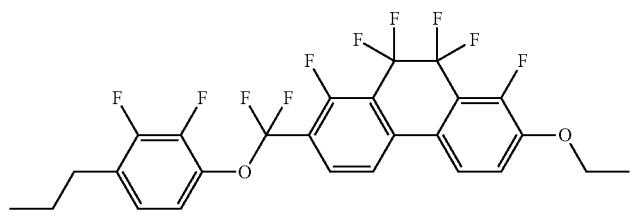 [SMILES: CCCc1ccc(OC(F)(F)c2ccc3c(c2F)C(F)(F)C(F)(F)c2c-3ccc(OCC)c2F)c(F)c1F] |
| 452 | 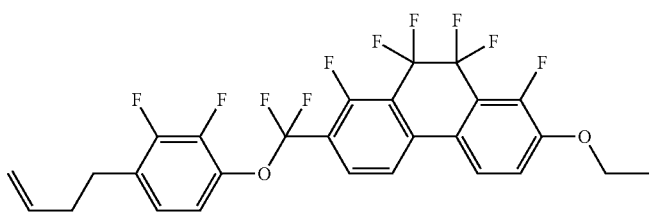 |
| 453 | 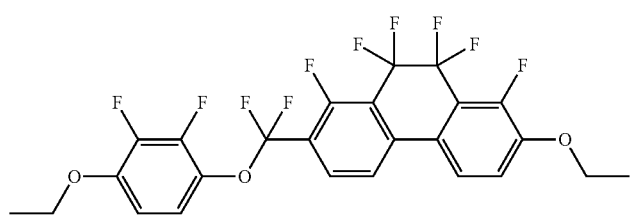 [SMILES: CCOc1ccc(OC(F)(F)c2ccc3c(c2F)C(F)(F)C(F)(F)c2c-3ccc(OCC)c2F)c(F)c1F] |
| 454 | 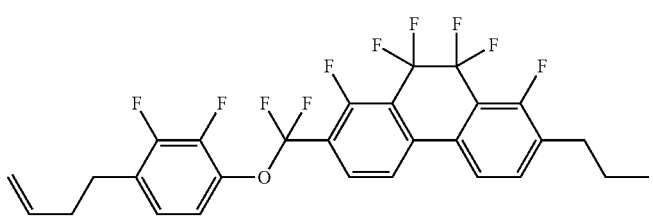 [SMILES: C=CCCc1ccc(OC(F)(F)c2ccc3c(c2F)C(F)(F)C(F)(F)c2c-3ccc(CCC)c2F)c(F)c1F] |
| 455 | 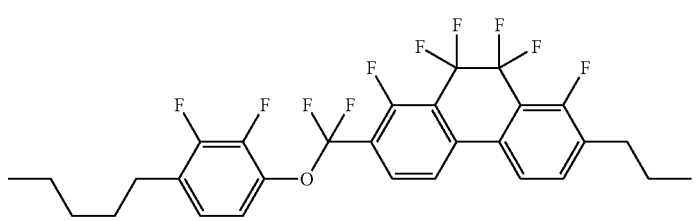 |
| 456 | 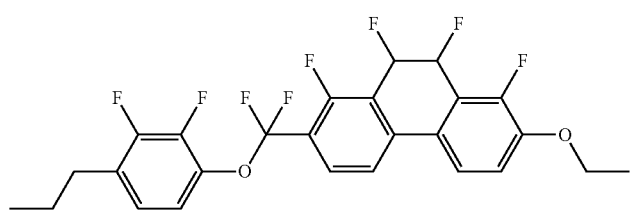 |

| No. | |
|---|---|
| 457 | 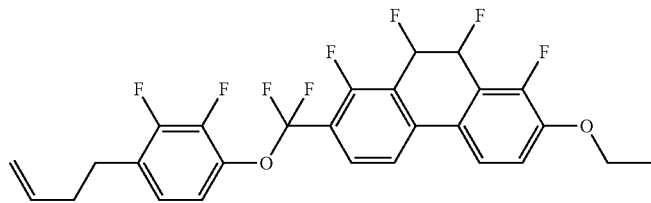 [SMILES: C=CCCc1ccc(OC(F)(F)c2ccc3c(c2F)C(F)C(F)c2c-3ccc(OCC)c2F)c(F)c1F] |
| 458 | 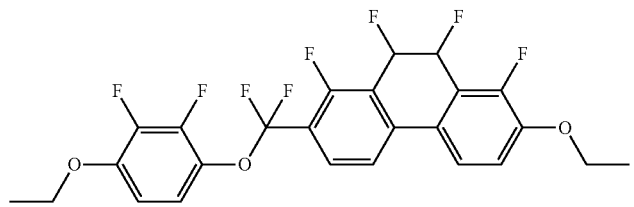 |
| 459 | 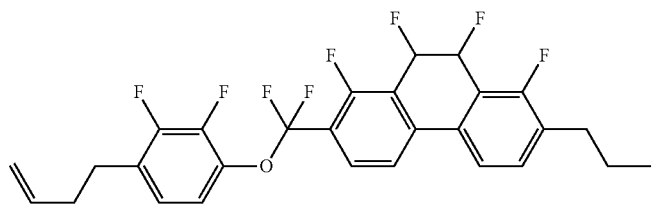 [SMILES: C=CCCc1ccc(OC(F)(F)c2ccc3c(c2F)C(F)C(F)c2c-3ccc(CCC)c2F)c(F)c1F] |
| 460 | 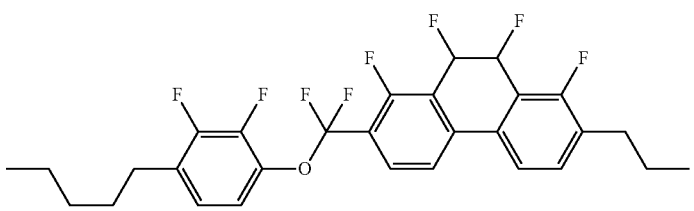 [SMILES: CCCCCc1ccc(OC(F)(F)c2ccc3c(c2F)C(F)C(F)c2c-3ccc(CCC)c2F)c(F)c1F] |
| 461 | 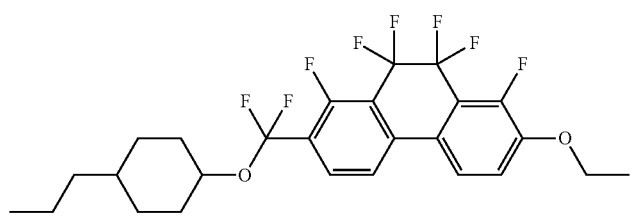 |
| 462 | 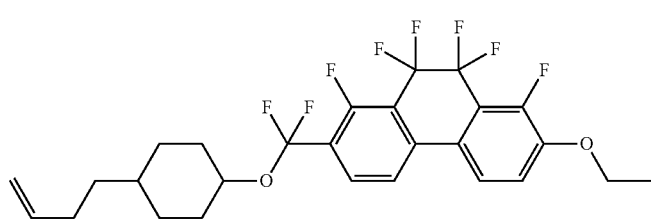 [SMILES: C=CCCC1CCC(OC(F)(F)c2ccc3c(c2F)C(F)(F)C(F)(F)c2c-3ccc(OCC)c2F)CC1] |
| 463 | 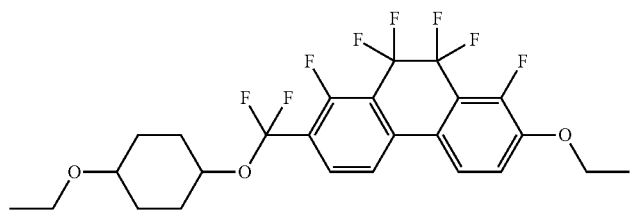 |

| No. |
|---|
| 464 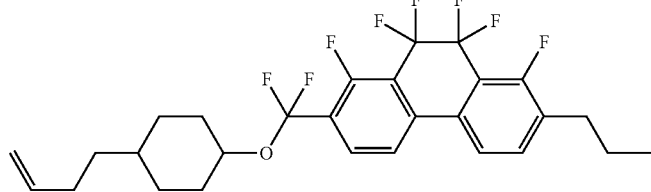 |
| 465 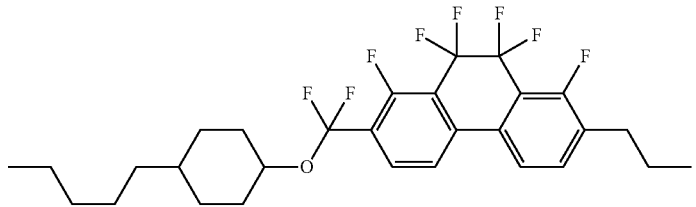 [SMILES: CCCCCC1CCC(OC(F)(F)c2ccc3c(c2F)C(F)(F)C(F)(F)c2c-3ccc(CCC)c2F)CC1] |
| 466 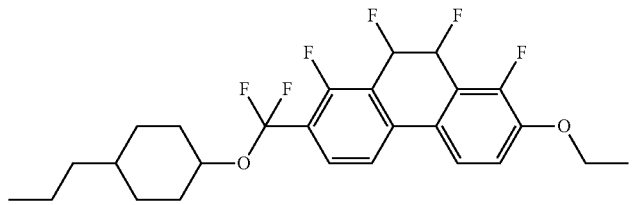 |
| 467 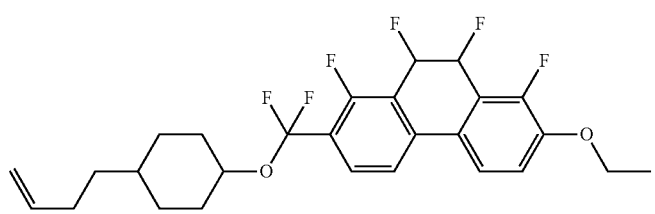 |
| 468 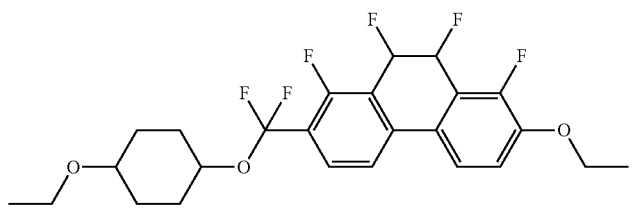 [SMILES: CCOc1ccc2c(c1F)C(F)C(F)c1c-2ccc(C(F)(F)OC2CCC(OCC)CC2)c1F] |
| 469 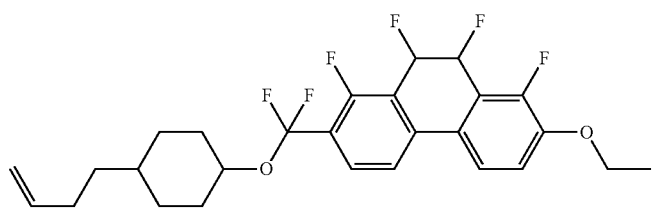 [SMILES: C=CCCC1CCC(OC(F)(F)c2ccc3c(c2F)C(F)C(F)c2c-3ccc(OCC)c2F)CC1] |
| 470 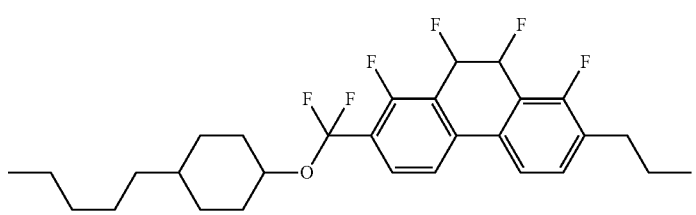 [SMILES: CCCCCC1CCC(OC(F)(F)c2ccc3c(c2F)C(F)C(F)c2c-3ccc(CCC)c2F)CC1] |

| No. |
|---|
| 471 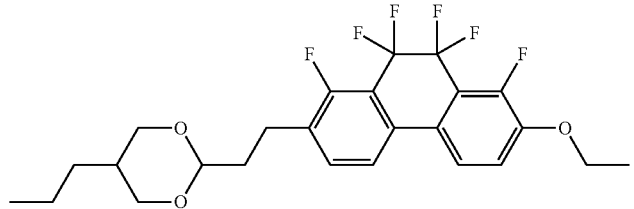 |
| 472 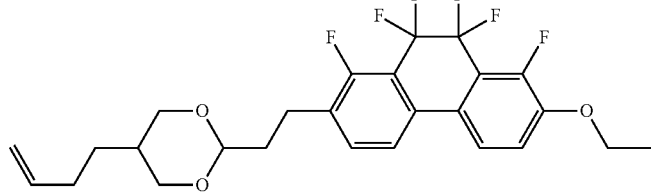 |
| 473 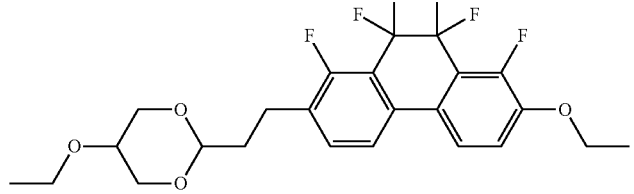 |
| 474 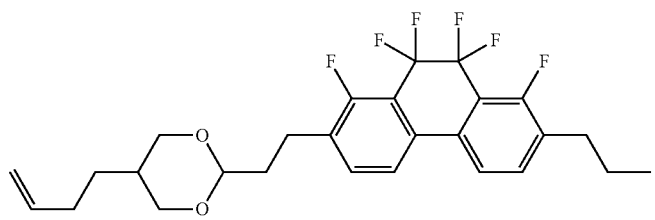 [SMILES: C=CCCC1COC(CCc2ccc3c(c2F)C(F)(F)C(F)(F)c2c-3ccc(CCC)c2F)OC1] |
| 475 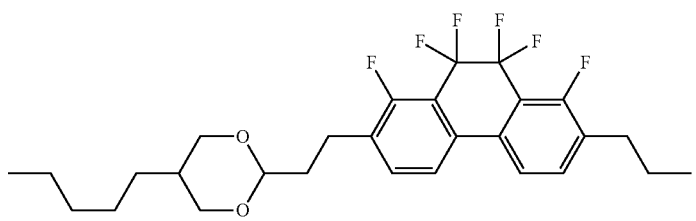 |
| 476 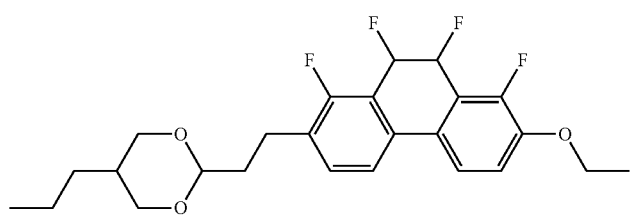 [SMILES: CCCC1COC(CCc2ccc3c(c2F)C(F)C(F)c2c-3ccc(OCC)c2F)OC1] |
| 477 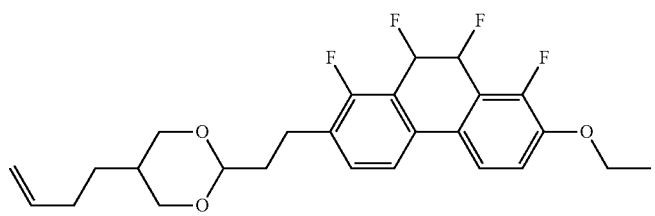 |

-continued
| No. |
|---|
| 478 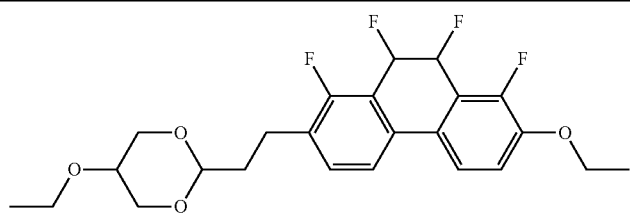 |
| 479 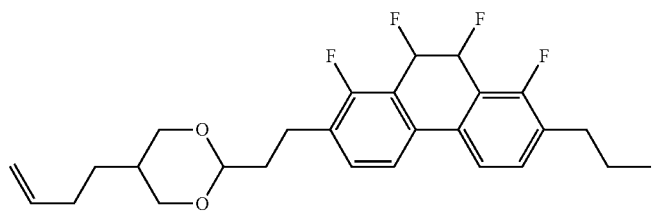 |
| 480 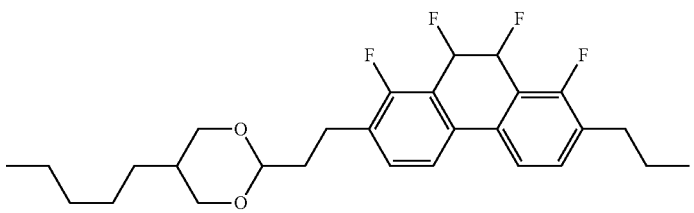 [SMILES: CCCCCC1COC(CCc2ccc3c(c2F)C(F)C(F)c2c-3ccc(CCC)c2F)OC1] |
| 481 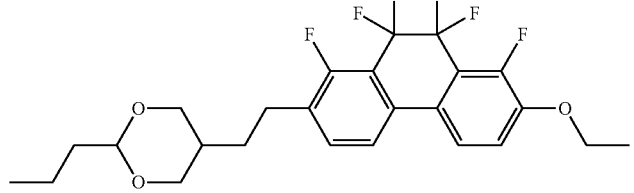 |
| 482 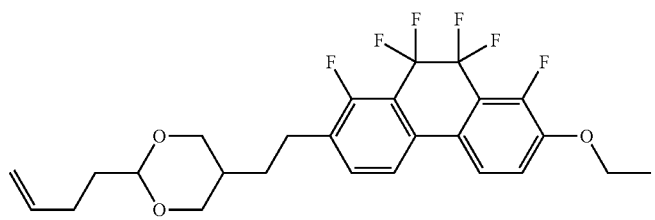 |
| 483 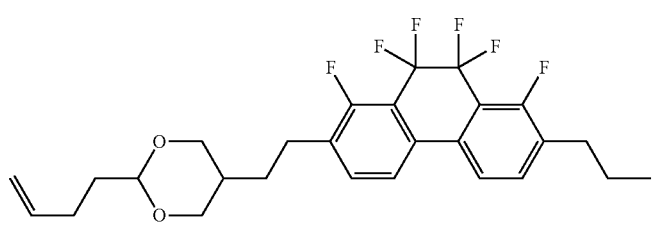 |
| 484 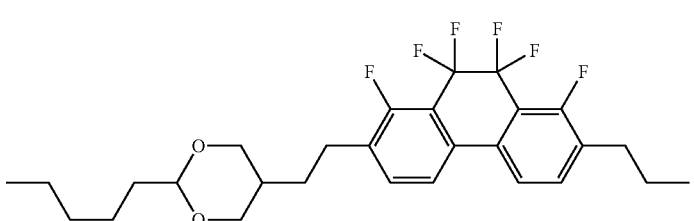 |

| No. |
|---|
| 485 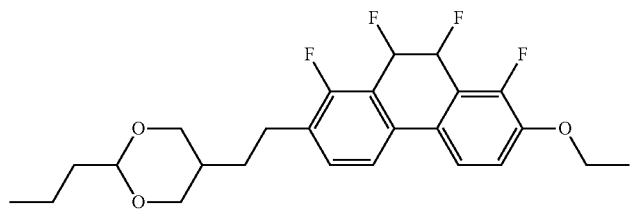 [SMILES: CCCC1OCC(CCc2ccc3c(c2F)C(F)C(F)c2c-3ccc(OCC)c2F)CO1] |
| 486 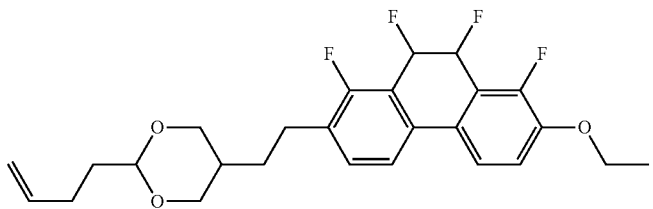 |
| 487 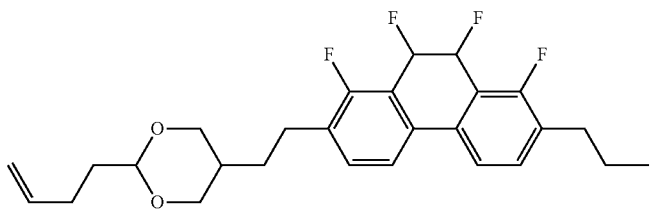 [SMILES: C=CCCC1OCC(CCc2ccc3c(c2F)C(F)C(F)c2c-3ccc(CCC)c2F)CO1] |
| 488 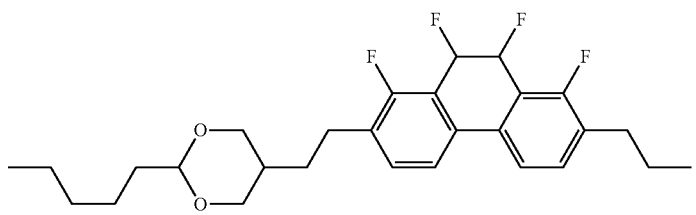 |
| 489 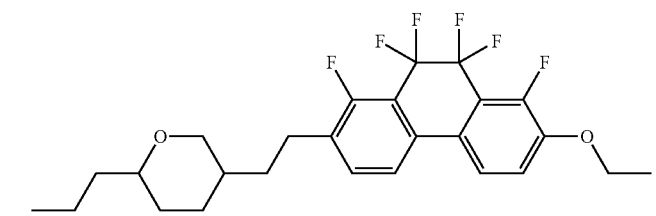 [SMILES: CCCC1CCC(CCc2ccc3c(c2F)C(F)(F)C(F)(F)c2c-3ccc(OCC)c2F)CO1] |
| 490 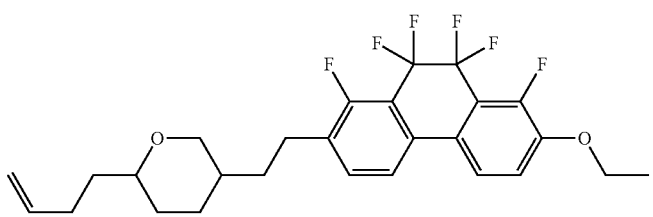 |
| 491 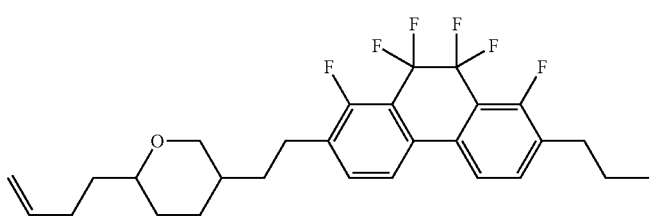 |

| No. |
|---|
| 492 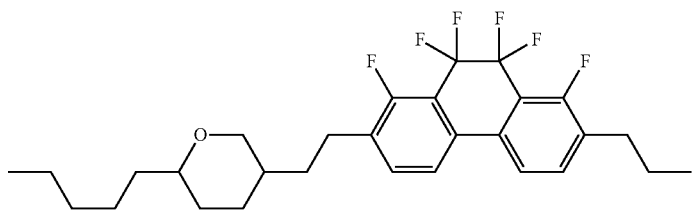 |
| 493 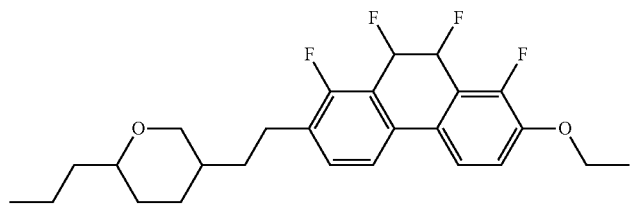 |
| 494 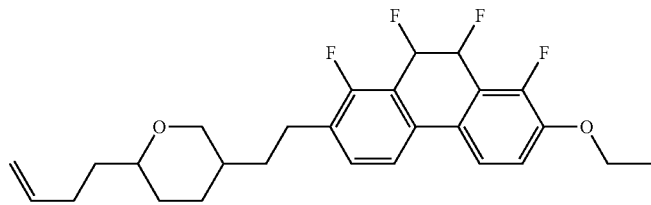 |
| 495 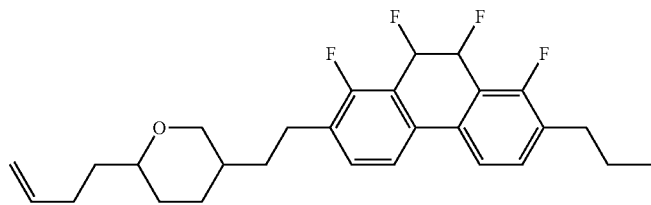 |
| 496 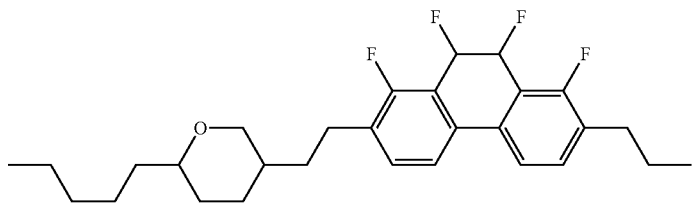 |
| 497 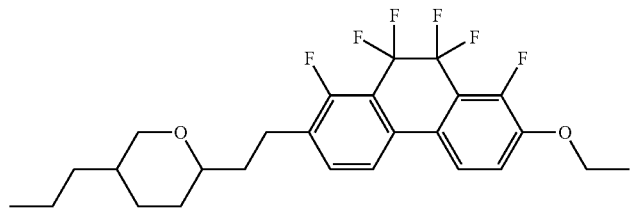 |
| 498 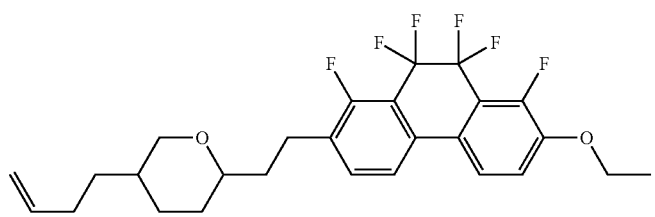 |

-continued
| No. |
|---|
| 499 |
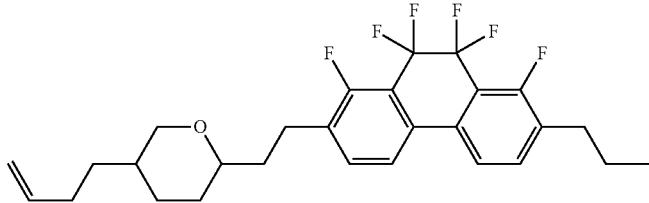
500
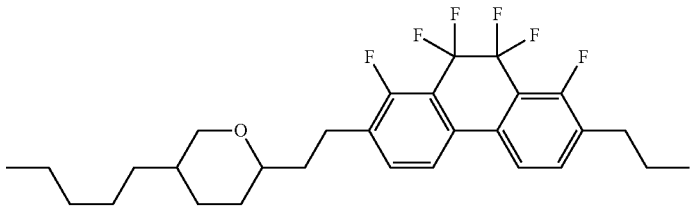
501
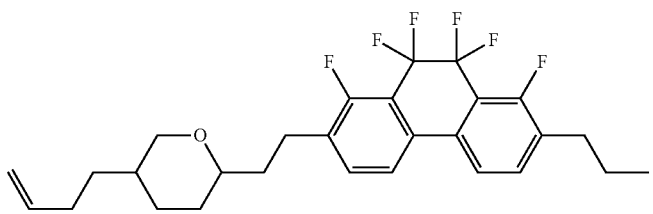 [SMILES: C=CCCC1CCC(CCc2ccc3c(c2F)C(F)(F)C(F)(F)c2c-3ccc(CCC)c2F)OC1]
502
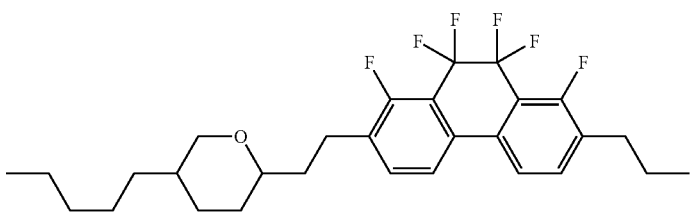
503
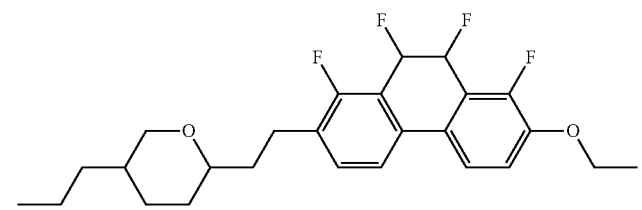
504
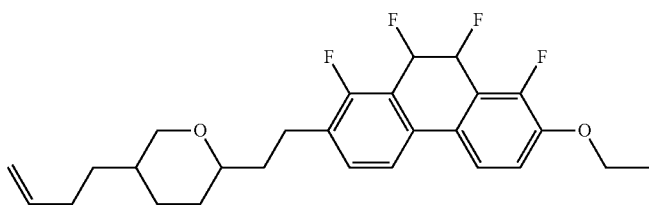 [SMILES: C=CCCC1CCC(CCc2ccc3c(c2F)C(F)C(F)c2c-3ccc(OCC)c2F)OC1]
505
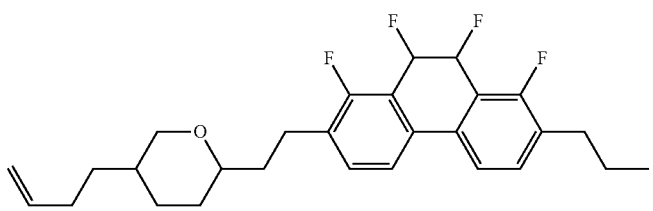 [SMILES: C=CCCC1CCC(CCc2ccc3c(c2F)C(F)C(F)c2c-3ccc(CCC)c2F)OC1]

-continued
| No. |
| --- |
506
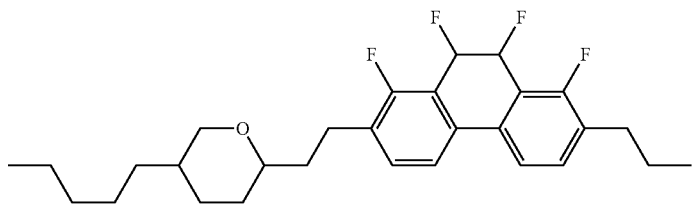
507
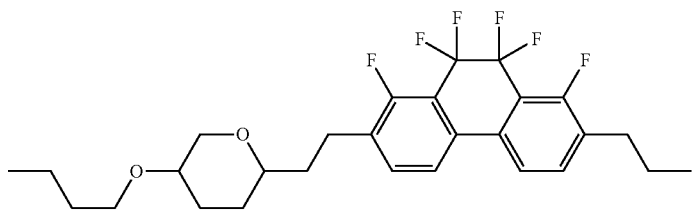
508
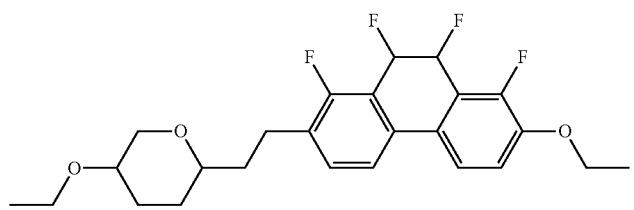
509
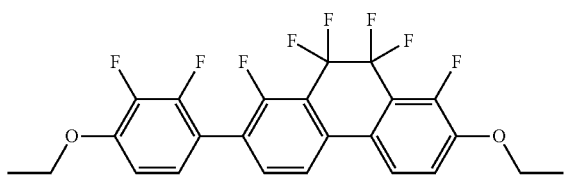 [SMILES: CCOc1ccc(-c2ccc3c(c2F)C(F)(F)C(F)(F)c2c-3ccc(OCC)c2F)c(F)c1F]
510
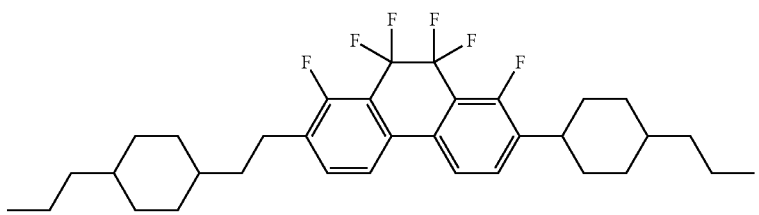 [SMILES: CCCC1CCC(CCc2ccc3c(c2F)C(F)(F)C(F)(F)c2c-3ccc(C3CCC(CCC)CC3)c2F)CC1]
511
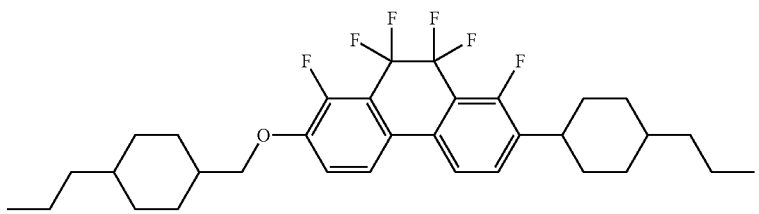 [SMILES: CCCC1CCC(COc2ccc3c(c2F)C(F)(F)C(F)(F)c2c-3ccc(C3CCC(CCC)CC3)c2F)CC1]
512
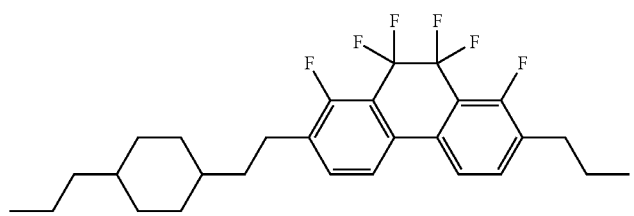

| No. | |
|---|---|
| 513 | 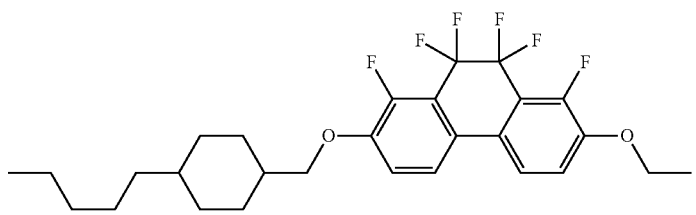 |
| 514 | 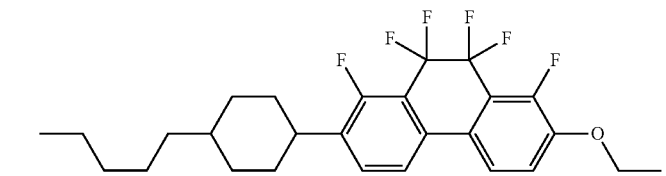 [SMILES: CCCCCC1CCC(c2ccc3c(c2F)C(F)(F)C(F)(F)c2c-3ccc(OCC)c2F)CC1] |

Comparative Example 1

Compound (C-11) that falls under a general formula described in JP H11-508890 A (Patent literature No. 5) was prepared. The compound is similar to compound (No. 211) of the invention, but has no fluorine on 1-position and 8-position of a dihydrophenanthrene ring.

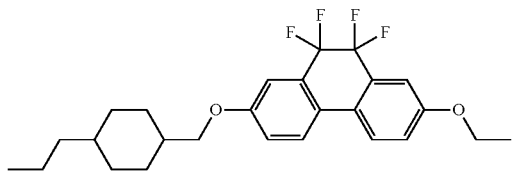

(C-11)

Chemical shifts (δ (ppm)) by $^1$H-NMR analysis were as described below to support a structure of compound (C-11).

$^1$H-NMR CDCl$_3$) δ: 7.68-7.67 (m, 2H), 7.26 (d, 2H), 7.08-7.04 (dd, 2H), 4.11 (q, 2H), 3.82 (d, 2H), 1.94-1.88 (m, 2H), 1.85-1.72 (m, 3H), 1.45 (t, 3H), 1.38-1.16 (m, 5H), 1.13-1.03 (m, 2H), 1.01-0.86 (m, 5H).

A liquid crystal composition was prepared using 15% of compound (C-11) and 85% of base liquid crystal A. Physical properties of the liquid crystal composition obtained were measured, and values of physical properties of compound (C-11) were determined by extrapolating measured values. The results were as described below.

Maximum temperature (NI)=67.9° C.; dielectric anisotropy (Δ∈)=−6.5; refractive index anisotropy (Δn)=0.1603; viscosity (η)=170.3 mPa·s.

Comparative Example 2

Compound (C-12) that falls under a general formula described in Patent literature No. 5 was prepared. The compound has no fluorine on 8-position of a dihydrophenanthrene ring.

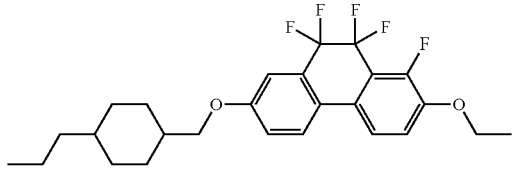

(C-12)

Chemical shifts (δ (ppm)) by $^1$H-NMR analysis were as described below to support a structure of compound (C-12).

$^1$H-NMR (CDCl$_3$) δ: 7.62 (d, 1H), 7.44 (d, 1H), 7.26 (d, 1H), 7.11 (dd, 1H), 7.06 (dd, 1H), 4.15 (q, 2H), 3.82 (d, 2H), 1.94-1.88 (m, 2H), 1.85-1.72 (m, 3H), 1.48 (t, 3H), 1.38-1.16 (m, 5H), 1.13-1.03 (m, 2H), 1.00-0.87 (m, 5H).

A liquid crystal composition was prepared using 15% of compound (C-12) and 85% of base liquid crystal A. Physical properties of the liquid crystal composition obtained were measured, and values of physical properties of compound (C-12) were determined by extrapolating measured values. The results were as described below.

Maximum temperature (NI)=73.3° C.; dielectric anisotropy (Δ∈)=−12.7; refractive index anisotropy (Δn)=0.1537; viscosity (η)=194.9 mPa·s.

Comparative Example 3

Compound (C-13) that falls under a general formula described in Patent literature No. 5 was prepared. The compound has no fluorine on 8-position of a dihydrophenanthrene ring.

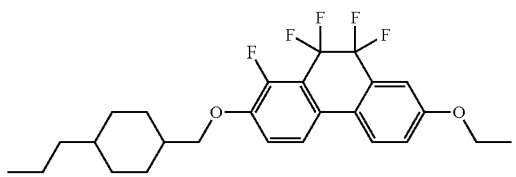

(C-13)

Chemical shifts (δ (ppm)) by $^1$H-NMR analysis were as described below to support a structure of compound (C-12).

$^1$H-NMR CDCl$_3$) δ: 7.63 (d, 1H), 7.43 (d, 1H), 7.26 (d, 1H), 7.13-7.04 (m, 2H), 4.11 (q, 2H), 3.85 (d, 2H), 1.95-1.89 (m, 2H), 1.85-1.75 (m, 3H), 1.45 (t, 3H), 1.38-1.15 (m, 5H), 1.13-1.03 (m, 2H), 1.01-0.86 (m, 5H).

A liquid crystal composition was prepared using 15% of compound (C-13) and 85% of base liquid crystal A. Physical properties of the liquid crystal composition obtained were measured, and values of physical properties of compound (C-13) were determined by extrapolating measured values. The results were as described below.

Maximum temperature (NI)=79.9° C.; dielectric anisotropy (Δ∈)-13.0; refractive index anisotropy (Δn)=0.163; viscosity (η)=174.5 mPa·s.

When the compounds according to Comparative Examples 1 to 3 are compared with compound (No. 211) according to Example 2, compound (No. 211) is found to be superior in view of having a higher maximum temperature (NI), a negatively larger dielectric anisotropy (Lc) and a lower viscosity (n).

The finding shows that having fluorine simultaneously on 1-position and on 8-position of the dihydrophenanthrene ring, as the features of the invention, is significantly important.

Examples of Liquid Crystal Compositions

Typical compositions of the invention are shown in Examples 15 and 16. First, a compound being a component of a composition and an amount (% by weight) thereof were shown. The compound was represented using symbols of a left-terminal group, a bonding group, a ring structure and a right-terminal group according to definitions in Table.

| Table Method for Description of Compounds using Symbols R—(A$_1$)—Z$_1$—...—Z$_n$—(A$_n$)—R | |
|---|---|
| 1) Left-terminal Group R— | Symbol |
| C$_n$H$_{2n+1}$— | n- |
| C$_n$H$_{2n+1}$O— | nO— |
| C$_m$H$_{2m+1}$OC$_n$H$_{2n}$— | mOn— |
| CH$_2$=CH— | V— |
| C$_n$H$_{2n+1}$—CH=CH— | nV— |
| CH$_2$=CH—C$_n$H$_{2n}$— | Vn— |
| C$_m$H$_{2m+1}$—CH=CH—C$_n$H$_{2n}$— | mVn— |
| CF$_2$=CH— | VFF— |
| CF$_2$=CH—C$_n$H$_{2n}$— | VFFn— |
| 2) Right-terminal Group —R' | Symbol |
| —C$_n$H$_{2n+1}$ | -n |
| —OC$_n$H$_{2n+1}$ | —On |
| —CH=CH$_2$ | —V |
| —CH=CH—C$_n$H$_{2n+1}$ | —Vn |
| —C$_n$H$_{2n}$—CH=CH$_2$ | —nV |
| —C$_m$H$_{2m}$—CH=CH—C$_n$H$_{2n+1}$ | —mVn |
| —CH=CF$_2$ | —VFF |
| —COOCH$_3$ | —EMe |
| —F | —F |
| —Cl | —CL |
| —CN | —C |
| —OCF$_3$ | —OCF3 |
| 3) Bonding Group —Z$_n$— | Symbol |
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C≡C— | T |
| 4) Ring Structure —A$_n$— | Symbol |
| 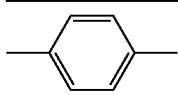 | B |
| 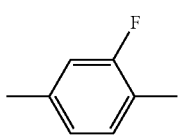 | B(F) |
| 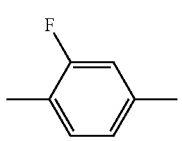 | B(2F) |

-continued
Table Method for Description of Compounds using Symbols
R—(A$_1$)—Z$_1$—...—Z$_n$—(A$_n$)—R
| | |
|---|---|
| 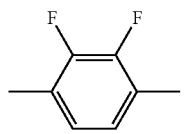 | B(2F,3F) |
| 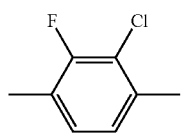 | B(2F,3CL) |
| 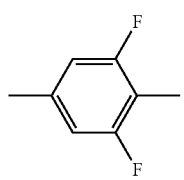 | B(F,F) |
| 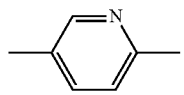 | Pr |
| 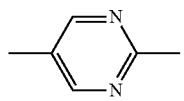 | Py |
| 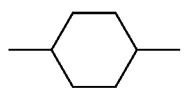 | H |
| 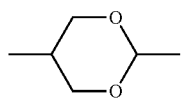 | G |
| 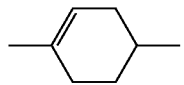 | Ch |
| 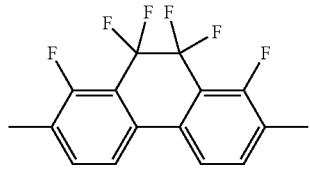 | Pnr(F6) |
5) Examples of Description
Example 1  3-Pnr(F6)—O2
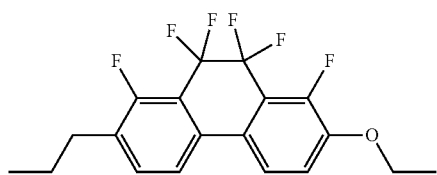 [SMILES: CCCc1ccc2c(c1F)C(F)(F)C(F)(F)c1c-2ccc(OCC)c1F]
Example 2  3-HHB(2F,3F)—O2

-continued

Table Method for Description of Compounds using Symbols
R—(A₁)—Z₁— ... —Zₙ—(Aₙ)—R

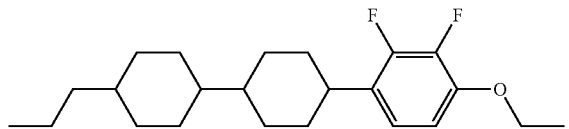 [SMILES: CCCC1CCC(C2CCC(c3ccc(OCC)c(F)c3F)CC2)CC1]

Example 3  5-HBB(F)B-3

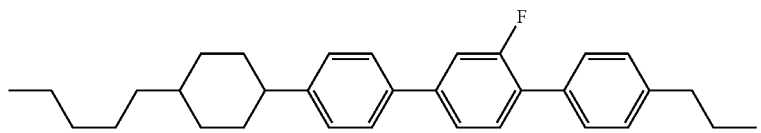 [SMILES: CCCCCC1CCC(c2ccc(-c3ccc(-c4ccc(CCC)cc4)c(F)c3)cc2)CC1]

Example 4  3-HH-4

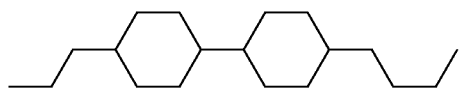 [SMILES: CCCCC1CCC(C2CCC(CCC)CC2)CC1]

Example 15

| | | |
|---|---|---|
| 3-Pnr(F6)-O2 | (No. 1) | 3% |
| 3-HB-O1 | (8-5) | 15% |
| 3-HH-4 | (8-1) | 5% |
| 3-HB(2F,3F)-O2 | (2-1) | 9% |
| 5-HB(2F,3F)-O2 | (2-1) | 12% |
| 2-HHB(2F,3F)-1 | (3-1) | 12% |
| 3-HHB(2F,3F)-1 | (3-1) | 12% |
| 3-HHB(2F,3F)-O2 | (3-1) | 13% |
| 5-HHB(2F,3F)-O2 | (3-1) | 13% |
| 6-HEB(2F,3F)-O2 | (2-6) | 6% |

NI = 81.0° C.; Δn = 0.088; η = 37.6 mPa · s; Δε = –4.1

A pitch when 0.25 part by weight of optically active compound (Op-5) was added to 100 parts by weight of the composition was 62.1 micrometers.

Example 16

| | | |
|---|---|---|
| 3-Pnr(F6)-O2 | (No. 1) | 3% |
| 2-HH-5 | (8-1) | 3% |
| 3-HH-4 | (8-1) | 15% |
| 3-HH-5 | (8-1) | 4% |
| 3-HB-O2 | (8-5) | 12% |
| 3-H2B(2F,3F)-O2 | (2-4) | 13% |
| 3-H2B(2F,3F)-O2 | (2-4) | 14% |
| 3-HHB(2F,3CL)-O2 | (3-12) | 5% |
| 3-HBB(2F,3F)-O2 | (3-7) | 3% |
| 3-HBB(2F,3F)-O2 | (3-7) | 9% |
| 5-HBB(2F,3F)-O2 | (3-7) | 9% |
| 3-HHB-1 | (9-1) | 3% |
| 3-HHB-3 | (9-1) | 4% |
| 3-HHB-O1 | (9-1) | 3% |

NI = 74.8° C.; Δn = 0.094; η = 22.8 mPa · s; Δε = –4.4

INDUSTRIAL APPLICABILITY

The invention provides a liquid crystal compound having an excellent compatibility with other liquid crystal compounds, and a large negative dielectric anisotropy (Δε). When a terminal group, a bonding group, a ring or the like constituting the compound is suitably selected, objective physical properties can be obtained. Furthermore, the invention provides a liquid crystal composition containing the compound and a liquid crystal display device using the composition.

What is claimed is:

1. A liquid crystal composition comprising:
a compound represented by formula (1) and a compound represented by formula (10):

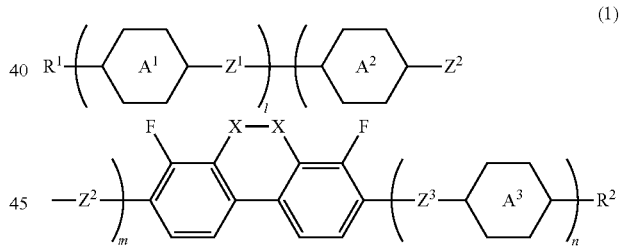

wherein, in formula (1), $R^1$ is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, and in the alkyl, the alkenyl, the alkoxy, the alkoxyalkyl and the alkenyloxy, at least one of hydrogen may be replaced by fluorine, and $R^2$ is alkoxy having 1 to 9 carbons or alkenyloxy having 2 to 9 carbons;
ring $A^1$, ring $A^2$ and ring $A^3$ are independently 1,4-cyclohexylene, 1,4-cyclohexenylene, 1,4-phenylene, tetrahydropyran-2,5-diyl or 1,3-dioxane-2,5-diyl, and in the rings, at least one of hydrogen may be replaced by fluorine;
$Z^1$ and $Z^2$ are independently a single bond, —(CH₂)₂—, —OCH₂—, —CH₂O—, —CF₂O— or —OCF₂—;
l and m are independently 0 or 1; and
a sum of 1 and m is 1 or 2; and
in formula (10), $R^5$ and $R^6$ are independently alkyl having 1 to 10 carbons or alkenyl having 2 to 10 carbons, and in the alkyl and the alkenyl, at least one of hydrogen may be replaced by fluorine, and at least one of —CH$_2$— may be replaced by —O—;

ring D$^1$, ring D$^2$ and ring D$^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and Z$^8$ is —C≡C—, —COO—, —(CH$_2$)$_2$—, —CH=CH— or a single bond.

2. The liquid crystal composition according to claim 1, wherein, in formula (1), R$^1$ is alkyl having 1 to 10 carbons, alkenyl having 2 to 10 carbons or alkoxy having 1 to 9 carbons and R$^2$ is alkoxy having 1 to 9 carbons; and ring A$^1$, ring A$^2$ and ring A$^3$ are independently 1,4-cyclohexylene, 1,4-cyclohexenylene, 1,4-phenylene, tetrahydropyran-2,5-diyl, 1,3-dioxane-2,5-diyl, 2-fluoro-1,4-phenylene, 3-fluoro-1,4-phenylene or 2,3-difluoro-1,4-phenylene.

3. The liquid crystal composition according to claim 2, wherein, in formula (1), ring A$^1$, ring A$^2$ and ring A$^3$ are independently 1,4-cyclohexylene, 1,4-cyclohexenylene, 1,4-phenylene, 2-fluoro-1,4-phenylene, 3-fluoro-1,4-phenylene or 2,3-difluoro-1,4-phenylene.

4. The liquid crystal composition according to claim 1, wherein the compound represented by formula (1) comprises a compound represented by formula (1-1):

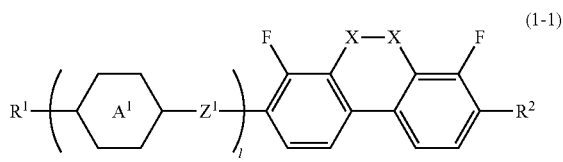

wherein, in formula (1-1), ring A$^1$ is 1,4-cyclohexylene, 1,4-cyclohexenylene, 1,4-phenylene, 2-fluoro-1,4-phenylene, 3-fluoro-1,4-phenylene or 2,3-difluoro-1,4-phenylene;

R$^1$ is alkyl having 1 to 10 carbons, alkenyl having 2 to 10 carbons or alkoxy having 1 to 9 carbons, and R$^2$ is alkoxy having 1 to 9 carbons;

Z$^1$ is a single bond, —(CH$_2$)$_2$—, —OCH$_2$—, —CH$_2$O—, CF$_2$O— or —OCF$_2$—; and l is 1.

5. The liquid crystal composition according to claim 4, wherein, in formula (1-1), Z$^1$ is a single bond, —(CH$_2$)$_2$—, —CH$_2$O—, or —CF$_2$O—.

6. The liquid crystal composition according to claim 5, wherein, in formula (1-1), ring A$^1$ is 1,4-cyclohexylene, 1,4-cyclohexenylene, 1,4-phenylene or 2,3-difluoro-1,4-phenylene.

7. The liquid crystal composition according to claim 1, further containing at least one compound selected from the group of compounds represented by formulas (2), (3), (4), (5), (6) and (7):

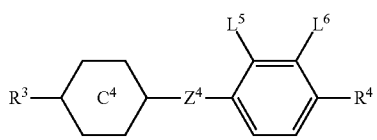

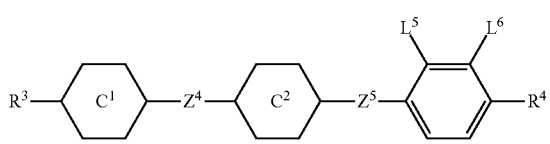

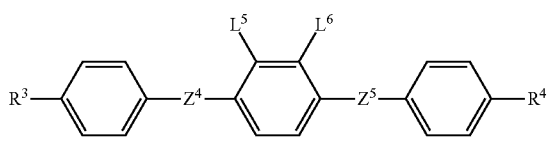

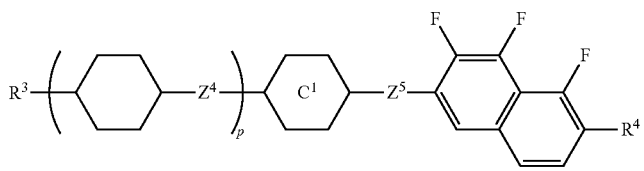

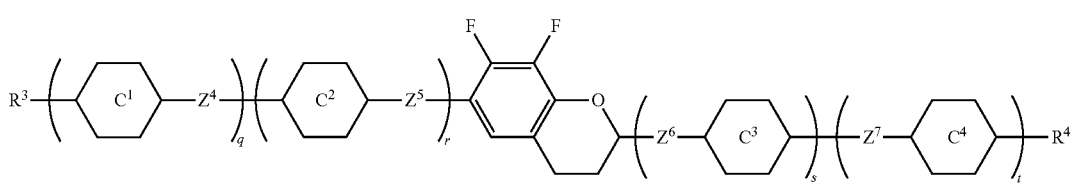

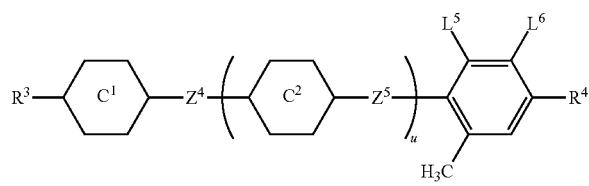

(7)

wherein, in the formulas, $R^3$ and $R^4$ are independently alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

ring $C^1$, ring $C^2$, ring $C^3$ and ring $C^4$ are independently 1,4-cyclohexylene, 1,4-cyclohexenylene, 1,4-phenylene in which at least one of hydrogen may be replaced by fluorine, tetrahydropyran-2,5-diyl or decahydro-2,6-naphthalene;

$Z^4$, $Z^5$, $Z^6$ and $Z^7$ are independently —$(CH_2)_2$—, —COO—, —$CH_2$—, —$OCF_2$—, —$OCF_2(CH_2)_2$— or a single bond;

$L^5$ and $L^6$ are independently fluorine or chlorine; and p, q, r, s, t and u are independently 0 or 1, and a sum of q, r, s and t is 1 or 2.

8. The liquid crystal composition according to claim 1, further containing at least one compound selected from the group of compounds represented by formulas (8) and (9):

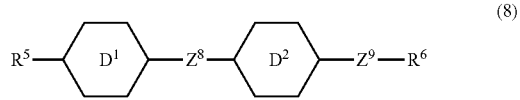

(8)

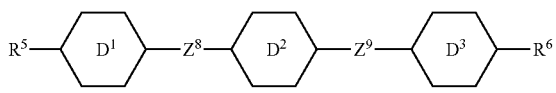

(9)

wherein, in the formulas, $R^5$ and $R^6$ are independently alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

ring $D^1$, ring $D^2$ and ring $D^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^8$ and $Z^9$ are independently —C≡C—, —COO—, —$(CH_2)_2$—, —CH=CH— or a single bond.

9. The liquid crystal composition according to claim 7, further containing at least one compound selected from the group of compounds represented by formulas (8) and (9).

10. The liquid crystal composition according to claim 1, further containing at least one optically active compound and/or one polymerizable compound.

11. The liquid crystal composition according to claim 1, containing at least one antioxidant and/or one ultraviolet light absorber.

12. A liquid crystal display device including the liquid crystal composition according to claim 1.

\* \* \* \* \*